US012188059B2

(12) United States Patent
Carr et al.

(10) Patent No.: US 12,188,059 B2
(45) Date of Patent: Jan. 7, 2025

(54) PROXIMITY-DEPENDENT BIOTINYLATION AND USES THEREOF

(71) Applicant: THE BROAD INSTITUTE, INC., Cambridge, MA (US)

(72) Inventors: Steven A. Carr, Cambridge, MA (US); Jason Wright, Cambridge, MA (US); Sam Myers, Cambridge, MA (US)

(73) Assignee: THE BROAD INSTITUTE, INC., Cambridge, MA (US)

(*) Notice: Subject to any disclaimer, the term of this patent is extended or adjusted under 35 U.S.C. 154(b) by 1279 days.

(21) Appl. No.: 16/333,185

(22) PCT Filed: Sep. 13, 2017

(86) PCT No.: PCT/US2017/051428
§ 371 (c)(1),
(2) Date: Mar. 13, 2019

(87) PCT Pub. No.: WO2018/053053
PCT Pub. Date: Mar. 22, 2018

(65) Prior Publication Data

US 2019/0241880 A1 Aug. 8, 2019

Related U.S. Application Data

(60) Provisional application No. 62/394,133, filed on Sep. 13, 2016.

(51) Int. Cl.

| | |
|---|---|
| ***C07H 21/04*** | (2006.01) |
| ***C12N 9/00*** | (2006.01) |
| ***C12N 9/08*** | (2006.01) |
| ***C12N 9/22*** | (2006.01) |
| ***C12N 15/10*** | (2006.01) |
| ***C12N 15/11*** | (2006.01) |
| ***C12N 15/63*** | (2006.01) |
| ***G16B 15/30*** | (2019.01) |
| *G16B 20/00* | (2019.01) |

(52) U.S. Cl.
CPC ............ *C12N 9/22* (2013.01); *C12N 9/0065* (2013.01); *C12N 9/93* (2013.01); *C12N 15/102* (2013.01); *C12N 15/11* (2013.01); *C12N 15/63* (2013.01); *C12Y 111/01011* (2013.01); *C12Y 603/04015* (2013.01); *G16B 15/30* (2019.02); *C07K 2319/09* (2013.01); *C07K 2319/85* (2013.01); *C12N 2310/20* (2017.05); *C12N 2740/16043* (2013.01); *G16B 20/00* (2019.02)

(58) Field of Classification Search
None
See application file for complete search history.

(56) References Cited

U.S. PATENT DOCUMENTS

2006/0248617 A1 11/2006 Imanaka et al.
2016/0024568 A1* 1/2016 May ...................... C12N 15/11 424/94.6
2019/0062736 A1* 2/2019 Liu ...................... C12N 15/111

FOREIGN PATENT DOCUMENTS

| | | | |
|---|---|---|---|
| WO | 2010079430 | A1 | 7/2010 |
| WO | 2013082519 | A2 | 6/2013 |
| WO | 2014070227 | A1 | 5/2014 |
| WO | 2014093622 | A2 | 6/2014 |
| WO | 2014204724 | A1 | 12/2014 |
| WO | 2014204725 | A1 | 12/2014 |
| WO | 2014204726 | A1 | 12/2014 |
| WO | 2014204727 | A1 | 12/2014 |
| WO | 2014204728 | A1 | 12/2014 |
| WO | 2014204729 | A1 | 12/2014 |
| WO | 2015065964 | A1 | 5/2015 |
| WO | 2015089419 | A2 | 6/2015 |
| WO | 2016161207 | A1 | 10/2016 |
| WO | 2018053053 | A1 | 3/2018 |

OTHER PUBLICATIONS

Gasiunas, Giedrius, et al. "A catalogue of biochemically diverse CRISPR-Cas9 orthologs." Nature communications 11.1 (2020): 5512.*
McDonald, James I., et al. ("Reprogrammable CRISPR/Cas9-based system for inducing site-specific DNA methylation." Biology open 5.6 (2016): 866-874).*
Mutwil, Marek et al. ("In vitro characterization of promiscuous biotinylation by biotin ligase." 2013).*
"International Preliminary Report on Patentability for International Application No. PCT/US2017/051428, filed Sep. 13, 2017", mailed Mar. 28, 2019, 7 pages.
Boyer, et al., "Core transcriptional regulatory circuitry in human embryonic stem cells. Cell 122, 947-956 (2005)."
Chen, et al., "Genome-wide CRISPR screen in a mouse model of tumor growth and metastasis", Cell, vol. 160, No. 6, pp. 1246-1260, Mar. 12, 2015., Mar. 12, 2015, 1246-1260.
Cong, et al., "Multiplex Genome Engineering Using CRISPR/Cas Systems", Science, vol. 339, No. 6121, Feb. 14, 2013, 819-823.
Doench, et al., "Rational design of highly active sgRNAs for CRISPR-Cas9-mediated gene inactivation", Nat Biotechnology, vol. 32, No. 12, pp. 1262-1267, Dec. 2014.
Fujita, "Efficient isolation of specific genomic regions and identification of associated proteins by engineered DNA-binding molecule-mediated chromatin immunoprecipitation (enChIP) using CRISPR.", Biochem Biophys Res Commun 439, 132-136 (2013).

(Continued)

*Primary Examiner* — Kimberly Chong
(74) *Attorney, Agent, or Firm* — Withers Bergman LLP; Christopher R. Cowles

(57) ABSTRACT

The present invention provides fusion proteins, polynucleotides, kits, as well as TALE- or CRISPR-Cas based systems and methods. The present invention relies on proximity-dependent biotinylation, which allows site-directed protein or DNA purification and identification. The present invention provides tools for delineating the genetics of disease mechanism and for the identification of therapeutic targets and markers.

26 Claims, 44 Drawing Sheets

Specification includes a Sequence Listing.

(56) References Cited

OTHER PUBLICATIONS

Fujita, et al., "Isolation of specific genomic regions and identification of associated molecules by engineered DNA-binding molecule-mediated chromatin immunoprecipitation (enChIP) using CRISPR", Methods Mol Biol. 2015;1288:43-52. doi: 10.1007/978-1-4939-2474-5_4).
Hsu, et al., "Development and Applications of CRISPR-Cas9 for Genome Engineering", Cell, vol. 157, No. 6,, Jun. 5, 2014, 1262-1278.
Hsu, et al., "DNA Targeting Specificity of RNA-Guided Cas9 Nucleases", Nat. Biotechnol. vol. 31, No. 9, Sep. 2013, 827-832.
Hung, et al., "Proteomic Mapping of the Human Mitochondrial Intermembrane Space in Live Cells via Ratiometric APEX tagging", Mol Cell. Jul. 17, 2014; 55(2): 332-341. doi:10.1016/j.molcel.2014.06.003., 20 pages.
Jiang, et al., "RNA-guided editing of bacterial genomes using CRISPR-Cas systems", Nature Biotechnology, vol. 31, Issue 3, Mar. 2013, 233-239.
Jinek, et al., "A Programmable Dual-RNA-Guided DNA Endonuclease in Adaptive Bacterial Immunity", Science, vol. 337, No. 6096,, Aug. 17, 2012, 816-821.
Kim, et al., "Probing nuclear pore complex architecture with proximity-dependent biotinylation.", Proc Natl Acad Sci U S A. Jun. 17, 2014;111(24):E2453-61. doi: 10.1073/pnas.1406459111. Epub Jun. 3, 2014.
Konermann, et al., "Genome-Scale Transcriptional Activation by an Engineered CRISPR-Cas9 Complex", Nature, vol. 517, No. 7536, Dec. 10, 2014, 583-588.
Konermann, et al., "Optical Control of Mammalian Endogenous Transcription and Epigenetic States", Nature, vol. 500, No. 7463, Aug. 22, 2013, 472-476.
Lam, "Directed evolution of APEX2 for electron microscopy and proteomics", Nat Methods. Jan. 2015 ; 12(1): 51-54. doi: 10.1038/nmeth.3179.
Nishimasu, et al., "Crystal Structure of Cas9 in Complex with Guide RNA and Target DNA", Cell, vol. 156, No. 5, Feb. 27, 2014, 935-949.
Nishimasu, et al., "Crystal Structure of *Staphylococcus aureus* Cas9", Cell, vol. 162, pp. 1113-11126, Aug. 27, 2015.
Parnas, et al., "A genome-wide CRISPR screen in primary immune cells to dissect regulatory networks", Cell, vol. 162, No. 3, pp. 675-686, Jul. 30, 2015.
Platt, et al., "CRISPR-Cas9 Knockin Mice for Genome Editing and Cancer Modelling", Cell, vol. 159, No. 2, Oct. 9, 2014, 440-455.
Qi, et al., "Repurposing CRISPR as an RNA-Guided Platform for Sequence-Specific Control of Gene Expression", Cell, vol. 152, No. 5, Feb. 28, 2013, 1173-1183.
Ramanan, et al., "CRISPR/Cas9 Cleavage of Viral DNA Efficiently Suppresses Hepatitis B Virus", Scientific Reports, vol. 5, Article No. 10833, 2015, 9 pages.
Ran, et al., "Double nicking by RNA-guided CRISPR Cas9 for enhanced genome editing specificity", Cell, vol. 154, No. 6, pp. 1-18, Available in PMC: Sep. 12, 2014.
Ran, et al., "Genome Engineering using the CRISPR-Cas9 System", Nature Protocols, vol. 8, No. 11, Nov. 2013, 2281-2308.
Ran, et al., "In Vivo Genome Editing using*Staphylococcus aureau* Cas9", Nature, vol. 520, No. 7546, Apr. 9, 2015, 186-191.
Rao, et al., "A 3D map of the human genome at kilobase resolution reveals principles of chromatin looping", Cell, Dec. 11:P.mhAr 2014 (Dec. 11, 2014), vol. 159, p. 1665-1600.
Roux, et al., "A promiscuous biotin ligase fusion protein identifies proximal and interacting proteins in mammalian cells.", J Cell Biol. Mar. 19, 2012;196(6):801-10. doi: 10.1083/jcb.201112098. Epub Mar. 12, 2012.
Sanjana, et al., "A Transcription Activator-like Effector Toolbox for Genome Engineering", Nature Protocol, vol. 7, Issue 1, Jan. 2012, 171-192.
Shalem, et al., "Genome-Scale CRISPR-Cas9 Knockout Screening in Human Cells", Science, vol. 343, No. 6166, 2014, 84-87.
Shalem, et al., "High-Throughput Functional Genomics Using CRISPR-Cas9", Nature Reviews Genetics, vol. 16, No. 5, May 2015, 299-311.
Shengdar, et al., "Dimeric CRISPR RNA-guided FokI nucleases for highly specific genome editing", Nature Biotechnology, vol. 32, No. 6, 2014, 569-576.
Swiech, et al., "In vivo interrogation of gene function in the mammalian brain using CRISPR-Cas9", Nat. Biotechnology, vol. 33, No. 1, pp. 102-106, Jan. 2015., Jan. 2015, 102-106.
Thakore, et al., "Highly specific epigenome editing by CRISPR-Cas9 repressors for silencing of distal regulatory elements.", Nature Methods 12, 1143-+ (2015).
Wang, et al., "Genetic screens in human cells using the CRISPR/Cas9 system", Science, vol. 343, No. 6166, pp. 80-84, Jan. 3, 2014.
Wang, et al., "One-Step Generation of Mice Carrying Mutations in Multiple Genes by CRISPR/Cas-Mediated Genome Engineering", Cell, vol. 153, pp. 910-918, May 9, 2013.
Wu, et al., "Genome-wide binding of the crisPr endonuclease cas9 in mammalian cells", Nature Biotechnology Letters, pp. 1-9, Published online: Apr. 20, 2014.
Xu, et al., "Sequence determinants of improved CRISPR sgRNA design", Genome Research, pp. 1147-1157, 2015.
Zetche, et al., "A Split Cas9 Architecture for Inducible Genome Editing and Transcription Modulation", Nat. Biotechnology, vol. 33, No. 2, pp. 139-142, Feb. 2015.
"PCT Notification of the International Search Report and Written Opinion", 1-10, PCT/US2017/051428, mailed Dec. 4, 2017.
Schmidtmann, et al., "Determination of Local Chromatin Composition by CasID", Nucleus, vol. 7, No. 5, pp. 476-484, Sep. 23, 2016, 475-484.

* cited by examiner pLenti2-EF1a-NLS-dCas9-BirAR118G-2A-WPRE 15.256 kb

15000

5000

10000

EF-1a hSpCsn1

BIRAR118G

EGFP

F) Native ChIP heatmap

SEQUENCE LISTING

<160> NUMBER OF SEQ ID NOS: 201

<210> SEQ ID NO 1
<211> LENGTH: 321
<212> TYPE: PRT
<213> ORGANISM: E. coli

<400> SEQUENCE: 1

```
Met Lys Asp Asn Thr Val Pro Leu Lys Leu Ile Ala Leu Leu Ala Asn
1               5                   10                  15

Gly Glu Phe His Ser Gly Glu Gln Leu Gly Glu Thr Leu Gly Met Ser
            20                  25                  30

Arg Ala Ala Ile Asn Lys His Ile Gln Thr Leu Arg Asp Trp Gly Val
        35                  40                  45

Asp Val Phe Thr Val Pro Gly Lys Gly Tyr Ser Leu Pro Glu Pro Ile
    50                  55                  60

Gln Leu Leu Asn Ala Lys Gln Ile Leu Gly Gln Leu Asp Gly Gly Ser
65                  70                  75                  80

Val Ala Val Leu Pro Val Ile Asp Ser Thr Asn Gln Tyr Leu Leu Asp
                85                  90                  95

Arg Ile Gly Glu Leu Lys Ser Gly Asp Ala Cys Ile Ala Glu Tyr Gln
            100                 105                 110

Gln Ala Gly Arg Gly Gly Arg Gly Arg Lys Trp Phe Ser Pro Phe Gly
        115                 120                 125

Ala Asn Leu Tyr Leu Ser Met Phe Trp Arg Leu Glu Gln Gly Pro Ala
    130                 135                 140

Ala Ala Ile Gly Leu Ser Leu Val Ile Gly Ile Val Met Ala Glu Val
145                 150                 155                 160

Leu Arg Lys Leu Gly Ala Asp Lys Val Arg Val Lys Trp Pro Asn Asp
                165                 170                 175

Leu Tyr Leu Gln Asp Arg Lys Leu Ala Gly Ile Leu Val Glu Leu Thr
            180                 185                 190

Gly Lys Thr Gly Asp Ala Ala Gln Ile Val Ile Gly Ala Gly Ile Asn
        195                 200                 205

Met Ala Met Arg Arg Val Glu Glu Ser Val Val Asn Gln Gly Trp Ile
    210                 215                 220

Thr Leu Gln Glu Ala Gly Ile Asn Leu Asp Arg Asn Thr Leu Ala Ala
225                 230                 235                 240

Met Leu Ile Arg Glu Leu Arg Ala Ala Leu Glu Leu Phe Glu Gln Glu
                245                 250                 255

Gly Leu Ala Pro Tyr Leu Ser Arg Trp Glu Lys Leu Asp Asn Phe Ile
            260                 265                 270

Asn Arg Pro Val Lys Leu Ile Ile Gly Asp Lys Glu Ile Phe Gly Ile
        275                 280                 285

Ser Arg Gly Ile Asp Lys Gln Gly Ala Leu Leu Leu Glu Gln Asp Gly
    290                 295                 300

Ile Ile Lys Pro Trp Met Gly Gly Glu Ile Ser Leu Arg Ser Ala Glu
305                 310                 315                 320

Lys
```

<210> SEQ ID NO 2
<211> LENGTH: 963
<212> TYPE: DNA
<213> ORGANISM: E. coli

<400> SEQUENCE: 2

```
atgaaggaca acaccgtgcc cctgaagctg atcgccctgc tggccaacgg cgagttccac     60

tctggcgagc agctgggaga gaccctggga atgagcagag ccgccatcaa caagcacatc    120

cagacactga gagactgggg agtggacgtg ttcaccgtgc ctggcaaggg ctacagcctg    180

cctgagccta tccagctgct gaacgccaag cagatcctgg gacagctgga tggcggaagc    240

gtggccgtgc tgcctgtgat cgactccacc aatcagtacc tgctggacag aatcggagag    300

ctgaagtccg gcgacgcctg catcgccgag taccagcagg ctggcagagg aggcagaggc    360

cggaagtggt tcagcccatt cggagccaac ctgtacctgt ccatgttctg gagactggag    420

cagggacctg ctgctgccat cggactgagt ctggtgatcg gaatcgtgat ggccgaggtg    480

ctgagaaagc tgggagccga caaggtgaga gtgaagtggc ctaatgacct gtacctccag    540

gaccgcaagc tggctggcat cctggtggag ctgacaggca agacaggcga tgccgctcag    600

atcgtgatcg gagccggaat caacatggcc atgagaagag tggaggagag cgtggtgaac    660

cagggctgga tcaccctgca ggaggctggc atcaacctgg accggaacac cctggccgcc    720

atgctgatca gagagctgag agccgctctg gagctgttcg agcaggaggg actggctcct    780

tacctgagca gatgggagaa gctggacaac ttcatcaaca gacctgtgaa gctgatcatc    840

ggcgacaagg aaatcttcgg catctccaga ggaatcgaca agcagggagc tctgctgctg    900

gagcaggacg gaatcatcaa gccctggatg ggcggagaaa tctccctgag aagcgcagag    960

aag                                                                  963
```

```
<210> SEQ ID NO 3
<211> LENGTH: 7
<212> TYPE: PRT
<213> ORGANISM: SV40

<400> SEQUENCE: 3

Pro Lys Lys Lys Arg Lys Val
1               5


<210> SEQ ID NO 4
<211> LENGTH: 16
<212> TYPE: PRT
<213> ORGANISM: Artificial Sequence
<220> FEATURE:
<223> OTHER INFORMATION: Synthetic

<400> SEQUENCE: 4

Lys Arg Pro Ala Ala Thr Lys Lys Ala Gly Gln Ala Lys Lys Lys Lys
1               5                   10                  15


<210> SEQ ID NO 5
<211> LENGTH: 9
<212> TYPE: PRT
<213> ORGANISM: Artificial Sequence
<220> FEATURE:
<223> OTHER INFORMATION: Synthetic

<400> SEQUENCE: 5

Pro Ala Ala Lys Arg Val Lys Leu Asp
1               5


<210> SEQ ID NO 6
<211> LENGTH: 11
<212> TYPE: PRT
<213> ORGANISM: Artificial Sequence
<220> FEATURE:
<223> OTHER INFORMATION: Synthetic
```

```
<400> SEQUENCE: 6

Arg Gln Arg Arg Asn Glu Leu Lys Arg Ser Pro
1               5                   10


<210> SEQ ID NO 7
<211> LENGTH: 38
<212> TYPE: PRT
<213> ORGANISM: Artificial Sequence
<220> FEATURE:
<223> OTHER INFORMATION: Synthetic

<400> SEQUENCE: 7

Asn Gln Ser Ser Asn Phe Gly Pro Met Lys Gly Gly Asn Phe Gly Gly
1               5                   10                  15

Arg Ser Ser Gly Pro Tyr Gly Gly Gly Gly Gln Tyr Phe Ala Lys Pro
            20                  25                  30

Arg Asn Gln Gly Gly Tyr
        35


<210> SEQ ID NO 8
<211> LENGTH: 42
<212> TYPE: PRT
<213> ORGANISM: Artificial Sequence
<220> FEATURE:
<223> OTHER INFORMATION: Synthetic

<400> SEQUENCE: 8

Arg Met Arg Ile Glx Phe Lys Asn Lys Gly Lys Asp Thr Ala Glu Leu
1               5                   10                  15

Arg Arg Arg Arg Val Glu Val Ser Val Glu Leu Arg Lys Ala Lys Lys
            20                  25                  30

Asp Glu Gln Ile Leu Lys Arg Arg Asn Val
        35                  40


<210> SEQ ID NO 9
<211> LENGTH: 8
<212> TYPE: PRT
<213> ORGANISM: Artificial Sequence
<220> FEATURE:
<223> OTHER INFORMATION: Synthetic

<400> SEQUENCE: 9

Val Ser Arg Lys Arg Pro Arg Pro
1               5


<210> SEQ ID NO 10
<211> LENGTH: 8
<212> TYPE: PRT
<213> ORGANISM: Artificial Sequence
<220> FEATURE:
<223> OTHER INFORMATION: Synthetic

<400> SEQUENCE: 10

Pro Pro Lys Lys Ala Arg Glu Asp
1               5


<210> SEQ ID NO 11
<211> LENGTH: 8
<212> TYPE: PRT
<213> ORGANISM: Homo sapiens

<400> SEQUENCE: 11

Pro Gln Pro Lys Lys Lys Pro Leu
```

```
1               5


<210> SEQ ID NO 12
<211> LENGTH: 12
<212> TYPE: PRT
<213> ORGANISM: Mus

<400> SEQUENCE: 12

Ser Ala Leu Ile Lys Lys Lys Lys Lys Met Ala Pro
1               5                   10


<210> SEQ ID NO 13
<211> LENGTH: 5
<212> TYPE: PRT
<213> ORGANISM: Influenza NS1

<400> SEQUENCE: 13

Asp Arg Leu Arg Arg
1               5


<210> SEQ ID NO 14
<211> LENGTH: 7
<212> TYPE: PRT
<213> ORGANISM: Influenza NS1

<400> SEQUENCE: 14

Pro Lys Gln Lys Lys Arg Lys
1               5


<210> SEQ ID NO 15
<211> LENGTH: 10
<212> TYPE: PRT
<213> ORGANISM: Hepatitis virus

<400> SEQUENCE: 15

Arg Lys Leu Lys Lys Lys Ile Lys Lys Leu
1               5                   10


<210> SEQ ID NO 16
<211> LENGTH: 10
<212> TYPE: PRT
<213> ORGANISM: Mus

<400> SEQUENCE: 16

Arg Glu Lys Lys Lys Phe Leu Lys Arg Arg
1               5                   10


<210> SEQ ID NO 17
<211> LENGTH: 20
<212> TYPE: PRT
<213> ORGANISM: Homo sapiens

<400> SEQUENCE: 17

Lys Arg Lys Gly Asp Glu Val Asp Gly Val Asp Glu Val Ala Lys Lys
1               5                   10                  15

Lys Ser Lys Lys
            20


<210> SEQ ID NO 18
<211> LENGTH: 17
<212> TYPE: PRT
<213> ORGANISM: Homo sapiens

<400> SEQUENCE: 18
```

Arg Lys Cys Leu Gln Ala Gly Met Asn Leu Glu Ala Arg Lys Thr Lys
1 5 10 15

Lys

<210> SEQ ID NO 19
<211> LENGTH: 34
<212> TYPE: DNA
<213> ORGANISM: Artificial Sequence
<220> FEATURE:
<223> OTHER INFORMATION: Synthetic

<400> SEQUENCE: 19
aaaccgaccc cggggaggcc cacctggcgg aagg 34

<210> SEQ ID NO 20
<211> LENGTH: 35
<212> TYPE: DNA
<213> ORGANISM: Artificial Sequence
<220> FEATURE:
<223> OTHER INFORMATION: Synthetic

<400> SEQUENCE: 20
caccgccctg ctgcgcagcc actaccgcga ggtgc 35

<210> SEQ ID NO 21
<211> LENGTH: 34
<212> TYPE: DNA
<213> ORGANISM: Artificial Sequence
<220> FEATURE:
<223> OTHER INFORMATION: Synthetic

<400> SEQUENCE: 21
aaacgcacct cgcggtagtg gctgcgcagc aggg 34

<210> SEQ ID NO 22
<211> LENGTH: 35
<212> TYPE: DNA
<213> ORGANISM: Artificial Sequence
<220> FEATURE:
<223> OTHER INFORMATION: Synthetic

<400> SEQUENCE: 22
caccggcagg tgacaccaca cagaaaccac ggtca 35

<210> SEQ ID NO 23
<211> LENGTH: 34
<212> TYPE: DNA
<213> ORGANISM: Artificial Sequence
<220> FEATURE:
<223> OTHER INFORMATION: Synthetic

<400> SEQUENCE: 23
aaactgaccg tggtttctgt gtggtgtcac ctgc 34

<210> SEQ ID NO 24
<211> LENGTH: 35
<212> TYPE: DNA
<213> ORGANISM: Artificial Sequence
<220> FEATURE:
<223> OTHER INFORMATION: Synthetic

<400> SEQUENCE: 24
caccgccttc cagctccgcc tcctccgcgc ggacc 35

<210> SEQ ID NO 25

<211> LENGTH: 34
<212> TYPE: DNA
<213> ORGANISM: Artificial Sequence
<220> FEATURE:
<223> OTHER INFORMATION: Synthetic

<400> SEQUENCE: 25
aaacggtccg cgcggaggag gcggagctgg aagg 34

<210> SEQ ID NO 26
<211> LENGTH: 35
<212> TYPE: DNA
<213> ORGANISM: Artificial Sequence
<220> FEATURE:
<223> OTHER INFORMATION: Synthetic

<400> SEQUENCE: 26
caccgctccg gatcaggcca gcggccaaag ggtcg 35

<210> SEQ ID NO 27
<211> LENGTH: 34
<212> TYPE: DNA
<213> ORGANISM: Artificial Sequence
<220> FEATURE:
<223> OTHER INFORMATION: Synthetic

<400> SEQUENCE: 27
aaaccgaccc tttggccgct ggcctgatcc ggag 34

<210> SEQ ID NO 28
<211> LENGTH: 35
<212> TYPE: DNA
<213> ORGANISM: Artificial Sequence
<220> FEATURE:
<223> OTHER INFORMATION: Synthetic

<400> SEQUENCE: 28
caccgcataa cgcgctctcc aagtatacgt ggcaa 35

<210> SEQ ID NO 29
<211> LENGTH: 34
<212> TYPE: DNA
<213> ORGANISM: Artificial Sequence
<220> FEATURE:
<223> OTHER INFORMATION: Synthetic

<400> SEQUENCE: 29
aaacttgcca cgtatacttg gagagcgcgt tatg 34

<210> SEQ ID NO 30
<211> LENGTH: 35
<212> TYPE: DNA
<213> ORGANISM: Artificial Sequence
<220> FEATURE:
<223> OTHER INFORMATION: Synthetic

<400> SEQUENCE: 30
caccgaggtg ctagacggga gaatatggga ggggc 35

<210> SEQ ID NO 31
<211> LENGTH: 34
<212> TYPE: DNA
<213> ORGANISM: Artificial Sequence
<220> FEATURE:
<223> OTHER INFORMATION: Synthetic

<400> SEQUENCE: 31
aaacgcccct cccatattct cccgtctagc acct 34

<210> SEQ ID NO 32
<211> LENGTH: 34
<212> TYPE: DNA
<213> ORGANISM: Artificial Sequence
<220> FEATURE:
<223> OTHER INFORMATION: Synthetic

<400> SEQUENCE: 32
caccgtccct gggactcttg atcaaagcgc ggcc 34

<210> SEQ ID NO 33
<211> LENGTH: 34
<212> TYPE: DNA
<213> ORGANISM: Artificial Sequence
<220> FEATURE:
<223> OTHER INFORMATION: Synthetic

<400> SEQUENCE: 33
aaacgggccg cgctttgatc aagagtccca ggga 34

<210> SEQ ID NO 34
<211> LENGTH: 35
<212> TYPE: DNA
<213> ORGANISM: Artificial Sequence
<220> FEATURE:
<223> OTHER INFORMATION: Synthetic

<400> SEQUENCE: 34
caccgcgaaa ctttgcccat agcagcgggc gggca 35

<210> SEQ ID NO 35
<211> LENGTH: 34
<212> TYPE: DNA
<213> ORGANISM: Artificial Sequence
<220> FEATURE:
<223> OTHER INFORMATION: Synthetic

<400> SEQUENCE: 35
aaactgcccg cccgctgcta tgggcaaagt ttcg 34

<210> SEQ ID NO 36
<211> LENGTH: 35
<212> TYPE: DNA
<213> ORGANISM: Artificial Sequence
<220> FEATURE:
<223> OTHER INFORMATION: Synthetic

<400> SEQUENCE: 36
caccgactcg ctgtagtaat tccagcgaga ggcag 35

<210> SEQ ID NO 37
<211> LENGTH: 34
<212> TYPE: DNA
<213> ORGANISM: Artificial Sequence
<220> FEATURE:
<223> OTHER INFORMATION: Synthetic

<400> SEQUENCE: 37
aaacctgcct ctcgctggaa ttactacagc gagt 34

<210> SEQ ID NO 38
<211> LENGTH: 35
<212> TYPE: DNA

<213> ORGANISM: Artificial Sequence
<220> FEATURE:
<223> OTHER INFORMATION: Synthetic

<400> SEQUENCE: 38
caccggaagg gagatccgga gcgaataggg ggctt 35

<210> SEQ ID NO 39
<211> LENGTH: 34
<212> TYPE: DNA
<213> ORGANISM: Artificial Sequence
<220> FEATURE:
<223> OTHER INFORMATION: Synthetic

<400> SEQUENCE: 39
aaacaagccc cctattcgct ccggatctcc cttc 34

<210> SEQ ID NO 40
<211> LENGTH: 35
<212> TYPE: DNA
<213> ORGANISM: Artificial Sequence
<220> FEATURE:
<223> OTHER INFORMATION: Synthetic

<400> SEQUENCE: 40
caccgatgtc cgcccgcata cgagttctgc ggagg 35

<210> SEQ ID NO 41
<211> LENGTH: 34
<212> TYPE: DNA
<213> ORGANISM: Artificial Sequence
<220> FEATURE:
<223> OTHER INFORMATION: Synthetic

<400> SEQUENCE: 41
aaaccctccg cagaactcgt atgcgggcgg acat 34

<210> SEQ ID NO 42
<211> LENGTH: 35
<212> TYPE: DNA
<213> ORGANISM: Artificial Sequence
<220> FEATURE:
<223> OTHER INFORMATION: Synthetic

<400> SEQUENCE: 42
caccgagacg ggtgggtaag caagaactga ggagt 35

<210> SEQ ID NO 43
<211> LENGTH: 34
<212> TYPE: DNA
<213> ORGANISM: Artificial Sequence
<220> FEATURE:
<223> OTHER INFORMATION: Synthetic

<400> SEQUENCE: 43
aaacactcct cagttcttgc ttacccaccc gtct 34

<210> SEQ ID NO 44
<211> LENGTH: 35
<212> TYPE: DNA
<213> ORGANISM: Artificial Sequence
<220> FEATURE:
<223> OTHER INFORMATION: Synthetic

<400> SEQUENCE: 44
caccgaaaca ctccttaaat tgggcatggt ggtag 35

<210> SEQ ID NO 45
<211> LENGTH: 34
<212> TYPE: DNA
<213> ORGANISM: Artificial Sequence
<220> FEATURE:
<223> OTHER INFORMATION: Synthetic

<400> SEQUENCE: 45
aaacctacca ccatgcccaa tttaaggagt gttt 34

<210> SEQ ID NO 46
<211> LENGTH: 35
<212> TYPE: DNA
<213> ORGANISM: Artificial Sequence
<220> FEATURE:
<223> OTHER INFORMATION: Synthetic

<400> SEQUENCE: 46
caccgcaaat cagcctatct gaaggccaac ggctc 35

<210> SEQ ID NO 47
<211> LENGTH: 34
<212> TYPE: DNA
<213> ORGANISM: Artificial Sequence
<220> FEATURE:
<223> OTHER INFORMATION: Synthetic

<400> SEQUENCE: 47
aaacgagccg ttggccttca gataggctga tttg 34

<210> SEQ ID NO 48
<211> LENGTH: 20
<212> TYPE: DNA
<213> ORGANISM: Artificial Sequence
<220> FEATURE:
<223> OTHER INFORMATION: Synthetic

<400> SEQUENCE: 48
ggtctcccta tgaagccata 20

<210> SEQ ID NO 49
<211> LENGTH: 20
<212> TYPE: DNA
<213> ORGANISM: Artificial Sequence
<220> FEATURE:
<223> OTHER INFORMATION: Synthetic

<400> SEQUENCE: 49
ggtctgctgt cccatctcca 20

<210> SEQ ID NO 50
<211> LENGTH: 20
<212> TYPE: DNA
<213> ORGANISM: Artificial Sequence
<220> FEATURE:
<223> OTHER INFORMATION: Synthetic

<400> SEQUENCE: 50
gtacttcaga caccagaaga 20

<210> SEQ ID NO 51
<211> LENGTH: 20
<212> TYPE: DNA
<213> ORGANISM: Artificial Sequence
<220> FEATURE:

<223> OTHER INFORMATION: Synthetic

<400> SEQUENCE: 51
atgaatgtat agaaattggg 20

<210> SEQ ID NO 52
<211> LENGTH: 20
<212> TYPE: DNA
<213> ORGANISM: Artificial Sequence
<220> FEATURE:
<223> OTHER INFORMATION: Synthetic

<400> SEQUENCE: 52
gaggacacta gactagagca 20

<210> SEQ ID NO 53
<211> LENGTH: 20
<212> TYPE: DNA
<213> ORGANISM: Artificial Sequence
<220> FEATURE:
<223> OTHER INFORMATION: Synthetic

<400> SEQUENCE: 53
atctgcctgt gtcttccaga 20

<210> SEQ ID NO 54
<211> LENGTH: 20
<212> TYPE: DNA
<213> ORGANISM: Artificial Sequence
<220> FEATURE:
<223> OTHER INFORMATION: Synthetic

<400> SEQUENCE: 54
ccaacttcac ggcattgggg 20

<210> SEQ ID NO 55
<211> LENGTH: 20
<212> TYPE: DNA
<213> ORGANISM: Artificial Sequence
<220> FEATURE:
<223> OTHER INFORMATION: Synthetic

<400> SEQUENCE: 55
gcgcatttaa acacgaccca 20

<210> SEQ ID NO 56
<211> LENGTH: 20
<212> TYPE: DNA
<213> ORGANISM: Artificial Sequence
<220> FEATURE:
<223> OTHER INFORMATION: Synthetic

<400> SEQUENCE: 56
cgattgggtt gaaaacccag 20

<210> SEQ ID NO 57
<211> LENGTH: 20
<212> TYPE: DNA
<213> ORGANISM: Artificial Sequence
<220> FEATURE:
<223> OTHER INFORMATION: Synthetic

<400> SEQUENCE: 57
gccattaaat gagcgcgccg 20

<210> SEQ ID NO 58
<211> LENGTH: 20
<212> TYPE: DNA
<213> ORGANISM: Artificial Sequence
<220> FEATURE:
<223> OTHER INFORMATION: Synthetic

<400> SEQUENCE: 58
ccgggagtgc agaataacag 20

<210> SEQ ID NO 59
<211> LENGTH: 20
<212> TYPE: DNA
<213> ORGANISM: Artificial Sequence
<220> FEATURE:
<223> OTHER INFORMATION: Synthetic

<400> SEQUENCE: 59
ggagacttcg agccgacaag 20

<210> SEQ ID NO 60
<211> LENGTH: 20
<212> TYPE: DNA
<213> ORGANISM: Artificial Sequence
<220> FEATURE:
<223> OTHER INFORMATION: Synthetic

<400> SEQUENCE: 60
cttcccacta gagatcgcca 20

<210> SEQ ID NO 61
<211> LENGTH: 20
<212> TYPE: DNA
<213> ORGANISM: Artificial Sequence
<220> FEATURE:
<223> OTHER INFORMATION: Synthetic

<400> SEQUENCE: 61
gtagtagtca ttaacataag 20

<210> SEQ ID NO 62
<211> LENGTH: 20
<212> TYPE: DNA
<213> ORGANISM: Artificial Sequence
<220> FEATURE:
<223> OTHER INFORMATION: Synthetic

<400> SEQUENCE: 62
atcaccggtc aaactcagag 20

<210> SEQ ID NO 63
<211> LENGTH: 20
<212> TYPE: DNA
<213> ORGANISM: Artificial Sequence
<220> FEATURE:
<223> OTHER INFORMATION: Synthetic

<400> SEQUENCE: 63
actgtggtag agtcttcaca 20

<210> SEQ ID NO 64
<211> LENGTH: 20
<212> TYPE: DNA
<213> ORGANISM: Artificial Sequence
<220> FEATURE:
<223> OTHER INFORMATION: Synthetic

<400> SEQUENCE: 64
gagtggtgtc ttcagtagca 20

<210> SEQ ID NO 65
<211> LENGTH: 20
<212> TYPE: DNA
<213> ORGANISM: Artificial Sequence
<220> FEATURE:
<223> OTHER INFORMATION: Synthetic

<400> SEQUENCE: 65
ataacctcac caaaaaaatg 20

<210> SEQ ID NO 66
<211> LENGTH: 20
<212> TYPE: DNA
<213> ORGANISM: Artificial Sequence
<220> FEATURE:
<223> OTHER INFORMATION: Synthetic

<400> SEQUENCE: 66
gcagaagtgc agcatgcagg 20

<210> SEQ ID NO 67
<211> LENGTH: 20
<212> TYPE: DNA
<213> ORGANISM: Artificial Sequence
<220> FEATURE:
<223> OTHER INFORMATION: Synthetic

<400> SEQUENCE: 67
ttaaagatgg aaaaaaagtg 20

<210> SEQ ID NO 68
<211> LENGTH: 20
<212> TYPE: DNA
<213> ORGANISM: Artificial Sequence
<220> FEATURE:
<223> OTHER INFORMATION: Synthetic

<400> SEQUENCE: 68
gctgttgcca ggtaactgtg 20

<210> SEQ ID NO 69
<211> LENGTH: 20
<212> TYPE: DNA
<213> ORGANISM: Artificial Sequence
<220> FEATURE:
<223> OTHER INFORMATION: Synthetic

<400> SEQUENCE: 69
gttcttagca cacatcaggc 20

<210> SEQ ID NO 70
<211> LENGTH: 20
<212> TYPE: DNA
<213> ORGANISM: Artificial Sequence
<220> FEATURE:
<223> OTHER INFORMATION: Synthetic

<400> SEQUENCE: 70
tctggcggag aatagttggg 20

<210> SEQ ID NO 71
<211> LENGTH: 20

<212> TYPE: DNA
<213> ORGANISM: Artificial Sequence
<220> FEATURE:
<223> OTHER INFORMATION: Synthetic

<400> SEQUENCE: 71
gcagggcgct gacgtcgtag 20

<210> SEQ ID NO 72
<211> LENGTH: 20
<212> TYPE: DNA
<213> ORGANISM: Artificial Sequence
<220> FEATURE:
<223> OTHER INFORMATION: Synthetic

<400> SEQUENCE: 72
gcgctgtgcc ccgaaccgcg 20

<210> SEQ ID NO 73
<211> LENGTH: 20
<212> TYPE: DNA
<213> ORGANISM: Artificial Sequence
<220> FEATURE:
<223> OTHER INFORMATION: Synthetic

<400> SEQUENCE: 73
actaatcaca acaatcgcgg 20

<210> SEQ ID NO 74
<211> LENGTH: 20
<212> TYPE: DNA
<213> ORGANISM: Artificial Sequence
<220> FEATURE:
<223> OTHER INFORMATION: Synthetic

<400> SEQUENCE: 74
gataagtaca cgcttcccgg 20

<210> SEQ ID NO 75
<211> LENGTH: 20
<212> TYPE: DNA
<213> ORGANISM: Artificial Sequence
<220> FEATURE:
<223> OTHER INFORMATION: Synthetic

<400> SEQUENCE: 75
cgttcatcga cgaggccaag 20

<210> SEQ ID NO 76
<211> LENGTH: 20
<212> TYPE: DNA
<213> ORGANISM: Artificial Sequence
<220> FEATURE:
<223> OTHER INFORMATION: Synthetic

<400> SEQUENCE: 76
ggccagctcc agcccccccg 20

<210> SEQ ID NO 77
<211> LENGTH: 20
<212> TYPE: DNA
<213> ORGANISM: Artificial Sequence
<220> FEATURE:
<223> OTHER INFORMATION: Synthetic

<400> SEQUENCE: 77
gggctctgtg gtcaagtccg 20

<210> SEQ ID NO 78
<211> LENGTH: 20
<212> TYPE: DNA
<213> ORGANISM: Artificial Sequence
<220> FEATURE:
<223> OTHER INFORMATION: Synthetic

<400> SEQUENCE: 78
ggaaagctag aaaggatgcg 20

<210> SEQ ID NO 79
<211> LENGTH: 20
<212> TYPE: DNA
<213> ORGANISM: Artificial Sequence
<220> FEATURE:
<223> OTHER INFORMATION: Synthetic

<400> SEQUENCE: 79
ccccttgcct tgcttccgaa 20

<210> SEQ ID NO 80
<211> LENGTH: 20
<212> TYPE: DNA
<213> ORGANISM: Artificial Sequence
<220> FEATURE:
<223> OTHER INFORMATION: Synthetic

<400> SEQUENCE: 80
cagaagcctg gataaccaga 20

<210> SEQ ID NO 81
<211> LENGTH: 20
<212> TYPE: DNA
<213> ORGANISM: Artificial Sequence
<220> FEATURE:
<223> OTHER INFORMATION: Synthetic

<400> SEQUENCE: 81
ttagtggtgc gaatagaggg 20

<210> SEQ ID NO 82
<211> LENGTH: 20
<212> TYPE: DNA
<213> ORGANISM: Artificial Sequence
<220> FEATURE:
<223> OTHER INFORMATION: Synthetic

<400> SEQUENCE: 82
tgaaggttca agcaaagaaa 20

<210> SEQ ID NO 83
<211> LENGTH: 20
<212> TYPE: DNA
<213> ORGANISM: Artificial Sequence
<220> FEATURE:
<223> OTHER INFORMATION: Synthetic

<400> SEQUENCE: 83
agagcagatc tccagccaag 20

<210> SEQ ID NO 84
<211> LENGTH: 20
<212> TYPE: DNA
<213> ORGANISM: Artificial Sequence
<220> FEATURE:
<223> OTHER INFORMATION: Synthetic

<400> SEQUENCE: 84
gctgcgcagc cgataccggg 20

<210> SEQ ID NO 85
<211> LENGTH: 20
<212> TYPE: DNA
<213> ORGANISM: Artificial Sequence
<220> FEATURE:
<223> OTHER INFORMATION: Synthetic

<400> SEQUENCE: 85
gcagcagaga gcgcaccgcg 20

<210> SEQ ID NO 86
<211> LENGTH: 20
<212> TYPE: DNA
<213> ORGANISM: Artificial Sequence
<220> FEATURE:
<223> OTHER INFORMATION: Synthetic

<400> SEQUENCE: 86
ccgcgctcct cgttgccccg 20

<210> SEQ ID NO 87
<211> LENGTH: 20
<212> TYPE: DNA
<213> ORGANISM: Artificial Sequence
<220> FEATURE:
<223> OTHER INFORMATION: Synthetic

<400> SEQUENCE: 87
gcgcagcaga gagcgcaccg 20

<210> SEQ ID NO 88
<211> LENGTH: 20
<212> TYPE: DNA
<213> ORGANISM: Artificial Sequence
<220> FEATURE:
<223> OTHER INFORMATION: Synthetic

<400> SEQUENCE: 88
acgcacccat agcaaggcca 20

<210> SEQ ID NO 89
<211> LENGTH: 20
<212> TYPE: DNA
<213> ORGANISM: Artificial Sequence
<220> FEATURE:
<223> OTHER INFORMATION: Synthetic

<400> SEQUENCE: 89
ccaccaggtg ggcctccagg 20

<210> SEQ ID NO 90
<211> LENGTH: 20
<212> TYPE: DNA
<213> ORGANISM: Artificial Sequence
<220> FEATURE:
<223> OTHER INFORMATION: Synthetic

<400> SEQUENCE: 90
acgttgtgtg aggttcctag 20

<210> SEQ ID NO 91
<211> LENGTH: 20
<212> TYPE: DNA
<213> ORGANISM: Artificial Sequence
<220> FEATURE:
<223> OTHER INFORMATION: Synthetic

<400> SEQUENCE: 91
gattcctttg gatatatacc 20

<210> SEQ ID NO 92
<211> LENGTH: 20
<212> TYPE: DNA
<213> ORGANISM: Artificial Sequence
<220> FEATURE:
<223> OTHER INFORMATION: Synthetic

<400> SEQUENCE: 92
aagaggattg ctggataacg 20

<210> SEQ ID NO 93
<211> LENGTH: 20
<212> TYPE: DNA
<213> ORGANISM: Artificial Sequence
<220> FEATURE:
<223> OTHER INFORMATION: Synthetic

<400> SEQUENCE: 93
gactgctgct tagaaattct 20

<210> SEQ ID NO 94
<211> LENGTH: 20
<212> TYPE: DNA
<213> ORGANISM: Artificial Sequence
<220> FEATURE:
<223> OTHER INFORMATION: Synthetic

<400> SEQUENCE: 94
ccgtgggaag aaacaaagaa 20

<210> SEQ ID NO 95
<211> LENGTH: 20
<212> TYPE: DNA
<213> ORGANISM: Artificial Sequence
<220> FEATURE:
<223> OTHER INFORMATION: Synthetic

<400> SEQUENCE: 95
ccagaagaat agttagtaaa 20

<210> SEQ ID NO 96
<211> LENGTH: 20
<212> TYPE: DNA
<213> ORGANISM: Artificial Sequence
<220> FEATURE:
<223> OTHER INFORMATION: Synthetic

<400> SEQUENCE: 96
aagtagcaag ggagattctt 20

<210> SEQ ID NO 97
<211> LENGTH: 20
<212> TYPE: DNA
<213> ORGANISM: Artificial Sequence
<220> FEATURE:
<223> OTHER INFORMATION: Synthetic

<400> SEQUENCE: 97
tgcaaagaag tcacattcac 20

<210> SEQ ID NO 98
<211> LENGTH: 20
<212> TYPE: DNA
<213> ORGANISM: Artificial Sequence
<220> FEATURE:
<223> OTHER INFORMATION: Synthetic

<400> SEQUENCE: 98
ttatcaactc aaagttctgg 20

<210> SEQ ID NO 99
<211> LENGTH: 20
<212> TYPE: DNA
<213> ORGANISM: Artificial Sequence
<220> FEATURE:
<223> OTHER INFORMATION: Synthetic

<400> SEQUENCE: 99
gcccgtcact ccgagcgcga 20

<210> SEQ ID NO 100
<211> LENGTH: 20
<212> TYPE: DNA
<213> ORGANISM: Artificial Sequence
<220> FEATURE:
<223> OTHER INFORMATION: Synthetic

<400> SEQUENCE: 100
ccgggtccgc gcgaggtacg 20

<210> SEQ ID NO 101
<211> LENGTH: 20
<212> TYPE: DNA
<213> ORGANISM: Artificial Sequence
<220> FEATURE:
<223> OTHER INFORMATION: Synthetic

<400> SEQUENCE: 101
ccgagagagc ccgtccaagt 20

<210> SEQ ID NO 102
<211> LENGTH: 20
<212> TYPE: DNA
<213> ORGANISM: Artificial Sequence
<220> FEATURE:
<223> OTHER INFORMATION: Synthetic

<400> SEQUENCE: 102
tcacgcgcgg cttgccggat 20

<210> SEQ ID NO 103
<211> LENGTH: 20
<212> TYPE: DNA
<213> ORGANISM: Artificial Sequence
<220> FEATURE:
<223> OTHER INFORMATION: Synthetic

<400> SEQUENCE: 103
ctatttccac gcgttggcgg 20

<210> SEQ ID NO 104

<211> LENGTH: 20
<212> TYPE: DNA
<213> ORGANISM: Artificial Sequence
<220> FEATURE:
<223> OTHER INFORMATION: Synthetic

<400> SEQUENCE: 104
tgcatgcgtg tgagtagggc 20

<210> SEQ ID NO 105
<211> LENGTH: 20
<212> TYPE: DNA
<213> ORGANISM: Artificial Sequence
<220> FEATURE:
<223> OTHER INFORMATION: Synthetic

<400> SEQUENCE: 105
ttacaggctt gcaccgcgcc 20

<210> SEQ ID NO 106
<211> LENGTH: 20
<212> TYPE: DNA
<213> ORGANISM: Artificial Sequence
<220> FEATURE:
<223> OTHER INFORMATION: Synthetic

<400> SEQUENCE: 106
gcggggaatc gcttgaaccc 20

<210> SEQ ID NO 107
<211> LENGTH: 20
<212> TYPE: DNA
<213> ORGANISM: Artificial Sequence
<220> FEATURE:
<223> OTHER INFORMATION: Synthetic

<400> SEQUENCE: 107
gatatggtgt ttcgccatgt 20

<210> SEQ ID NO 108
<211> LENGTH: 20
<212> TYPE: DNA
<213> ORGANISM: Artificial Sequence
<220> FEATURE:
<223> OTHER INFORMATION: Synthetic

<400> SEQUENCE: 108
gctggaggtg agctgctgac 20

<210> SEQ ID NO 109
<211> LENGTH: 20
<212> TYPE: DNA
<213> ORGANISM: Artificial Sequence
<220> FEATURE:
<223> OTHER INFORMATION: Synthetic

<400> SEQUENCE: 109
gcgcttattg acaaagaaaa 20

<210> SEQ ID NO 110
<211> LENGTH: 20
<212> TYPE: DNA
<213> ORGANISM: Artificial Sequence
<220> FEATURE:
<223> OTHER INFORMATION: Synthetic

<400> SEQUENCE: 110
gctgtcttaa tcaacaaaat 20

<210> SEQ ID NO 111
<211> LENGTH: 20
<212> TYPE: DNA
<213> ORGANISM: Artificial Sequence
<220> FEATURE:
<223> OTHER INFORMATION: Synthetic

<400> SEQUENCE: 111
gtatgttgaa aagaaaatta 20

<210> SEQ ID NO 112
<211> LENGTH: 20
<212> TYPE: DNA
<213> ORGANISM: Artificial Sequence
<220> FEATURE:
<223> OTHER INFORMATION: Synthetic

<400> SEQUENCE: 112
gtcccccgcc tgccagcaaa 20

<210> SEQ ID NO 113
<211> LENGTH: 20
<212> TYPE: DNA
<213> ORGANISM: Artificial Sequence
<220> FEATURE:
<223> OTHER INFORMATION: Synthetic

<400> SEQUENCE: 113
gcgcacacag ggcgggaaag 20

<210> SEQ ID NO 114
<211> LENGTH: 20
<212> TYPE: DNA
<213> ORGANISM: Artificial Sequence
<220> FEATURE:
<223> OTHER INFORMATION: Synthetic

<400> SEQUENCE: 114
ggtccgctgt gatcgccggg 20

<210> SEQ ID NO 115
<211> LENGTH: 20
<212> TYPE: DNA
<213> ORGANISM: Artificial Sequence
<220> FEATURE:
<223> OTHER INFORMATION: Synthetic

<400> SEQUENCE: 115
gtacttttat atgatctcaa 20

<210> SEQ ID NO 116
<211> LENGTH: 20
<212> TYPE: DNA
<213> ORGANISM: Artificial Sequence
<220> FEATURE:
<223> OTHER INFORMATION: Synthetic

<400> SEQUENCE: 116
gctcgtggaa aatataacta 20

<210> SEQ ID NO 117
<211> LENGTH: 20
<212> TYPE: DNA

<213> ORGANISM: Artificial Sequence
<220> FEATURE:
<223> OTHER INFORMATION: Synthetic

<400> SEQUENCE: 117
gtattttaaa actcagctcg 20

<210> SEQ ID NO 118
<211> LENGTH: 20
<212> TYPE: DNA
<213> ORGANISM: Artificial Sequence
<220> FEATURE:
<223> OTHER INFORMATION: Synthetic

<400> SEQUENCE: 118
gaaaatatgt ataaagtctg 20

<210> SEQ ID NO 119
<211> LENGTH: 19
<212> TYPE: DNA
<213> ORGANISM: Artificial Sequence
<220> FEATURE:
<223> OTHER INFORMATION: Synthetic

<400> SEQUENCE: 119
aaaagtagct taaaatcat 19

<210> SEQ ID NO 120
<211> LENGTH: 20
<212> TYPE: DNA
<213> ORGANISM: Artificial Sequence
<220> FEATURE:
<223> OTHER INFORMATION: Synthetic

<400> SEQUENCE: 120
ctgagaagtt caacggctaa 20

<210> SEQ ID NO 121
<211> LENGTH: 20
<212> TYPE: DNA
<213> ORGANISM: Artificial Sequence
<220> FEATURE:
<223> OTHER INFORMATION: Synthetic

<400> SEQUENCE: 121
ggctgcgtgt tagtggcttc 20

<210> SEQ ID NO 122
<211> LENGTH: 20
<212> TYPE: DNA
<213> ORGANISM: Artificial Sequence
<220> FEATURE:
<223> OTHER INFORMATION: Synthetic

<400> SEQUENCE: 122
cccactaaca ggaaacctac 20

<210> SEQ ID NO 123
<211> LENGTH: 20
<212> TYPE: DNA
<213> ORGANISM: Artificial Sequence
<220> FEATURE:
<223> OTHER INFORMATION: Synthetic

<400> SEQUENCE: 123
gaatgggcgc atgcgtaagg 20

<210> SEQ ID NO 124
<211> LENGTH: 20
<212> TYPE: DNA
<213> ORGANISM: Artificial Sequence
<220> FEATURE:
<223> OTHER INFORMATION: Synthetic

<400> SEQUENCE: 124
gtagggcccc acgtgacgcg 20

<210> SEQ ID NO 125
<211> LENGTH: 20
<212> TYPE: DNA
<213> ORGANISM: Artificial Sequence
<220> FEATURE:
<223> OTHER INFORMATION: Synthetic

<400> SEQUENCE: 125
agctcgccaa tgaggacgcg 20

<210> SEQ ID NO 126
<211> LENGTH: 20
<212> TYPE: DNA
<213> ORGANISM: Artificial Sequence
<220> FEATURE:
<223> OTHER INFORMATION: Synthetic

<400> SEQUENCE: 126
acaccgaacc gggaccgatc 20

<210> SEQ ID NO 127
<211> LENGTH: 20
<212> TYPE: DNA
<213> ORGANISM: Artificial Sequence
<220> FEATURE:
<223> OTHER INFORMATION: Synthetic

<400> SEQUENCE: 127
ttcccaaggc ggggcgatat 20

<210> SEQ ID NO 128
<211> LENGTH: 20
<212> TYPE: DNA
<213> ORGANISM: Artificial Sequence
<220> FEATURE:
<223> OTHER INFORMATION: Synthetic

<400> SEQUENCE: 128
gaggtgcggc gtccagaacc 20

<210> SEQ ID NO 129
<211> LENGTH: 20
<212> TYPE: DNA
<213> ORGANISM: Artificial Sequence
<220> FEATURE:
<223> OTHER INFORMATION: Synthetic

<400> SEQUENCE: 129
gtttgagctc agcagatgaa 20

<210> SEQ ID NO 130
<211> LENGTH: 20
<212> TYPE: DNA
<213> ORGANISM: Artificial Sequence
<220> FEATURE:

<223> OTHER INFORMATION: Synthetic

<400> SEQUENCE: 130
ggactttatt ttattttatg 20

<210> SEQ ID NO 131
<211> LENGTH: 20
<212> TYPE: DNA
<213> ORGANISM: Artificial Sequence
<220> FEATURE:
<223> OTHER INFORMATION: Synthetic

<400> SEQUENCE: 131
gtttcatctg ctgagctcaa 20

<210> SEQ ID NO 132
<211> LENGTH: 20
<212> TYPE: DNA
<213> ORGANISM: Artificial Sequence
<220> FEATURE:
<223> OTHER INFORMATION: Synthetic

<400> SEQUENCE: 132
gccccgagct gtgctgctcg 20

<210> SEQ ID NO 133
<211> LENGTH: 20
<212> TYPE: DNA
<213> ORGANISM: Artificial Sequence
<220> FEATURE:
<223> OTHER INFORMATION: Synthetic

<400> SEQUENCE: 133
gtcccgggtt cccaaagcag 20

<210> SEQ ID NO 134
<211> LENGTH: 20
<212> TYPE: DNA
<213> ORGANISM: Artificial Sequence
<220> FEATURE:
<223> OTHER INFORMATION: Synthetic

<400> SEQUENCE: 134
gcgcgcgtag ttaattcatg 20

<210> SEQ ID NO 135
<211> LENGTH: 20
<212> TYPE: DNA
<213> ORGANISM: Artificial Sequence
<220> FEATURE:
<223> OTHER INFORMATION: Synthetic

<400> SEQUENCE: 135
aagaagggcc gtacccgaaa 20

<210> SEQ ID NO 136
<211> LENGTH: 20
<212> TYPE: DNA
<213> ORGANISM: Artificial Sequence
<220> FEATURE:
<223> OTHER INFORMATION: Synthetic

<400> SEQUENCE: 136
aggtcaagcc gacctcgaac 20

<210> SEQ ID NO 137
<211> LENGTH: 20
<212> TYPE: DNA
<213> ORGANISM: Artificial Sequence
<220> FEATURE:
<223> OTHER INFORMATION: Synthetic

<400> SEQUENCE: 137
gcgagcgcta tcccggtgga 20

<210> SEQ ID NO 138
<211> LENGTH: 15
<212> TYPE: DNA
<213> ORGANISM: Artificial Sequence
<220> FEATURE:
<223> OTHER INFORMATION: Synthetic

<400> SEQUENCE: 138
ggggsggggs ggggs 15

<210> SEQ ID NO 139
<211> LENGTH: 30
<212> TYPE: DNA
<213> ORGANISM: Artificial Sequence
<220> FEATURE:
<223> OTHER INFORMATION: Synthetic

<400> SEQUENCE: 139
ggggsggggs ggggsggggs ggggsggggs 30

<210> SEQ ID NO 140
<211> LENGTH: 45
<212> TYPE: DNA
<213> ORGANISM: Artificial Sequence
<220> FEATURE:
<223> OTHER INFORMATION: Synthetic

<400> SEQUENCE: 140
ggggsggggs ggggsggggs ggggsggggs ggggsggggs ggggs 45

<210> SEQ ID NO 141
<211> LENGTH: 60
<212> TYPE: DNA
<213> ORGANISM: Artificial Sequence
<220> FEATURE:
<223> OTHER INFORMATION: Synthetic

<400> SEQUENCE: 141
ggggsggggs ggggsggggs ggggsggggs ggggsggggs ggggsggggs ggggsggggs 60

<210> SEQ ID NO 142
<211> LENGTH: 15239
<212> TYPE: DNA
<213> ORGANISM: Artificial Sequence
<220> FEATURE:
<223> OTHER INFORMATION: Synthetic

<400> SEQUENCE: 142
gtcgacggat cgggagatct cccgatcccc tatggtgcac tctcagtaca atctgctctg 60
atgccgcata gttaagccag tatctgctcc ctgcttgtgt gttggaggtc gctgagtagt 120
gcgcgagcaa aatttaagct acaacaaggc aaggcttgac cgacaattgc atgaagaatc 180
tgcttagggt taggcgtttt gcgctgcttc gcgatgtacg ggccagatat acgcgttgac 240
attgattatt gactagttat taatagtaat caattacggg gtcattagtt catagcccat 300

-continued

```
atatggagtt ccgcgttaca taacttacgg taaatggccc gcctggctga ccgcccaacg    360
acccccgccc attgacgtca ataatgacgt atgttcccat agtaacgcca atagggactt    420
tccattgacg tcaatgggtg gagtatttac ggtaaactgc ccacttggca gtacatcaag    480
tgtatcatat gccaagtacg ccccctattg acgtcaatga cggtaaatgg cccgcctggc    540
attatgccca gtacatgacc ttatgggact ttcctacttg gcagtacatc tacgtattag    600
tcatcgctat taccatggtg atgcggtttt ggcagtacat caatgggcgt ggatagcggt    660
ttgactcacg gggatttcca agtctccacc ccattgacgt caatgggagt ttgttttggc    720
accaaaatca acgggacttt ccaaaatgtc gtaacaactc cgccccattg acgcaaatgg    780
gcggtaggcg tgtacggtgg gaggtctata taagcagcgc gttttgcctg tactgggtct    840
ctctggttag accagatctg agcctgggag ctctctggct aactagggaa cccactgctt    900
aagcctcaat aaagcttgcc ttgagtgctt caagtagtgt gtgcccgtct gttgtgtgac    960
tctggtaact agagatccct cagacccttt tagtcagtgt ggaaaatctc tagcagtggc   1020
gcccgaacag ggacttgaaa gcgaaaggga aaccagagga gctctctcga cgcaggactc   1080
ggcttgctga agcgcgcacg gcaagaggcg aggggcggcg actggtgagt acgccaaaaa   1140
ttttgactag cggaggctag aaggagagag atgggtgcga gagcgtcagt attaagcggg   1200
ggagaattag atcgcgatgg gaaaaaattc ggttaaggcc agggggaaag aaaaaatata   1260
aattaaaaca tatagtatgg gcaagcaggg agctagaacg attcgcagtt aatcctggcc   1320
tgttagaaac atcagaaggc tgtagacaaa tactgggaca gctacaacca tcccttcaga   1380
caggatcaga agaacttaga tcattatata atacagtagc aaccctctat tgtgtgcatc   1440
aaaggataga gataaaagac accaaggaag ctttagacaa gatagaggaa gagcaaaaca   1500
aaagtaagac caccgcacag caagcggccg ctgatcttca gacctggagg aggagatatg   1560
agggacaatt ggagaagtga attatataaa tataaagtag taaaaattga accattagga   1620
gtagcaccca ccaaggcaaa gagaagagtg gtgcagagag aaaaaagagc agtgggaata   1680
ggagctttgt tccttgggtt cttgggagca gcaggaagca ctatgggcgc agcgtcaatg   1740
acgctgacgg tacaggccag acaattattg tctggtatag tgcagcagca gaacaatttg   1800
ctgagggcta ttgaggcgca acagcatctg ttgcaactca cagtctgggg catcaagcag   1860
ctccaggcaa gaatcctggc tgtggaaaga tacctaaagg atcaacagct cctggggatt   1920
tggggttgct ctggaaaact catttgcacc actgctgtgc cttggaatgc tagttggagt   1980
aataaatctc tggaacagat ttggaatcac acgacctgga tggagtggga cagagaaatt   2040
aacaattaca caagcttaat acactcctta attgaagaat cgcaaaacca gcaagaaaag   2100
aatgaacaag aattattgga attagataaa tgggcaagtt tgtggaattg gtttaacata   2160
acaaattggc tgtggtatat aaaattattc ataatgatag taggaggctt ggtaggttta   2220
agaatagttt ttgctgtact ttctatagtg aatagagtta ggcagggata ttcaccatta   2280
tcgtttcaga cccacctccc aaccccgagg ggacccgaca ggcccgaagg aatagaagaa   2340
gaaggtggag agagagacag agacagatcc attcgattag tgaacggatc ggcactgcgt   2400
gcgccaattc tgcagacaaa tggcagtatt catccacaat tttaaaagaa aaggggggat   2460
tggggggtac agtgcagggg aaagaatagt agacataata gcaacagaca tacaaactaa   2520
agaattacaa aaacaaatta caaaaattca aaattttcgg gtttattaca gggacagcag   2580
agatccagtt tggttaatta atgcaaagat ggataaagtt ttaaacagag aggaatcttt   2640
gcagctaatg gaccttctag gtcttgaaag gagtgggaat tggctccggt gcccgtcagt   2700
```

```
gggcagagcg cacatcgccc acagtccccg agaagttggg gggaggggtc ggcaattgaa   2760
ccggtgccta gagaaggtgg cgcggggtaa actgggaaag tgatgtcgtg tactggctcc   2820
gcctttttcc cgagggtggg ggagaaccgt atataagtgc agtagtcgcc gtgaacgttc   2880
tttttcgcaa cgggtttgcc gccagaacac aggtaagtgc cgtgtgtggt tcccgcgggc   2940
ctggcctctt tacgggttat ggcccttgcg tgccttgaat tacttccact ggctgcagta   3000
cgtgattctt gatcccgagc ttcgggttgg aagtgggtgg gagagttcga ggccttgcgc   3060
ttaaggagcc ccttcgcctc gtgcttgagt tgaggcctgg cctgggcgct ggggccgccg   3120
cgtgcgaatc tggtggcacc ttcgcgcctg tctcgctgct ttcgataagt ctctagccat   3180
ttaaaatttt tgatgacctg ctgcgacgct ttttttctgg caagatagtc ttgtaaatgc   3240
gggccaagat ctgcacactg gtatttcggt ttttggggcc gcgggcggcg acggggcccg   3300
tgcgtcccag cgcacatgtt cggcgaggcg gggcctgcga gcgcggccac cgagaatcgg   3360
acgggggtag tctcaagctg gccggcctgc tctggtgcct ggcctcgcgc cgccgtgtat   3420
cgccccgccc tgggcggcaa ggctggcccg gtcggcacca gttgcgtgag cggaaagatg   3480
gccgcttccc ggccctgctg cagggagctc aaaatggagg acgcggcgct cgggagagcg   3540
ggcgggtgag tcacccacac aaaggaaaag ggcctttccg tcctcagccg tcgcttcatg   3600
tgactccacg gagtaccggg cgccgtccag gcacctcgat tagttctcga gcttttggag   3660
tacgtcgtct ttaggttggg gggaggggtt ttatgcgatg gagtttcccc acactgagtg   3720
ggtggagact gaagttaggc cagcttggca cttgatgtaa ttctccttgg aatttgccct   3780
ttttgagttt ggatcttggt tcattctcaa gcctcagaca gtggttcaaa gtttttttct   3840
tccatttcag gtgtcgtgac gtacggccac catgagcccc aagaagaaga gaaaggtgga   3900
ggccagcgac aagaagtaca gcatcggcct ggccatcggc accaactctg tgggctgggc   3960
cgtgatcacc gacgagtaca aggtgcccag caagaaattc aaggtgctgg gcaacaccga   4020
ccggcacagc atcaagaaga acctgatcgg agccctgctg ttcgacagcg gcgaaacagc   4080
cgaggccacc cggctgaaga gaaccgccag aagaagatac accagacgga agaaccggat   4140
ctgctatctg caagagatct tcagcaacga gatggccaag gtggacgaca gcttcttcca   4200
cagactggaa gagtccttcc tggtggaaga ggataagaag cacgagcggc accccatctt   4260
cggcaacatc gtggacgagg tggcctacca cgagaagtac cccaccatct accacctgag   4320
aaagaaactg gtggacagca ccgacaaggc cgacctgcgg ctgatctatc tggccctggc   4380
ccacatgatc aagttccggg gccacttcct gatcgagggc gacctgaacc ccgacaacag   4440
cgacgtggac aagctgttca tccagctggt gcagacctac aaccagctgt tcgaggaaaa   4500
ccccatcaac gccagcggcg tggacgccaa ggccatcctg tctgccagac tgagcaagag   4560
cagacggctg gaaaatctga tcgcccagct gcccggcgag aagaagaatg gcctgttcgg   4620
caacctgatt gccctgagcc tgggcctgac ccccaacttc aagagcaact tcgacctggc   4680
cgaggatgcc aaactgcagc tgagcaagga cacctacgac gacgacctgg acaacctgct   4740
ggcccagatc ggcgaccagt acgccgacct gtttctggcc gccaagaacc tgtccgacgc   4800
catcctgctg agcgacatcc tgagagtgaa caccgagatc accaaggccc ccctgagcgc   4860
ctctatgatc aagagatacg acgagcacca ccaggacctg accctgctga aagctctcgt   4920
gcggcagcag ctgcctgaga agtacaaaga gattttcttc gaccagagca agaacggcta   4980
cgccggctac attgacggcg gagccagcca ggaagagttc tacaagttca tcaagcccat   5040
```

```
cctggaaaag atggacggca ccgaggaact gctcgtgaag ctgaacagag aggacctgct   5100
gcggaagcag cggaccttcg acaacggcag catcccccac cagatccacc tgggagagct   5160
gcacgccatt ctgcggcggc aggaagattt ttacccattc ctgaaggaca accgggaaaa   5220
gatcgagaag atcctgacct tccgcatccc ctactacgtg ggccctctgg ccaggggaaa   5280
cagcagattc gcctggatga ccagaaagag cgaggaaacc atcaccccct ggaacttcga   5340
ggaagtggtg gacaagggcg cttccgccca gagcttcatc gagcggatga ccaacttcga   5400
taagaacctg cccaacgaga aggtgctgcc caagcacagc ctgctgtacg agtacttcac   5460
cgtgtataac gagctgacca aagtgaaata cgtgaccgag ggaatgagaa agcccgcctt   5520
cctgagcggc gagcagaaaa aggccatcgt ggacctgctg ttcaagacca accggaaagt   5580
gaccgtgaag cagctgaaag aggactactt caagaaaatc gagtgcttcg actccgtgga   5640
aatctccggc gtggaagatc ggttcaacgc ctccctgggc acataccacg atctgctgaa   5700
aattatcaag gacaaggact tcctggacaa tgaggaaaac gaggacattc tggaagatat   5760
cgtgctgacc ctgacactgt ttgaggacag agagatgatc gaggaacggc tgaaaaccta   5820
tgcccacctg ttcgacgaca aagtgatgaa gcagctgaag cggcggagat acaccggctg   5880
ggcaggctg agccggaagc tgatcaacgg catccgggac aagcagtccg gcaagacaat   5940
cctggatttc ctgaagtccg acggcttcgc caacagaaac ttcatgcagc tgatccacga   6000
cgacagcctg acctttaaag aggacatcca gaaagcccag gtgtccggcc agggcgatag   6060
cctgcacgag cacattgcca atctggccgg cagccccgcc attaagaagg gcatcctgca   6120
gacagtgaag gtggtggacg agctcgtgaa agtgatgggc cggcacaagc ccgagaacat   6180
cgtgatcgaa atggccagag agaaccagac caccccagaag ggacagaaga acagccgcga   6240
gagaatgaag cggatcgaag agggcatcaa agagctgggc agccagatcc tgaaagaaca   6300
ccccgtggaa aacacccagc tgcagaacga gaagctgtac ctgtactacc tgcagaatgg   6360
gcgggatatg tacgtggacc aggaactgga catcaaccgg ctgtccgact acgatgtgga   6420
cgctatcgtg cctcagagct ttctgaagga cgactccatc gacaacaagg tgctgaccag   6480
aagcgacaag aaccggggca agagcgacaa cgtgccctcc gaagaggtcg tgaagaagat   6540
gaagaactac tggcggcagc tgctgaacgc caagctgatt acccagagaa agttcgacaa   6600
tctgaccaag gccgagagag gcggcctgag cgaactggat aaggccggct tcatcaagag   6660
acagctggtg gaaacccggc agatcacaaa gcacgtggca cagatcctgg actcccggat   6720
gaacactaag tacgacgaga atgacaagct gatccgggaa gtgaaagtga tcaccctgaa   6780
gtccaagctg gtgtccgatt tccggaagga tttccagttt tacaaagtgc gcgagatcaa   6840
caactaccac cacgcccacg acgcctacct gaacgccgtc gtgggaaccg ccctgatcaa   6900
aaagtaccct aagctggaaa gcgagttcgt gtacggcgac tacaaggtgt acgacgtgcg   6960
gaagatgatc gccaagagcg agcaggaaat cggcaaggct accgccaagt acttcttcta   7020
cagcaacatc atgaactttt tcaagaccga gattaccctg gccaacggcg agatccggaa   7080
gcggcctctg atcgagacaa acggcgaaac cggggagatc gtgtgggata agggccggga   7140
ttttgccacc gtgcggaaag tgctgagcat gccccaagtg aatatcgtga aaaagaccga   7200
ggtgcagaca ggcggcttca gcaaagagtc tatcctgccc aagaggaaca gcgataagct   7260
gatcgccaga aagaaggact gggaccctaa gaagtacggc ggcttcgaca gccccaccgt   7320
ggcctattct gtgctggtgg tggccaaagt ggaaaagggc aagtccaaga aactgaagag   7380
tgtgaaagag ctgctgggga tcaccatcat ggaaagaagc agcttcgaga agaatcccat   7440
```

```
cgactttctg gaagccaagg gctacaaaga agtgaaaaag gacctgatca tcaagctgcc   7500
taagtactcc ctgttcgagc tggaaaacgg ccggaagaga atgctggcct ctgccggcga   7560
actgcagaag ggaaacgaac tggccctgcc ctccaaatat gtgaacttcc tgtacctggc   7620
cagccactat gagaagctga agggctcccc cgaggataat gagcagaaac agctgtttgt   7680
ggaacagcac aagcactacc tggacgagat catcgagcag atcagcgagt tctccaagag   7740
agtgatcctg gccgacgcta atctggacaa agtgctgtcc gcctacaaca agcaccggga   7800
taagcccatc agagagcagg ccgagaatat catccacctg tttaccctga ccaatctggg   7860
agcccctgcc gccttcaagt actttgacac caccatcgac cggaagaggt acaccagcac   7920
caaagaggtg ctggacgcca ccctgatcca ccagagcatc accggcctgt acgagacacg   7980
gatcgacctg tctcagctgg gaggcgacag cgctggagga ggtggaagcg gaggaggagg   8040
aagcggagga ggaggtagcg gacctaagaa aaagaggaag gtggcggccg ctggatccaa   8100
ggacaacacc gtgcccctga agctgatcgc cctgctggcc aacggcgagt tccactctgg   8160
cgagcagctg ggagagaccc tgggaatgag cagagccgcc atcaacaagc acatccagac   8220
actgagagac tggggagtgg acgtgttcac cgtgcctggc aagggctaca gcctgcctga   8280
gcctatccag ctgctgaacg ccaagcagat cctgggacag ctggatggcg gaagcgtggc   8340
cgtgctgcct gtgatcgact ccaccaatca gtacctgctg gacagaatcg gagagctgaa   8400
gtccggcgac gcctgcatcg ccgagtacca gcaggctggc agaggaggca gaggccagat   8460
tacgctcgga agtggttcag cccattcgga gccaacctgt acctgtccat gttctggaga   8520
ctggagcagg gacctgctgc tgccatcgga ctgagtctgg tgatcggaat cgtgatggcc   8580
gaggtgctga gaaagctggg agccgacaag gtgagagtga agtggcctaa tgacctgtac   8640
ctccaggacc gcaagctggc tggcatcctg gtggagctga caggcaagac aggcgatgcc   8700
gctcagatcg tgatcggagc cggaatcaac atggccatga gaagagtgga ggagagcgtg   8760
gtgaaccagg gctggatcac cctgcaggag gctggcatca acctggaccg gaacaccctg   8820
gccgccatgc tgatcagaga gctgagagcc gctctggagc tgttcgagca ggagggactg   8880
gctccttacc tgagcagatg ggagaagctg gacaacttca tcaacagacc tgtgaagctg   8940
atcatcggcg acaaggaaat cttcggcatc tccagaggaa tcgacaagca gggagctctg   9000
ctgctggagc aggacggaat catcaagccc tggatgggcg gagaaatctc cctgagaagc   9060
gcagagaagg cttaccctta cgatgtaccg gattacgcat aggcggcctt aagttgctag   9120
cctagcggca gtggagaggg cagaggaagt ctgctaacat gcggtgacgt cgaggagaat   9180
cctggcccag tgagcaaggg cgaggagctg ttcaccgggg tggtgcccat cctggtcgag   9240
ctggacggcg acgtaaacgg ccacaagttc agcgtgtccg gcgagggcga gggcgatgcc   9300
acctacggca agctgaccct gaagttcatc tgcaccaccg gcaagctgcc cgtgccctgg   9360
cccaccctcg tgaccaccct gacctacggc gtgcagtgct tcagccgcta ccccgaccac   9420
atgaagcagc acgacttctt caagtccgcc atgcccgaag gctacgtcca ggagcgcacc   9480
atcttcttca aggacgacgg caactacaag acccgcgccg aggtgaagtt cgagggcgac   9540
accctggtga accgcatcga gctgaagggc atcgacttca aggaggacgg caacatcctg   9600
gggcacaagc tggagtacaa ctacaacagc cacaacgtct atatcatggc cgacaagcag   9660
aagaacggca tcaaggtgaa cttcaagatc cgccacaaca tcgaggacgg cagcgtgcag   9720
ctcgccgacc actaccagca gaacaccccc atcggcgacg gccccgtgct gctgcccgac   9780
```

```
aaccactacc tgagcaccca gtccgccctg agcaaagacc ccaacgagaa gcgcgatcac   9840
atggtcctgc tggagttcgt gaccgccgcc gggatcactc tcggcatgga cgagctgtac   9900
aagtaagaat tcgatatcaa gcttatcgat aatcaacctc tggattacaa aatttgtgaa   9960
agattgactg gtattcttaa ctatgttgct ccttttacgc tatgtggata cgctgcttta  10020
atgcctttgt atcatgctat tgcttcccgt atggctttca ttttctcctc cttgtataaa  10080
tcctggttgc tgtctcttta tgaggagttg tggcccgttg tcaggcaacg tggcgtggtg  10140
tgcactgtgt ttgctgacgc aacccccact ggttggggca ttgccaccac ctgtcagctc  10200
ctttccggga ctttcgcttt ccccctccct attgccacgg cggaactcat cgccgcctgc  10260
cttgcccgct gctggacagg ggctcggctg ttgggcactg acaattccgt ggtgttgtcg  10320
gggaaatcat cgtcctttcc ttggctgctc gcctgtgttg ccacctggat tctgcgcggg  10380
acgtccttct gctacgtccc ttcggccctc aatccagcgg accttccttc ccgcggcctg  10440
ctgccggctc tgcggcctct tccgcgtctt cgccttcgcc ctcagacgag tcggatctcc  10500
ctttgggccg cctccccgca tcgataccgt cgacctcgag acctagaaaa acatggagca  10560
atcacaagta gcaatacagc agctaccaat gctgattgtg cctggctaga agcacaagag  10620
gaggaggagg tgggttttcc agtcacacct caggtacctt taagaccaat gacttacaag  10680
gcagctgtag atcttagcca ctttttaaaa gaaaaggggg gactggaagg gctaattcac  10740
tcccaacgaa gacaagatat ccttgatctg tggatctacc acacacaagg ctacttccct  10800
gattggcaga actacacacc agggccaggg atcagatatc cactgacctt tggatggtgc  10860
tacaagctag taccagttga gcaagagaag gtagaagaag ccaatgaagg agagaacacc  10920
cgcttgttac accctgtgag cctgcatggg atggatgacc cggagagaga agtattagag  10980
tggaggtttg acagccgcct agcatttcat cacatggccc gagagctgca tccggactgt  11040
actgggtctc tctggttaga ccagatctga gcctgggagc tctctggcta actagggaac  11100
ccactgctta agcctcaata aagcttgcct tgagtgcttc aagtagtgtg tgcccgtctg  11160
ttgtgtgact ctggtaacta gagatccctc agaccctttt agtcagtgtg gaaaatctct  11220
agcagggccc gtttaaaccc gctgatcagc ctcgactgtg ccttctagtt gccagccatc  11280
tgttgtttgc ccctcccccg tgccttcctt gaccctggaa ggtgccactc ccactgtcct  11340
ttcctaataa aatgaggaaa ttgcatcgca ttgtctgagt aggtgtcatt ctattctggg  11400
gggtggggtg gggcaggaca gcaaggggga ggattgggaa gacaatagca ggcatgctgg  11460
ggatgcggtg ggctctatgg cttctgaggc ggaaagaacc agctggggct ctagggggta  11520
tccccacgcg ccctgtagcg gcgcattaag cgcggcgggt gtggtggtta cgcgcagcgt  11580
gaccgctaca cttgccagcg ccctagcgcc cgctcctttc gctttcttcc cttcctttct  11640
cgccacgttc gccggctttc cccgtcaagc tctaaatcgg gggctccctt tagggttccg  11700
atttagtgct ttacggcacc tcgaccccaa aaaacttgat tagggtgatg gttcacgtag  11760
tgggccatcg ccctgataga cggtttttcg ccctttgacg ttggagtcca cgttctttaa  11820
tagtggactc ttgttccaaa ctggaacaac actcaaccct atctcggtct attcttttga  11880
tttataaggg attttgccga tttcggccta ttggttaaaa aatgagctga tttaacaaaa  11940
atttaacgcg aattaattct gtggaatgtg tgtcagttag ggtgtggaaa gtccccaggc  12000
tccccagcag gcagaagtat gcaaagcatg catctcaatt agtcagcaac caggtgtgga  12060
aagtccccag gctccccagc aggcagaagt atgcaaagca tgcatctcaa ttagtcagca  12120
accatagtcc cgcccctaac tccgcccatc ccgcccctaa ctccgcccag ttccgcccat  12180
```

```
tctccgcccc atggctgact aattttttt atttatgcag aggccgaggc cgcctctgcc 12240
tctgagctat tccagaagta gtgaggaggc tttttggag gcctaggctt ttgcaaaaag 12300
ctcccgggag cttgtatatc cattttcgga tctgatcagc acgtgttgac aattaatcat 12360
cggcatagta tatcggcata gtataatacg acaaggtgag gaactaaacc atggccaagt 12420
tgaccagtgc cgttccggtg ctcaccgcgc gcgacgtcgc cggagcggtc gagttctgga 12480
ccgaccggct cgggttctcc cgggacttcg tggaggacga cttcgccggt gtggtccggg 12540
acgacgtgac cctgttcatc agcgcggtcc aggaccaggt ggtgccggac aacaccctgg 12600
cctgggtgtg ggtgcgcggc ctggacgagc tgtacgccga gtggtcggag gtcgtgtcca 12660
cgaacttccg ggacgcctcc gggccggcca tgaccgagat cggcgagcag ccgtgggggc 12720
gggagttcgc cctgcgcgac ccggccggca actgcgtgca cttcgtggcc gaggagcagg 12780
actgacacgt gctacgagat ttcgattcca ccgccgcctt ctatgaaagg ttgggcttcg 12840
gaatcgtttt ccgggacgcc ggctggatga tcctccagcg cggggatctc atgctggagt 12900
tcttcgccca ccccaacttg tttattgcag cttataatgg ttacaaataa agcaatagca 12960
tcacaaattt cacaaataaa gcattttttt cactgcattc tagttgtggt ttgtccaaac 13020
tcatcaatgt atcttatcat gtctgtatac cgtcgacctc tagctagagc ttggcgtaat 13080
catggtcata gctgtttcct gtgtgaaatt gttatccgct cacaattcca cacaacatac 13140
gagccggaag cataaagtgt aaagcctggg gtgcctaatg agtgagctaa ctcacattaa 13200
ttgcgttgcg ctcactgccc gctttccagt cgggaaacct gtcgtgccag ctgcattaat 13260
gaatcggcca acgcgcgggg agaggcggtt tgcgtattgg gcgctcttcc gcttcctcgc 13320
tcactgactc gctgcgctcg gtcgttcggc tgcggcgagc ggtatcagct cactcaaagg 13380
cggtaatacg gttatccaca gaatcagggg ataacgcagg aaagaacatg tgagcaaaag 13440
gccagcaaaa ggccaggaac cgtaaaaagg ccgcgttgct ggcgtttttc cataggctcc 13500
gcccccctga cgagcatcac aaaaatcgac gctcaagtca gaggtggcga aacccgacag 13560
gactataaag ataccaggcg tttccccctg gaagctccct cgtgcgctct cctgttccga 13620
ccctgccgct taccggatac ctgtccgcct ttctcccttc gggaagcgtg gcgctttctc 13680
atagctcacg ctgtaggtat ctcagttcgg tgtaggtcgt tcgctccaag ctgggctgtg 13740
tgcacgaacc ccccgttcag cccgaccgct gcgccttatc cggtaactat cgtcttgagt 13800
ccaacccggt aagacacgac ttatcgccac tggcagcagc cactggtaac aggattagca 13860
gagcgaggta tgtaggcggt gctacagagt tcttgaagtg gtggcctaac tacggctaca 13920
ctagaagaac agtatttggt atctgcgctc tgctgaagcc agttaccttc ggaaaaagag 13980
ttggtagctc ttgatccggc aaacaaacca ccgctggtag cggtggtttt tttgtttgca 14040
agcagcagat tacgcgcaga aaaaaaggat ctcaagaaga tcctttgatc ttttctacgg 14100
ggtctgacgc tcagtggaac gaaaactcac gttaagggat tttggtcatg agattatcaa 14160
aaaggatctt cacctagatc cttttaaatt aaaaatgaag ttttaaatca atctaaagta 14220
tatatgagta aacttggtct gacagttacc aatgcttaat cagtgaggca cctatctcag 14280
cgatctgtct atttcgttca tccatagttg cctgactccc cgtcgtgtag ataactacga 14340
tacgggaggg cttaccatct ggccccagtg ctgcaatgat accgcgagac ccacgctcac 14400
cggctccaga tttatcagca ataaaccagc cagccggaag ggccgagcgc agaagtggtc 14460
ctgcaacttt atccgcctcc atccagtcta ttaattgttg ccgggaagct agagtaagta 14520
```

gttcgccagt taatagtttg cgcaacgttg ttgccattgc tacaggcatc gtggtgtcac 14580
gctcgtcgtt tggtatggct tcattcagct ccggttccca acgatcaagg cgagttacat 14640
gatcccccat gttgtgcaaa aaagcggtta gctccttcgg tcctccgatc gttgtcagaa 14700
gtaagttggc cgcagtgtta tcactcatgg ttatggcagc actgcataat tctcttactg 14760
tcatgccatc cgtaagatgc ttttctgtga ctggtgagta ctcaaccaag tcattctgag 14820
aatagtgtat gcggcgaccg agttgctctt gcccggcgtc aatacgggat aataccgcgc 14880
cacatagcag aactttaaaa gtgctcatca ttggaaaacg ttcttcgggg cgaaaactct 14940
caaggatctt accgctgttg agatccagtt cgatgtaacc cactcgtgca cccaactgat 15000
cttcagcatc ttttactttc accagcgttt ctgggtgagc aaaaacagga aggcaaaatg 15060
ccgcaaaaaa gggaataagg gcgacacgga aatgttgaat actcatactc ttcctttttc 15120
aatattattg aagcatttat cagggttatt gtctcatgag cggatacata tttgaatgta 15180
tttagaaaaa taaacaaata ggggttccgc gcacatttcc ccgaaaagtg ccacctgac 15239

<210> SEQ ID NO 143
<211> LENGTH: 11487
<212> TYPE: DNA
<213> ORGANISM: Artificial Sequence
<220> FEATURE:
<223> OTHER INFORMATION: Synthetic

<400> SEQUENCE: 143
gtcgacggat cgggagatct cccgatcccc tatggtgcac tctcagtaca atctgctctg 60
atgccgcata gttaagccag tatctgctcc ctgcttgtgt gttggaggtc gctgagtagt 120
gcgcgagcaa aatttaagct acaacaaggc aaggcttgac cgacaattgc atgaagaatc 180
tgcttagggt taggcgtttt gcgctgcttc gcgatgtacg ggccagatat acgcgttgac 240
attgattatt gactagttat taatagtaat caattacggg gtcattagtt catagcccat 300
atatggagtt ccgcgttaca taacttacgg taaatggccc gcctggctga ccgcccaacg 360
acccccgccc attgacgtca ataatgacgt atgttcccat agtaacgcca atagggactt 420
tccattgacg tcaatgggtg gagtatttac ggtaaactgc ccacttggca gtacatcaag 480
tgtatcatat gccaagtacg ccccctattg acgtcaatga cggtaaatgg cccgcctggc 540
attatgccca gtacatgacc ttatgggact ttcctacttg gcagtacatc tacgtattag 600
tcatcgctat taccatggtg atgcggtttt ggcagtacat caatgggcgt ggatagcggt 660
ttgactcacg gggatttcca agtctccacc ccattgacgt caatgggagt ttgttttggc 720
accaaaatca acgggacttt ccaaaatgtc gtaacaactc cgccccattg acgcaaatgg 780
gcggtaggcg tgtacggtgg gaggtctata taagcagcgc gttttgcctg tactgggtct 840
ctctggttag accagatctg agcctgggag ctctctggct aactagggaa cccactgctt 900
aagcctcaat aaagcttgcc ttgagtgctt caagtagtgt gtgcccgtct gttgtgtgac 960
tctggtaact agagatccct cagacccttt tagtcagtgt ggaaaatctc tagcagtggc 1020
gcccgaacag ggacttgaaa gcgaaaggga aaccagagga gctctctcga cgcaggactc 1080
ggcttgctga agcgcgcacg gcaagaggcg aggggcggcg actggtgagt acgccaaaaa 1140
ttttgactag cggaggctag aaggagagag atgggtgcga gagcgtcagt attaagcggg 1200
ggagaattag atcgcgatgg gaaaaaattc ggttaaggcc agggggaaag aaaaaatata 1260
aattaaaaca tatagtatgg gcaagcaggg agctagaacg attcgcagtt aatcctggcc 1320
tgttagaaac atcagaaggc tgtagacaaa tactgggaca gctacaacca tcccttcaga 1380

```
caggatcaga agaacttaga tcattatata atacagtagc aaccctctat tgtgtgcatc   1440
aaaggataga gataaaagac accaaggaag ctttagacaa gatagaggaa gagcaaaaca   1500
aaagtaagac caccgcacag caagcggccg ctgatcttca gacctggagg aggagatatg   1560
agggacaatt ggagaagtga attatataaa tataaagtag taaaaattga accattagga   1620
gtagcaccca ccaaggcaaa gagaagagtg gtgcagagag aaaaaagagc agtgggaata   1680
ggagctttgt tccttgggtt cttgggagca gcaggaagca ctatgggcgc agcgtcaatg   1740
acgctgacgg tacaggccag acaattattg tctggtatag tgcagcagca gaacaatttg   1800
ctgagggcta ttgaggcgca acagcatctg ttgcaactca cagtctgggg catcaagcag   1860
ctccaggcaa gaatcctggc tgtggaaaga tacctaaagg atcaacagct cctggggatt   1920
tggggttgct ctggaaaact catttgcacc actgctgtgc cttggaatgc tagttggagt   1980
aataaatctc tggaacagat ttggaatcac acgacctgga tggagtggga cagagaaatt   2040
aacaattaca caagcttaat acactcctta attgaagaat cgcaaaacca gcaagaaaag   2100
aatgaacaag aattattgga attagataaa tgggcaagtt tgtggaattg gtttaacata   2160
acaaattggc tgtggtatat aaaattattc ataatgatag taggaggctt ggtaggttta   2220
agaatagttt ttgctgtact ttctatagtg aatagagtta ggcagggata ttcaccatta   2280
tcgtttcaga cccacctccc aaccccgagg ggacccgaca ggcccgaagg aatagaagaa   2340
gaaggtggag agagagacag agacagatcc attcgattag tgaacggatc ggcactgcgt   2400
gcgccaattc tgcagacaaa tggcagtatt catccacaat tttaaaagaa aaggggggat   2460
tggggggtac agtgcagggg aaagaatagt agacataata gcaacagaca tacaaactaa   2520
agaattacaa aaacaaatta caaaaattca aaattttcgg gtttattaca gggacagcag   2580
agatccagtt tggttaatta atgcaaagat ggataaagtt ttaaacagag aggaatcttt   2640
gcagctaatg gaccttctag gtcttgaaag gagtgggaat tggctccggt gcccgtcagt   2700
gggcagagcg cacatcgccc acagtccccg agaagttggg gggaggggtc ggcaattgaa   2760
ccggtgccta gagaaggtgg cgcggggtaa actgggaaag tgatgtcgtg tactggctcc   2820
gcctttttcc cgagggtggg ggagaaccgt atataagtgc agtagtcgcc gtgaacgttc   2880
tttttcgcaa cgggtttgcc gccagaacac aggtaagtgc cgtgtgtggt tcccgcgggc   2940
ctggcctctt tacgggttat ggcccttgcg tgccttgaat tacttccact ggctgcagta   3000
cgtgattctt gatcccgagc ttcgggttgg aagtgggtgg gagagttcga ggccttgcgc   3060
ttaaggagcc ccttcgcctc gtgcttgagt tgaggcctgg cctgggcgct ggggccgccg   3120
cgtgcgaatc tggtggcacc ttcgcgcctg tctcgctgct ttcgataagt ctctagccat   3180
ttaaaatttt tgatgacctg ctgcgacgct ttttttctgg caagatagtc ttgtaaatgc   3240
gggccaagat ctgcacactg gtatttcggt ttttggggcc gcgggcggcg acggggcccg   3300
tgcgtcccag cgcacatgtt cggcgaggcg gggcctgcga gcgcggccac cgagaatcgg   3360
acgggggtag tctcaagctg gccggcctgc tctggtgcct ggcctcgcgc cgccgtgtat   3420
cgccccgccc tgggcggcaa ggctggcccg gtcggcacca gttgcgtgag cggaaagatg   3480
gccgcttccc ggccctgctg cagggagctc aaaatggagg acgcggcgct cgggagagcg   3540
ggcgggtgag tcacccacac aaaggaaaag ggcctttccg tcctcagccg tcgcttcatg   3600
tgactccacg gagtaccggg cgccgtccag gcacctcgat tagttctcga gcttttggag   3660
tacgtcgtct ttaggttggg gggaggggtt ttatgcgatg gagtttcccc acactgagtg   3720
```

-continued

```
ggtggagact gaagttaggc cagcttggca cttgatgtaa ttctccttgg aatttgccct   3780
ttttgagttt ggatcttggt tcattctcaa gcctcagaca gtggttcaaa gttttttttct   3840
tccatttcag gtgtcgtgac gtacggccac catggcttca aactttactc agttcgtgct   3900
cgtggacaat ggtgggacag ggatgtgac agtggctcct tctaatttcg ctaatggggt   3960
ggcagagtgg atcagctcca actcacggag ccaggcctac aaggtgacat gcagcgtcag   4020
gcagtctagt gcccagaaga gaaagtatac catcaaggtg gaggtcccca aagtggctac   4080
ccagacagtg ggcggagtcg aactgcctgt cgccgcttgg aggtcctacc tgaacatgga   4140
gctcactatc ccaatttcg ctaccaattc tgactgtgaa ctcatcgtga aggcaatgca   4200
ggggctcctc aaagacggta atcctatccc ttccgccatc gccgctaact caggtatcta   4260
cagcgctgga ggaggtggaa gcggaggagg aggaagcgga ggaggaggta gcggacctaa   4320
gaaaaagagg aaggtggcgg ccgctggatc caaggacaac accgtgcccc tgaagctgat   4380
cgccctgctg gccaacggcg agttccactc tggcgagcag ctgggagaga ccctgggaat   4440
gagcagagcc gccatcaaca agcacatcca gacactgaga gactggggag tggacgtgtt   4500
caccgtgcct ggcaagggct acagcctgcc tgagcctatc cagctgctga acgccaagca   4560
gatcctggga cagctggatg gcggaagcgt ggccgtgctg cctgtgatcg actccaccaa   4620
tcagtacctg ctggacagaa tcggagagct gaagtccggc gacgcctgca tcgccgagta   4680
ccagcaggct ggcagaggag gcagaggcca gattacgctc ggaagtggtt cagcccattc   4740
ggagccaacc tgtacctgtc catgttctgg agactggagc agggacctgc tgctgccatc   4800
ggactgagtc tggtgatcgg aatcgtgatg gccgaggtgc tgagaaagct gggagccgac   4860
aaggtgagag tgaagtggcc taatgacctg tacctccagg accgcaagct ggctggcatc   4920
ctggtggagc tgacaggcaa gacaggcgat gccgctcaga tcgtgatcgg agccggaatc   4980
aacatggcca tgagaagagt ggaggagagc gtggtgaacc agggctggat caccctgcag   5040
gaggctggca tcaacctgga ccggaacacc ctggccgcca tgctgatcag agagctgaga   5100
gccgctctgg agctgttcga gcaggaggga ctggctcctt acctgagcag atgggagaag   5160
ctggacaact tcatcaacag acctgtgaag ctgatcatcg gcgacaagga aatcttcggc   5220
atctccagag gaatcgacaa gcagggagct ctgctgctgg agcaggacgg aatcatcaag   5280
ccctggatgg gcggagaaat ctccctgaga agcgcagaga aggcttaccc ttacgatgta   5340
ccggattacg cataggcggc cttaagttgc tagcggcagt ggagagggca gaggaagtct   5400
gctaacatgc ggtgacgtcg aggagaatcc tggcccagtg agcaagggcg aggagctgtt   5460
caccggggtg gtgcccatcc tggtcgagct ggacggcgac gtaaacggcc acaagttcag   5520
cgtgtccggc gagggcgagg gcgatgccac ctacggcaag ctgaccctga agttcatctg   5580
caccaccggc aagctgcccg tgccctggcc caccctcgtg accaccctga cctacggcgt   5640
gcagtgcttc agccgctacc ccgaccacat gaagcagcac gacttcttca agtccgccat   5700
gcccgaaggc tacgtccagg agcgcaccat cttcttcaag gacgacggca actacaagac   5760
ccgcgccgag gtgaagttcg agggcgacac cctggtgaac cgcatcgagc tgaagggcat   5820
cgacttcaag gaggacggca acatcctggg gcacaagctg gagtacaact acaacagcca   5880
caacgtctat atcatggccg acaagcagaa gaacggcatc aaggtgaact tcaagatccg   5940
ccacaacatc gaggacggca gcgtgcagct cgccgaccac taccagcaga acacccccat   6000
cggcgacggc cccgtgctgc tgcccgacaa ccactacctg agcacccagt ccgccctgag   6060
caaagacccc aacgagaagc gcgatcacat ggtcctgctg gagttcgtga ccgccgccgg   6120
```

```
gatcactctc ggcatggacg agctgtacaa gtaagaattc gatatcaagc ttatcgataa   6180
tcaacctctg gattacaaaa tttgtgaaag attgactggt attcttaact atgttgctcc   6240
ttttacgcta tgtggatacg ctgctttaat gcctttgtat catgctattg cttcccgtat   6300
ggctttcatt ttctcctcct tgtataaatc ctggttgctg tctctttatg aggagttgtg   6360
gcccgttgtc aggcaacgtg gcgtggtgtg cactgtgttt gctgacgcaa cccccactgg   6420
ttggggcatt gccaccacct gtcagctcct ttccgggact ttcgctttcc ccctccctat   6480
tgccacggcg gaactcatcg ccgcctgcct tgcccgctgc tggacagggg ctcggctgtt   6540
gggcactgac aattccgtgg tgttgtcggg gaaatcatcg tcctttcctt ggctgctcgc   6600
ctgtgttgcc acctggattc tgcgcgggac gtccttctgc tacgtccctt cggccctcaa   6660
tccagcggac cttccttccc gcggcctgct gccggctctg cggcctcttc cgcgtcttcg   6720
ccttcgccct cagacgagtc ggatctccct ttgggccgcc tccccgcatc gataccgtcg   6780
acctcgagac ctagaaaaac atggagcaat cacaagtagc aatacagcag ctaccaatgc   6840
tgattgtgcc tggctagaag cacaagagga ggaggaggtg ggttttccag tcacacctca   6900
ggtaccttta agaccaatga cttacaaggc agctgtagat cttagccact ttttaaaaga   6960
aaagggggga ctggaagggc taattcactc ccaacgaaga caagatatcc ttgatctgtg   7020
gatctaccac acacaaggct acttccctga ttggcagaac tacacaccag ggccagggat   7080
cagatatcca ctgacctttg gatggtgcta caagctagta ccagttgagc aagagaaggt   7140
agaagaagcc aatgaaggag agaacacccg cttgttacac cctgtgagcc tgcatgggat   7200
ggatgacccg gagagagaag tattagagtg gaggtttgac agccgcctag catttcatca   7260
catggcccga gagctgcatc cggactgtac tgggtctctc tggttagacc agatctgagc   7320
ctgggagctc tctggctaac tagggaaccc actgcttaag cctcaataaa gcttgccttg   7380
agtgcttcaa gtagtgtgtg cccgtctgtt gtgtgactct ggtaactaga gatccctcag   7440
acccttttag tcagtgtgga aaatctctag cagggcccgt ttaaacccgc tgatcagcct   7500
cgactgtgcc ttctagttgc cagccatctg ttgtttgccc ctcccccgtg ccttccttga   7560
ccctggaagg tgccactccc actgtccttt cctaataaaa tgaggaaatt gcatcgcatt   7620
gtctgagtag gtgtcattct attctggggg gtggggtggg gcaggacagc aagggggagg   7680
attgggaaga caatagcagg catgctgggg atgcggtggg ctctatggct tctgaggcgg   7740
aaagaaccag ctggggctct agggggtatc cccacgcgcc ctgtagcggc gcattaagcg   7800
cggcgggtgt ggtggttacg cgcagcgtga ccgctacact tgccagcgcc ctagcgcccg   7860
ctcctttcgc tttcttccct tcctttctcg ccacgttcgc cggctttccc cgtcaagctc   7920
taaatcgggg gctcccttta gggttccgat ttagtgcttt acggcacctc gaccccaaaa   7980
aacttgatta gggtgatggt tcacgtagtg ggccatcgcc ctgatagacg gtttttcgcc   8040
ctttgacgtt ggagtccacg ttctttaata gtggactctt gttccaaact ggaacaacac   8100
tcaaccctat ctcggtctat tcttttgatt tataagggat tttgccgatt tcggcctatt   8160
ggttaaaaaa tgagctgatt taacaaaaat ttaacgcgaa ttaattctgt ggaatgtgtg   8220
tcagttaggg tgtggaaagt ccccaggctc cccagcaggc agaagtatgc aaagcatgca   8280
tctcaattag tcagcaacca ggtgtggaaa gtccccaggc tccccagcag gcagaagtat   8340
gcaaagcatg catctcaatt agtcagcaac catagtcccg cccctaactc cgcccatccc   8400
gcccctaact ccgcccagtt ccgcccattc tccgccccat ggctgactaa ttttttttat   8460
```

```
ttatgcagag gccgaggccg cctctgcctc tgagctattc cagaagtagt gaggaggctt   8520
ttttggaggc ctaggctttt gcaaaaagct cccgggagct tgtatatcca ttttcggatc   8580
tgatcagcac gtgttgacaa ttaatcatcg gcatagtata tcggcatagt ataatacgac   8640
aaggtgagga actaaaccat ggccaagttg accagtgccg ttccggtgct caccgcgcgc   8700
gacgtcgccg gagcggtcga gttctggacc gaccggctcg ggttctcccg ggacttcgtg   8760
gaggacgact tcgccggtgt ggtccgggac gacgtgaccc tgttcatcag cgcggtccag   8820
gaccaggtgg tgccggacaa caccctggcc tgggtgtggg tgcgcggcct ggacgagctg   8880
tacgccgagt ggtcggaggt cgtgtccacg aacttccggg acgcctccgg gccggccatg   8940
accgagatcg gcgagcagcc gtgggggcgg gagttcgccc tgcgcgaccc ggccggcaac   9000
tgcgtgcact tcgtggccga ggagcaggac tgacacgtgc tacgagattt cgattccacc   9060
gccgccttct atgaaaggtt gggcttcgga atcgttttcc gggacgccgg ctggatgatc   9120
ctccagcgcg gggatctcat gctggagttc ttcgcccacc ccaacttgtt tattgcagct   9180
tataatggtt acaaataaag caatagcatc acaaatttca caaataaagc atttttttca   9240
ctgcattcta gttgtggttt gtccaaactc atcaatgtat cttatcatgt ctgtataccg   9300
tcgacctcta gctagagctt ggcgtaatca tggtcatagc tgtttcctgt gtgaaattgt   9360
tatccgctca caattccaca caacatacga gccggaagca taaagtgtaa agcctggggt   9420
gcctaatgag tgagctaact cacattaatt gcgttgcgct cactgcccgc tttccagtcg   9480
ggaaacctgt cgtgccagct gcattaatga atcggccaac gcgcggggag aggcggtttg   9540
cgtattgggc gctcttccgc ttcctcgctc actgactcgc tgcgctcggt cgttcggctg   9600
cggcgagcgg tatcagctca ctcaaaggcg gtaatacggt tatccacaga atcaggggat   9660
aacgcaggaa agaacatgtg agcaaaaggc cagcaaaagg ccaggaaccg taaaaaggcc   9720
gcgttgctgg cgtttttcca taggctccgc ccccctgacg agcatcacaa aaatcgacgc   9780
tcaagtcaga ggtggcgaaa cccgacagga ctataaagat accaggcgtt tccccctgga   9840
agctccctcg tgcgctctcc tgttccgacc ctgccgctta ccggatacct gtccgccttt   9900
ctcccttcgg gaagcgtggc gctttctcat agctcacgct gtaggtatct cagttcggtg   9960
taggtcgttc gctccaagct gggctgtgtg cacgaacccc ccgttcagcc cgaccgctgc  10020
gccttatccg gtaactatcg tcttgagtcc aacccggtaa gacacgactt atcgccactg  10080
gcagcagcca ctggtaacag gattagcaga gcgaggtatg taggcggtgc tacagagttc  10140
ttgaagtggt ggcctaacta cggctacact agaagaacag tatttggtat ctgcgctctg  10200
ctgaagccag ttaccttcgg aaaaagagtt ggtagctctt gatccggcaa acaaaccacc  10260
gctggtagcg gtggtttttt tgtttgcaag cagcagatta cgcgcagaaa aaaaggatct  10320
caagaagatc ctttgatctt ttctacgggg tctgacgctc agtggaacga aaactcacgt  10380
taagggattt tggtcatgag attatcaaaa aggatcttca cctagatcct tttaaattaa  10440
aaatgaagtt ttaaatcaat ctaaagtata tatgagtaaa cttggtctga cagttaccaa  10500
tgcttaatca gtgaggcacc tatctcagcg atctgtctat ttcgttcatc catagttgcc  10560
tgactccccg tcgtgtagat aactacgata cgggagggct taccatctgg ccccagtgct  10620
gcaatgatac cgcgagaccc acgctcaccg gctccagatt tatcagcaat aaaccagcca  10680
gccggaaggg ccgagcgcag aagtggtcct gcaactttat ccgcctccat ccagtctatt  10740
aattgttgcc gggaagctag agtaagtagt tcgccagtta atagtttgcg caacgttgtt  10800
gccattgcta caggcatcgt ggtgtcacgc tcgtcgtttg gtatggcttc attcagctcc  10860
```

```
ggttcccaac gatcaaggcg agttacatga tcccccatgt tgtgcaaaaa agcggttagc  10920

tccttcggtc ctccgatcgt tgtcagaagt aagttggccg cagtgttatc actcatggtt  10980

atggcagcac tgcataattc tcttactgtc atgccatccg taagatgctt ttctgtgact  11040

ggtgagtact caaccaagtc attctgagaa tagtgtatgc ggcgaccgag ttgctcttgc  11100

ccggcgtcaa tacgggataa taccgcgcca catagcagaa ctttaaaagt gctcatcatt  11160

ggaaaacgtt cttcggggcg aaaactctca aggatcttac cgctgttgag atccagttcg  11220

atgtaaccca ctcgtgcacc caactgatct tcagcatctt ttactttcac cagcgtttct  11280

gggtgagcaa aaacaggaag gcaaaatgcc gcaaaaaagg gaataagggc gacacggaaa  11340

tgttgaatac tcatactctt cctttttcaa tattattgaa gcatttatca gggttattgt  11400

ctcatgagcg gatacatatt tgaatgtatt tagaaaaata aacaaatagg ggttccgcgc  11460

acatttcccc gaaaagtgcc acctgac                                     11487
```

<210> SEQ ID NO 144
<211> LENGTH: 14630
<212> TYPE: DNA
<213> ORGANISM: Artificial Sequence
<220> FEATURE:
<223> OTHER INFORMATION: Synthetic

<400> SEQUENCE: 144

```
gtcgacggat cgggagatct cccgatcccc tatggtgcac tctcagtaca atctgctctg     60

atgccgcata gttaagccag tatctgctcc ctgcttgtgt gttggaggtc gctgagtagt    120

gcgcgagcaa aatttaagct acaacaaggc aaggcttgac cgacaattgc atgaagaatc    180

tgcttagggt taggcgtttt gcgctgcttc gcgatgtacg ggccagatat acgcgttgac    240

attgattatt gactagttat taatagtaat caattacggg gtcattagtt catagcccat    300

atatggagtt ccgcgttaca taacttacgg taaatggccc gcctggctga ccgcccaacg    360

acccccgccc attgacgtca ataatgacgt atgttcccat agtaacgcca atagggactt    420

tccattgacg tcaatgggtg gagtatttac ggtaaactgc ccacttggca gtacatcaag    480

tgtatcatat gccaagtacg ccccctattg acgtcaatga cggtaaatgg cccgcctggc    540

attatgccca gtacatgacc ttatgggact ttcctacttg gcagtacatc tacgtattag    600

tcatcgctat taccatggtg atgcggtttt ggcagtacat caatgggcgt ggatagcggt    660

ttgactcacg gggatttcca agtctccacc ccattgacgt caatgggagt ttgttttggc    720

accaaaatca acgggacttt ccaaaatgtc gtaacaactc cgccccattg acgcaaatgg    780

gcggtaggcg tgtacggtgg gaggtctata taagcagcgc gttttgcctg tactgggtct    840

ctctggttag accagatctg agcctgggag ctctctggct aactagggaa cccactgctt    900

aagcctcaat aaagcttgcc ttgagtgctt caagtagtgt gtgcccgtct gttgtgtgac    960

tctggtaact agagatccct cagacccttt tagtcagtgt ggaaaatctc tagcagtggc   1020

gcccgaacag ggacttgaaa gcgaaaggga aaccagagga gctctctcga cgcaggactc   1080

ggcttgctga agcgcgcacg gcaagaggcg aggggcggcg actggtgagt acgccaaaaa   1140

ttttgactag cggaggctag aaggagagag atgggtgcga gagcgtcagt attaagcggg   1200

ggagaattag atcgcgatgg gaaaaaattc ggttaaggcc agggggaaag aaaaaatata   1260

aattaaaaca tatagtatgg gcaagcaggg agctagaacg attcgcagtt aatcctggcc   1320

tgttagaaac atcagaaggc tgtagacaaa tactgggaca gctacaacca tcccttcaga   1380
```

```
caggatcaga agaacttaga tcattatata atacagtagc aaccctctat tgtgtgcatc   1440
aaaggataga gataaaagac accaaggaag ctttagacaa gatagaggaa gagcaaaaca   1500
aaagtaagac caccgcacag caagcggccg ctgatcttca gacctggagg aggagatatg   1560
agggacaatt ggagaagtga attatataaa tataaagtag taaaaattga accattagga   1620
gtagcaccca ccaaggcaaa gagaagagtg gtgcagagag aaaaaagagc agtgggaata   1680
ggagctttgt tccttgggtt cttgggagca gcaggaagca ctatgggcgc agcgtcaatg   1740
acgctgacgg tacaggccag acaattattg tctggtatag tgcagcagca gaacaatttg   1800
ctgagggcta ttgaggcgca acagcatctg ttgcaactca cagtctgggg catcaagcag   1860
ctccaggcaa gaatcctggc tgtggaaaga tacctaaagg atcaacagct cctggggatt   1920
tggggttgct ctggaaaact catttgcacc actgctgtgc cttggaatgc tagttggagt   1980
aataaatctc tggaacagat ttggaatcac acgacctgga tggagtggga cagagaaatt   2040
aacaattaca caagcttaat acactcctta attgaagaat cgcaaaacca gcaagaaaag   2100
aatgaacaag aattattgga attagataaa tgggcaagtt tgtggaattg gtttaacata   2160
acaaattggc tgtggtatat aaaattattc ataatgatag taggaggctt ggtaggttta   2220
agaatagttt ttgctgtact ttctatagtg aatagagtta ggcagggata ttcaccatta   2280
tcgtttcaga cccacctccc aaccccgagg ggacccgaca ggcccgaagg aatagaagaa   2340
gaaggtggag agagagacag agacagatcc attcgattag tgaacggatc ggcactgcgt   2400
gcgccaattc tgcagacaaa tggcagtatt catccacaat tttaaaagaa aaggggggat   2460
tggggggtac agtgcagggg aaagaatagt agacataata gcaacagaca tacaaactaa   2520
agaattacaa aaacaaatta caaaaattca aaattttcgg gtttattaca gggacagcag   2580
agatccagtt tggttaatta atgcaaagat ggataaagtt ttaaacagag aggaatcttt   2640
gcagctaatg gaccttctag gtcttgaaag gagtgggaat tggctccggt gcccgtcagt   2700
gggcagagcg cacatcgccc acagtccccg agaagttggg gggaggggtc ggcaattgaa   2760
ccggtgccta gagaaggtgg cgcggggtaa actgggaaag tgatgtcgtg tactggctcc   2820
gcctttttcc cgagggtggg ggagaaccgt atataagtgc agtagtcgcc gtgaacgttc   2880
tttttcgcaa cgggtttgcc gccagaacac aggtaagtgc cgtgtgtggt tcccgcgggc   2940
ctggcctctt tacgggttat ggcccttgcg tgccttgaat tacttccact ggctgcagta   3000
cgtgattctt gatcccgagc ttcgggttgg aagtgggtgg gagagttcga ggccttgcgc   3060
ttaaggagcc ccttcgcctc gtgcttgagt tgaggcctgg cctgggcgct ggggccgccg   3120
cgtgcgaatc tggtggcacc ttcgcgcctg tctcgctgct ttcgataagt ctctagccat   3180
ttaaaatttt tgatgacctg ctgcgacgct ttttttctgg caagatagtc ttgtaaatgc   3240
gggccaagat ctgcacactg gtatttcggt ttttggggcc gcgggcggcg acggggcccg   3300
tgcgtcccag cgcacatgtt cggcgaggcg gggcctgcga gcgcggccac cgagaatcgg   3360
acgggggtag tctcaagctg gccggcctgc tctggtgcct ggcctcgcgc cgccgtgtat   3420
cgccccgccc tgggcggcaa ggctggcccg gtcggcacca gttgcgtgag cggaaagatg   3480
gccgcttccc ggccctgctg cagggagctc aaaatggagg acgcggcgct cgggagagcg   3540
ggcgggtgag tcacccacac aaaggaaaag ggcctttccg tcctcagccg tcgcttcatg   3600
tgactccacg gagtaccggg cgccgtccag gcacctcgat tagttctcga gcttttggag   3660
tacgtcgtct ttaggttggg gggaggggtt ttatgcgatg gagtttcccc acactgagtg   3720
ggtggagact gaagttaggc cagcttggca cttgatgtaa ttctccttgg aatttgccct   3780
```

```
ttttgagttt ggatcttggt tcattctcaa gcctcagaca gtggttcaaa gtttttttct   3840
tccatttcag gtgtcgtgac gtacggccac catgagcccc aagaagaaga gaaaggtgga   3900
ggccagcgac aagaagtaca gcatcggcct ggccatcggc accaactctg tgggctgggc   3960
cgtgatcacc gacgagtaca aggtgcccag caagaaattc aaggtgctgg gcaacaccga   4020
ccggcacagc atcaagaaga acctgatcgg agccctgctg ttcgacagcg gcgaaacagc   4080
cgaggccacc cggctgaaga gaaccgccag aagaagatac accagacgga agaaccggat   4140
ctgctatctg caagagatct tcagcaacga gatggccaag gtggacgaca gcttcttcca   4200
cagactggaa gagtccttcc tggtggaaga ggataagaag cacgagcggc accccatctt   4260
cggcaacatc gtggacgagg tggcctacca cgagaagtac cccaccatct accacctgag   4320
aaagaaactg gtggacagca ccgacaaggc cgacctgcgg ctgatctatc tggccctggc   4380
ccacatgatc aagttccggg gccacttcct gatcgagggc gacctgaacc ccgacaacag   4440
cgacgtggac aagctgttca tccagctggt gcagacctac aaccagctgt tcgaggaaaa   4500
ccccatcaac gccagcggcg tggacgccaa ggccatcctg tctgccagac tgagcaagag   4560
cagacggctg gaaaatctga tcgcccagct gcccggcgag aagaagaatg gcctgttcgg   4620
caacctgatt gccctgagcc tgggcctgac ccccaacttc aagagcaact tcgacctggc   4680
cgaggatgcc aaactgcagc tgagcaagga cacctacgac gacgacctgg acaacctgct   4740
ggcccagatc ggcgaccagt acgccgacct gtttctggcc gccaagaacc tgtccgacgc   4800
catcctgctg agcgacatcc tgagagtgaa caccgagatc accaaggccc ccctgagcgc   4860
ctctatgatc aagagatacg acgagcacca ccaggacctg accctgctga aagctctcgt   4920
gcggcagcag ctgcctgaga agtacaaaga gattttcttc gaccagagca agaacggcta   4980
cgccggctac attgacggcg gagccagcca ggaagagttc tacaagttca tcaagcccat   5040
cctggaaaag atggacggca ccgaggaact gctcgtgaag ctgaacagag aggacctgct   5100
gcggaagcag cggaccttcg acaacggcag catcccccac cagatccacc tgggagagct   5160
gcacgccatt ctgcggcggc aggaagattt ttacccattc ctgaaggaca accgggaaaa   5220
gatcgagaag atcctgacct tccgcatccc ctactacgtg ggccctctgg ccaggggaaa   5280
cagcagattc gcctggatga ccagaaagag cgaggaaacc atcaccccct ggaacttcga   5340
ggaagtggtg gacaagggcg cttccgccca gagcttcatc gagcggatga ccaacttcga   5400
taagaacctg cccaacgaga aggtgctgcc caagcacagc ctgctgtacg agtacttcac   5460
cgtgtataac gagctgacca aagtgaaata cgtgaccgag ggaatgagaa agcccgcctt   5520
cctgagcggc gagcagaaaa aggccatcgt ggacctgctg ttcaagacca accggaaagt   5580
gaccgtgaag cagctgaaag aggactactt caagaaaatc gagtgcttcg actccgtgga   5640
aatctccggc gtggaagatc ggttcaacgc ctccctgggc acataccacg atctgctgaa   5700
aattatcaag gacaaggact tcctggacaa tgaggaaaac gaggacattc tggaagatat   5760
cgtgctgacc ctgacactgt ttgaggacag agagatgatc gaggaacggc tgaaaaccta   5820
tgcccacctg ttcgacgaca aagtgatgaa gcagctgaag cggcggagat acaccggctg   5880
ggcaggctg agccggaagc tgatcaacgg catccgggac aagcagtccg gcaagacaat   5940
cctggatttc ctgaagtccg acggcttcgc caacagaaac ttcatgcagc tgatccacga   6000
cgacagcctg acctttaaag aggacatcca gaaagcccag gtgtccggcc agggcgatag   6060
cctgcacgag cacattgcca atctggccgg cagccccgcc attaagaagg gcatcctgca   6120
```

```
gacagtgaag gtggtggacg agctcgtgaa agtgatgggc cggcacaagc ccgagaacat   6180
cgtgatcgaa atggccagag agaaccagac cacccagaag ggacagaaga acagccgcga   6240
gagaatgaag cggatcgaag agggcatcaa agagctgggc agccagatcc tgaaagaaca   6300
ccccgtggaa aacacccagc tgcagaacga gaagctgtac ctgtactacc tgcagaatgg   6360
gcgggatatg tacgtggacc aggaactgga catcaaccgg ctgtccgact acgatgtgga   6420
cgctatcgtg cctcagagct ttctgaagga cgactccatc gacaacaagg tgctgaccag   6480
aagcgacaag aaccggggca agagcgacaa cgtgccctcc gaagaggtcg tgaagaagat   6540
gaagaactac tggcggcagc tgctgaacgc caagctgatt acccagagaa agttcgacaa   6600
tctgaccaag gccgagagag gcggcctgag cgaactggat aaggccggct tcatcaagag   6660
acagctggtg gaaacccggc agatcacaaa gcacgtggca cagatcctgg actcccggat   6720
gaacactaag tacgacgaga atgacaagct gatccgggaa gtgaaagtga tcaccctgaa   6780
gtccaagctg gtgtccgatt tccggaagga tttccagttt tacaaagtgc gcgagatcaa   6840
caactaccac cacgcccacg acgcctacct gaacgccgtc gtgggaaccg ccctgatcaa   6900
aaagtaccct aagctggaaa gcgagttcgt gtacggcgac tacaaggtgt acgacgtgcg   6960
gaagatgatc gccaagagcg agcaggaaat cggcaaggct accgccaagt acttcttcta   7020
cagcaacatc atgaactttt tcaagaccga gattaccctg gccaacggcg agatccggaa   7080
gcggcctctg atcgagacaa acggcgaaac cggggagatc gtgtgggata agggccggga   7140
ttttgccacc gtgcggaaag tgctgagcat gccccaagtg aatatcgtga aaaagaccga   7200
ggtgcagaca ggcggcttca gcaaagagtc tatcctgccc aagaggaaca gcgataagct   7260
gatcgccaga aagaaggact gggaccctaa gaagtacggc ggcttcgaca gccccaccgt   7320
ggcctattct gtgctggtgg tggccaaagt ggaaaagggc aagtccaaga aactgaagag   7380
tgtgaaagag ctgctgggga tcaccatcat ggaaagaagc agcttcgaga agaatcccat   7440
cgactttctg gaagccaagg gctacaaaga agtgaaaaag gacctgatca tcaagctgcc   7500
taagtactcc ctgttcgagc tggaaaacgg ccggaagaga atgctggcct ctgccggcga   7560
actgcagaag ggaaacgaac tggccctgcc ctccaaatat gtgaacttcc tgtacctggc   7620
cagccactat gagaagctga agggctcccc cgaggataat gagcagaaac agctgtttgt   7680
ggaacagcac aagcactacc tggacgagat catcgagcag atcagcgagt tctccaagag   7740
agtgatcctg gccgacgcta atctggacaa agtgctgtcc gcctacaaca agcaccggga   7800
taagcccatc agagagcagg ccgagaatat catccacctg tttaccctga ccaatctggg   7860
agcccctgcc gccttcaagt actttgacac caccatcgac cggaagaggt acaccagcac   7920
caaagaggtg ctggacgcca ccctgatcca ccagagcatc accggcctgt acgagacacg   7980
gatcgacctg tctcagctgg gaggcgacag cgctggagga ggtggaagcg gaggaggagg   8040
aagcggagga ggaggtagcg gacctaagaa aaagaggaag gtggcggccg ctggatccaa   8100
ggacaacacc gtgcccctga agctgatcgc cctgctggcc aacggcgagt tccactctgg   8160
cgagcagctg ggagagaccc tgggaatgag cagagccgcc atcaacaagc acatccagac   8220
actgagagac tggggagtgg acgtgttcac cgtgcctggc aagggctaca gcctgcctga   8280
gcctatccag ctgctgaacg ccaagcagat cctgggacag ctggatggcg gaagcgtggc   8340
cgtgctgcct gtgatcgact ccaccaatca gtacctgctg gacagaatcg gagagctgaa   8400
gtccggcgac gcctgcatcg ccgagtacca gcaggctggc agaggaggca gaggccagat   8460
tacgctcgga agtggttcag cccattcgga gccaacctgt acctgtccat gtttagcggc   8520
```

```
agtggagagg gcagaggaag tctgctaaca tgcggtgacg tcgaggagaa tcctggccca   8580
gtgagcaagg gcgaggagct gttcaccggg gtggtgccca tcctggtcga gctggacggc   8640
gacgtaaacg gccacaagtt cagcgtgtcc ggcgagggcg agggcgatgc cacctacggc   8700
aagctgaccc tgaagttcat ctgcaccacc ggcaagctgc ccgtgccctg gcccaccctc   8760
gtgaccaccc tgacctacgg cgtgcagtgc ttcagccgct accccgacca catgaagcag   8820
cacgacttct tcaagtccgc catgcccgaa ggctacgtcc aggagcgcac catcttcttc   8880
aaggacgacg gcaactacaa gacccgcgcc gaggtgaagt tcgagggcga caccctggtg   8940
aaccgcatcg agctgaaggg catcgacttc aaggaggacg gcaacatcct ggggcacaag   9000
ctggagtaca actacaacag ccacaacgtc tatatcatgg ccgacaagca gaagaacggc   9060
atcaaggtga acttcaagat ccgccacaac atcgaggacg gcagcgtgca gctcgccgac   9120
cactaccagc agaacacccc catcggcgac ggccccgtgc tgctgcccga caaccactac   9180
ctgagcaccc agtccgccct gagcaaagac cccaacgaga agcgcgatca catggtcctg   9240
ctggagttcg tgaccgccgc cgggatcact ctcggcatgg acgagctgta caagtaagaa   9300
ttcgatatca agcttatcga taatcaacct ctggattaca aaatttgtga aagattgact   9360
ggtattctta actatgttgc tccttttacg ctatgtggat acgctgcttt aatgcctttg   9420
tatcatgcta ttgcttcccg tatggctttc attttctcct ccttgtataa atcctggttg   9480
ctgtctcttt atgaggagtt gtggcccgtt gtcaggcaac gtggcgtggt gtgcactgtg   9540
tttgctgacg caacccccac tggttggggc attgccacca cctgtcagct cctttccggg   9600
actttcgctt tccccctccc tattgccacg gcggaactca tcgccgcctg ccttgcccgc   9660
tgctggacag gggctcggct gttgggcact gacaattccg tggtgttgtc ggggaaatca   9720
tcgtcctttc cttggctgct cgcctgtgtt gccacctgga ttctgcgcgg gacgtccttc   9780
tgctacgtcc cttcggccct caatccagcg gaccttcctt cccgcggcct gctgccggct   9840
ctgcggcctc ttccgcgtct tcgccttcgc cctcagacga gtcggatctc cctttgggcc   9900
gcctccccgc atcgataccg tcgacctcga gacctagaaa aacatggagc aatcacaagt   9960
agcaatacag cagctaccaa tgctgattgt gcctggctag aagcacaaga ggaggaggag  10020
gtgggttttc cagtcacacc tcaggtacct ttaagaccaa tgacttacaa ggcagctgta  10080
gatcttagcc actttttaaa agaaaagggg ggactggaag ggctaattca ctcccaacga  10140
agacaagata tccttgatct gtggatctac cacacacaag gctacttccc tgattggcag  10200
aactacacac cagggccagg gatcagatat ccactgacct ttggatggtg ctacaagcta  10260
gtaccagttg agcaagagaa ggtagaagaa gccaatgaag gagagaacac ccgcttgtta  10320
caccctgtga gcctgcatgg gatggatgac ccggagagag aagtattaga gtggaggttt  10380
gacagccgcc tagcatttca tcacatggcc cgagagctgc atccggactg tactgggtct  10440
ctctggttag accagatctg agcctgggag ctctctggct aactagggaa cccactgctt  10500
aagcctcaat aaagcttgcc ttgagtgctt caagtagtgt gtgcccgtct gttgtgtgac  10560
tctggtaact agagatccct cagacccttt tagtcagtgt ggaaaatctc tagcagggcc  10620
cgtttaaacc cgctgatcag cctcgactgt gccttctagt tgccagccat ctgttgtttg  10680
cccctccccc gtgccttcct tgaccctgga aggtgccact cccactgtcc tttcctaata  10740
aaatgaggaa attgcatcgc attgtctgag taggtgtcat tctattctgg ggggtggggt  10800
ggggcaggac agcaaggggg aggattggga agacaatagc aggcatgctg gggatgcggt  10860
```

```
gggctctatg gcttctgagg cggaaagaac cagctggggc tctagggggt atccccacgc  10920
gccctgtagc ggcgcattaa gcgcggcggg tgtggtggtt acgcgcagcg tgaccgctac  10980
acttgccagc gccctagcgc ccgctccttt cgctttcttc ccttcctttc tcgccacgtt  11040
cgccggcttt ccccgtcaag ctctaaatcg ggggctccct ttagggttcc gatttagtgc  11100
tttacggcac ctcgacccca aaaaacttga ttagggtgat ggttcacgta gtgggccatc  11160
gccctgatag acggtttttc gccctttgac gttggagtcc acgttcttta atagtggact  11220
cttgttccaa actggaacaa cactcaaccc tatctcggtc tattcttttg atttataagg  11280
gattttgccg atttcggcct attggttaaa aaatgagctg atttaacaaa aatttaacgc  11340
gaattaattc tgtggaatgt gtgtcagtta gggtgtggaa agtccccagg ctccccagca  11400
ggcagaagta tgcaaagcat gcatctcaat tagtcagcaa ccaggtgtgg aaagtcccca  11460
ggctccccag caggcagaag tatgcaaagc atgcatctca attagtcagc aaccatagtc  11520
ccgcccctaa ctccgcccat cccgccccta actccgccca gttccgccca ttctccgccc  11580
catggctgac taattttttt tatttatgca gaggccgagg ccgcctctgc ctctgagcta  11640
ttccagaagt agtgaggagg cttttttgga ggcctaggct tttgcaaaaa gctcccggga  11700
gcttgtatat ccattttcgg atctgatcag cacgtgttga caattaatca tcggcatagt  11760
atatcggcat agtataatac gacaaggtga ggaactaaac catggccaag ttgaccagtg  11820
ccgttccggt gctcaccgcg cgcgacgtcg ccggagcggt cgagttctgg accgaccggc  11880
tcgggttctc ccgggacttc gtggaggacg acttcgccgg tgtggtccgg gacgacgtga  11940
ccctgttcat cagcgcggtc caggaccagg tggtgccgga caacaccctg gcctgggtgt  12000
gggtgcgcgg cctggacgag ctgtacgccg agtggtcgga ggtcgtgtcc acgaacttcc  12060
gggacgcctc cgggccggcc atgaccgaga tcggcgagca gccgtggggg cgggagttcg  12120
ccctgcgcga cccggccggc aactgcgtgc acttcgtggc cgaggagcag gactgacacg  12180
tgctacgaga tttcgattcc accgccgcct tctatgaaag gttgggcttc ggaatcgttt  12240
tccgggacgc cggctggatg atcctccagc gcggggatct catgctggag ttcttcgccc  12300
accccaactt gtttattgca gcttataatg gttacaaata aagcaatagc atcacaaatt  12360
tcacaaataa agcatttttt tcactgcatt ctagttgtgg tttgtccaaa ctcatcaatg  12420
tatcttatca tgtctgtata ccgtcgacct ctagctagag cttggcgtaa tcatggtcat  12480
agctgtttcc tgtgtgaaat tgttatccgc tcacaattcc acacaacata cgagccggaa  12540
gcataaagtg taaagcctgg ggtgcctaat gagtgagcta actcacatta attgcgttgc  12600
gctcactgcc cgctttccag tcgggaaacc tgtcgtgcca gctgcattaa tgaatcggcc  12660
aacgcgcggg gagaggcggt ttgcgtattg ggcgctcttc cgcttcctcg ctcactgact  12720
cgctgcgctc ggtcgttcgg ctgcggcgag cggtatcagc tcactcaaag gcggtaatac  12780
ggttatccac agaatcaggg gataacgcag gaaagaacat gtgagcaaaa ggccagcaaa  12840
aggccaggaa ccgtaaaaag gccgcgttgc tggcgttttt ccataggctc cgcccccctg  12900
acgagcatca caaaaatcga cgctcaagtc agaggtggcg aaacccgaca ggactataaa  12960
gataccaggc gtttccccct ggaagctccc tcgtgcgctc tcctgttccg accctgccgc  13020
ttaccggata cctgtccgcc tttctccctt cgggaagcgt ggcgctttct catagctcac  13080
gctgtaggta tctcagttcg gtgtaggtcg ttcgctccaa gctgggctgt gtgcacgaac  13140
cccccgttca gcccgaccgc tgcgccttat ccggtaacta tcgtcttgag tccaacccgg  13200
taagacacga cttatcgcca ctggcagcag ccactggtaa caggattagc agagcgaggt  13260
```

```
atgtaggcgg tgctacagag ttcttgaagt ggtggcctaa ctacggctac actagaagaa  13320

cagtatttgg tatctgcgct ctgctgaagc cagttacctt cggaaaaaga gttggtagct  13380

cttgatccgg caaacaaacc accgctggta gcggtggttt ttttgtttgc aagcagcaga  13440

ttacgcgcag aaaaaaagga tctcaagaag atcctttgat cttttctacg gggtctgacg  13500

ctcagtggaa cgaaaactca cgttaaggga ttttggtcat gagattatca aaaaggatct  13560

tcacctagat ccttttaaat taaaaatgaa gttttaaatc aatctaaagt atatatgagt  13620

aaacttggtc tgacagttac caatgcttaa tcagtgaggc acctatctca gcgatctgtc  13680

tatttcgttc atccatagtt gcctgactcc ccgtcgtgta gataactacg atacgggagg  13740

gcttaccatc tggccccagt gctgcaatga taccgcgaga cccacgctca ccggctccag  13800

atttatcagc aataaaccag ccagccggaa gggccgagcg cagaagtggt cctgcaactt  13860

tatccgcctc catccagtct attaattgtt gccgggaagc tagagtaagt agttcgccag  13920

ttaatagttt gcgcaacgtt gttgccattg ctacaggcat cgtggtgtca cgctcgtcgt  13980

ttggtatggc ttcattcagc tccggttccc aacgatcaag gcgagttaca tgatccccca  14040

tgttgtgcaa aaaagcggtt agctccttcg gtcctccgat cgttgtcaga agtaagttgg  14100

ccgcagtgtt atcactcatg gttatggcag cactgcataa ttctcttact gtcatgccat  14160

ccgtaagatg cttttctgtg actggtgagt actcaaccaa gtcattctga gaatagtgta  14220

tgcggcgacc gagttgctct tgcccggcgt caatacggga taataccgcg ccacatagca  14280

gaactttaaa agtgctcatc attggaaaac gttcttcggg gcgaaaactc tcaaggatct  14340

taccgctgtt gagatccagt tcgatgtaac ccactcgtgc acccaactga tcttcagcat  14400

cttttacttt caccagcgtt tctgggtgag caaaaacagg aaggcaaaat gccgcaaaaa  14460

agggaataag ggcgacacgg aaatgttgaa tactcatact cttccttttt caatattatt  14520

gaagcattta tcagggttat tgtctcatga gcggatacat atttgaatgt atttagaaaa  14580

ataaacaaat aggggttccg cgcacatttc cccgaaaagt gccacctgac             14630
```

<210> SEQ ID NO 145
<211> LENGTH: 14819
<212> TYPE: DNA
<213> ORGANISM: Artificial Sequence
<220> FEATURE:
<223> OTHER INFORMATION: Synthetic

<400> SEQUENCE: 145

```
gtcgacggat cgggagatct cccgatcccc tatggtgcac tctcagtaca atctgctctg     60

atgccgcata gttaagccag tatctgctcc ctgcttgtgt gttggaggtc gctgagtagt    120

gcgcgagcaa aatttaagct acaacaaggc aaggcttgac cgacaattgc atgaagaatc    180

tgcttagggt taggcgtttt gcgctgcttc gcgatgtacg ggccagatat acgcgttgac    240

attgattatt gactagttat taatagtaat caattacggg gtcattagtt catagcccat    300

atatggagtt ccgcgttaca taacttacgg taaatggccc gcctggctga ccgcccaacg    360

acccccgccc attgacgtca ataatgacgt atgttcccat agtaacgcca atagggactt    420

tccattgacg tcaatgggtg gagtatttac ggtaaactgc ccacttggca gtacatcaag    480

tgtatcatat gccaagtacg ccccctattg acgtcaatga cggtaaatgg cccgcctggc    540

attatgccca gtacatgacc ttatgggact ttcctacttg gcagtacatc tacgtattag    600

tcatcgctat taccatggtg atgcggtttt ggcagtacat caatgggcgt ggatagcggt    660
```

```
ttgactcacg gggatttcca agtctccacc ccattgacgt caatgggagt ttgttttggc    720
accaaaatca acgggacttt ccaaaatgtc gtaacaactc cgccccattg acgcaaatgg    780
gcggtaggcg tgtacggtgg gaggtctata taagcagcgc gttttgcctg tactgggtct    840
ctctggttag accagatctg agcctgggag ctctctggct aactagggaa cccactgctt    900
aagcctcaat aaagcttgcc ttgagtgctt caagtagtgt gtgcccgtct gttgtgtgac    960
tctggtaact agagatccct cagacccttt tagtcagtgt ggaaaatctc tagcagtggc   1020
gcccgaacag ggacttgaaa gcgaaaggga aaccagagga gctctctcga cgcaggactc   1080
ggcttgctga agcgcgcacg gcaagaggcg aggggcggcg actggtgagt acgccaaaaa   1140
ttttgactag cggaggctag aaggagagag atgggtgcga gagcgtcagt attaagcggg   1200
ggagaattag atcgcgatgg gaaaaaattc ggttaaggcc agggggaaag aaaaaatata   1260
aattaaaaca tatagtatgg gcaagcaggg agctagaacg attcgcagtt aatcctggcc   1320
tgttagaaac atcagaaggc tgtagacaaa tactgggaca gctacaacca tcccttcaga   1380
caggatcaga agaacttaga tcattatata atacagtagc aaccctctat tgtgtgcatc   1440
aaaggataga gataaaagac accaaggaag ctttagacaa gatagaggaa gagcaaaaca   1500
aaagtaagac caccgcacag caagcggccg ctgatcttca gacctggagg aggagatatg   1560
agggacaatt ggagaagtga attatataaa tataaagtag taaaaattga accattagga   1620
gtagcaccca ccaaggcaaa gagaagagtg gtgcagagag aaaaaagagc agtgggaata   1680
ggagctttgt tccttgggtt cttgggagca gcaggaagca ctatgggcgc agcgtcaatg   1740
acgctgacgg tacaggccag acaattattg tctggtatag tgcagcagca gaacaatttg   1800
ctgagggcta ttgaggcgca acagcatctg ttgcaactca cagtctgggg catcaagcag   1860
ctccaggcaa gaatcctggc tgtggaaaga tacctaaagg atcaacagct cctggggatt   1920
tggggttgct ctggaaaact catttgcacc actgctgtgc cttggaatgc tagttggagt   1980
aataaatctc tggaacagat ttggaatcac acgacctgga tggagtggga cagagaaatt   2040
aacaattaca caagcttaat acactcctta attgaagaat cgcaaaacca gcaagaaaag   2100
aatgaacaag aattattgga attagataaa tgggcaagtt tgtggaattg gtttaacata   2160
acaaattggc tgtggtatat aaaattattc ataatgatag taggaggctt ggtaggttta   2220
agaatagttt ttgctgtact ttctatagtg aatagagtta ggcagggata ttcaccatta   2280
tcgtttcaga cccacctccc aaccccgagg ggacccgaca ggcccgaagg aatagaagaa   2340
gaaggtggag agagagacag agacagatcc attcgattag tgaacggatc ggcactgcgt   2400
gcgccaattc tgcagacaaa tggcagtatt catccacaat tttaaaagaa aaggggggat   2460
tggggggtac agtgcagggg aaagaatagt agacataata gcaacagaca tacaaactaa   2520
agaattacaa aaacaaatta caaaaattca aaattttcgg gtttattaca gggacagcag   2580
agatccagtt tggttaatta atgcaaagat ggataaagtt ttaaacagag aggaatcttt   2640
gcagctaatg gaccttctag gtcttgaaag gagtgggaat tggctccggt gcccgtcagt   2700
gggcagagcg cacatcgccc acagtccccg agaagttggg gggaggggtc ggcaattgaa   2760
ccggtgccta gagaaggtgg cgcggggtaa actgggaaag tgatgtcgtg tactggctcc   2820
gcctttttcc cgagggtggg ggagaaccgt atataagtgc agtagtcgcc gtgaacgttc   2880
tttttcgcaa cgggtttgcc gccagaacac aggtaagtgc cgtgtgtggt tcccgcgggc   2940
ctggcctctt tacgggttat ggcccttgcg tgccttgaat tacttccact ggctgcagta   3000
cgtgattctt gatcccgagc ttcgggttgg aagtgggtgg gagagttcga ggccttgcgc   3060
```

```
ttaaggagcc ccttcgcctc gtgcttgagt tgaggcctgg cctgggcgct ggggccgccg   3120
cgtgcgaatc tggtggcacc ttcgcgcctg tctcgctgct ttcgataagt ctctagccat   3180
ttaaaatttt tgatgacctg ctgcgacgct ttttttctgg caagatagtc ttgtaaatgc   3240
gggccaagat ctgcacactg gtatttcggt ttttggggcc gcgggcggcg acggggcccg   3300
tgcgtcccag cgcacatgtt cggcgaggcg gggcctgcga gcgcggccac cgagaatcgg   3360
acgggggtag tctcaagctg gccggcctgc tctggtgcct ggcctcgcgc cgccgtgtat   3420
cgccccgccc tgggcggcaa ggctggcccg gtcggcacca gttgcgtgag cggaaagatg   3480
gccgcttccc ggccctgctg cagggagctc aaaatggagg acgcggcgct cgggagagcg   3540
ggcgggtgag tcacccacac aaaggaaaag ggcctttccg tcctcagccg tcgcttcatg   3600
tgactccacg gagtaccggg cgccgtccag gcacctcgat tagttctcga gcttttggag   3660
tacgtcgtct ttaggttggg gggaggggtt ttatgcgatg gagtttcccc acactgagtg   3720
ggtggagact gaagttaggc cagcttggca cttgatgtaa ttctccttgg aatttgccct   3780
ttttgagttt ggatcttggt tcattctcaa gcctcagaca gtggttcaaa gtttttttct   3840
tccatttcag gtgtcgtgac gtacggccac catgagcccc aagaagaaga gaaaggtgga   3900
ggccagcgac aagaagtaca gcatcggcct ggccatcggc accaactctg tgggctgggc   3960
cgtgatcacc gacgagtaca aggtgcccag caagaaattc aaggtgctgg gcaacaccga   4020
ccggcacagc atcaagaaga acctgatcgg agccctgctg ttcgacagcg gcgaaacagc   4080
cgaggccacc cggctgaaga gaaccgccag aagaagatac accagacgga agaaccggat   4140
ctgctatctg caagagatct tcagcaacga gatggccaag gtggacgaca gcttcttcca   4200
cagactggaa gagtccttcc tggtggaaga ggataagaag cacgagcggc accccatctt   4260
cggcaacatc gtggacgagg tggcctacca cgagaagtac cccaccatct accacctgag   4320
aaagaaactg gtggacagca ccgacaaggc cgacctgcgg ctgatctatc tggccctggc   4380
ccacatgatc aagttccggg gccacttcct gatcgagggc gacctgaacc ccgacaacag   4440
cgacgtggac aagctgttca tccagctggt gcagacctac aaccagctgt tcgaggaaaa   4500
ccccatcaac gccagcggcg tggacgccaa ggccatcctg tctgccagac tgagcaagag   4560
cagacggctg gaaaatctga tcgcccagct gcccggcgag aagaagaatg gcctgttcgg   4620
caacctgatt gccctgagcc tgggcctgac ccccaacttc aagagcaact tcgacctggc   4680
cgaggatgcc aaactgcagc tgagcaagga cacctacgac gacgacctgg acaacctgct   4740
ggcccagatc ggcgaccagt acgccgacct gtttctggcc gccaagaacc tgtccgacgc   4800
catcctgctg agcgacatcc tgagagtgaa caccgagatc accaaggccc ccctgagcgc   4860
ctctatgatc aagagatacg acgagcacca ccaggacctg accctgctga aagctctcgt   4920
gcggcagcag ctgcctgaga agtacaaaga gattttcttc gaccagagca agaacggcta   4980
cgccggctac attgacggcg gagccagcca ggaagagttc tacaagttca tcaagcccat   5040
cctggaaaag atggacggca ccgaggaact gctcgtgaag ctgaacagag aggacctgct   5100
gcggaagcag cggaccttcg acaacggcag catcccccac cagatccacc tgggagagct   5160
gcacgccatt ctgcggcggc aggaagattt ttacccattc ctgaaggaca accgggaaaa   5220
gatcgagaag atcctgacct tccgcatccc ctactacgtg ggccctctgg ccaggggaaa   5280
cagcagattc gcctggatga ccagaaagag cgaggaaacc atcaccccct ggaacttcga   5340
ggaagtggtg gacaagggcg cttccgccca gagcttcatc gagcggatga ccaacttcga   5400
```

-continued

```
taagaacctg cccaacgaga aggtgctgcc caagcacagc ctgctgtacg agtacttcac   5460
cgtgtataac gagctgacca aagtgaaata cgtgaccgag ggaatgagaa agcccgcctt   5520
cctgagcggc gagcagaaaa aggccatcgt ggacctgctg ttcaagacca accggaaagt   5580
gaccgtgaag cagctgaaag aggactactt caagaaaatc gagtgcttcg actccgtgga   5640
aatctccggc gtggaagatc ggttcaacgc ctccctgggc acataccacg atctgctgaa   5700
aattatcaag gacaaggact tcctggacaa tgaggaaaac gaggacattc tggaagatat   5760
cgtgctgacc ctgacactgt ttgaggacag agagatgatc gaggaacggc tgaaaaccta   5820
tgcccacctg ttcgacgaca aagtgatgaa gcagctgaag cggcggagat acaccggctg   5880
gggcaggctg agccggaagc tgatcaacgg catccgggac aagcagtccg gcaagacaat   5940
cctggatttc ctgaagtccg acggcttcgc caacagaaac ttcatgcagc tgatccacga   6000
cgacagcctg acctttaaag aggacatcca gaaagcccag gtgtccggcc agggcgatag   6060
cctgcacgag cacattgcca atctggccgg cagccccgcc attaagaagg gcatcctgca   6120
gacagtgaag gtggtggacg agctcgtgaa agtgatgggc cggcacaagc ccgagaacat   6180
cgtgatcgaa atggccagag agaaccagac cacccagaag ggacagaaga acagccgcga   6240
gagaatgaag cggatcgaag agggcatcaa agagctgggc agccagatcc tgaaagaaca   6300
ccccgtggaa aacacccagc tgcagaacga gaagctgtac ctgtactacc tgcagaatgg   6360
gcgggatatg tacgtggacc aggaactgga catcaaccgg ctgtccgact acgatgtgga   6420
cgctatcgtg cctcagagct ttctgaagga cgactccatc gacaacaagg tgctgaccag   6480
aagcgacaag aaccggggca agagcgacaa cgtgccctcc gaagaggtcg tgaagaagat   6540
gaagaactac tggcggcagc tgctgaacgc caagctgatt acccagagaa agttcgacaa   6600
tctgaccaag gccgagagag gcggcctgag cgaactggat aaggccggct tcatcaagag   6660
acagctggtg gaaacccggc agatcacaaa gcacgtggca cagatcctgg actcccggat   6720
gaacactaag tacgacgaga atgacaagct gatccgggaa gtgaaagtga tcaccctgaa   6780
gtccaagctg gtgtccgatt tccggaagga tttccagttt tacaaagtgc gcgagatcaa   6840
caactaccac cacgcccacg acgcctacct gaacgccgtc gtgggaaccg ccctgatcaa   6900
aaagtaccct aagctggaaa gcgagttcgt gtacggcgac tacaaggtgt acgacgtgcg   6960
gaagatgatc gccaagagcg agcaggaaat cggcaaggct accgccaagt acttcttcta   7020
cagcaacatc atgaactttt tcaagaccga gattaccctg gccaacggcg agatccggaa   7080
gcggcctctg atcgagacaa acggcgaaac cggggagatc gtgtgggata agggccggga   7140
ttttgccacc gtgcggaaag tgctgagcat gccccaagtg aatatcgtga aaaagaccga   7200
ggtgcagaca ggcggcttca gcaaagagtc tatcctgccc aagaggaaca gcgataagct   7260
gatcgccaga aagaaggact gggaccctaa gaagtacggc ggcttcgaca gccccaccgt   7320
ggcctattct gtgctggtgg tggccaaagt ggaaaagggc aagtccaaga aactgaagag   7380
tgtgaaagag ctgctgggga tcaccatcat ggaaagaagc agcttcgaga agaatcccat   7440
cgactttctg gaagccaagg gctacaaaga agtgaaaaag gacctgatca tcaagctgcc   7500
taagtactcc ctgttcgagc tggaaaacgg ccggaagaga atgctggcct ctgccggcga   7560
actgcagaag ggaaacgaac tggccctgcc ctccaaatat gtgaacttcc tgtacctggc   7620
cagccactat gagaagctga agggctcccc cgaggataat gagcagaaac agctgtttgt   7680
ggaacagcac aagcactacc tggacgagat catcgagcag atcagcgagt tctccaagag   7740
agtgatcctg gccgacgcta atctggacaa agtgctgtcc gcctacaaca agcaccggga   7800
```

```
taagcccatc agagagcagg ccgagaatat catccacctg tttaccctga ccaatctggg   7860
agcccctgcc gccttcaagt actttgacac caccatcgac cggaagaggt acaccagcac   7920
caaagaggtg ctggacgcca ccctgatcca ccagagcatc accggcctgt acgagacacg   7980
gatcgacctg tctcagctgg gaggcgacag cgctggagga ggtggaagcg gaggaggagg   8040
aagcggagga ggaggtagcg gacctaagaa aaagaggaag gtggcggccg ctgctggaga   8100
ctggagcagg gacctgctgc tgccatcgga ctgagtctgg tgatcggaat cgtgatggcc   8160
gaggtgctga gaaagctggg agccgacaag gtgagagtga agtggcctaa tgacctgtac   8220
ctccaggacc gcaagctggc tggcatcctg gtggagctga caggcaagac aggcgatgcc   8280
gctcagatcg tgatcggagc cggaatcaac atggccatga gaagagtgga ggagagcgtg   8340
gtgaaccagg gctggatcac cctgcaggag gctggcatca acctggaccg gaacaccctg   8400
gccgccatgc tgatcagaga gctgagagcc gctctggagc tgttcgagca ggagggactg   8460
gctccttacc tgagcagatg ggagaagctg gacaacttca tcaacagacc tgtgaagctg   8520
atcatcggcg acaaggaaat cttcggcatc tccagaggaa tcgacaagca gggagctctg   8580
ctgctggagc aggacggaat catcaagccc tggatgggcg gagaaatctc cctgagaagc   8640
gcagagaagg cttaccctta cgatgtaccg gattacgcat aggcggcctt aagttgctag   8700
cctagcggca gtggagaggg cagaggaagt ctgctaacat gcggtgacgt cgaggagaat   8760
cctggcccag tgagcaaggg cgaggagctg ttcaccgggg tggtgcccat cctggtcgag   8820
ctggacggcg acgtaaacgg ccacaagttc agcgtgtccg gcgagggcga gggcgatgcc   8880
acctacggca agctgaccct gaagttcatc tgcaccaccg gcaagctgcc cgtgccctgg   8940
cccaccctcg tgaccaccct gacctacggc gtgcagtgct tcagccgcta ccccgaccac   9000
atgaagcagc acgacttctt caagtccgcc atgcccgaag gctacgtcca ggagcgcacc   9060
atcttcttca aggacgacgg caactacaag acccgcgccg aggtgaagtt cgagggcgac   9120
accctggtga accgcatcga gctgaagggc atcgacttca aggaggacgg caacatcctg   9180
gggcacaagc tggagtacaa ctacaacagc cacaacgtct atatcatggc cgacaagcag   9240
aagaacggca tcaaggtgaa cttcaagatc cgccacaaca tcgaggacgg cagcgtgcag   9300
ctcgccgacc actaccagca gaacaccccc atcggcgacg gccccgtgct gctgcccgac   9360
aaccactacc tgagcaccca gtccgccctg agcaaagacc ccaacgagaa gcgcgatcac   9420
atggtcctgc tggagttcgt gaccgccgcc gggatcactc tcggcatgga cgagctgtac   9480
aagtaagaat tcgatatcaa gcttatcgat aatcaacctc tggattacaa aatttgtgaa   9540
agattgactg gtattcttaa ctatgttgct ccttttacgc tatgtggata cgctgcttta   9600
atgcctttgt atcatgctat tgcttcccgt atggctttca ttttctcctc cttgtataaa   9660
tcctggttgc tgtctcttta tgaggagttg tggcccgttg tcaggcaacg tggcgtggtg   9720
tgcactgtgt ttgctgacgc aacccccact ggttggggca ttgccaccac ctgtcagctc   9780
ctttccggga ctttcgcttt ccccctccct attgccacgg cggaactcat cgccgcctgc   9840
cttgcccgct gctggacagg ggctcggctg ttgggcactg acaattccgt ggtgttgtcg   9900
gggaaatcat cgtcctttcc ttggctgctc gcctgtgttg ccacctggat tctgcgcggg   9960
acgtccttct gctacgtccc ttcggccctc aatccagcgg accttccttc ccgcggcctg  10020
ctgccggctc tgcggcctct tccgcgtctt cgccttcgcc ctcagacgag tcggatctcc  10080
ctttgggccg cctccccgca tcgataccgt cgacctcgag acctagaaaa acatggagca  10140
```

```
atcacaagta gcaatacagc agctaccaat gctgattgtg cctggctaga agcacaagag  10200
gaggaggagg tgggttttcc agtcacacct caggtacctt taagaccaat gacttacaag  10260
gcagctgtag atcttagcca ctttttaaaa gaaaaggggg gactggaagg gctaattcac  10320
tcccaacgaa gacaagatat ccttgatctg tggatctacc acacacaagg ctacttccct  10380
gattggcaga actacacacc agggccaggg atcagatatc cactgacctt tggatggtgc  10440
tacaagctag taccagttga gcaagagaag gtagaagaag ccaatgaagg agagaacacc  10500
cgcttgttac accctgtgag cctgcatggg atggatgacc cggagagaga agtattagag  10560
tggaggtttg acagccgcct agcatttcat cacatggccc gagagctgca tccggactgt  10620
actgggtctc tctggttaga ccagatctga gcctgggagc tctctggcta actagggaac  10680
ccactgctta agcctcaata aagcttgcct tgagtgcttc aagtagtgtg tgcccgtctg  10740
ttgtgtgact ctggtaacta gagatccctc agaccctttt agtcagtgtg gaaaatctct  10800
agcagggccc gtttaaaccc gctgatcagc ctcgactgtg ccttctagtt gccagccatc  10860
tgttgtttgc ccctcccccg tgccttcctt gaccctggaa ggtgccactc ccactgtcct  10920
ttcctaataa aatgaggaaa ttgcatcgca ttgtctgagt aggtgtcatt ctattctggg  10980
gggtggggtg gggcaggaca gcaaggggga ggattgggaa gacaatagca ggcatgctgg  11040
ggatgcggtg ggctctatgg cttctgaggc ggaaagaacc agctggggct ctagggggta  11100
tccccacgcg ccctgtagcg gcgcattaag cgcggcgggt gtggtggtta cgcgcagcgt  11160
gaccgctaca cttgccagcg ccctagcgcc cgctcctttc gctttcttcc cttcctttct  11220
cgccacgttc gccggctttc cccgtcaagc tctaaatcgg gggctccctt tagggttccg  11280
atttagtgct ttacggcacc tcgaccccaa aaaacttgat tagggtgatg gttcacgtag  11340
tgggccatcg ccctgataga cggtttttcg ccctttgacg ttggagtcca cgttctttaa  11400
tagtggactc ttgttccaaa ctggaacaac actcaaccct atctcggtct attcttttga  11460
tttataaggg attttgccga tttcggccta ttggttaaaa aatgagctga tttaacaaaa  11520
atttaacgcg aattaattct gtggaatgtg tgtcagttag ggtgtggaaa gtccccaggc  11580
tccccagcag gcagaagtat gcaaagcatg catctcaatt agtcagcaac caggtgtgga  11640
aagtccccag gctccccagc aggcagaagt atgcaaagca tgcatctcaa ttagtcagca  11700
accatagtcc cgcccctaac tccgcccatc ccgcccctaa ctccgcccag ttccgcccat  11760
tctccgcccc atggctgact aatttttttt atttatgcag aggccgaggc cgcctctgcc  11820
tctgagctat tccagaagta gtgaggaggc ttttttggag gcctaggctt ttgcaaaaag  11880
ctcccgggag cttgtatatc cattttcgga tctgatcagc acgtgttgac aattaatcat  11940
cggcatagta tatcggcata gtataatacg acaaggtgag gaactaaacc atggccaagt  12000
tgaccagtgc cgttccggtg ctcaccgcgc gcgacgtcgc cggagcggtc gagttctgga  12060
ccgaccggct cgggttctcc cgggacttcg tggaggacga cttcgccggt gtggtccggg  12120
acgacgtgac cctgttcatc agcgcggtcc aggaccaggt ggtgccggac aacaccctgg  12180
cctgggtgtg ggtgcgcggc ctggacgagc tgtacgccga gtggtcggag gtcgtgtcca  12240
cgaacttccg ggacgcctcc gggccggcca tgaccgagat cggcgagcag ccgtgggggc  12300
gggagttcgc cctgcgcgac ccggccggca actgcgtgca cttcgtggcc gaggagcagg  12360
actgacacgt gctacgagat ttcgattcca ccgccgcctt ctatgaaagg ttgggcttcg  12420
gaatcgtttt ccgggacgcc ggctggatga tcctccagcg cggggatctc atgctggagt  12480
tcttcgccca ccccaacttg tttattgcag cttataatgg ttacaaataa agcaatagca  12540
```

```
tcacaaattt cacaaataaa gcattttttt cactgcattc tagttgtggt ttgtccaaac  12600
tcatcaatgt atcttatcat gtctgtatac cgtcgacctc tagctagagc ttggcgtaat  12660
catggtcata gctgtttcct gtgtgaaatt gttatccgct cacaattcca cacaacatac  12720
gagccggaag cataaagtgt aaagcctggg gtgcctaatg agtgagctaa ctcacattaa  12780
ttgcgttgcg ctcactgccc gctttccagt cgggaaacct gtcgtgccag ctgcattaat  12840
gaatcggcca acgcgcgggg agaggcggtt tgcgtattgg gcgctcttcc gcttcctcgc  12900
tcactgactc gctgcgctcg gtcgttcggc tgcggcgagc ggtatcagct cactcaaagg  12960
cggtaatacg gttatccaca gaatcagggg ataacgcagg aaagaacatg tgagcaaaag  13020
gccagcaaaa ggccaggaac cgtaaaaagg ccgcgttgct ggcgtttttc cataggctcc  13080
gcccccctga cgagcatcac aaaaatcgac gctcaagtca gaggtggcga aacccgacag  13140
gactataaag ataccaggcg tttccccctg gaagctccct cgtgcgctct cctgttccga  13200
ccctgccgct taccggatac ctgtccgcct ttctcccttc gggaagcgtg gcgctttctc  13260
atagctcacg ctgtaggtat ctcagttcgg tgtaggtcgt tcgctccaag ctgggctgtg  13320
tgcacgaacc ccccgttcag cccgaccgct gcgccttatc cggtaactat cgtcttgagt  13380
ccaacccggt aagacacgac ttatcgccac tggcagcagc cactggtaac aggattagca  13440
gagcgaggta tgtaggcggt gctacagagt tcttgaagtg gtggcctaac tacggctaca  13500
ctagaagaac agtatttggt atctgcgctc tgctgaagcc agttaccttc ggaaaaagag  13560
ttggtagctc ttgatccggc aaacaaacca ccgctggtag cggtggtttt tttgtttgca  13620
agcagcagat tacgcgcaga aaaaaaggat ctcaagaaga tcctttgatc ttttctacgg  13680
ggtctgacgc tcagtggaac gaaaactcac gttaagggat tttggtcatg agattatcaa  13740
aaaggatctt cacctagatc cttttaaatt aaaaatgaag ttttaaatca atctaaagta  13800
tatatgagta aacttggtct gacagttacc aatgcttaat cagtgaggca cctatctcag  13860
cgatctgtct atttcgttca tccatagttg cctgactccc cgtcgtgtag ataactacga  13920
tacgggaggg cttaccatct ggccccagtg ctgcaatgat accgcgagac ccacgctcac  13980
cggctccaga tttatcagca ataaaccagc cagccggaag ggccgagcgc agaagtggtc  14040
ctgcaacttt atccgcctcc atccagtcta ttaattgttg ccgggaagct agagtaagta  14100
gttcgccagt taatagtttg cgcaacgttg ttgccattgc tacaggcatc gtggtgtcac  14160
gctcgtcgtt tggtatggct tcattcagct ccggttccca acgatcaagg cgagttacat  14220
gatcccccat gttgtgcaaa aaagcggtta gctccttcgg tcctccgatc gttgtcagaa  14280
gtaagttggc cgcagtgtta tcactcatgg ttatggcagc actgcataat tctcttactg  14340
tcatgccatc cgtaagatgc ttttctgtga ctggtgagta ctcaaccaag tcattctgag  14400
aatagtgtat gcggcgaccg agttgctctt gcccggcgtc aatacgggat aataccgcgc  14460
cacatagcag aactttaaaa gtgctcatca ttggaaaacg ttcttcgggg cgaaaactct  14520
caaggatctt accgctgttg agatccagtt cgatgtaacc cactcgtgca cccaactgat  14580
cttcagcatc ttttactttc accagcgttt ctgggtgagc aaaaacagga aggcaaaatg  14640
ccgcaaaaaa gggaataagg gcgacacgga aatgttgaat actcatactc ttcctttttc  14700
aatattattg aagcatttat cagggttatt gtctcatgag cggatacata tttgaatgta  14760
tttagaaaaa taaacaaata ggggttccgc gcacatttcc ccgaaaagtg ccacctgac   14819
```

<210> SEQ ID NO 146

<211> LENGTH: 9747
<212> TYPE: DNA
<213> ORGANISM: Artificial Sequence
<220> FEATURE:
<223> OTHER INFORMATION: Synthetic

<400> SEQUENCE: 146

```
ctcatgacca aaatccctta acgtgagtta cgcgcgcgtc gttccactga gcgtcagacc     60
ccgtagaaaa gatcaaagga tcttcttgag atcctttttt tctgcgcgta atctgctgct    120
tgcaaacaaa aaaaccaccg ctaccagcgg tggtttgttt gccggatcaa gagctaccaa    180
ctctttttcc gaaggtaact ggcttcagca gagcgcagat accaaatact gttcttctag    240
tgtagccgta gttagcccac cacttcaaga actctgtagc accgcctaca tacctcgctc    300
tgctaatcct gttaccagtg gctgctgcca gtggcgataa gtcgtgtctt accgggttgg    360
actcaagacg atagttaccg gataaggcgc agcggtcggg ctgaacgggg ggttcgtgca    420
cacagcccag cttggagcga acgacctaca ccgaactgag atacctacag cgtgagctat    480
gagaaagcgc cacgcttccc gaagggagaa aggcggacag gtatccggta agcggcaggg    540
tcggaacagg agagcgcacg agggagcttc caggggggaaa cgcctggtat ctttatagtc    600
ctgtcgggtt tcgccacctc tgacttgagc gtcgattttt gtgatgctcg tcaggggggc    660
ggagcctatg gaaaaacgcc agcaacgcgg cctttttacg gttcctggcc ttttgctggc    720
cttttgctca catgttcttt cctgcgttat cccctgattc tgtggataac cgtattaccg    780
cctttgagtg agctgatacc gctcgccgca gccgaacgac cgagcgcagc gagtcagtga    840
gcgaggaagc ggaaggcgag agtagggaac tgccaggcat caaactaagc agaaggcccc    900
tgacggatgg cctttttgcg tttctacaaa ctctttctgt gttgtaaaac gacggccagt    960
cttaagctcg ggccccctgg gcggttctga taacgagtaa tcgttaatcc gcaaataacg   1020
taaaaacccg cttcggcggg tttttttatg gggggagttt agggaaagag catttgtcag   1080
aatatttaag ggcgcctgtc actttgcttg atatatgaga attatttaac cttataaatg   1140
agaaaaaagc aacgcacttt aaataagata cgttgctttt tcgattgatg aacacctata   1200
attaaactat tcatctatta tttatgattt tttgtatata caatatttct agtttgttaa   1260
agagaattaa gaaaataaat ctcgaaaata ataaagggaa aatcagtttt tgatatcaaa   1320
attatacatg tcaacgataa tacaaaatat aatacaaact ataagatgtt atcagtattt   1380
attatcattt agaataaatt ttgtgtcgcc cttaattgtg agcggataac aattacgagc   1440
ttcatgcaca gtggcgttga cattgattat tgactagtta ttaatagtaa tcaattacgg   1500
ggtcattagt tcatagccca tatatggagt tccgcgttac ataacttacg gtaaatggcc   1560
cgcctggctg accgcccaac gacccccgcc cattgacgtc aataatgacg tatgttccca   1620
tagtaacgcc aatagggact ttccattgac gtcaatgggt ggagtattta cggtaaactg   1680
cccacttggc agtacatcaa gtgtatcata tgccaagtac gccccctatt gacgtcaatg   1740
acggtaaatg gcccgcctgg cattatgccc agtacatgac cttatgggac tttcctactt   1800
ggcagtacat ctacgtatta gtcatcgcta ttaccatggt gatgcggttt tggcagtaca   1860
tcaatgggcg tggatagcgg tttgactcac ggggatttcc aagtctccac cccattgacg   1920
tcaatgggag tttgttttgg caccaaaatc aacgggactt tccaaaatgt cgtaacaact   1980
ccgccccatt gacgcaaatg ggcggtaggc gtgtacggtg ggaggtctat ataagcagag   2040
ctctctggct aactagagaa cccactgctt actggcttat cgaaattaat acgactcact   2100
atagggggcgt acggccacca tgtcgcggac ccggctccct tccccacccg cacccagccc   2160
```

```
agcgttttcg gccgactcgt tctcagacct gcttaggcag ttcgacccct cactgtttaa   2220
cacatcgttg ttcgactccc ttcctccgtt tggggcgcac catacggagg cggccaccgg   2280
ggagtgggat gaggtgcagt cgggattgag agctgcggat gcaccacccc caaccatgcg   2340
ggtggccgtc accgctgccc gaccgccgag ggcgaagccc gcaccaaggc ggagggcagc   2400
gcaaccgtcc gacgcaagcc ccgcagcgca agtagatttg agaactttgg gatattcaca   2460
gcagcagcag gaaaagatca agcccaaagt gaggtcgaca gtcgcgcagc atcacgaagc   2520
gctggtgggt catgggttta cacatgccca catcgtagcc ttgtcgcagc accctgcagc   2580
ccttggcacg gtcgccgtca agtaccagga catgattgcg gcgttgccgg aagccacaca   2640
tgaggcgatc gtcggtgtgg ggaaacagtg gagcggagcc cgagcgcttg aggccctgtt   2700
gacggtcgcg ggagagctga gagggcctcc ccttcagctg gacacgggcc agttgctgaa   2760
gatcgcgaag cggggaggag tcacggcggt cgaggcggtg cacgcgtggc gcaatgcgct   2820
cacgggagca cccctcaacc tgacagagac cgcggccgca ttaggcaccc caggctttac   2880
actttatgct tccggctcgt ataatgtgtg gattttgagt taggatccgt cgagattttc   2940
aggagctaag gaagctaaaa tggagaaaaa aatcactgga tataccaccg ttgatatatc   3000
ccaatggcat cgtaaagaac attttgaggc atttcagtca gttgctcaat gtacctataa   3060
ccagaccgtt cagctggata ttacggcctt tttaaagacc gtaaagaaaa ataagcacaa   3120
gttttatccg gcctttattc acattcttgc ccgcctgatg aatgctcatc cggaattccg   3180
tatggcaatg aaagacggtg agctggtgat atgggatagt gttcaccctt gttacaccgt   3240
tttccatgag caaactgaaa cgttttcatc gctctggagt gaataccacg acgatttccg   3300
gcagtttcta cacatatatt cgcaagatgt ggcgtgttac ggtgaaaacc tggcctattt   3360
ccctaaaggg tttattgaga atatgttttt cgtctcagcc aatccctggg tgagtttcac   3420
cagttttgat ttaaacgtgg ccaatatgga caacttcttc gcccccgttt tcaccatggg   3480
caaatattat acgcaaggcg acaaggtgct gatgccgctg gcgattcagg ttcatcatgc   3540
cgtttgtgat ggcttccatg tcggcagaat gcttaatgaa ttacaacagt actgcgatga   3600
gtggcagggc ggggcgtaaa gatctggatc cggcttacta aaagccagat aacagtatgc   3660
gtatttgcgc gctgattttt gcggtataag aatatatact gatatgtata cccgaagtat   3720
gtcaaaaaga ggtatgctat gaagcagcgt attacagtga cagttgacag cgacagctat   3780
cagttgctca aggcatatat gatgtcaata tctccggtct ggtaagcaca accatgcaga   3840
atgaagcccg tcgtctgcgt gccgaacgct ggaaagcgga aaatcaggaa gggatggctg   3900
aggtcgcccg gtttattgaa atgaacggct cttttgctga cgagaacagg ggctggtgaa   3960
atgcagttta aggtttacac ctataaaaga gagagccgtt atcgtctgtt tgtggatgta   4020
cagagtgata ttattgacac gcccgggcga cggatggtga tccccctggc cagtgcacgt   4080
ctgctgtcag ataaagtctc ccgtgaactt tacccggtgg tgcatatcgg ggatgaaagc   4140
tggcgcatga tgaccaccga tatggccagt gtgccggtct ccgttatcgg ggaagaagtg   4200
gctgatctca gccaccgcga aaatgacatc aaaaacgcca ttaacctgat gttctgggga   4260
atataaatgt caggctccct tatacacagc cagtctgcag gtcgacggtc tcgactcacg   4320
cctgagcagg tagtggctat tgcatccaat atcgggggca gacccgcact ggagtcaatc   4380
gtggcccagc tttcgaggcc ggaccccgcg ctggccgcac tcactaatga tcatcttgta   4440
gcgctggcct gcctcggcgg acgacccgcc ttggatgcgg tgaagaaggg gctcccgcac   4500
```

```
gcgcctgcat tgattaagcg gaccaacaga aggattcccg agaggacatc acatcgagtg   4560
gcagatcacg cgcaagtggt ccgcgtgctc ggattcttcc agtgtcactc ccaccccgca   4620
caagcgttcg atgacgccat gactcaattt ggtatgtcga gacacggact gctgcagctc   4680
tttcgtagag tcggtgtcac agaactcgag gcccgctcgg gcacactgcc tcccgcctcc   4740
cagcggtggg acaggattct ccaagcgagc ggtatgaaac gcgcgaagcc ttcacctacg   4800
tcaactcaga cacctgacca ggcgagcctt catgcgttcg cagactcgct ggagagggat   4860
ttggacgcgc cctcgcccat gcatgaaggg gaccaaactc gcgcgtcagc tagccccaag   4920
aagaagagaa aggtggaggc cagcgatcca aggacaacac cgtgcccctg aagctgatcg   4980
ccctgctggc caacggcgag ttccactctg gcgagcagct gggagagacc ctgggaatga   5040
gcagagccgc catcaacaag cacatccaga cactgagaga ctggggagtg gacgtgttca   5100
ccgtgcctgg caagggctac agcctgcctg agcctatcca gctgctgaac gccaagcaga   5160
tcctgggaca gctggatggc ggaagcgtgg ccgtgctgcc tgtgatcgac tccaccaatc   5220
agtacctgct ggacagaatc ggagagctga agtccggcga cgcctgcatc gccgagtacc   5280
agcaggctgg cagaggaggc agaggccaga ttacgctcgg aagtggttca gcccattcgg   5340
agccaacctg tacctgtcca tgttctggag actggagcag ggacctgctg ctgccatcgg   5400
actgagtctg gtgatcggaa tcgtgatggc cgaggtgctg agaaagctgg gagccgacaa   5460
ggtgagagtg aagtggccta atgacctgta cctccaggac cgcaagctgg ctggcatcct   5520
ggtggagctg acaggcaaga caggcgatgc cgctcagatc gtgatcggag ccggaatcaa   5580
catggccatg agaagagtgg aggagagcgt ggtgaaccag ggctggatca ccctgcagga   5640
ggctggcatc aacctggacc ggaacaccct ggccgccatg ctgatcagag agctgagagc   5700
cgctctggag ctgttcgagc aggagggact ggctccttac ctgagcagat gggagaagct   5760
ggacaacttc atcaacagac ctgtgaagct gatcatcggc gacaaggaaa tcttcggcat   5820
ctccagagga atcgacaagc agggagctct gctgctggag caggacggaa tcatcaagcc   5880
ctggatgggc ggagaaatct ccctgagaag cgcagagaag gcttaccctt acgatgtacc   5940
ggattacgca taggcggcct taagttgggc agtggagagg gcagaggaag tctgctaaca   6000
tgcggtgacg tcgaggagaa tcctggccca gtgagcaagg gcgaggagct gttcaccggg   6060
gtggtgccca tcctggtcga gctggacggc gacgtaaacg gccacaagtt cagcgtgtcc   6120
ggcgagggcg agggcgatgc cacctacggc aagctgaccc tgaagttcat ctgcaccacc   6180
ggcaagctgc ccgtgccctg gcccaccctc gtgaccaccc tgacctacgg cgtgcagtgc   6240
ttcagccgct accccgacca catgaagcag cacgacttct tcaagtccgc catgcccgaa   6300
ggctacgtcc aggagcgcac catcttcttc aaggacgacg gcaactacaa gacccgcgcc   6360
gaggtgaagt tcgagggcga caccctggtg aaccgcatcg agctgaaggg catcgacttc   6420
aaggaggacg gcaacatcct ggggcacaag ctggagtaca actacaacag ccacaacgtc   6480
tatatcatgg ccgacaagca gaagaacggc atcaaggtga acttcaagat ccgccacaac   6540
atcgaggacg gcagcgtgca gctcgccgac cactaccagc agaacacccc catcggcgac   6600
ggccccgtgc tgctgcccga caaccactac ctgagcaccc agtccgccct gagcaaagac   6660
cccaacgaga agcgcgatca catggtcctg ctggagttcg tgaccgccgc cgggatcact   6720
ctcggcatgg acgagctgta caagtaagaa ttcaaaatca gcctcgactg tgccttctag   6780
ttgccagcca tctgttgttt gcccctcccc cgtgccttcc ttgaccctgg aaggtgccac   6840
tcccactgtc ctttcctaat aaaatgagga aattgcatca caacactcaa ccctatctcg   6900
```

```
gtctattctt ttgatttata agggattttg ccgatttcgg cctattggtt aaaaaatgag   6960
ctgatttaac aaaaatttaa cgcgaattaa ttctgtggaa tgtgtgtcag ttagggtgtg   7020
gaaagtcccc aggctcccca gcaggcagaa gtatgcaaag catgcatctc aattagtcag   7080
caaccaggtg tggaaagtcc ccaggctccc cagcaggcag aagtatgcaa agcatgcatc   7140
tcaattagtc agcaaccata gtcccgcccc taactccgcc catcccgccc ctaactccgc   7200
ccagttccgc ccattctccg ccccatggct gactaatttt ttttatttat gcagaggccg   7260
aggccgcctc tgcctctgag ctattccaga agtagtgagg aggctttttt ggaggcctag   7320
gcttttgcaa aaagctcccg ggagcttgta tatccatttt cggatctgat cagcacgtga   7380
tgaaaaagcc tgaactcacc gcgacgtctg tcgagaagtt tctgatcgaa aagttcgaca   7440
gcgtctccga cctgatgcag ctctcggagg gcgaagaatc tcgtgctttc agcttcgatg   7500
taggagggcg tggatatgtc ctgcgggtaa atagctgcgc cgatggtttc tacaaagatc   7560
gttatgttta tcggcacttt gcatcggccg cgctcccgat tccggaagtg cttgacattg   7620
gggaattcag cgagagcctg acctattgca tctcccgccg tgcacagggt gtcacgttgc   7680
aagacctgcc tgaaaccgaa ctgcccgctg ttctgcagcc ggtcgcggag gccatggatg   7740
cgatcgctgc ggccgatctt agccagacga gcgggttcgg cccattcgga ccgcaaggaa   7800
tcggtcaata cactacatgg cgtgatttca tatgcgcgat tgctgatccc catgtgtatc   7860
actggcaaac tgtgatggac gacaccgtca gtgcgtccgt cgcgcaggct ctcgatgagc   7920
tgatgctttg ggccgaggac tgccccgaag tccggcacct cgtgcacgcg gatttcggct   7980
ccaacaatgt cctgacggac aatggccgca taacagcggt cattgactgg agcgaggcga   8040
tgttcgggga ttcccaatac gaggtcgcca acatcttctt ctggaggccg tggttggctt   8100
gtatggagca gcagacgcgc tacttcgagc ggaggcatcc ggagcttgca ggatcgccgc   8160
ggctccgggc gtatatgctc cgcattggtc ttgaccaact ctatcagagc ttggttgacg   8220
gcaatttcga tgatgcagct tgggcgcagg gtcgatgcga cgcaatcgtc cgatccggag   8280
ccgggactgt cgggcgtaca caaatcgccc gcagaagcgc ggccgtctgg accgatggct   8340
gtgtagaagt actcgccgat agtggaaacc gacgccccag cactcgtccg agggcaaagg   8400
aatagcacgt gctacgagat ttcgattcca ccgccgcctt ctatgaaagg ttgggcttcg   8460
gaatcgtttt ccgggacgcc ggctggatga tcctccagcg cggggatctc atgctggagt   8520
tcttcgccca ccccaacttg tttattgcag cttataatgg ttacaaataa agcaatagca   8580
tcacaaattt cacaaataaa gcattttttt cactgcattc tagttgtggt ttgtccaaac   8640
tcatcaatgt atcttatcat gtctgtatac cgtcgacctc tagctagagc ttggcgtaat   8700
catggtcatt accaatgctt aatcagtgag gcacctatct cagcgatctg tctatttcgt   8760
tcatccatag ttgcctgact ccccgtcgtg tagataacta cgatacggga gggcttacca   8820
tctggcccca gcgctgcgat gataccgcga gaaccacgct caccggctcc ggatttatca   8880
gcaataaacc agccagccgg aagggccgag cgcagaagtg gtcctgcaac tttatccgcc   8940
tccatccagt ctattaattg ttgccgggaa gctagagtaa gtagttcgcc agttaatagt   9000
ttgcgcaacg ttgttgccat cgctacaggc atcgtggtgt cacgctcgtc gtttggtatg   9060
gcttcattca gctccggttc ccaacgatca aggcgagtta catgatcccc catgttgtgc   9120
aaaaaagcgg ttagctcctt cggtcctccg atcgttgtca gaagtaagtt ggccgcagtg   9180
ttatcactca tggttatggc agcactgcat aattctctta ctgtcatgcc atccgtaaga   9240
```

```
tgcttttctg tgactggtga gtactcaacc aagtcattct gagaatagtg tatgcggcga   9300

ccgagttgct cttgcccggc gtcaatacgg gataataccg cgccacatag cagaacttta   9360

aaagtgctca tcattggaaa acgttcttcg gggcgaaaac tctcaaggat cttaccgctg   9420

ttgagatcca gttcgatgta acccactcgt gcacccaact gatcttcagc atcttttact   9480

ttcaccagcg tttctgggtg agcaaaaaca ggaaggcaaa atgccgcaaa aaagggaata   9540

agggcgacac ggaaatgttg aatactcata ttcttccttt ttcaatatta ttgaagcatt   9600

tatcagggtt attgtctcat gagcggatac atatttgaat gtatttagaa aaataaacaa   9660

ataggggtca gtgttacaac caattaacca attctgaaca ttatcgcgag cccatttata   9720

cctgaatatg gctcataaca ccccttg                                        9747
```

<210> SEQ ID NO 147
<211> LENGTH: 8039
<212> TYPE: DNA
<213> ORGANISM: Artificial Sequence
<220> FEATURE:
<223> OTHER INFORMATION: Synthetic

<400> SEQUENCE: 147

```
gacggatcgg gagatctccc gatcccctat ggtgcactct cagtacaatc tgctctgatg     60

ccgcatagtt aagccagtat ctgctccctg cttgtgtgtt ggaggtcgct gagtagtgcg    120

cgagcaaaat ttaagctaca acaaggcaag gcttgaccga caattgcatg aagaatctgc    180

ttagggttag gcgttttgcg ctgcttcgcg atgtacgggc cagatatacg cgttgacatt    240

gattattgac tagttattaa tagtaatcaa ttacggggtc attagttcat agcccatata    300

tggagttccg cgttacataa cttacggtaa atggcccgcc tggctgaccg cccaacgacc    360

cccgcccatt gacgtcaata atgacgtatg ttcccatagt aacgccaata gggactttcc    420

attgacgtca atgggtggag tatttacggt aaactgccca cttggcagta catcaagtgt    480

atcatatgcc aagtacgccc cctattgacg tcaatgacgg taaatggccc gcctggcatt    540

atgcccagta catgacctta tgggactttc ctacttggca gtacatctac gtattagtca    600

tcgctattac catggtgatg cggttttggc agtacatcaa tgggcgtgga tagcggtttg    660

actcacgggg atttccaagt ctccacccca ttgacgtcaa tgggagtttg ttttggcacc    720

aaaatcaacg ggactttcca aaatgtcgta acaactccgc cccattgacg caaatgggcg    780

gtaggcgtgt acggtgggag gtctatataa gcagagctct ctggctaact agagaaccca    840

ctgcttactg gcttatcgaa attaatacga ctcactatag ggagacccaa gctggctagc    900

gtttaaactt aagcttgcca ccatgggtga ctggagtgcc ttggggaaat tactggacaa    960

ggtccaagcc tactccaccg ctggagggaa ggtgtggctg tcagtgctct tcatattcag   1020

aatcctgctc ctggggacag ctgttgagtc agcttggggt gatgaacagt ctgcctttcg   1080

ctgtaacact caacaacctg gctgcgaaaa cgtctgctat gacaagtcct tccccatctc   1140

tcacgtgcgc ttctgggtcc ttcagatcat attcgtgtct gtgcccacac tcctgtactt   1200

ggcccatgtg ttctatgtga tgaggaagga agagaagcta aacaagaaag aagaggagct   1260

caaagtggcc cagactgacg gggtcaacgt ggagatgcac ctgaagcaga ttgaaatcaa   1320

gaagttcaag tacgggattg aagagcacgg caaggtgaaa atgaggggcg gcttgctgag   1380

aacctacatc atcagcatcc tcttcaagtc tgtcttcgag gtggccttcc tgctcatcca   1440

gtggtacatc tatgggttca gcttgagcgc ggtctacacc tgcaagagag atccctgccc   1500

ccaccaggta gactgcttcc tctcacgtcc cacggagaaa accatcttca tcatcttcat   1560
```

```
gctggtggtg tccttggtgt ctctcgcttt gaacatcatt gagctcttct acgtcttctt   1620
caagggcgtt aaggatcgcg tgaagggaag aagcgatcct taccacgcca ccactggccc   1680
actgagccca tcaaaagact gcggatctcc aaaatacgcc tacttcaatg gctgctcctc   1740
accaacggct ccactctcgc ctatgtctcc tcctgggtac aagctggtta ctggtgacag   1800
aaacaattcc tcgtgccgca attacaacaa gcaagctagc gagcaaaact gggcgaacta   1860
cagcgcagag caaaatcgca tggggcaggc cggaagcacc atctccaact cgcacgccca   1920
gccgttcgat ttccccgacg acaaccagaa tgccaaaaaa gttgctgctg gacatgaact   1980
ccagccatta gccatcgtgg accaacgacc ttccagcaga gccagcagcc gcgccagcag   2040
caggcctcgg cctgatgacc tggagattgg atccgggggt ggtgggtcta tggtgagcaa   2100
gggcgaggag ctgttcaccg gggtggtgcc catcctggtc gagctggacg gcgacgtaaa   2160
cggccacaag ttcagcgtgt ccggcgaggg cgagggcgat gccacctacg gcaagctgac   2220
cctgaagttc atctgcacca ccggcaagct gcccgtgccc tggcccaccc tcgtgaccac   2280
cctgacctac ggcgtgcagt gcttcagccg ctaccccgac cacatgaagc agcacgactt   2340
cttcaagtcc gccatgcccg aaggctacgt ccaggagcgc accatcttct tcaaggacga   2400
cggcaactac aagacccgcg ccgaggtgaa gttcgagggc gacaccctgg tgaaccgcat   2460
cgagctgaag ggcatcgact tcaaggagga cggcaacatc ctggggcaca agctggagta   2520
caactacaac agccacaacg tctatatcat ggccgacaag cagaagaacg gcatcaaggc   2580
caacttcaag atccgccaca acatcgagga cggcagcgtg cagctcgccg accactacca   2640
gcagaacacc cccatcggcg acggccccgt gctgctgccc gacaaccact acctgagcac   2700
ccagtccgcc ctgagcaaag accccaacga gaagcgcgat cacatggtcc tgctggagtt   2760
cgtgaccgcc gccgggatca ctctcggcat ggacgagctg tacaaggggc gcgccaaggg   2820
ctcgggctcg acctcgggct cgggcggaaa gtcttaccca actgtgagtg ctgattacca   2880
ggacgccgtt gagaaggcga agaagaagct cagaggcttc atcgctgaga agagatgcgc   2940
tcctctaatg ctccgtttgg cattccactc tgctggaacc tttgacaagg gcacgaagac   3000
cggtggaccc ttcggaacca tcaagcaccc tgccgaactg gctcacagcg ctaacaacgg   3060
tcttgacatc gctgttaggc ttttggagcc actcaaggcg gagttcccta ttttgagcta   3120
cgccgatttc taccagttgg ctggcgttgt tgccgttgag gtcacgggtg gacctaaggt   3180
tccattccac cctggaagag aggacaagcc tgagccacca ccagagggtc gcttgcccga   3240
tcccactaag ggttctgacc atttgagaga tgtgtttggc aaagctatgg ggcttactga   3300
ccaagatatc gttgctctat ctgggggtca cactattgga gctgcacaca aggagcgttc   3360
tggatttgag ggtccctgga cctctaatcc tcttattttc gacaactcat acttcacgga   3420
gttgttgagt ggtgagaagg aaggtctcct tcagctacct tctgacaagg ctcttttgtc   3480
tgaccctgta ttccgccctc tcgttgacaa atatgcagcg gacgaagatg ccttctttgc   3540
tgattacgct gaggctcacc aaaagctttc cgagcttggg tttgctgatg cctaactcga   3600
gtctagaggg cccgtttaaa cccgctgatc agcctcgact gtgccttcta gttgccagcc   3660
atctgttgtt tgcccctccc ccgtgccttc cttgaccctg gaaggtgcca ctcccactgt   3720
cctttcctaa taaaatgagg aaattgcatc gcattgtctg agtaggtgtc attctattct   3780
ggggggtggg gtggggcagg acagcaaggg ggaggattgg gaagacaata gcaggcatgc   3840
tggggatgcg gtgggctcta tggcttctga ggcggaaaga accagctggg gctctagggg   3900
```

```
gtatccccac gcgccctgta gcggcgcatt aagcgcggcg ggtgtggtgg ttacgcgcag   3960
cgtgaccgct acacttgcca gcgccctagc gcccgctcct ttcgctttct tcccttcctt   4020
tctcgccacg ttcgccggct ttccccgtca agctctaaat cgggggctcc ctttagggtt   4080
ccgatttagt gctttacggc acctcgaccc caaaaaactt gattagggtg atggttcacg   4140
tagtgggcca tcgccctgat agacggtttt tcgccctttg acgttggagt ccacgttctt   4200
taatagtgga ctcttgttcc aaactggaac aacactcaac cctatctcgg tctattcttt   4260
tgatttataa gggattttgc cgatttcggc ctattggtta aaaaatgagc tgatttaaca   4320
aaaatttaac gcgaattaat tctgtggaat gtgtgtcagt tagggtgtgg aaagtcccca   4380
ggctccccag caggcagaag tatgcaaagc atgcatctca attagtcagc aaccaggtgt   4440
ggaaagtccc caggctcccc agcaggcaga agtatgcaaa gcatgcatct caattagtca   4500
gcaaccatag tcccgcccct aactccgccc atcccgcccc taactccgcc cagttccgcc   4560
cattctccgc cccatggctg actaattttt tttatttatg cagaggccga ggccgcctct   4620
gcctctgagc tattccagaa gtagtgagga ggcttttttg gaggcctagg cttttgcaaa   4680
aagctcccgg gagcttgtat atccattttc ggatctgatc aagagacagg atgaggatcg   4740
tttcgcatga ttgaacaaga tggattgcac gcaggttctc cggccgcttg ggtggagagg   4800
ctattcggct atgactgggc acaacagaca atcggctgct ctgatgccgc cgtgttccgg   4860
ctgtcagcgc aggggcgccc ggttcttttt gtcaagaccg acctgtccgg tgccctgaat   4920
gaactgcagg acgaggcagc gcggctatcg tggctggcca cgacgggcgt tccttgcgca   4980
gctgtgctcg acgttgtcac tgaagcggga agggactggc tgctattggg cgaagtgccg   5040
gggcaggatc tcctgtcatc tcaccttgct cctgccgaga aagtatccat catggctgat   5100
gcaatgcggc ggctgcatac gcttgatccg gctacctgcc cattcgacca ccaagcgaaa   5160
catcgcatcg agcgagcacg tactcggatg gaagccggtc ttgtcgatca ggatgatctg   5220
gacgaagagc atcaggggct cgcgccagcc gaactgttcg ccaggctcaa ggcgcgcatg   5280
cccgacggcg aggatctcgt cgtgacccat ggcgatgcct gcttgccgaa tatcatggtg   5340
gaaaatggcc gcttttctgg attcatcgac tgtggccggc tgggtgtggc ggaccgctat   5400
caggacatag cgttggctac ccgtgatatt gctgaagagc ttggcggcga atgggctgac   5460
cgcttcctcg tgctttacgg tatcgccgct cccgattcgc agcgcatcgc cttctatcgc   5520
cttcttgacg agttcttctg agcgggactc tggggttcga aatgaccgac caagcgacgc   5580
ccaacctgcc atcacgagat ttcgattcca ccgccgcctt ctatgaaagg ttgggcttcg   5640
gaatcgtttt ccgggacgcc ggctggatga tcctccagcg cggggatctc atgctggagt   5700
tcttcgccca ccccaacttg tttattgcag cttataatgg ttacaaataa agcaatagca   5760
tcacaaattt cacaaataaa gcattttttt cactgcattc tagttgtggt ttgtccaaac   5820
tcatcaatgt atcttatcat gtctgtatac cgtcgacctc tagctagagc ttggcgtaat   5880
catggtcata gctgtttcct gtgtgaaatt gttatccgct cacaattcca cacaacatac   5940
gagccggaag cataaagtgt aaagcctggg gtgcctaatg agtgagctaa ctcacattaa   6000
ttgcgttgcg ctcactgccc gctttccagt cgggaaacct gtcgtgccag ctgcattaat   6060
gaatcggcca acgcgcgggg agaggcggtt tgcgtattgg gcgctcttcc gcttcctcgc   6120
tcactgactc gctgcgctcg gtcgttcggc tgcggcgagc ggtatcagct cactcaaagg   6180
cggtaatacg gttatccaca gaatcagggg ataacgcagg aaagaacatg tgagcaaaag   6240
gccagcaaaa ggccaggaac cgtaaaaagg ccgcgttgct ggcgtttttc cataggctcc   6300
```

gccccccctga cgagcatcac aaaaatcgac gctcaagtca gaggtggcga aacccgacag 6360
gactataaag ataccaggcg tttccccctg gaagctccct cgtgcgctct cctgttccga 6420
ccctgccgct taccggatac ctgtccgcct ttctcccttc gggaagcgtg gcgctttctc 6480
atagctcacg ctgtaggtat ctcagttcgg tgtaggtcgt tcgctccaag ctgggctgtg 6540
tgcacgaacc ccccgttcag cccgaccgct gcgccttatc cggtaactat cgtcttgagt 6600
ccaacccggt aagacacgac ttatcgccac tggcagcagc cactggtaac aggattagca 6660
gagcgaggta tgtaggcggt gctacagagt tcttgaagtg gtggcctaac tacggctaca 6720
ctagaagaac agtatttggt atctgcgctc tgctgaagcc agttaccttc ggaaaaagag 6780
ttggtagctc ttgatccggc aaacaaacca ccgctggtag cggttttttt gtttgcaagc 6840
agcagattac gcgcagaaaa aaaggatctc aagaagatcc tttgatcttt tctacggggt 6900
ctgacgctca gtggaacgaa aactcacgtt aagggatttt ggtcatgaga ttatcaaaaa 6960
ggatcttcac ctagatcctt ttaaattaaa aatgaagttt taaatcaatc taaagtatat 7020
atgagtaaac ttggtctgac agttaccaat gcttaatcag tgaggcacct atctcagcga 7080
tctgtctatt tcgttcatcc atagttgcct gactccccgt cgtgtagata actacgatac 7140
gggagggctt accatctggc cccagtgctg caatgatacc gcgagaccca cgctcaccgg 7200
ctccagattt atcagcaata aaccagccag ccggaagggc cgagcgcaga agtggtcctg 7260
caactttatc cgcctccatc cagtctatta attgttgccg ggaagctaga gtaagtagtt 7320
cgccagttaa tagtttgcgc aacgttgttg ccattgctac aggcatcgtg gtgtcacgct 7380
cgtcgtttgg tatggcttca ttcagctccg gttcccaacg atcaaggcga gttacatgat 7440
cccccatgtt gtgcaaaaaa gcggttagct ccttcggtcc tccgatcgtt gtcagaagta 7500
agttggccgc agtgttatca ctcatggtta tggcagcact gcataattct cttactgtca 7560
tgccatccgt aagatgcttt tctgtgactg gtgagtactc aaccaagtca ttctgagaat 7620
agtgtatgcg gcgaccgagt tgctcttgcc cggcgtcaat acgggataat accgcgccac 7680
atagcagaac tttaaaagtg ctcatcattg gaaaacgttc ttcggggcga aaactctcaa 7740
ggatcttacc gctgttgaga tccagttcga tgtaacccac tcgtgcaccc aactgatctt 7800
cagcatcttt tactttcacc agcgtttctg ggtgagcaaa aacaggaagg caaaatgccg 7860
caaaaaaggg aataagggcg acacggaaat gttgaatact catactcttc ctttttcaat 7920
attattgaag catttatcag ggttattgtc tcatgagcgg atacatattt gaatgtattt 7980
agaaaaataa acaaataggg gttccgcgca catttccccg aaaagtgcca cctgacgtc 8039

<210> SEQ ID NO 148
<211> LENGTH: 6198
<212> TYPE: DNA
<213> ORGANISM: Artificial Sequence
<220> FEATURE:
<223> OTHER INFORMATION: Synthetic

<400> SEQUENCE: 148
gacggatcgg gagatctccc gatcccctat ggtcgactct cagtacaatc tgctctgatg 60
ccgcatagtt aagccagtat ctgctccctg cttgtgtgtt ggaggtcgct gagtagtgcg 120
cgagcaaaat ttaagctaca acaaggcaag gcttgaccga caattgcatg aagaatctgc 180
ttagggttag gcgttttgcg ctgcttcgcg atgtacgggc cagatatacg cgttgacatt 240
gattattgac tagttattaa tagtaatcaa ttacggggtc attagttcat agcccatata 300

```
tggagttccg cgttacataa cttacggtaa atggcccgcc tggctgaccg cccaacgacc    360
cccgcccatt gacgtcaata atgacgtatg ttcccatagt aacgccaata gggactttcc    420
attgacgtca atgggtggac tatttacggt aaactgccca cttggcagta catcaagtgt    480
atcatatgcc aagtacgccc cctattgacg tcaatgacgg taaatggccc gcctggcatt    540
atgcccagta catgacctta tgggactttc ctacttggca gtacatctac gtattagtca    600
tcgctattac catggtgatg cggttttggc agtacatcaa tgggcgtgga tagcggtttg    660
actcacgggg atttccaagt ctccacccca ttgacgtcaa tgggagtttg ttttggcacc    720
aaaatcaacg ggactttcca aaatgtcgta acaactccgc cccattgacg caaatgggcg    780
gtaggcgtgt acggtgggag gtctatataa gcagagctct ctggctaact agagaaccca    840
ctgcttactg gcttatcgaa attaatacga ctcactatag ggagacccaa gcttgcggcc    900
gccaccatgg actacaagga tgacgacgat aagggaaagt cttacccaac tgtgagtgct    960
gattaccagg acgccgttga gaaggcgaag aagaagctca gaggcttcat cgctgagaag   1020
agatgcgctc ctctaatgct ccgtttggca ttccactctg ctggaacctt tgacaagggc   1080
acgaagaccg gtggaccctt cggaaccatc aagcaccctg ccgaactggc tcacagcgct   1140
aacaacggtc ttgacatcgc tgttaggctt ttggagccac tcaaggcgga gttccctatt   1200
ttgagctacg ccgatttcta ccagttggct ggcgttgttg ccgttgaggt cacgggtgga   1260
cctaaggttc cattccaccc tggaagagag gacaagcctg agccaccacc agagggtcgc   1320
ttgcccgatc ccactaaggg ttctgaccat ttgagagatg tgtttggcaa agctatgggg   1380
cttactgacc aagatatcgt tgctctatct ggggggtcaca ctattggagc tgcacacaag   1440
gagcgttctg gatttgaggg tccctggacc tctaatcctc ttattttcga caactcatac   1500
ttcacggagt tgttgagtgg tgagaaggaa ggtctccttc agctaccttc tgacaaggct   1560
cttttgtctg accctgtatt ccgccctctc gttgacaaat atgcagcgga cgaagatgcc   1620
ttctttgctg attacgctga ggctcaccaa aagctttccg agcttgggtt tgctgatgcc   1680
ctgcagctgc ctcccctgga gcgcctgacc ctggactaat agctcgagca tgcatctaga   1740
gggccctatt ctatagtgtc acctaaatgc tagagctcgc tgatcagcct cgactgtgcc   1800
ttctagttgc cagccatctg ttgtttgccc ctcccccgtg ccttccttga ccctggaagg   1860
tgccactccc actgtccttt cctaataaaa tgaggaaatt gcatcgcatt gtctgagtag   1920
gtgtcattct attctggggg gtggggtggg gcaggacagc aagggggagg attgggaaga   1980
caatagcagg catgctgggg atgcggtggg ctctatggct tctgaggcgg aaagaaccag   2040
ctggggctct agggggtatc cccacgcgcc ctgtagcggc gcattaagcg cggcgggtgt   2100
ggtggttacg cgcagcgtga ccgctacact tgccagcgcc ctagcgcccg ctcctttcgc   2160
tttcttccct tcctttctcg ccacgttcgc cggctttccc cgtcaagctc taaatcgggg   2220
catcccttta gggttccgat ttagtgcttt acggcacctc gaccccaaaa aacttgatta   2280
gggtgatggt tcacgtagtg ggccatcgcc ctgatagacg gtttttcgcc ctttgacgtt   2340
ggagtccacg ttctttaata gtggactctt gttccaaact ggaacaacac tcaaccctat   2400
ctcggtctat tcttttgatt tataagggat tttggggatt tcggcctatt ggttaaaaaa   2460
tgagctgatt taacaaaaat ttaacgcgaa ttaattctgt ggaatgtgtg tcagttaggg   2520
tgtggaaagt ccccaggctc cccaggcagg cagaagtatg caaagcatgc atctcaatta   2580
gtcagcaacc aggtgtggaa agtccccagg ctccccagca ggcagaagta tgcaaagcat   2640
gcatctcaat tagtcagcaa ccatagtccc gcccctaact ccgcccatcc cgcccctaac   2700
```

```
tccgcccagt tccgcccatt ctccgcccca tggctgacta attttttta tttatgcaga   2760
ggccgaggcc gcctctgcct ctgagctatt ccagaagtag tgaggaggct tttttggagg  2820
cctaggcttt tgcaaaaagc tcccgggagc ttgtatatcc attttcggat ctgatcaaga  2880
gacaggatga ggatcgtttc gcatgattga acaagatgga ttgcacgcag gttctccggc  2940
cgcttgggtg gagaggctat tcggctatga ctgggcacaa cagacaatcg gctgctctga  3000
tgccgccgtg ttccggctgt cagcgcaggg gcgcccggtt ctttttgtca agaccgacct  3060
gtccggtgcc ctgaatgaac tgcaggacga ggcagcgcgg ctatcgtggc tggccacgac  3120
gggcgttcct tgcgcagctg tgctcgacgt tgtcactgaa gcgggaaggg actggctgct  3180
attgggcgaa gtgccggggc aggatctcct gtcatctcac cttgctcctg ccgagaaagt  3240
atccatcatg gctgatgcaa tgcggcggct gcatacgctt gatccggcta cctgcccatt  3300
cgaccaccaa gcgaaacatc gcatcgagcg agcacgtact cggatggaag ccggtcttgt  3360
cgatcaggat gatctggacg aagagcatca ggggctcgcg ccagccgaac tgttcgccag  3420
gctcaaggcg cgcatgcccg acggcgagga tctcgtcgtg acccatggcg atgcctgctt  3480
gccgaatatc atggtggaaa atggccgctt ttctggattc atcgactgtg gccggctggg  3540
tgtggcggac cgctatcagg acatagcgtt ggctacccgt gatattgctg aagagcttgg  3600
cggcgaatgg gctgaccgct tcctcgtgct ttacggtatc gccgctcccg attcgcagcg  3660
catcgccttc tatcgccttc ttgacgagtt cttctgagcg ggactctggg gttcgaaatg  3720
accgaccaag cgacgcccaa cctgccatca cgagatttcg attccaccgc cgccttctat  3780
gaaaggttgg gcttcggaat cgttttccgg gacgccggct ggatgatcct ccagcgcggg  3840
gatctcatgc tggagttctt cgcccacccc aacttgttta ttgcagctta taatggttac  3900
aaataaagca atagcatcac aaatttcaca aataaagcat ttttttcact gcattctagt  3960
tgtggtttgt ccaaactcat caatgtatct tatcatgtct gtataccgtc gacctctagc  4020
tagagcttgg cgtaatcatg gtcatagctg tttcctgtgt gaaattgtta tccgctcaca  4080
attccacaca acatacgagc cggaagcata aagtgtaaag cctggggtgc ctaatgagtg  4140
agctaactca cattaattgc gttgcgctca ctgcccgctt tccagtcggg aaacctgtcg  4200
tgccagctgc attaatgaat cggccaacgc gcggggagag gcggtttgcg tattgggcgc  4260
tcttccgctt cctcgctcac tgactcgctg cgctcggtcg ttcggctgcg gcgagcggta  4320
tcagctcact caaaggcggt aatacggtta tccacagaat caggggataa cgcaggaaag  4380
aacatgtgag caaaaggcca gcaaaaggcc aggaaccgta aaaaggccgc gttgctggcg  4440
tttttccata ggctccgccc ccctgacgag catcacaaaa atcgacgctc aagtcagagg  4500
tggcgaaacc cgacaggact ataaagatac caggcgtttc cccctggaag ctccctcgtg  4560
cgctctcctg ttccgaccct gccgcttacc ggatacctgt ccgcctttct cccttcggga  4620
agcgtggcgc tttctcaatg ctcacgctgt aggtatctca gttcggtgta ggtcgttcgc  4680
tccaagctgg gctgtgtgca cgaacccccc gttcagcccg accgctgcgc cttatccggt  4740
aactatcgtc ttgagtccaa cccggtaaga cacgacttat cgccactggc agcagccact  4800
ggtaacagga ttagcagagc gaggtatgta ggcggtgcta cagagttctt gaagtggtgg  4860
cctaactacg gctacactag aaggacagta tttggtatct gcgctctgct gaagccagtt  4920
accttcggaa aaagagttgg tagctcttga tccggcaaac aaaccaccgc tggtagcggt  4980
ggtttttttg tttgcaagca gcagattacg cgcagaaaaa aaggatctca agaagatcct  5040
```

ttgatctttt ctacggggtc tgacgctcag tggaacgaaa actcacgtta agggattttg 5100
gtcatgagat tatcaaaaag gatcttcacc tagatccttt taaattaaaa atgaagtttt 5160
aaatcaatct aaagtatata tgagtaaact tggtctgaca gttaccaatg cttaatcagt 5220
gaggcaccta tctcagcgat ctgtctattt cgttcatcca tagttgcctg actccccgtc 5280
gtgtagataa ctacgatacg ggagggctta ccatctggcc ccagtgctgc aatgataccg 5340
cgagacccac gctcaccggc tccagattta tcagcaataa accagccagc cggaagggcc 5400
gagcgcagaa gtggtcctgc aactttatcc gcctccatcc agtctattaa ttgttgccgg 5460
gaagctagag taagtagttc gccagttaat agtttgcgca acgttgttgc cattgctaca 5520
ggcatcgtgg tgtcacgctc gtcgtttggt atggcttcat tcagctccgg ttcccaacga 5580
tcaaggcgag ttacatgatc ccccatgttg tgcaaaaaag cggttagctc cttcggtcct 5640
ccgatcgttg tcagaagtaa gttggccgca gtgttatcac tcatggttat ggcagcactg 5700
cataattctc ttactgtcat gccatccgta agatgctttt ctgtgactgg tgagtactca 5760
accaagtcat tctgagaata gtgtatgcgg cgaccgagtt gctcttgccc ggcgtcaata 5820
cgggataata ccgcgccaca tagcagaact ttaaaagtgc tcatcattgg aaaacgttct 5880
tcggggcgaa aactctcaag gatcttaccg ctgttgagat ccagttcgat gtaacccact 5940
cgtgcaccca actgatcttc agcatctttt actttcacca gcgtttctgg gtgagcaaaa 6000
acaggaaggc aaaatgccgc aaaaaaggga ataagggcga cacggaaatg ttgaatactc 6060
atactcttcc tttttcaata ttattgaagc atttatcagg gttattgtct catgagcgga 6120
tacatatttg aatgtattta gaaaaataaa caaatagggg ttccgcgcac atttccccga 6180
aaagtgccac ctgacgtc 6198

<210> SEQ ID NO 149
<211> LENGTH: 19
<212> TYPE: DNA
<213> ORGANISM: Artificial Sequence
<220> FEATURE:
<223> OTHER INFORMATION: Synthetic

<400> SEQUENCE: 149
ccccgagctg tgctgctcg 19

<210> SEQ ID NO 150
<211> LENGTH: 21
<212> TYPE: DNA
<213> ORGANISM: Artificial Sequence
<220> FEATURE:
<223> OTHER INFORMATION: Synthetic

<400> SEQUENCE: 150
gtgggcggag attagcgaga g 21

<210> SEQ ID NO 151
<211> LENGTH: 19
<212> TYPE: DNA
<213> ORGANISM: Artificial Sequence
<220> FEATURE:
<223> OTHER INFORMATION: Synthetic

<400> SEQUENCE: 151
tcccgggttc ccaaagcag 19

<210> SEQ ID NO 152
<211> LENGTH: 20

<212> TYPE: DNA
<213> ORGANISM: Artificial Sequence
<220> FEATURE:
<223> OTHER INFORMATION: Synthetic

<400> SEQUENCE: 152
gcgcgcgtag ttaattcatg 20

<210> SEQ ID NO 153
<211> LENGTH: 20
<212> TYPE: DNA
<213> ORGANISM: Artificial Sequence
<220> FEATURE:
<223> OTHER INFORMATION: Synthetic

<400> SEQUENCE: 153
tgggactctt gatcaaagcg 20

<210> SEQ ID NO 154
<211> LENGTH: 30
<212> TYPE: DNA
<213> ORGANISM: Artificial Sequence
<220> FEATURE:
<223> OTHER INFORMATION: Synthetic

<400> SEQUENCE: 154
gcccctccca tattctcccg tctagcacct 30

<210> SEQ ID NO 155
<211> LENGTH: 30
<212> TYPE: DNA
<213> ORGANISM: Artificial Sequence
<220> FEATURE:
<223> OTHER INFORMATION: Synthetic

<400> SEQUENCE: 155
gcaggtgaca ccacacagaa accacggtca 30

<210> SEQ ID NO 156
<211> LENGTH: 30
<212> TYPE: DNA
<213> ORGANISM: Artificial Sequence
<220> FEATURE:
<223> OTHER INFORMATION: Synthetic

<400> SEQUENCE: 156
ccttccgcca ggtgggcctc cccggggtcg 30

<210> SEQ ID NO 157
<211> LENGTH: 30
<212> TYPE: DNA
<213> ORGANISM: Artificial Sequence
<220> FEATURE:
<223> OTHER INFORMATION: Synthetic

<400> SEQUENCE: 157
ccctgctgcg cagccactac cgcgaggtgc 30

<210> SEQ ID NO 158
<211> LENGTH: 30
<212> TYPE: DNA
<213> ORGANISM: Artificial Sequence
<220> FEATURE:
<223> OTHER INFORMATION: Synthetic

<400> SEQUENCE: 158
ccttccagct ccgcctcctc cgcgcggacc 30

<210> SEQ ID NO 159
<211> LENGTH: 30
<212> TYPE: DNA
<213> ORGANISM: Artificial Sequence
<220> FEATURE:
<223> OTHER INFORMATION: Synthetic

<400> SEQUENCE: 159
ctccggatca ggccagcggc caaagggtcg 30

<210> SEQ ID NO 160
<211> LENGTH: 20
<212> TYPE: DNA
<213> ORGANISM: Artificial Sequence
<220> FEATURE:
<223> OTHER INFORMATION: Synthetic

<400> SEQUENCE: 160
gggagatccg gagcgaatag 20

<210> SEQ ID NO 161
<211> LENGTH: 20
<212> TYPE: DNA
<213> ORGANISM: Artificial Sequence
<220> FEATURE:
<223> OTHER INFORMATION: Synthetic

<400> SEQUENCE: 161
ggagagtcgc gtccttgctc 20

<210> SEQ ID NO 162
<211> LENGTH: 23
<212> TYPE: DNA
<213> ORGANISM: Artificial Sequence
<220> FEATURE:
<223> OTHER INFORMATION: Synthetic

<400> SEQUENCE: 162
agggatcgcg ctgagtataa aag 23

<210> SEQ ID NO 163
<211> LENGTH: 20
<212> TYPE: DNA
<213> ORGANISM: Artificial Sequence
<220> FEATURE:
<223> OTHER INFORMATION: Synthetic

<400> SEQUENCE: 163
ctattcgctc cggatctccc 20

<210> SEQ ID NO 164
<211> LENGTH: 23
<212> TYPE: DNA
<213> ORGANISM: Artificial Sequence
<220> FEATURE:
<223> OTHER INFORMATION: Synthetic

<400> SEQUENCE: 164
aagatcctct ctcgctaatc tcc 23

<210> SEQ ID NO 165
<211> LENGTH: 20
<212> TYPE: DNA
<213> ORGANISM: Artificial Sequence
<220> FEATURE:
<223> OTHER INFORMATION: Synthetic

<400> SEQUENCE: 165
ctgcccttct cgaggcagga 20

<210> SEQ ID NO 166
<211> LENGTH: 25
<212> TYPE: DNA
<213> ORGANISM: Artificial Sequence
<220> FEATURE:
<223> OTHER INFORMATION: Synthetic

<400> SEQUENCE: 166
gtttgtcaaa cagtactgct acgga 25

<210> SEQ ID NO 167
<211> LENGTH: 20
<212> TYPE: DNA
<213> ORGANISM: Artificial Sequence
<220> FEATURE:
<223> OTHER INFORMATION: Synthetic

<400> SEQUENCE: 167
gaggagactc agccgggcag 20

<210> SEQ ID NO 168
<211> LENGTH: 22
<212> TYPE: DNA
<213> ORGANISM: Artificial Sequence
<220> FEATURE:
<223> OTHER INFORMATION: Synthetic

<400> SEQUENCE: 168
tacactaaca tcccacgctc tg 22

<210> SEQ ID NO 169
<211> LENGTH: 23
<212> TYPE: DNA
<213> ORGANISM: Artificial Sequence
<220> FEATURE:
<223> OTHER INFORMATION: Synthetic

<400> SEQUENCE: 169
gtataaatca tcgcaggcgg aac 23

<210> SEQ ID NO 170
<211> LENGTH: 21
<212> TYPE: DNA
<213> ORGANISM: Artificial Sequence
<220> FEATURE:
<223> OTHER INFORMATION: Synthetic

<400> SEQUENCE: 170
caggacccgc ttctctgaaa g 21

<210> SEQ ID NO 171
<211> LENGTH: 25
<212> TYPE: DNA
<213> ORGANISM: Artificial Sequence
<220> FEATURE:
<223> OTHER INFORMATION: Synthetic

<400> SEQUENCE: 171
gacaccctat ttaggcattc gactc 25

<210> SEQ ID NO 172
<211> LENGTH: 21
<212> TYPE: DNA
<213> ORGANISM: Artificial Sequence
<220> FEATURE:
<223> OTHER INFORMATION: Synthetic

<400> SEQUENCE: 172
ggtccacaag ctctccactt g 21

<210> SEQ ID NO 173
<211> LENGTH: 20
<212> TYPE: DNA
<213> ORGANISM: Artificial Sequence
<220> FEATURE:
<223> OTHER INFORMATION: Synthetic

<400> SEQUENCE: 173
ccggtttgca acagtctcgg 20

<210> SEQ ID NO 174
<211> LENGTH: 26
<212> TYPE: DNA
<213> ORGANISM: Artificial Sequence
<220> FEATURE:
<223> OTHER INFORMATION: Synthetic

<400> SEQUENCE: 174
cagcaggagc gcctggctcc atttcc 26

<210> SEQ ID NO 175
<211> LENGTH: 25
<212> TYPE: DNA
<213> ORGANISM: Artificial Sequence
<220> FEATURE:
<223> OTHER INFORMATION: Synthetic

<400> SEQUENCE: 175
gacgaacccg aggacgcatt gctcc 25

<210> SEQ ID NO 176
<211> LENGTH: 25
<212> TYPE: DNA
<213> ORGANISM: Artificial Sequence
<220> FEATURE:
<223> OTHER INFORMATION: Synthetic

<400> SEQUENCE: 176
ggagcaatgc gtcctcgggt tcgtc 25

<210> SEQ ID NO 177
<211> LENGTH: 23
<212> TYPE: DNA
<213> ORGANISM: Artificial Sequence
<220> FEATURE:
<223> OTHER INFORMATION: Synthetic

<400> SEQUENCE: 177
catgatgtgg aggccctggg aac 23

<210> SEQ ID NO 178
<211> LENGTH: 23
<212> TYPE: DNA
<213> ORGANISM: Artificial Sequence
<220> FEATURE:
<223> OTHER INFORMATION: Synthetic

<400> SEQUENCE: 178
gttcccaggg cctccacatc atg 23

<210> SEQ ID NO 179
<211> LENGTH: 25
<212> TYPE: DNA
<213> ORGANISM: Artificial Sequence
<220> FEATURE:
<223> OTHER INFORMATION: Synthetic

<400> SEQUENCE: 179
ggaagcgcgg tcctgggcgt ctgtg 25

<210> SEQ ID NO 180
<211> LENGTH: 25
<212> TYPE: DNA
<213> ORGANISM: Artificial Sequence
<220> FEATURE:
<223> OTHER INFORMATION: Synthetic

<400> SEQUENCE: 180
cacagacgcc caggaccgcg cttcc 25

<210> SEQ ID NO 181
<211> LENGTH: 28
<212> TYPE: DNA
<213> ORGANISM: Artificial Sequence
<220> FEATURE:
<223> OTHER INFORMATION: Synthetic

<400> SEQUENCE: 181
cagcaggacg cagcgctgcc tgaaactc 28

<210> SEQ ID NO 182
<211> LENGTH: 28
<212> TYPE: DNA
<213> ORGANISM: Artificial Sequence
<220> FEATURE:
<223> OTHER INFORMATION: Synthetic

<400> SEQUENCE: 182
gagtttcagg cagcgctgcg tcctgctg 28

<210> SEQ ID NO 183
<211> LENGTH: 23
<212> TYPE: DNA
<213> ORGANISM: Artificial Sequence
<220> FEATURE:
<223> OTHER INFORMATION: Synthetic

<400> SEQUENCE: 183
cagcacctcg cggtagtggc tgc 23

<210> SEQ ID NO 184
<211> LENGTH: 23
<212> TYPE: DNA
<213> ORGANISM: Artificial Sequence
<220> FEATURE:
<223> OTHER INFORMATION: Synthetic

<400> SEQUENCE: 184
gcagccacta ccgcgaggtg ctg 23

<210> SEQ ID NO 185

<211> LENGTH: 27
<212> TYPE: DNA
<213> ORGANISM: Artificial Sequence
<220> FEATURE:
<223> OTHER INFORMATION: Synthetic

<400> SEQUENCE: 185
caccagctcc ttcaggcagg acacctg 27

<210> SEQ ID NO 186
<211> LENGTH: 27
<212> TYPE: DNA
<213> ORGANISM: Artificial Sequence
<220> FEATURE:
<223> OTHER INFORMATION: Synthetic

<400> SEQUENCE: 186
caggtgtcct gcctgaagga gctggtg 27

<210> SEQ ID NO 187
<211> LENGTH: 27
<212> TYPE: DNA
<213> ORGANISM: Artificial Sequence
<220> FEATURE:
<223> OTHER INFORMATION: Synthetic

<400> SEQUENCE: 187
cagtgcgtcg gtcaccgtgt tgggcag 27

<210> SEQ ID NO 188
<211> LENGTH: 27
<212> TYPE: DNA
<213> ORGANISM: Artificial Sequence
<220> FEATURE:
<223> OTHER INFORMATION: Synthetic

<400> SEQUENCE: 188
ctgcccaaca cggtgaccga cgcactg 27

<210> SEQ ID NO 189
<211> LENGTH: 22
<212> TYPE: DNA
<213> ORGANISM: Artificial Sequence
<220> FEATURE:
<223> OTHER INFORMATION: Synthetic

<400> SEQUENCE: 189
cttcggggtc cactagcgtg tg 22

<210> SEQ ID NO 190
<211> LENGTH: 21
<212> TYPE: DNA
<213> ORGANISM: Artificial Sequence
<220> FEATURE:
<223> OTHER INFORMATION: Synthetic

<400> SEQUENCE: 190
gaagaagcca cctctttgga g 21

<210> SEQ ID NO 191
<211> LENGTH: 21
<212> TYPE: DNA
<213> ORGANISM: Artificial Sequence
<220> FEATURE:
<223> OTHER INFORMATION: Synthetic

<400> SEQUENCE: 191
ctccaaagag gtggcttctt c 21

<210> SEQ ID NO 192
<211> LENGTH: 21
<212> TYPE: DNA
<213> ORGANISM: Artificial Sequence
<220> FEATURE:
<223> OTHER INFORMATION: Synthetic

<400> SEQUENCE: 192
gaagaagcca cctctttgga g 21

<210> SEQ ID NO 193
<211> LENGTH: 29
<212> TYPE: DNA
<213> ORGANISM: Artificial Sequence
<220> FEATURE:
<223> OTHER INFORMATION: Synthetic

<400> SEQUENCE: 193
ctggaaccca gaaagatggt ctccacgag 29

<210> SEQ ID NO 194
<211> LENGTH: 29
<212> TYPE: DNA
<213> ORGANISM: Artificial Sequence
<220> FEATURE:
<223> OTHER INFORMATION: Synthetic

<400> SEQUENCE: 194
ctcgtggaga ccatctttct gggttccag 29

<210> SEQ ID NO 195
<211> LENGTH: 22
<212> TYPE: DNA
<213> ORGANISM: Artificial Sequence
<220> FEATURE:
<223> OTHER INFORMATION: Synthetic

<400> SEQUENCE: 195
ccacagagcc ctggggcttc tc 22

<210> SEQ ID NO 196
<211> LENGTH: 60
<212> TYPE: DNA
<213> ORGANISM: Artificial Sequence
<220> FEATURE:
<223> OTHER INFORMATION: Synthetic

<400> SEQUENCE: 196
taccacttcc taccctcgta aaggtctaga gctagccacc atggactaca aagaccatga 60

<210> SEQ ID NO 197
<211> LENGTH: 50
<212> TYPE: DNA
<213> ORGANISM: Artificial Sequence
<220> FEATURE:
<223> OTHER INFORMATION: Synthetic

<400> SEQUENCE: 197
gttggggatg ggcttgccag aaccccgcac gtctccaccg agctgagaga 50

<210> SEQ ID NO 198
<211> LENGTH: 49
<212> TYPE: DNA

```
<213> ORGANISM: Artificial Sequence
<220> FEATURE:
<223> OTHER INFORMATION: Synthetic

<400> SEQUENCE: 198

agaatcgacc tctctcagct cggtggagac gtgcggggtt ctggcaagc               49


<210> SEQ ID NO 199
<211> LENGTH: 51
<212> TYPE: DNA
<213> ORGANISM: Artificial Sequence
<220> FEATURE:
<223> OTHER INFORMATION: Synthetic

<400> SEQUENCE: 199

accgcatgtt agaagacttc ctctgccctc caccttcctc ttcttcttgg g            51


<210> SEQ ID NO 200
<211> LENGTH: 50
<212> TYPE: DNA
<213> ORGANISM: Artificial Sequence
<220> FEATURE:
<223> OTHER INFORMATION: Synthetic

<400> SEQUENCE: 200

agggccgacc ccaagaagaa gaggaaggtg gagggcagag gaagtcttct              50


<210> SEQ ID NO 201
<211> LENGTH: 51
<212> TYPE: DNA
<213> ORGANISM: Artificial Sequence
<220> FEATURE:
<223> OTHER INFORMATION: Synthetic

<400> SEQUENCE: 201

cctcccccgt ttaaactcat tactaaccgg tcaaccggtc ttgtacagct c            51
```

PROXIMITY-DEPENDENT BIOTINYLATION AND USES THEREOF

CROSS-REFERENCE TO RELATED APPLICATIONS

This application is a U.S. National Stage of International Application No. PCT/US2017/051428, filed Sep. 13, 2017, which claims the benefit of U.S. Provisional Application No. 62/394,133 filed on Sep. 13, 2016. The entire contents of the above-identified priority applications are hereby fully incorporated herein by reference.

STATEMENT REGARDING FEDERALLY SPONSORED RESEARCH

This invention was made with government support under grant number DK097768 granted by National Institutes of Health. The government has certain rights in the invention.

FIELD OF THE INVENTION

The present invention relies on proximity-dependent biotinylation, allowing site-directed protein or DNA purification and identification. The present invention further provides fusion proteins, polynucleotides, kits, as well as TALE- or CRISPR-Cas based systems and methods. The present invention provides tools for delineating the genetics of disease mechanism and for the identification of therapeutic targets and markers.

BACKGROUND OF THE INVENTION

Over 2600 locations across the human genome have been identified as altering the risk of a vast spectrum of diseases including cancer, diabetes and heart disease. Over 95% of these genomic locations do not include protein coding genes, suggesting that alterations in unidentified regulatory proteins (transcription factors) that bind to the DNA of these sites cause disease pathogenesis. Therefore, in order to fully utilize current knowledge of disease genetics and guide future therapeutic efforts, it would be useful to first determine which proteins are bound to these locations. At present, chromatin immuno-precipitation (ChIP) is used to identify protein-DNA interactions. This method is restricted to detecting only the proteins that are specifically purified using antibodies. Because of this limitation only about 160 out of over 2000 known transcription factors, have been queried by ChIP across the human genome. Taken together there is an unmet need to identify all proteins at a given genomic location by "reverse-ChIP", where the DNA itself provides the specificity and bound proteins are determined in an unbiased manner.

It has long been acknowledged that there is a great need for the unbiased identification of proteins at specific sites in the genome (Rusk, Nature Methods, vol. 6 no. 3, March 2009, 187). Previous attempts to address this problem include delivering modified-DNA probes to genomic locations for protein identification by mass-spectrometry (Cell. 2009 Jan. 9; 136 (1): 175-86. doi: 10.1016/j.cell.2008.11.045. *Purification of proteins associated with specific genomic Loci*. Déjardin J et al.). These methods were successful at identifying abundant proteins bound to repetitive elements in the genome such as telomeres, but even at these repetitive sites require tremendous technical optimization. Moreover, application of this method has too low of a signal to noise ratio for practical application to the majority of single-copy disease relevant sites across the genome. Therefore previous methods have not been adequately robust or tractable to meet the massive and ever growing number of disease relevant sites identified by modern human disease genomics.

There thus lies a major unmet need in the interrogation of disease relevant genomic locations, so as to provide inroads to identifying novel therapeutic targets as well as exposing novel markers of disease. The present invention aims at providing for an efficient non-biased identification of proteins and pathways at targeted locations in the genome.

Citation or identification of any document in this application is not an admission that such document is available as prior art to the present invention.

SUMMARY OF THE INVENTION

In one embodiment, the present invention involves a fusion protein and nucleic acid constructs encoding same. The fusion protein may comprise (a) a genome-editing protein or a fragment thereof, and (b) a proximity-dependent biotin protein ligase, an ATP-biotin interaction loop or a biotin pocket thereof, or an engineered ascorbate-peroxidase (e.g. APEX, APEX2). In certain example embodiments, the fusion protein may comprise: (a) an MS2 bacteriophage coat protein, and (b) a proximity-dependent biotin protein ligase, or an engineered ascorbate-peroxidase (APEX, APEX2) or an ATP-biotin interaction loop or a biotin pocket thereof. The present invention also involves a polynucleotide which may comprise a nucleotide sequence encoding any of the herein disclosed fusion proteins.

In another embodiment, the present invention relates to a TALE system for targeting a genomic locus of interest, wherein said TALE system may comprise a herein disclosed fusion protein or a polynucleotide encoding a herein disclosed fusion protein, wherein said genome-editing protein thereof is selected from Transcription activator-like effector (TALE) DNA binding domains.

In yet another embodiment, the present invention relates to a CRISPR-Cas system for targeting a genomic locus of interest. The CRISPR-Cas system may comprise a herein disclosed fusion protein or a polynucleotide encoding a herein disclosed fusion protein, wherein said genome-editing protein is selected from Type-II Clustered Regularly Interspaced Short Palindromic Repeats (CRISPR) associated proteins (Cas), and (ii) one or more CRISPR guide RNA(s) that hybridize(s) with a target sequence within the genomic locus of interest, wherein (each of) said guide RNA comprise(s) a guide sequence, a tracr sequence and a tracr mate sequence. The CRISPR-Cas system may comprise a herein disclosed fusion protein or a polynucleotide encoding a herein disclosed fusion protein, wherein said genome-editing protein is selected from Type-II Clustered Regularly Interspaced Short Palindromic Repeats (CRISPR) associated proteins (Cas), and (ii) one or more polynucleotide(s) encoding one or more CRISPR guide RNA(s) that hybridize(s) with a target sequence within the genomic locus of interest, wherein (each of) said guide RNA may comprise a guide sequence, a tracr sequence and a tracr mate sequence. The CRISPR-Cas system may comprise a herein disclosed fusion protein or a polynucleotide encoding a herein disclosed fusion protein, wherein said genome-editing protein is selected from Type-II Clustered Regularly Interspaced Short Palindromic Repeats (CRISPR) associated proteins (Cas), and (ii) target sequence within the respective genomic loci, wherein each of said guide RNAs may comprise a guide sequence, a tracr sequence and a tracr mate sequence. The CRISPR-Cas system may comprise a herein disclosed fusion protein or a polynucleotide encoding a herein disclosed fusion protein, wherein said genome-editing protein is selected from Type-II Clustered Regularly Interspaced Short Palindromic Repeats (CRISPR) associated proteins (Cas), and (ii) one or more polynucleotide(s) encoding a plurality of CRISPR guide RNAs that hybridize respectively with a target sequence within the respective genomic loci, wherein each of said guide RNAs may comprise a guide sequence, a tracr sequence and a tracr mate sequence.

In another embodiment, the invention relates to a method for protein purification, which may comprise (A) selecting a genomic locus of interest in a cell, (B) providing a TALE or a CRISPR-Cas system comprising the fusion proteins disclosed herein, (C) contacting said genomic locus of interest with the component(s) of the system provided at step (B), wherein the proximity-dependent biotin protein ligase, or an ATP-biotin interaction loop or a biotin pocket thereof, is directed to the genomic locus of interest, (D) causing endogenous ATP and free biotin uptake by said cell, so as to allow proximity-dependent biotinylation of one or more proteins located at the genomic locus of interest, and (E) following flushing of free biotin, perform streptavidin-mediated purification of said one or more proteins biotinylated at step (D).

In another embodiment, the invention relates to a method for DNA purification, which may comprise (A) selecting a genomic locus of interest in a cell, (B) providing a TALE or a CRISPR-Cas system, (C) contacting said genomic locus of interest with the component(s) of the system provided at step (B), wherein the proximity-dependent biotin protein ligase, or an ATP-biotin interaction loop or a biotin pocket thereof, is directed to the genomic locus of interest, (D) causing endogenous ATP and free biotin uptake by said cell, so as to allow proximity-dependent biotinylation of DNA at the genomic locus of interest, and possibly proximity-dependent biotinylation of DNA present at other genomic locations, and (E) following flushing of free biotin, perform streptavidin-mediated purification of said DNA biotinylated at step (D).

The present invention also encompases a kit which may comprise any of the herein disclosed fusion proteins, polynucleotides or systems; free biotin; ATP; streptavidin, optionally in a form bound to a solid support such as magnetic beads; and optionally, a set of instructions.

Accordingly, it is an object of the invention not to encompass within the invention any previously known product, process of making the product, or method of using the product such that Applicants reserve the right and hereby disclose a disclaimer of any previously known product, process, or method. It is further noted that the invention does not intend to encompass within the scope of the invention any product, process, or making of the product or method of using the product, which does not meet the written description and enablement requirements of the USPTO (35 U.S.C. § 112, first paragraph) or the EPO (Article 83 of the EPC), such that Applicants reserve the right and hereby disclose a disclaimer of any previously described product, process of making the product, or method of using the product. It may be advantageous in the practice of the invention to be in compliance with Art. 53 (c) EPC and Rule 28 (b) and (c) EPC. Nothing herein is to be construed as a promise.

It is noted that in this disclosure and particularly in the claims and/or paragraphs, terms such as "comprises", "comprised", "comprising" and the like can have the meaning attributed to it in U.S. Patent law; e.g., they can mean "includes", "included", "including", and the like; and that terms such as "consisting essentially of" and "consists essentially of" have the meaning ascribed to them in U.S. Patent law, e.g., they allow for elements not explicitly recited, but exclude elements that are found in the prior art or that affect a basic or novel characteristic of the invention.

These and other embodiments are disclosed or are obvious from and encompassed by, the following Detailed Description.

BRIEF DESCRIPTION OF THE DRAWINGS

The following detailed description, given by way of example, but not intended to limit the invention solely to the specific embodiments described, may best be understood in conjunction with the accompanying drawings.

FIG. 1—depicts a vector map of pLenti2-EF1a-NLS-dCas9-BirAR118G-2A-WPRE.

DETAILED DESCRIPTION OF THE INVENTION

General Definitions

Figure 2:
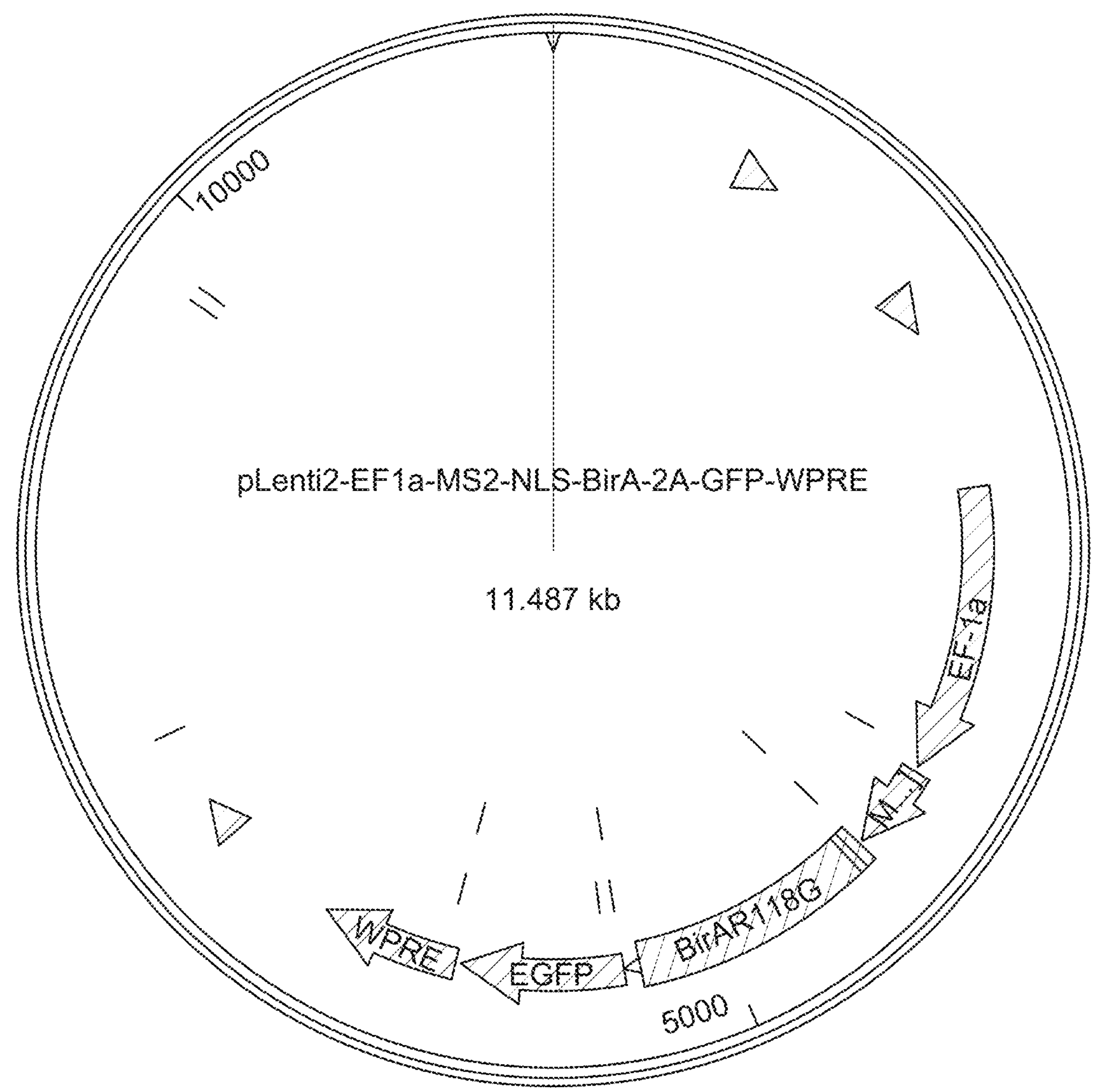
FIG. 2—depicts a vector map of pLenti2-EF1a-MS2-NLS-BirA-2A-GFP-WPRE

Unless defined otherwise, technical and scientific terms used herein have the same meaning as commonly understood by one of ordinary skill in the art to which this disclosure pertains. Definitions of common terms and techniques in molecular biology may be found in Molecular Cloning: A Laboratory Manual, $2^{nd}$ edition (1989) (Sambrook, Fritsch, and Maniatis); Molecular Cloning: A Laboratory Manual, $4^{th}$ edition (2012) (Green and Sambrook); Current Protocols in Molecular Biology (1987) (F. M. Ausubel et al. eds.); the series Methods in Enzymology (Academic Press, Inc.): PCR 2: A Practical Approach (1995) (M. J. MacPherson, B. D. Hames, and G. R. Taylor eds.): Antibodies, A Laboratory Manual (1988) (Harlow and Lane, eds.): Antibodies A Laboratory Manual, $2^{nd}$ edition 2013 (E. A. Greenfield ed.); Animal Cell Culture (1987) (R. I. Freshney, ed.); Benjamin Lewin, Genes IX, published by Jones and Bartlett, 2008 (ISBN 0763752223); Kendrew et al. (eds.), The Encyclopedia of Molecular Biology, published by Blackwell Science Ltd., 1994 (ISBN 0632021829); Robert A. Meyers (ed.), Molecular Biology and Biotechnology: a Comprehensive Desk Reference, published by VCH Publishers, Inc., 1995 (ISBN 9780471185710); Singleton et al., Dictionary of Microbiology and Molecular Biology 2nd ed., J. Wiley & Sons (New York, N.Y. 1994), March, Advanced Organic Chemistry Reactions, Mechanisms and Structure 4th ed., John Wiley & Sons (New York, N.Y. 1992); and Marten H. Hofker and Jan van Deursen, Transgenic Mouse Methods and Protocols, $2^{nd}$ edition (2011).

As used herein, the singular forms "a", "an", and "the" include both singular and plural referents unless the context clearly dictates otherwise.

The term "optional" or "optionally" means that the subsequent described event, circumstance or substituent may or may not occur, and that the description includes instances where the event or circumstance occurs and instances where it does not.

The recitation of numerical ranges by endpoints includes all numbers and fractions subsumed within the respective ranges, as well as the recited endpoints.

The terms "about" or "approximately" as used herein when referring to a measurable value such as a parameter, an amount, a temporal duration, and the like, are meant to encompass variations of and from the specified value, such as variations of +/−10% or less, +/−5% or less, +/−1% or less, and +/−0.1% or less of and from the specified value, insofar such variations are appropriate to perform in the disclosed invention. It is to be understood that the value to which the modifier "about" or "approximately" refers is itself also specifically, and preferably, disclosed.

Reference throughout this specification to "one embodiment", "an embodiment," "an example embodiment," means that a particular feature, structure or characteristic described in connection with the embodiment is included in at least one embodiment of the present invention. Thus, appearances of the phrases "in one embodiment," "in an embodiment," or "an example embodiment" in various places throughout this specification are not necessarily all referring to the same embodiment, but may. Furthermore, the particular features, structures or characteristics may be combined in any suitable manner, as would be apparent to a person skilled in the art from this disclosure, in one or more embodiments. Furthermore, while some embodiments described herein include some but not other features included in other embodiments, combinations of features of different embodiments are meant to be within the scope of the invention. For example, in the appended claims, any of the claimed embodiments can be used in any combination.

All publications, published patent documents, and patent applications cited herein are hereby incorporated by reference to the same extent as though each individual publication, published patent document, or patent application was specifically and individually indicated as being incorporated by reference.

Overview

Embodiments disclosed herein are direction compositions, fusion proteins, polynucleotide constructs, systems, and methods for identifying proteins located at a genomic locus of interest. In one aspect, the embodiments are directed to fusion proteins comprising a nucleotide-editing protein or fragment thereof, and a proximity-dependent protein to catalyze ligation of biotin and variants therefor, or an ATP-biotin interaction loop or a biotin pocket there. In other example embodiments, the fusion protein may comprise a MS2 bacteriophage coat protein or other RNA sequence specific RNA binding proteins and a proximity-dependent enzyme.

In another aspect, the embodiments are directed to polynucleotides encoding the fusion proteins described herein.

In yet another aspects, the embodiments disclosed herein are directed to CRISPR-Cas system comprising the fusion proteins disclosed herein and one or more guide sequences that hybridize to a target sequence. In certain example embodiments, the guide sequence may comprise a tracr sequence and a tracr mate sequence. In certain example embodiments, the buide sequence does not comprise a tracr sequence and/or tracr mate sequence. In certain example embodiments, the CRISPR-Cas sequence may comprise a polynucleotide encoding the one or more guide sequences.

In another aspect, the embodiments disclosed herein are directed to TALE systems comprising the fusion proteins disclosed herein.

In another aspect, the embodiments disclosed herein are directed to methods for protein purification, including from a genomic locus of interest, comprising providing a TALE or CRISPR-Cas system disclosed herein, causing endogenous ATP and free biotin uptake by a cell or population of cells in a sample so as to allow proximity-dependent biotinylation of one or more proteins located at the genomic locus of interest, followed by purification of the biotin labeled proteins in order to identify proteins present at the target locus. In other embodiments, the method may be adapted for biotinylation of DNA at a target locus and isolation of said labeled DNA via the biotin label. Further embodiments are disclosed in detail below.

Proximity-Dependent Protein

Biotin Protein Ligase, BirA and Mutants Thereof.

In certain example embodiments, the proximity-dependent protein is a native or engineered BirA protein, or an orthologue or variant thereof. Proximity dependent protein purification has recently seen some important advances through the application of an enzyme purified from *E. coli* termed BirA. This enzyme in the presence a non-toxic, small molecule (Biotin) and ATP catalyzes a covalent bond between biotin and an amine-group on proximal molecules. Molecules that are covalently bound by biotin can be easily isolated by "pulling-down" the complex using a protein (streptavidin) isolated from the bacterium *Streptomyces*. Streptavidin affinity for biotin is one of the strongest non-covalent bonds found in nature, making it an extremely robust and effective method of purification (Green et al., Adv. Prot. Chem, 1975).

The native (wild-type) BirA displays stringent target specificity requiring the presence of a precise peptide sequence in order for biotinylation to take place. However, a modified form of BirA termed (BirAR118G), has been shown to catalyze biotinylation of any protein within ~10 nm of the enzyme both in vivo and in vitro (Protein Sci. 2004 November; 13 (11): 3043-50. Epub 2004 Sep. 30. *Promiscuous protein biotinylation by Escherichia coli biotin protein ligase*. Choi-Rhee E et al.; Proc Natl Acad Sci USA. 2014 Jun. 17; 111 (24): E2453-61. doi: 10.1073/pnas.1406459111. Epub 2014 Jun. 3. *Probing nuclear pore complex architecture with proximity-dependent biotinylation*. Kim D I et al.). Proximity dependent biotinylation using BirA118G, has successfully been used to purify and identify known and novel protein constituents of large and complicated protein complexes (Proc Natl Acad Sci USA. 2014 Jun. 17; 111 (24): E2453-61. doi: 10.1073/pnas.1406459111. Epub 2014 Jun. 3. *Probing nuclear pore complex architecture with proximity-dependent biotinylation*. Kim D I et al.; J Cell Biol. 2012 Mar. 19; 196 (6): 801-10. doi: 10.1083/jcb.201112098. Epub 2012 Mar. 12. *A promiscuous biotin ligase fusion protein identifies proximal and interacting proteins in mammalian cells*. Roux K J et al.). This system has not as yet been applied to transcription factor complex purification.

In certain example embodiments, the BirA is SEQ ID NO: 1 or a functional variant thereof. In certain example embodiments, the BirA protein is encoded by SEQ. I.D. No. 2.

In certain example embodiments, "proximity-dependent" may refer to nucleic acids or proteins within 10 nm of the fusion proteins disclosed herein.

A "split BirA" by ATP-biotin interaction loop refers to a catalytic and inhibitory loop (residues 112-130) that may partially comprise an active site of BirA. A mutation of R118 to G on this loop significantly decreases substrate specificity permitting promiscuous protein biotinylation by BirA.

In one embodiment, a split biotin protein ligase may be separated at amino acid positions 1-149 and/or 141-320.

A biotin pocket may include a 3 dimensional fold of BirA protein that immobilizes ATP, biotin and biotinyl-AMP within the BirA protein.

Biotin variants and alternative purification tags include, but are not limited to, modified biotin (DSB-X biotin), desthiobiotin, biotin cadaverine, biotin alkyne, D-biotin, DNP-X-Biocytin-X, biocytin hydrazide, ARP (N-(aminooxyacetyl)-N'-(D-Biotinoyl) hydrazine, N-(Biotinoyl)-N'-(Iodoacetyl)Ethylenediamine, Na-(3-Maleimidylpropionyl) Biocytin, sulfo-NHS-LC-Biotin, APEX™ Biotin-XX and biotin ethylenediamine.

Ascorbate Peroxidase

In certain example embodiments, the proximity-dependent protein a native or engineered ascorbate peroxidase, or an orthologue thereof. An example engineered ascorbate peroxidase include APEX, (Hung et al., 2014 Molecular Cell, Proteomic Mapping of the Human Mitochondrial Intermembrane Space in Live Cells via Ratiometric APEX tagging). APEX is an orthogonal approach to using a biotin protein ligase in which upon the addition of biotin-phenol, and $H_2O_2$, proximal tyrosine residues are covalently tagged with biotin, a reaction catalyzed by the dCas9-delivered ascorbate peroxidase. The advantage to this approach is it is precisely induced by peroxide treatment allowing greater control over the timing of biotin labeling, thus mitigating the risk of off target biotinylation. Another example of an engineered ascorbate peroxidase suitable for use in the embodiments disclosed herein is APEX2 (Addgene Ascension Codes: Cx43-GFP-APEX2, 49385; APEX2-NES, 49386). Lam et al. Nature Methods 2015, 12 (1): 51-54. APEX is a triple mutant of wild-type soybean ascorbate peroxidase derived by structure-guided mutagenesis and screening. Example APEX2 sequences are provided in the Sequence Listing submitted herewith at SEQ. I.D. No. 147 and SEQ. I.D. No. 148

Nucleotide-Editing Proteins

TALE Systems

The present invention provides for methods of targeted manipulation of a gene or genomic locus. The manipulation can occur by means of either altering gene expression, particularly by repression or activation or by means of site-specific gene-editing particularly by the generation of site specific double-strand breaks followed by non-homologous repair or homology directed repair. In some embodiments, the methods of the invention use deoxyribonucleic acid (DNA)-bind ing polypeptides or proteins comprising one or more Transcription activator-like effector (TALE) monomers and half-monomers attached to additional sequences which include functional protein domains, to function as proteins that include but are not limited to engineered transcription factors (TALE-TFs) such as repressors and activators, engineered nucleases (TALENs), recombinases, transposases, integrases, methylases, demethylases and invertases. With regards to TALEs, mention is also made of U.S. patent application Ser. Nos. 13/016,297, 13/019,526, 13/362,660, 13/218,050, 12/965,590, 13/068,735 and PCT application PCT/IB2010/000154, the disclosures of which are incorporated by reference herein in their entirety. In a preferred embodiment the gene or genomic locus is present in an animal or non-plant cell. Reference is made to U.S. Pat. Nos. 8,450,107; 8,481,309; 8,507,272 and 8,614,092; U.S. Ser. No. 13/554,922 filed on Jul. 20, 2012; Ser. No. 13/732,287 filed on Dec. 31, 2012 and Ser. No. 14/292,278 filed on May 30, 2014 and international application serial no. PCT/US12/67428 filed on Nov. 30, 2012, the disclosures of which are incorporated by reference. In a preferred embodiment the gene or genomic locus is present in an animal or non-plant cell.

The present invention provides for a method of repressing expression of a genomic locus of interest in an animal cell, comprising contacting the genomic locus with a non-naturally occurring or engineered composition comprising a DNA binding polypeptide comprising: a N-terminal capping region, a DNA binding domain comprising at least five or more TALE monomers and at least one or more half-monomers specifically ordered to target the genomic locus of interest, and a C-terminal capping region, wherein these three parts of the polypeptide are arranged in a predetermined N-terminus to C-terminus orientation, wherein the polypeptide includes at least one or more repressor domains, and wherein the polypeptide is encoded by and translated from a codon optimized nucleic acid molecule so that the polypeptide preferentially binds to DNA of the genomic locus. In a preferred embodiment the animal is a mammal.

The present invention provides for a method of selectively targeting a genomic locus of interest in an animal cell, comprising contacting the genomic locus with a non-naturally occurring or engineered composition comprising a DNA binding polypeptide comprising: a N-terminal capping region, a DNA binding domain comprising at least five or more TALE monomers and at least one or more half-monomers specifically ordered to target the genomic locus of interest, and a C-terminal capping region, wherein these three parts of the polypeptide are arranged in a predetermined N-terminus to C-terminus orientation, wherein the polypeptide includes at least one or more effector domains, wherein the polypeptide is encoded by and translated from a codon optimized nucleic acid molecule so that the polypeptide preferentially binds to DNA of the genomic locus, wherein the DNA binding domain comprises $(X_{1-11}\text{-}X_{12}\text{-}X_{13}\text{-}X_{14\text{-}33\ or\ 34\ or\ 35})_z$, wherein $X_{1-11}$ is a chain of 11 contiguous amino acids, wherein $X_{12}X_{13}$ is a repeat variable diresidue (RVD), wherein $X_{14\text{-}33\ or\ 34\ or\ 35}$ is a chain of 21, 22 or 23 contiguous amino acids, wherein z is at least 5 to 40, more preferably at least 10 to 26 and wherein at least one RVD is selected from the group consisting of (a) HH, KH, NH, NK, NQ, RH, RN, SS for recognition of guanine (G); (b) SI for recognition of adenine (A); (c) HG, KG, RG for recognition of thymine (T); (d) RD, SD for recognition of cytosine (C); (e) NV, HN for recognition of A or G and (f) H*, HA, KA, N*, NA, NC, NS, RA, S*for recognition of A or T or G or C, wherein (*) means that the amino acid at $X_{13}$ is absent. In a preferred embodiment the animal is a mammal.

The present invention provides for a method of selectively targeting a genomic locus of interest in an animal cell, comprising contacting the genomic locus with a non-naturally occurring or engineered composition comprising a DNA binding polypeptide comprising: a N-terminal capping region, a DNA binding domain comprising at least five or more TALE monomers and at least one or more half-monomers specifically ordered to target the genomic locus of interest, and a C-terminal capping region, wherein these three parts of the polypeptide are arranged in a predetermined N-terminus to C-terminus orientation, wherein the polypeptide includes at least one or more effector domains, wherein the polypeptide is encoded by and translated from a codon optimized nucleic acid molecule so that the polypeptide preferentially binds to DNA of the genomic locus, wherein the DNA binding domain comprises $(X_{1-11}\text{-}X_{12}X_{13}\text{-}X_{14-33\ or\ 34\ or\ 35})_z$, wherein $X_{1-11}$ is a chain of 11 contiguous amino acids, wherein $X_{12}X_{13}$ is a repeat variable diresidue (RVD), wherein $X_{14-33\ or\ 34\ or\ 35}$ is a chain of 21, 22 or 23 contiguous amino acids, wherein z is at least 5 to 40, more preferably at least 10 to 26 and wherein at least one RVD is selected from the group consisting of (a) HH, KH, NH, NK, NQ, RH, RN, SS for recognition of guanine (G); (b) SI for recognition of adenine (A); (c) HG, KG, RG for recognition of thymine (T); (d) RD, SD for recognition of cytosine (C); (e) NV, HN for recognition of A or G and (f) H*, HA, KA, N*, NA, NC, NS, RA, S*for recognition of A or T or G or C, wherein (*) means that the amino acid at $X_{13}$ is absent. In a preferred embodiment the animal is a mammal.

The present invention provides for a method of altering expression of a genomic locus of interest, preferably in an animal or non-plant cell, comprising contacting the genomic locus with a non-naturally occurring or engineered composition comprising a DNA binding polypeptide comprising a N-terminal capping region, a DNA binding domain comprising at least one or more TALE monomers or half-monomers specifically ordered to target the genomic locus of interest and a C-terminal capping region, wherein these three parts of the polypeptide are arranged in a predetermined N-terminus to C-terminus orientation and wherein the polypeptide includes at least one or more regulatory or functional protein domains. In an advantageous embodiment of the invention the polypeptide is encoded by and expressed from a codon optimized nucleic acid molecule so that the polypeptide preferentially binds to DNA of the genomic locus. In a preferred embodiment the animal is a mammal.

The present invention provides for a method of repressing expression of a genomic locus of interest, preferably in a mammalian cell, comprising contacting the genomic locus with a non-naturally occurring or engineered composition comprising a DNA binding polypeptide comprising a N-terminal capping region, a DNA binding domain comprising at least one or more TALE monomers or half-monomers specifically ordered to target the genomic locus of interest and a C-terminal capping region, wherein these three parts of the polypeptide are arranged in a predetermined N-terminus to C-terminus orientation and wherein the polypeptide includes at least one or more repressor domains. In an advantageous embodiment of the invention the polypeptide is encoded by and expressed from a codon optimized nucleic acid molecule so that the polypeptide preferentially binds to the DNA of the genomic locus.

The present invention provides for a method of repressing expression of a gene in a cell or cell line (preferably of mammalian origin), comprising contacting specific nucleic acids associated with the gene with a non-naturally occurring or engineered composition comprising a DNA binding polypeptide comprising a N-terminal capping region, a DNA binding domain comprising at least one or more TALE monomers or half-monomers specifically ordered to target the genomic locus of interest and a C-terminal capping region, wherein these three parts of the polypeptide are arranged in a predetermined N-terminus to C-terminus orientation and wherein the polypeptide includes at least one or more repressor domains. In an advantageous embodiment of the invention the polypeptide is encoded by and expressed from a codon optimized nucleic acid molecule so that the polypeptide preferentially binds to DNA of the genomic locus.

The present invention also provides for a method of activating expression of a genomic locus of interest, preferably in a mammalian cell, comprising contacting the genomic locus with a non-naturally occurring or engineered composition comprising a DNA binding polypeptide comprising a N-terminal capping region, a DNA binding domain comprising at least one or more TALE monomers or half-monomers specifically ordered to target the genomic locus of interest and a C-terminal capping region, wherein these three parts are arranged in a predetermined N-terminus to C-terminus orientation and wherein the polypeptide includes at least one or more activator domains. In an advantageous embodiment of the invention the polypeptide is encoded by and expressed from a codon optimized nucleic acid molecule so that the polypeptide preferentially binds to the DNA of the genomic locus.

The present invention also provides for a method of activating expression of a gene in a cell or cell line (preferably of mammalian origin), comprising contacting specific nucleic acids associated with the gene with a non-naturally occurring or engineered composition comprising a DNA binding polypeptide comprising a N-terminal capping region, a DNA binding domain comprising at least one or more TALE monomers or half-monomers specifically ordered to target the genomic locus of interest and a C-terminal capping region, wherein these three parts are arranged in a predetermined N-terminus to C-terminus orientation and wherein the polypeptide includes at least one or more activator domains. In an advantageous embodiment of the invention the polypeptide is encoded by and expressed from a codon optimized nucleic acid molecule so that the polypeptide preferentially binds to DNA of the genomic locus.

The present invention also provides for a non-naturally occurring or engineered composition for preferentially binding to DNA of a genomic locus or of a gene in a cell or cell line, preferably of an animal or non-plant origin, wherein the composition comprises a DNA binding polypeptide comprising: a N-terminal capping region, a DNA binding domain comprising at least one or more TALE monomers or half-monomers specifically ordered to target the genomic locus of interest and a C-terminal capping region, wherein these three parts of the polypeptide are arranged in a predetermined N-terminus to C-terminus orientation and wherein the polypeptide includes at least one or more regulatory or functional protein domains. In an advantageous embodiment of the invention the polypeptide is encoded by and expressed from a codon optimized nucleic acid molecule so that the polypeptide preferentially binds to DNA of the genomic locus or gene.

The present invention also provides for a non-naturally occurring or engineered composition for preferentially binding to DNA of a genomic locus or of a gene in a cell or cell line, preferably of mammalian origin, wherein the composition comprises a DNA binding polypeptide comprising: a N-terminal capping region, a DNA binding domain comprising at least one or more TALE monomers or half-monomers specifically ordered to target the genomic locus of interest and a C-terminal capping region, wherein these three parts of the polypeptide are arranged in a predetermined N-terminus to C-terminus orientation and wherein the polypeptide includes at least one or more repressor domains. In an advantageous embodiment of the invention the polypeptide is encoded by and expressed from a codon optimized nucleic acid molecule so that the polypeptide preferentially binds to DNA of the genomic locus or gene.

The present invention also provides for a non-naturally occurring or engineered composition for preferentially binding to DNA of a genomic locus or of a gene in a cell or cell line, preferably of mammalian origin, wherein the composition comprises a DNA binding polypeptide comprising: a N-terminal capping region, a DNA binding domain comprising at least one or more TALE monomers or half-monomers specifically ordered to target the genomic locus of interest and a C-terminal capping region, wherein these three parts of the polypeptide are arranged in a predetermined N-terminus to C-terminus orientation and wherein the polypeptide includes at least one or more activator domains. In an advantageous embodiment of the invention the polypeptide is encoded by and expressed from a codon optimized nucleic acid molecule so that the polypeptide preferentially binds to DNA of the genomic locus or gene.

The present invention also provides for a method of modifying the sequence of a mammalian genomic locus of interest, comprising contacting the genomic locus with a non-naturally occurring or engineered composition comprising a DNA binding polypeptide comprising a N-terminal capping region, a DNA binding domain comprising at least one or more TALE monomers or half-monomers specifically ordered to target the genomic locus of interest and a C-terminal capping region, wherein these three parts are arranged in a predetermined N-terminus to C-terminus orientation and wherein the DNA binding domain is attached to a catalytic domain of a restriction endonuclease. In an advantageous embodiment of the invention the polypeptide is encoded by and expressed from a codon optimized nucleic acid molecule so that the polypeptide preferentially binds to mammalian DNA. In an advantageous embodiment of the invention the sequence is modified by the introduction of a site-specific double strand break in the sequence which facilitates genome editing through non-homologous repair or homology directed repair. In an advantageous embodiment, an exogenous nucleic acid or DNA is introduced into the genomic locus. In an additional advantageous embodiment, integration into the genome occurs through non-homology dependent targeted integration. In certain preferred embodiments, the exogenous polynucleotide comprises a recombinase recognition site (e.g. loxP or FLP) for recognition by a cognate recombinase (e.g. Cre or FRT, respectively). In certain embodiments, the exogenous sequence is integrated into the genome of an animal.

The present invention also provides for a method of modifying the sequence of a gene in a cell or cell line (preferably of mammalian origin), comprising contacting specific nucleic acids associated with the gene with a non-naturally occurring or engineered composition comprising a DNA binding polypeptide comprising a N-terminal capping region, a DNA binding domain comprising at least one or more TALE monomers or half-monomers specifically ordered to target the genomic locus of interest and a C-terminal capping region, wherein these three parts are arranged in a predetermined N-terminus to C-terminus orientation and wherein the DNA binding domain is attached to a catalytic domain of a restriction endonuclease. In an advantageous embodiment of the invention the polypeptide is encoded by and expressed from a codon optimized nucleic acid molecule so that the polypeptide preferentially binds to mammalian DNA. In an advantageous embodiment of the invention the sequence is modified by the introduction of a site-specific double strand break in the sequence which facilitates genome editing through non-homologous repair or homology directed repair. In an advantageous embodiment, an exogenous nucleic acid or DNA is introduced into the gene present in the cell or cell line. In an advantageous embodiment, an exogenous nucleic acid or DNA is introduced into the genomic locus. In an additional advantageous embodiment, integration into the genome occurs through non-homology dependent targeted integration. In certain preferred embodiments, the exogenous polynucleotide comprises a recombinase recognition site (e.g. loxP or FLP) for recognition by a cognate recombinase (e.g. Cre or FRT, respectively). In certain embodiments, the exogenous sequence is integrated into the genome of an animal.

The present invention also provides for a method of construction and generation of the DNA binding polypeptides described herein comprising a N-terminal capping region, a DNA binding domain comprising at least one or more TALE monomers or half-monomers specifically ordered to target the genomic locus of interest and a C-terminal capping region. In an advantageous embodiment of the invention the polypeptide is encoded by and expressed from a codon optimized nucleic acid molecule so that the polypeptide preferentially binds to mammalian DNA. In a further advantageous embodiment, the construction of the DNA binding domain in the polypeptide uses hierarchical ligation assembly.

The present invention also provides for a method of selectively recognizing a specific nucleic acid sequence with a DNA binding polypeptide, wherein the polypeptide is constructed to include at least one or more TALE monomers and half monomers ordered or arranged in a particular orientation dictated by the sequence of the specific nucleic acid linked to additional TALE protein sequences, for efficiently recognizing the specific nucleic acid sequence.

The present invention also provides for pharmaceutical compositions comprising the DNA binding polypeptide or the nucleic acids encoding them. In a preferred embodiment the composition comprises one or more pharmaceutically acceptable excipients.

In addition, advantageous embodiments of the invention include host cells, cell lines and transgenic organisms (e.g., plants, fungi, animals) comprising these DNA-binding polypeptides/nucleic acids and/or modified by these polypeptides (e.g., genomic modification that is passed into the next generation). Further preferred embodiments include cells and cell lines which include but are not limited to plant cells, insect cells, bacterial cells, yeast cells, viral cells, human cells, primate cells, rat cells, mouse cells, zebrafish cells, madin-darby canine cells, hamster cells, *xenopus* cells and stem cells. An advantageous embodiment of the invention is the cell and cell lines being of mammalian origin. In a preferred embodiment, the DNA binding polypeptide further comprises a reporter or selection marker. In advantageous embodiments the selection marker may be a fluorescent marker, while in other aspects, the reporter is an enzyme.

Further advantageous embodiments of the invention include host cells comprising these polypeptides/nucleic acids and/or modified by these polypeptides (e.g., genomic modification that is passed into the next generation). The host cell may be stably transformed or transiently transfected or a combination thereof with one or more of these protein expression vectors. In other embodiments, the one or more protein expression vectors express one or more fusion proteins in the host cell. In another embodiment, the host cell may further comprise an exogenous polynucleotide donor sequence. Any prokaryotic or eukaryotic host cells can be employed, including, but not limited to, bacterial, plant, fish, yeast, algae, insect, worm or mammalian cells. In some embodiments, the host cell is a plant cell. In other aspects, the host cell is part of a plant tissue such as the vegetative parts of the plant, storage organs, fruit, flower and/or seed tissues. In further embodiments, the host cell is an algae cell. In other embodiments, the host cell is a fibroblast. In any of the embodiments, described herein, the host cell may comprise a stem cell, for example an embryonic stem cell. The stem cell may be a mammalian stem cell, for example, a hematopoietic stem cell, a mesenchymal stem cell, an embryonic stem cell, a neuronal stem cell, a muscle stem cell, a liver stem cell, a skin stem cell, an induced pluripotent stem cell and/or combinations thereof. In certain embodiments, the stem cell is a human induced pluripotent stem cell (hiPSC) or a human embryonic stem cell (hESC). In any of the embodiments, described herein, the host cell can comprise an embryo cell, for example one or more mouse, rat, rabbit or other mammal cell embryos. In some aspects, stem cells or embryo cells are used in the development of transgenic animals, including, for example, animals with TALE-mediated genomic modifications that are integrated into the germline such that the mutations are heritable. In further aspects, these transgenic animals are used for research purposes, i.e., mice, rats, rabbits; while in other aspects, the transgenic animals are livestock animals, i.e., cows, chickens, pigs, sheep, etc. In still further aspects, the transgenic animals are those used for therapeutic purposes, i.e. goats, cows, chickens, pigs; and in other aspects, the transgenic animals are companion animals, i.e. cats, dogs, horses, birds or fish.

The present invention also provides a method for identifying suitable or novel target sequences or binding sites for engineered or designed DNA binding proteins. In some advantageous embodiments, the target site identified has an increased number of guanine nucleotides ("G") as compared to a natural or wild-type TALE target sequence. In other embodiments, the target does not require flanking thymidine nucleotides ("T"), as typical in naturally occurring TALE proteins. In some embodiments, the repeat-variable diresidues (RVDs) (the 2 hypervariable amino acids at position 12 and 13 in the TALE monomer the combination of which dictate nucleotide specificity) selected for use in the engineered DNA-binding polypeptides of the invention are one or more of NH (asparagine-histidine), RN (arginine-asparagine) or KH (lysine-histidine) RVDs for the recognition of G nucleotides in the target sequence. Hence, additionally provided in this invention are novel (non-naturally occurring) RVDs, differing from those found in nature, which are capable of recognizing nucleotide bases. Non-limiting examples of atypical or non-naturally occurring RVDs (amino acid sequences at positions 12 and 13 of the TALE monomer), selection of RVDs may be made on the basis of their measured activity, specificity or affinity for a particular nucleotide (as described in Example 3).

Another advantageous embodiment of the invention is that in any of the compositions or methods described herein, the regulatory or functional domain may be selected from the group consisting of a transcriptional repressor, a transcriptional activator, a nuclease domain, a DNA methyl transferase, a protein acetyltransferase, a protein deacetylase, a protein methyltransferase, a protein deaminase, a protein kinase, and a protein phosphatase. In some aspects, the functional domain is an epigenetic regulator. In plants, such a TALE fusion can be removed by out-crossing using standard techniques.

A further advantageous embodiment of the invention is that in any of the compositions or methods described herein, the DNA-binding polypeptide may be encoded by a nucleic acid operably linked to a promoter, wherein the methods of altering gene expression comprise the step of first administering the nucleic acid encoding the polypeptide to a cell. In preferred embodiments the promoter may be constitutive, inducible or tissue-specific. The polypeptide of the invention may be expressed from an expression vector which include but are not limited a retroviral expression vector, an adenoviral expression vector, a lentiviral vector, a DNA plasmid expression vector and an AAV expression vector.

The present invention also provides DNA binding polypeptides with effector domains that may be constructed to specifically target nucleic acids associated with genes that encode for proteins which include but are not limited to transcription factors, proteins that may be involved with the transport of neurotransmitters, neurotransmitter synthases, synaptic proteins, plasticity proteins, presynaptic active zone proteins, post synaptic density proteins, neurotransmitter receptors, epigenetic modifiers, neural fate specification factors, axon guidance molecules, ion channels, CpG binding proteins, proteins involved in ubiquitination, hormones, homeobox proteins, growth factors, oncogenes, and proto-oncogenes.

Nucleic acids associated with a gene may be upstream of, or adjacent to, a transcription initiation site of the gene. Alternatively, the target site may be adjacent to an RNA polymerase pause site downstream of a transcription initiation site of the endogenous cellular gene. In still further embodiments, certain DNA binding proteins, e.g., TALENs bind to a site within the coding sequence of a gene or in a non-coding sequence within or adjacent to the gene; such as for example, a leader sequence, trailer sequence or intron, or within a non-transcribed region, either upstream or downstream of the coding region. Hence in preferred embodiments, polypeptides of the invention may be constructed to function as nucleases, activators or repressors to alter the expression of any of the genes which encode proteins that include but are not limited to those listed in the previous paragraph.

The present invention also provides compositions and methods for in vivo genomic manipulation. In certain embodiments, mRNAs encoding DNA binding proteins comprising one or more functional or regulatory protein domains may be injected into germ line cells or embryos for introducing specific double strand breaks as required.

CRISPR-Cas Systems: Enzymes and Guides

In certain example embodiments, the nucleotide-editing protein or fragment thereof is a CRISPR-Cas protein. With respect to general information on CRISPR-Cas Systems, components thereof, and delivery of such components, including methods, materials, delivery vehicles, vectors, particles, AAV, and making and using thereof, including as to amounts and formulations, all useful in the practice of the instant invention, reference is made to: U.S. Pat. Nos. 8,999,641, 8,993,233, 8,945,839, 8,932,814, 8,906,616, 8,895,308, 8,889,418, 8,889,356, 8,871,445, 8,865,406, 8,795,965, 8,771,945 and 8,697,359; US Patent Publications US 2014-0310830 (U.S. application Ser. No. 14/105,031), US 2014-0287938 A1 (U.S. application Ser. No. 14/213,991), US 2014-0273234 A1 (U.S. application Ser. No. 14/293,674), US2014-0273232 A1 (U.S. application Ser. No. 14/290,575), US 2014-0273231 (U.S. application Ser. No. 14/259,420), US 2014-0256046 A1 (U.S. application Ser. No. 14/226,274), US 2014-0248702 A1 (U.S. application Ser. No. 14/258,458), US 2014-0242700 A1 (U.S. application Ser. No. 14/222,930), US 2014-0242699 A1 (U.S. application Ser. No. 14/183,512), US 2014-0242664 A1 (U.S. application Ser. No. 14/104,990), US 2014-

0234972 A1 (U.S. application Ser. No. 14/183,471), US 2014-0227787 A1 (U.S. application Ser. No. 14/256,912), US 2014-0189896 A1 (U.S. application Ser. No. 14/105, 035), US 2014-0186958 (U.S. application Ser. No. 14/105, 017), US 2014-0186919 A1 (U.S. application Ser. No. 14/104,977), US 2014-0186843 A1 (U.S. application Ser. No. 14/104,900), US 2014-0179770 A1 (U.S. application Ser. No. 14/104,837) and US 2014-0179006 A1 (U.S. application Ser. No. 14/183,486), US 2014-0170753 (U.S. application Ser. No. 14/183,429); European Patents EP 2 784 162 B1 and EP 2 771 468 B1; European Patent Applications EP 2 771 468 (EP13818570.7), EP 2 764 103 (EP13824232.6), and EP 2 784 162 (EP14170383.5); and PCT Patent Publications PCT Patent Publications WO 2014/093661 (PCT/US2013/074743), WO 2014/093694 (PCT/US2013/074790), WO 2014/093595 (PCT/US2013/074611), WO 2014/093718 (PCT/US2013/074825), WO 2014/093709 (PCT/US2013/074812), WO 2014/093622 (PCT/US2013/074667), WO 2014/093635 (PCT/US2013/074691), WO 2014/093655 (PCT/US2013/074736), WO 2014/093712 (PCT/US2013/074819), WO 2014/093701 (PCT/US2013/074800), WO 2014/018423 (PCT/US2013/051418), WO 2014/204723 (PCT/US2014/041790), WO 2014/204724 (PCT/US2014/041800), WO 2014/204725 (PCT/US2014/041803), WO 2014/204726 (PCT/US2014/041804), WO 2014/204727 (PCT/US2014/041806), WO 2014/204728 (PCT/US2014/041808), WO 2014/204729 (PCT/US2014/041809). Reference is also made to U.S. provisional patent applications 61/758,468; 61/802,174; 61/806,375; 61/814, 263; 61/819,803 and 61/828,130, filed on Jan. 30, 2013; Mar. 15, 2013; Mar. 28, 2013; Apr. 20, 2013; May 6, 2013 and May 28, 2013 respectively. Reference is also made to U.S. provisional patent application 61/836,123, filed on Jun. 17, 2013. Reference is additionally made to U.S. provisional patent applications 61/835,931, 61/835,936, 61/836,127, 61/836,101, 61/836,080 and 61/835,973, each filed Jun. 17, 2013. Further reference is made to U.S. provisional patent applications 61/862,468 and 61/862,355 filed on Aug. 5, 2013; 61/871,301 filed on Aug. 28, 2013; 61/960,777 filed on Sep. 25, 2013 and 61/961,980 filed on Oct. 28, 2013. Reference is yet further made to: PCT Patent applications Nos: PCT/US2014/041803, PCT/US2014/041800, PCT/US2014/041809, PCT/US2014/041804 and PCT/US2014/041806, each filed Jun. 10, 2014 Jun. 10, 2014; PCT/US2014/041808 filed Jun. 11, 2014; and PCT/US2014/62558 filed Oct. 28, 2014, and U.S. Provisional Patent Applications Ser. Nos. 61/915,150, 61/915,301, 61/915,267 and 61/915,260, each filed Dec. 12, 2013; 61/757,972 and 61/768,959, filed on Jan. 29, 2013 and Feb. 25, 2013; 61/835,936, 61/836,127, 61/836,101, 61/836,080, 61/835, 973, and 61/835,931, filed Jun. 17, 2013; 62/010,888 and 62/010,879, both filed Jun. 11, 2014; 62/010,329 and 62/010,441, each filed Jun. 10, 2014; 61/939,228 and 61/939,242, each filed Feb. 12, 2014; 61/980,012, filed Apr. 15,2014; 62/038,358, filed Aug. 17, 2014; 62/054,490, 62/055,484, 62/055,460 and 62/055,487, each filed Sep. 25, 2014; and 62/069,243, filed Oct. 27, 2014. Reference is also made to U.S. provisional patent applications Nos. 62/055, 484, 62/055,460, and 62/055,487, filed Sep. 25, 2014; U.S. provisional patent application 61/980,012, filed Apr. 15, 2014; and U.S. provisional patent application 61/939,242 filed Feb. 12, 2014. Reference is made to PCT application designating, inter alia, the United States, application No. PCT/US14/41806, filed Jun. 10, 2014. Reference is made to U.S. provisional patent application 61/930,214 filed on Jan. 22, 2014. Reference is made to U.S. provisional patent applications 61/915,251; 61/915,260 and 61/915,267, each filed on Dec. 12, 2013. Reference is made to US provisional patent application U.S. Ser. No. 61/980,012 filed Apr. 15, 2014. Reference is made to PCT application designating, inter alia, the United States, application No. PCT/US14/41806, filed Jun. 10, 2014. Reference is made to U.S. provisional patent application 61/930,214 filed on Jan. 22, 2014. Reference is made to U.S. provisional patent applications 61/915,251; 61/915,260 and 61/915,267, each filed on Dec. 12, 2013.

Mention is also made of U.S. application 62/091,455, filed, 12 Dec. 2014, PROTECTED GUIDE RNAS (PGRNAS); US application 62/096,708, 24 Dec. 2014, PROTECTED GUIDE RNAS (PGRNAS); U.S. application 62/091,462, 12 Dec. 2014, DEAD GUIDES FOR CRISPR TRANSCRIPTION FACTORS; U.S. application 62/096, 324, 23 Dec. 2014, DEAD GUIDES FOR CRISPR TRANSCRIPTION FACTORS; U.S. application 62/091,456, 12 Dec. 2014, ESCORTED AND FUNCTIONALIZED GUIDES FOR CRISPR-CAS SYSTEMS; U.S. application 62/091,461, 12 Dec. 2014, DELIVERY, USE AND THERAPEUTIC APPLICATIONS OF THE CRISPR-CAS SYSTEMS AND COMPOSITIONS FOR GENOME EDITING AS TO HEMATOPOETIC STEM CELLS (HSCs); U.S. application 62/094,903, 19 Dec. 2014, UNBIASED IDENTIFICATION OF DOUBLE-STRAND BREAKS AND GENOMIC REARRANGEMENT BY GENOME-WISE INSERT CAPTURE SEQUENCING; US application 62/096,761, 24 Dec. 2014, ENGINEERING OF SYSTEMS, METHODS AND OPTIMIZED ENZYME AND GUIDE SCAFFOLDS FOR SEQUENCE MANIPULATION; U.S. application 62/098,059, 30 Dec. 2014, RNA-TARGETING SYSTEM; U.S. application 62/096,656, 24 Dec. 2014, CRISPR HAVING OR ASSOCIATED WITH DESTABILIZATION DOMAINS; U.S. application 62/096,697, 24 Dec. 2014, CRISPR HAVING OR ASSOCIATED WITH AAV; US application 62/098,158, 30 Dec. 2014, ENGINEERED CRISPR COMPLEX INSERTIONAL TARGETING SYSTEMS; U.S. application 62/151,052, 22 Apr. 2015, CELLULAR TARGETING FOR EXTRACELLULAR EXOSOMAL REPORTING; U.S. application 62/054,490, 24 Sep. 2014, DELIVERY, USE AND THERAPEUTIC APPLICATIONS OF THE CRISPR-CAS SYSTEMS AND COMPOSITIONS FOR TARGETING DISORDERS AND DISEASES USING PARTICLE DELIVERY COMPONENTS; U.S. application 62/055,484, 25 Sep. 2014, SYSTEMS, METHODS AND COMPOSITIONS FOR SEQUENCE MANIPULATION WITH OPTIMIZED FUNCTIONAL CRISPR-CAS SYSTEMS; U.S. application 62/087,537, 4 Dec. 2014, SYSTEMS, METHODS AND COMPOSITIONS FOR SEQUENCE MANIPULATION WITH OPTIMIZED FUNCTIONAL CRISPR-CAS SYSTEMS; U.S. application 62/054,651, 24 Sep. 2014, DELIVERY, USE AND THERAPEUTIC APPLICATIONS OF THE CRISPR-CAS SYSTEMS AND COMPOSITIONS FOR MODELING COMPETITION OF MULTIPLE CANCER MUTATIONS IN VIVO; U.S. application 62/067,886, 23 Oct. 2014, DELIVERY, USE AND THERAPEUTIC APPLICATIONS OF THE CRISPR-CAS SYSTEMS AND COMPOSITIONS FOR MODELING COMPETITION OF MULTIPLE CANCER MUTATIONS IN VIVO; US application 24 Sep. 2014, DELIVERY, USE AND THERAPEUTIC APPLICATIONS OF THE CRISPR-CAS SYSTEMS AND COMPOSITIONS IN NEURONAL CELLS/TISSUES; U.S. application 62/054,528, 24 Sep. 2014, DELIVERY, USE AND THERAPEUTIC APPLICATIONS OF THE CRISPR-CAS SYSTEMS AND COMPOSITIONS IN IMMUNE DISEASES OR DISORDERS; U.S. application 62/055,454, 25 Sep. 2014, DELIVERY, USE AND THERAPEUTIC APPLICATIONS OF THE CRISPR-CAS SYSTEMS AND COMPOSITIONS FOR TARGETING DISORDERS AND DISEASES USING CELL PENETRATION PEPTIDES (CPP); U.S. application 62/055,460, 25 Sep. 2014, MULTIFUNCTIONAL-CRISPR COMPLEXES AND/OR OPTIMIZED ENZYME LINKED FUNCTIONAL-CRISPR COMPLEXES; U.S. application 62/087,475, 4 Dec. 2014, FUNCTIONAL SCREENING WITH OPTIMIZED FUNCTIONAL CRISPR-CAS SYSTEMS; U.S. application 62/055,487, 25 Sep. 2014, FUNCTIONAL SCREENING WITH OPTIMIZED FUNCTIONAL CRISPR-CAS SYSTEMS; U.S. application 62/087,546, 4 Dec. 2014, MULTIFUNCTIONAL CRISPR COMPLEXES AND/OR OPTIMIZED ENZYME LINKED FUNCTIONAL-CRISPR COMPLEXES; and U.S. application 62/098,285, 30 Dec. 2014, CRISPR MEDIATED IN VIVO MODELING AND GENETIC SCREENING OF TUMOR GROWTH AND METASTASIS.

Each of these patents, patent publications, and applications, and all documents cited therein or during their prosecution ("appln cited documents") and all documents cited or referenced in the appln cited documents, together with any instructions, descriptions, product specifications, and product sheets for any products mentioned therein or in any document therein and incorporated by reference herein, are hereby incorporated herein by reference, and may be employed in the practice of the invention. All documents (e.g., these patents, patent publications and applications and the appln cited documents) are incorporated herein by reference to the same extent as if each individual document was specifically and individually indicated to be incorporated by reference.

Also with respect to general information on CRISPR-Cas Systems, mention is made of the following (also hereby incorporated herein by reference):

Multiplex genome engineering using CRISPR/Cas systems. Cong, L., Ran, F. A., Cox, D., Lin, S., Barretto, R., Habib, N., Hsu, P. D., Wu, X., Jiang, W., Marraffini, L. A., & Zhang, F. Science February 15; 339 (6121): 819-23 (2013);

RNA-guided editing of bacterial genomes using CRISPR-Cas systems. Jiang W., Bikard D., Cox D., Zhang F, Marraffini L A. Nat Biotechnol March; 31 (3): 233-9 (2013);

One-Step Generation of Mice Carrying Mutations in Multiple Genes by CRISPR/Cas-Mediated Genome Engineering. Wang H., Yang H., Shivalila C S., Dawlaty M M., Cheng A W., Zhang F., Jaenisch R. Cell May 9; 153 (4): 910-8 (2013);

Optical control of mammalian endogenous transcription and epigenetic states. Konermann S, Brigham M D, Trevino A E, Hsu P D, Heidenreich M, Cong L, Platt R J, Scott D A, Church G M, Zhang F. Nature. August 22; 500 (7463): 472-6. doi: 10.1038/Nature12466. Epub 2013 Aug. 23 (2013);

Double Nicking by RNA-Guided CRISPR Cas9 for Enhanced Genome Editing Specificity. Ran, F A., Hsu, P D., Lin, C Y., Gootenberg, J S., Konermann, S., Trevino, A E., Scott, D A., Inoue, A., Matoba, S., Zhang, Y., & Zhang, F. Cell August 28. pii: S0092-8674 (13) 01015-5 (2013-A);

DNA targeting specificity of RNA-guided Cas9 nucleases. Hsu, P., Scott, D., Weinstein, J., Ran, F A., Konermann, S., Agarwala, V., Li, Y., Fine, E., Wu, X., Shalem, O., Cradick, T J., Marraffini, L A., Bao, G., & Zhang, F. Nat Biotechnol doi: 10.1038/nbt.2647 (2013);

Genome engineering using the CRISPR-Cas9 system. Ran, F A., Hsu, P D., Wright, J., Agarwala, V., Scott, D A., Zhang, F. Nature Protocols November; 8 (11): 2281-308 (2013-B);

Genome-Scale CRISPR-Cas9 Knockout Screening in Human Cells. Shalem, O., Sanjana, N E., Hartenian, E., Shi, X., Scott, D A., Mikkelson, T., Heckl, D., Ebert, B L., Root, D E., Doench, J G., Zhang, F. Science December 12. (2013). [Epub ahead of print];

Crystal structure of cas9 in complex with guide RNA and target DNA. Nishimasu, H., Ran, F A., Hsu, P D., Konermann, S., Shehata, S I., Dohmae, N., Ishitani, R., Zhang, F., Nureki, O. Cell February 27, 156 (5): 935-49 (2014);

Genome-wide binding of the CRISPR endonuclease Cas9 in mammalian cells. Wu X., Scott D A., Kriz A J., Chiu A C., Hsu P D., Dadon D B., Cheng A W., Trevino A E., Konermann S., Chen S., Jaenisch R., Zhang F., Sharp P A. Nat Biotechnol. April 20. doi: 10.1038/nbt.2889 (2014);

CRISPR-Cas9 Knockin Mice for Genome Editing and Cancer Modeling. Platt R J, Chen S, Zhou Y, Yim M J, Swiech L, Kempton H R, Dahlman J E, Parnas O, Eisenhaure T M, Jovanovic M, Graham D B, Jhunjhunwala S, Heidenreich M, Xavier R J, Langer R, Anderson D G, Hacohen N, Regev A, Feng G, Sharp P A, Zhang F. Cell 159 (2): 440-455 DOI: 10.1016/j.cell.2014.09.014 (2014);

Development and Applications of CRISPR-Cas9 for Genome Engineering, Hsu P D, Lander E S, Zhang F., Cell. June 5; 157 (6): 1262-78 (2014);

Genetic screens in human cells using the CRISPR/Cas9 system, Wang T, Wei J J, Sabatini D M, Lander E S., Science. January 3; 343 (6166): 80-84. doi: 10.1126/science. 1246981 (2014);

Rational design of highly active sgRNAs for CRISPR-Cas9-mediated gene inactivation, Doench J G, Hartenian E, Graham D B, Tothova Z, Hegde M, Smith I, Sullender M, Ebert B L, Xavier R J, Root D E., (published online 3 Sep. 2014) Nat Biotechnol. December; 32 (12): 1262-7 (2014);

In vivo interrogation of gene function in the mammalian brain using CRISPR-Cas9, Swiech L, Heidenreich M, Banerjee A, Habib N, Li Y, Trombetta J, Sur M, Zhang F., (published online 19 Oct. 2014) Nat Biotechnol. January; 33 (1): 102-6 (2015);

Genome-scale transcriptional activation by an engineered CRISPR-Cas9 complex, Konermann S, Brigham M D, Trevino A E, Joung J, Abudayyeh O O, Barcena C, Hsu P D, Habib N, Gootenberg J S, Nishimasu H, Nureki O, Zhang F., Nature. January 29; 517 (7536): 583-8 (2015);

A split-Cas9 architecture for inducible genome editing and transcription modulation, Zetsche B, Volz S E, Zhang F., (published online 2 Feb. 2015) Nat Biotechnol. February; 33 (2): 139-42 (2015);

Genome-wide CRISPR Screen in a Mouse Model of Tumor Growth and Metastasis, Chen S, Sanjana N E, Zheng K, Shalem O, Lee K, Shi X, Scott D A, Song J, Pan J Q, Weissleder R, Lee H, Zhang F, Sharp P A. Cell 160, 1246-1260 Mar. 12, 2015 (multiplex screen in mouse); and In vivo genome editing using *Staphylococcus aureus* Cas9, Ran F A, Cong L, Yan W X, Scott D A, Gootenberg J S, Kriz A J, Zetsche B, Shalem O, Wu X, Makarova K S, Koonin E V, Sharp P A, Zhang F., (published online 1 Apr. 2015), Nature. April 9; 520 (7546): 186-91 (2015).

Shalem et al., "High-throughput functional genomics using CRISPR-Cas9," Nature Reviews Genetics 16, 299-311 (May 2015).

Xu et al., "Sequence determinants of improved CRISPR sgRNA design," Genome Research 25, 1147-1157 (August 2015).

Parnas et al., "A Genome-wide CRISPR Screen in Primary Immune Cells to Dissect Regulatory Networks," Cell 162, 675-686 (Jul. 30, 2015).

Ramanan et al., "CRISPR/Cas9 cleavage of viral DNA efficiently suppresses hepatitis B virus," Scientific Reports 5:10833. doi: 10.1038/srep10833 (Jun. 2, 2015).

Nishimasu et al., "Crystal Structure of *Staphylococcus aureus* Cas9," Cell 162, 1113-1126 (Aug. 27, 2015).

each of which is incorporated herein by reference, may be considered in the practice of the instant invention, and discussed briefly below:

Cong et al. engineered type II CRISPR-Cas systems for use in eukaryotic cells based on both *Streptococcus thermophilus* Cas9 and also *Streptococcus pyogenes* Cas9 and demonstrated that Cas9 nucleases can be directed by short RNAs to induce precise cleavage of DNA in human and mouse cells. Their study further showed that Cas9 as converted into a nicking enzyme can be used to facilitate homology-directed repair in eukaryotic cells with minimal mutagenic activity. Additionally, their study demonstrated that multiple guide sequences can be encoded into a single CRISPR array to enable simultaneous editing of several at endogenous genomic loci sites within the mammalian genome, demonstrating easy programmability and wide applicability of the RNA-guided nuclease technology. This ability to use RNA to program sequence specific DNA cleavage in cells defined a new class of genome engineering tools. These studies further showed that other CRISPR loci are likely to be transplantable into mammalian cells and can also mediate mammalian genome cleavage. Importantly, it can be envisaged that several aspects of the CRISPR-Cas system can be further improved to increase its efficiency and versatility.

Jiang et al. used the clustered, regularly interspaced, short palindromic repeats (CRISPR)-associated Cas9 endonuclease complexed with dual-RNAs to introduce precise mutations in the genomes of *Streptococcus pneumoniae* and *Escherichia coli*. The approach relied on dual-RNA: Cas9-directed cleavage at the targeted genomic site to kill unmutated cells and circumvents the need for selectable markers or counter-selection systems. The study reported reprogramming dual-RNA: Cas9 specificity by changing the sequence of short CRISPR RNA (crRNA) to make single- and multi-nucleotide changes carried on editing templates. The study showed that simultaneous use of two crRNAs enabled multiplex mutagenesis. Furthermore, when the approach was used in combination with recombineering, in *S. pneumoniae*, nearly 100% of cells that were recovered using the described approach contained the desired mutation, and in *E. coli,* 65% that were recovered contained the mutation.

Wang et al. (2013) used the CRISPR/Cas system for the one-step generation of mice carrying mutations in multiple genes which were traditionally generated in multiple steps by sequential recombination in embryonic stem cells and/or time-consuming intercrossing of mice with a single mutation. The CRISPR/Cas system will greatly accelerate the in vivo study of functionally redundant genes and of epistatic gene interactions.

Konermann et al. (2013) addressed the need in the art for versatile and robust technologies that enable optical and chemical modulation of DNA-binding domains based CRISPR Cas9 enzyme and also Transcriptional Activator Like Effectors.

Ran et al. (2013-A) described an approach that combined a Cas9 nickase mutant with paired guide RNAs to introduce targeted double-strand breaks. This addresses the issue of the Cas9 nuclease from the microbial CRISPR-Cas system being targeted to specific genomic loci by a guide sequence, which can tolerate certain mismatches to the DNA target and thereby promote undesired off-target mutagenesis. Because individual nicks in the genome are repaired with high fidelity, simultaneous nicking via appropriately offset guide RNAs is required for double-stranded breaks and extends the number of specifically recognized bases for target cleavage. The authors demonstrated that using paired nicking can reduce off-target activity by 50- to 1,500-fold in cell lines and to facilitate gene knockout in mouse zygotes without sacrificing on-target cleavage efficiency. This versatile strategy enables a wide variety of genome editing applications that require high specificity.

Hsu et al. (2013) characterized SpCas9 targeting specificity in human cells to inform the selection of target sites and avoid off-target effects. The study evaluated >700 guide RNA variants and SpCas9-induced indel mutation levels at >100 predicted genomic off-target loci in 293T and 293 FT cells. The authors that SpCas9 tolerates mismatches between guide RNA and target DNA at different positions in a sequence-dependent manner, sensitive to the number, position and distribution of mismatches. The authors further showed that SpCas9-mediated cleavage is unaffected by DNA methylation and that the dosage of SpCas9 and sgRNA can be titrated to minimize off-target modification. Additionally, to facilitate mammalian genome engineering applications, the authors reported providing a web-based software tool to guide the selection and validation of target sequences as well as off-target analyses.

Ran et al. (2013-B) described a set of tools for Cas9-mediated genome editing via non-homologous end joining (NHEJ) or homology-directed repair (HDR) in mammalian cells, as well as generation of modified cell lines for downstream functional studies. To minimize off-target cleavage, the authors further described a double-nicking strategy using the Cas9 nickase mutant with paired guide RNAs. The protocol provided by the authors experimentally derived guidelines for the selection of target sites, evaluation of cleavage efficiency and analysis of off-target activity. The studies showed that beginning with target design, gene modifications can be achieved within as little as 1-2 weeks, and modified clonal cell lines can be derived within 2-3 weeks.

Shalem et al. described a new way to interrogate gene function on a genome-wide scale. Their studies showed that delivery of a genome-scale CRISPR-Cas9 knockout (GeCKO) library targeted 18,080 genes with 64,751 unique guide sequences enabled both negative and positive selection screening in human cells. First, the authors showed use of the GeCKO library to identify genes essential for cell viability in cancer and pluripotent stem cells. Next, in a melanoma model, the authors screened for genes whose loss is involved in resistance to vemurafenib, a therapeutic that inhibits mutant protein kinase BRAF. Their studies showed that the highest-ranking candidates included previously validated genes NF1 and MED12 as well as novel hits NF2, CUL3, TADA2B, and TADA1. The authors observed a high level of consistency between independent guide RNAs targeting the same gene and a high rate of hit confirmation, and thus demonstrated the promise of genome-scale screening with Cas9.

Nishimasu et al. reported the crystal structure of *Streptococcus pyogenes* Cas9 in complex with sgRNA and its target DNA at 2.5 A° resolution. The structure revealed a bilobed architecture composed of target recognition and nuclease lobes, accommodating the sgRNA: DNA heteroduplex in a positively charged groove at their interface. Whereas the recognition lobe is essential for binding sgRNA and DNA, the nuclease lobe contains the HNH and RuvC nuclease domains, which are properly positioned for cleavage of the complementary and non-complementary strands of the target DNA, respectively. The nuclease lobe also contains a carboxyl-terminal domain responsible for the interaction with the protospacer adjacent motif (PAM). This high-resolution structure and accompanying functional analyses have revealed the molecular mechanism of RNA-guided DNA targeting by Cas9, thus paving the way for the rational design of new, versatile genome-editing technologies.

Wu et al. mapped genome-wide binding sites of a catalytically inactive Cas9 (dCas9) from *Streptococcus pyogenes* loaded with single guide RNAs (sgRNAs) in mouse embryonic stem cells (mESCs). The authors showed that each of the four sgRNAs tested targets dCas9 to between tens and thousands of genomic sites, frequently characterized by a 5-nucleotide seed region in the sgRNA and an NGG protospacer adjacent motif (PAM). Chromatin inaccessibility decreases dCas9 binding to other sites with matching seed sequences; thus 70% of off-target sites are associated with genes. The authors showed that targeted sequencing of 295 dCas9 binding sites in mESCs transfected with catalytically active Cas9 identified only one site mutated above background levels. The authors proposed a two-state model for Cas9 binding and cleavage, in which a seed match triggers binding but extensive pairing with target DNA is required for cleavage.

Platt et al. established a Cre-dependent Cas9 knockin mouse. The authors demonstrated in vivo as well as ex vivo genome editing using adeno-associated virus (AAV)-, lentivirus-, or particle-mediated delivery of guide RNA in neurons, immune cells, and endothelial cells.

Hsu et al. (2014) is a review article that discusses generally CRISPR-Cas9 history from yogurt to genome editing, including genetic screening of cells.

Wang et al. (2014) relates to a pooled, loss-of-function genetic screening approach suitable for both positive and negative selection that uses a genome-scale lentiviral single guide RNA (sgRNA) library.

Doench et al. created a pool of sgRNAs, tiling across all possible target sites of a panel of six endogenous mouse and three endogenous human genes and quantitatively assessed their ability to produce null alleles of their target gene by antibody staining and flow cytometry. The authors showed that optimization of the PAM improved activity and also provided an on-line tool for designing sgRNAs.

Swiech et al. demonstrate that AAV-mediated SpCas9 genome editing can enable reverse genetic studies of gene function in the brain.

Konermann et al. (2015) discusses the ability to attach multiple effector domains, e.g., transcriptional activator, functional and epigenomic regulators at appropriate positions on the guide such as stem or tetraloop with and without linkers.

Zetsche et al. demonstrates that the Cas9 enzyme can be split into two and hence the assembly of Cas9 for activation can be controlled.

Chen et al. relates to multiplex screening by demonstrating that a genome-wide in vivo CRISPR-Cas9 screen in mice reveals genes regulating lung metastasis.

Ran et al. (2015) relates to SaCas9 and its ability to edit genomes and demonstrates that one cannot extrapolate from biochemical assays. Shalem et al. (2015) described ways in which catalytically inactive Cas9 (dCas9) fusions are used to synthetically repress (CRISPRi) or activate (CRISPRa) expression, showing. advances using Cas9 for genome-scale screens, including arrayed and pooled screens, knockout approaches that inactivate genomic loci and strategies that modulate transcriptional activity.

Shalem et al. (2015) described ways in which catalytically inactive Cas9 (dCas9) fusions are used to synthetically repress (CRISPRi) or activate (CRISPRa) expression, showing. advances using Cas9 for genome-scale screens, including arrayed and pooled screens, knockout approaches that inactivate genomic loci and strategies that modulate transcriptional activity.

Xu et al. (2015) assessed the DNA sequence features that contribute to single guide RNA (sgRNA) efficiency in CRISPR-based screens. The authors explored efficiency of CRISPR/Cas9 knockout and nucleotide preference at the cleavage site. The authors also found that the sequence preference for CRISPRi/a is substantially different from that for CRISPR/Cas9 knockout.

Parnas et al. (2015) introduced genome-wide pooled CRISPR-Cas9 libraries into dendritic cells (DCs) to identify genes that control the induction of tumor necrosis factor (Tnf) by bacterial lipopolysaccharide (LPS). Known regulators of Tlr4 signaling and previously unknown candidates were identified and classified into three functional modules with distinct effects on the canonical responses to LPS.

Ramanan et al (2015) demonstrated cleavage of viral episomal DNA (cccDNA) in infected cells. The HBV genome exists in the nuclei of infected hepatocytes as a 3.2 kb double-stranded episomal DNA species called covalently closed circular DNA (cccDNA), which is a key component in the HBV life cycle whose replication is not inhibited by current therapies. The authors showed that sgRNAs specifically targeting highly conserved regions of HBV robustly suppresses viral replication and depleted cccDNA.

Nishimasu et al. (2015) reported the crystal structures of SaCas9 in complex with a single guide RNA (sgRNA) and its double-stranded DNA targets, containing the 5'-TTGAAT-3' PAM and the 5'-TTGGGT-3' PAM. A structural comparison of SaCas9 with SpCas9 highlighted both structural conservation and divergence, explaining their distinct PAM specificities and orthologous sgRNA recognition.

Also, "Dimeric CRISPR RNA-guided FokI nucleases for highly specific genome editing", Shengdar Q. Tsai, Nicolas Wyvekens, Cyd Khayter, Jennifer A. Foden, Vishal Thapar, Deepak Reyon, Mathew J. Goodwin, Martin J. Aryee, J. Keith Joung Nature Biotechnology 32 (6): 569-77 (2014), relates to dimeric RNA-guided FokI Nucleases that recognize extended sequences and can edit endogenous genes with high efficiencies in human cells.

In addition, mention is made of PCT application PCT/US14/70057, entitled "DELIVERY, USE AND THERAPEUTIC APPLICATIONS OF THE CRISPR-CAS SYSTEMS AND COMPOSITIONS FOR TARGETING DISORDERS AND DISEASES USING PARTICLE DELIVERY COMPONENTS (claiming priority from one or more or all of US provisional patent applications: 62/054,490, filed Sep. 24, 2014; 62/010,441, filed Jun. 10, 2014; and 61/915,118, 61/915,215 and 61/915,148, each filed on Dec. 12, 2013) ("the Particle Delivery PCT"), incorporated herein by reference, with respect to a method of preparing an sgRNA-and-Cas9 protein containing particle comprising admixing a mixture comprising an sgRNA and Cas9 protein (and optionally HDR template) with a mixture comprising or consisting essentially of or consisting of surfactant, phospholipid, biodegradable polymer, lipoprotein and alcohol; and particles from such a process. For example, wherein Cas9 protein and sgRNA were mixed together at a suitable, e.g., 3:1 to 1:3 or 2:1 to 1:2 or 1:1 molar ratio, at a suitable temperature, e.g., 15-30° C., e.g., 20-25° C., e.g., room temperature, for a suitable time, e.g., 15-45, such as 30 minutes, advantageously in sterile, nuclease free buffer, e.g., 1×PBS. Separately, particle components such as or comprising: a surfactant, e.g., cationic lipid, e.g., 1,2-dioleoyl-3-trimethylammonium-propane (DOTAP); phospholipid, e.g., dimyristoylphosphatidylcholine (DMPC); biodegradable polymer, such as an ethylene-glycol polymer or PEG, and a lipoprotein, such as a low-density lipoprotein, e.g., cholesterol were dissolved in an alcohol, advantageously a $C_{1-6}$ alkyl alcohol, such as methanol, ethanol, isopropanol, e.g., 100% ethanol. The two solutions were mixed together to form particles containing the Cas9-sgRNA complexes. Accordingly, sgRNA may be pre-complexed with the Cas9 protein, before formulating the entire complex in a particle. Formulations may be made with a different molar ratio of different components known to promote delivery of nucleic acids into cells (e.g. 1,2-dioleoyl-3-trimethylammonium-propane (DOTAP), 1,2-ditetradecanoyl-sn-glycero-3-phosphocholine (DMPC), polyethylene glycol (PEG), and cholesterol) For example DOTAP: DMPC: PEG: Cholesterol Molar Ratios may be DOTAP 100, DMPC 0, PEG 0, Cholesterol 0; or DOTAP 90, DMPC 0, PEG 10, Cholesterol 0; or DOTAP 90, DMPC 0, PEG 5, Cholesterol 5. DOTAP 100, DMPC 0, PEG 0, Cholesterol 0. That application accordingly comprehends admixing sgRNA, Cas9 protein and components that form a particle; as well as particles from such admixing. Aspects of the instant invention can involve particles; for example, particles using a process analogous to that of the Particle Delivery PCT, e.g., by admixing a mixture comprising sgRNA and/or Cas9 as in the instant invention and components that form a particle, e.g., as in the Particle Delivery PCT, to form a particle and particles from such admixing (or, of course, other particles involving sgRNA and/or Cas9 as in the instant invention).

In general, the CRISPR-Cas or CRISPR system is as used in the foregoing documents, such as WO 2014/093622 (PCT/US2013/074667) and refers collectively to transcripts and other elements involved in the expression of or directing the activity of CRISPR-associated ("Cas") genes, including sequences encoding a Cas gene, a tracr (transactivating CRISPR) sequence (e.g. tracrRNA or an active partial tracrRNA), a tracr-mate sequence (encompassing a "direct repeat" and a tracrRNA-processed partial direct repeat in the context of an endogenous CRISPR system), a guide sequence (also referred to as a "spacer" in the context of an endogenous CRISPR system), or "RNA(s)" as that term is herein used (e.g., RNA(s) to guide Cas, such as Cas9, e.g. CRISPR RNA and transactivating (tracr) RNA or a single guide RNA (sgRNA) (chimeric RNA)) or other sequences and transcripts from a CRISPR locus. In general, a CRISPR system is characterized by elements that promote the formation of a CRISPR complex at the site of a target sequence (also referred to as a protospacer in the context of an endogenous CRISPR system). In the context of formation of a CRISPR complex, "target sequence" refers to a sequence to which a guide sequence is designed to have complementarity, where hybridization between a target sequence and a guide sequence promotes the formation of a CRISPR complex. A target sequence may comprise any polynucleotide, such as DNA or RNA polynucleotides. In some embodiments, a target sequence is located in the nucleus or cytoplasm of a cell. In some embodiments, direct repeats may be identified in silico by searching for repetitive motifs that fulfill any or all of the following criteria: 1. found in a 2 Kb window of genomic sequence flanking the type II CRISPR locus; 2. span from 20 to 50 bp; and 3. interspaced by 20 to 50 bp. In some embodiments, 2 of these criteria may be used, for instance 1 and 2, 2 and 3, or 1 and 3. In some embodiments, all 3 criteria may be used.

In embodiments of the invention the terms guide sequence and guide RNA, i.e. RNA capable of guiding Group 29 or Group 30 proteins to a target locus, are used interchangeably as in foregoing cited documents such as WO 2014/093622 (PCT/US2013/074667). In general, a guide sequence (or spacer sequence) is any polynucleotide sequence having sufficient complementarity with a target polynucleotide sequence to hybridize with the target sequence and direct sequence-specific binding of a CRISPR complex to the target sequence. In some embodiments, the degree of complementarity between a guide sequence and its corresponding target sequence, when optimally aligned using a suitable alignment algorithm, is about or more than about 50%, 60%, 75%, 80%, 85%, 90%, 95%, 97.5%, 99%, or more. Optimal alignment may be determined with the use of any suitable algorithm for aligning sequences, non-limiting example of which include the Smith-Waterman algorithm, the Needleman-Wunsch algorithm, algorithms based on the Burrows-Wheeler Transform (e.g. the Burrows Wheeler Aligner), ClustalW, Clustal X, BLAT, Novoalign (Novocraft Technologies; available at www.novocraft.com), ELAND (Illumina, San Diego, CA), SOAP (available at soap.genomics.org.cn), and Maq (available at maq.sourceforge.net). In some embodiments, a guide sequence (or spacer sequence) is about or more than about 5, 10, 11, 12, 13, 14, 15, 16, 17, 18, 19, 20, 21, 22, 23, 24, 25, 26, 27, 28, 29, 30, 35, 40, 45, 50, 75, or more nucleotides in length. In some embodiments, a guide sequence is less than about 75, 50, 45, 40, 35, 30, 25, 20, 15, 12, or fewer nucleotides in length. Preferably the guide sequence is 10-30 nucleotides long, such as 20-30 nucleotides long, such as 30 nucleotides long or about 30 nucleotides long. In certain embodiments, the guide sequence is 10 10-30 nucleotides long, such as 20-30 nucleotides long, such as 30 nucleotides long or about 30 nucleotides long for Group 29 or Group 30 effectors. In certain embodiments, the guide sequence is 10-30 nucleotides long, such as 20-30 nucleotides long, such as 30 nucleotides long or about 30 nucleotides long for Group 29 effectors originating from Bergeyella zoohelcum (such as Bergeyella zoohelcum ATCC 43767). The ability of a guide sequence to direct sequence-specific binding of a CRISPR complex to a target sequence may be assessed by any suitable assay. For example, the components of a CRISPR system sufficient to form a CRISPR complex, including the guide sequence to be tested, may be provided to a host cell having the corresponding target sequence, such as by transfection with vectors encoding the components of the CRISPR sequence, followed by an assessment of preferential cleavage within the target sequence, such as by Surveyor assay as described herein. Similarly, cleavage of a target polynucleotide sequence may be evaluated in a test tube by providing the target sequence, components of a CRISPR complex, including the guide sequence to be tested and a control guide sequence different from the test guide sequence, and comparing binding or rate of cleavage at the target sequence between the test and control guide sequence reactions. Other assays are possible, and will occur to those skilled in the art.

In a classic CRISPR-Cas systems, the degree of complementarity between a guide sequence and its corresponding target sequence can be about or more than about 50%, 60%, 75%, 80%, 85%, 90%, 95%, 97.5%, 99%, or 100%; a guide or RNA or sgRNA can be about or more than about 5, 10, 11, 12, 13, 14, 15, 16, 17, 18, 19, 20, 21, 22, 23, 24, 25, 26, 27, 28, 29, 30, 35, 40, 45, 50, 75, or more nucleotides in length; or guide or RNA or sgRNA can be less than about 75, 50, 45, 40, 35, 30, 25, 20, 15, 12, or fewer nucleotides in length; and advantageously tracr RNA is 30 or 50 nucleotides in length. However, an aspect of the invention is to reduce off-target interactions, e.g., reduce the guide interacting with a target sequence having low complementarity. Indeed, in the examples, it is shown that the invention involves mutations that result in the CRISPR-Cas system being able to distinguish between target and off-target sequences that have greater than 80% to about 95% complementarity, e.g., 83%-84% or 88-89% or 94-95% complementarity (for instance, distinguishing between a target having 18 nucleotides from an off-target of 18 nucleotides having 1, 2 or 3 mismatches). Accordingly, in the context of the present invention the degree of complementarity between a guide sequence and its corresponding target sequence is greater than 94.5% or 95% or 95.5% or 96% or 96.5% or 97% or 97.5% or 98% or 98.5% or 99% or 99.5% or 99.9%, or 100%. Off target is less than 100% or 99.9% or 99.5% or 99% or 99% or 98.5% or 98% or 97.5% or 97% or 96.5% or 96% or 95.5% or 95% or 94.5% or 94% or 93% or 92% or 91% or 90% or 89% or 88% or 87% or 86% or 85% or 84% or 83% or 82% or 81% or 80% complementarity between the sequence and the guide, with it advantageous that off target is 100% or 99.9% or 99.5% or 99% or 99% or 98.5% or 98% or 97.5% or 97% or 96.5% or 96% or 95.5% or 95% or 94.5% complementarity between the sequence and the guide.

In particularly preferred embodiments according to the invention, the guide RNA (capable of guiding Cas to a target locus) may comprise (1) a guide sequence capable of hybridizing to a target locus (a polynucleotide target locus, such as an RNA target locus) in the eukaryotic cell; (2) a direct repeat (DR) sequence which reside in a single RNA, i.e. an sgRNA (arranged in a 5' to 3' orientation).

In particular embodiments, the wildtype group29/group30 effector protein has RNA binding and cleaving function.

In particular embodiments, the group29/group30 effector protein may have DNA cleaving function. In these embodiments, methods may be provided based on the effector proteins provided herein which comprehend inducing one or more mutations in a eukaryotic cell (in vitro, i.e. in an isolated eukaryotic cell) as herein discussed comprising delivering to cell a vector as herein discussed. The mutation(s) can include the introduction, deletion, or substitution of one or more nucleotides at each target sequence of cell(s) via the guide(s) RNA(s) or sgRNA(s). The mutations can include the introduction, deletion, or substitution of 1-75 nucleotides at each target sequence of said cell(s) via the guide(s) RNA(s) or sgRNA(s). The mutations can include the introduction, deletion, or substitution of 1, 5, 10, 11, 12, 13, 14, 15, 16, 17, 18, 19, 20, 21, 22, 23, 24, 25, 26, 27, 28, 29, 30, 35, 40, 45, 50, or 75 nucleotides at each target sequence of said cell(s) via the guide(s) RNA(s) or sgRNA(s). The mutations can include the introduction, deletion, or substitution of 5, 10, 11, 12, 13, 14, 15, 16, 17, 18, 19, 20, 21, 22, 23, 24, 25, 26, 27, 28, 29, 30, 35, 40, 45, 50, or 75 nucleotides at each target sequence of said cell(s) via the guide(s) RNA(s) or sgRNA(s). The mutations include the introduction, deletion, or substitution of 10, 11, 12, 13, 14, 15, 16, 17, 18, 19, 20, 21, 22, 23, 24, 25, 26, 27, 28, 29, 30, 35, 40, 45, 50, or 75 nucleotides at each target sequence of said cell(s) via the guide(s) RNA(s) or sgRNA(s). The mutations can include the introduction, deletion, or substitution of 20, 21, 22, 23, 24, 25, 26, 27, 28, 29, 30, 35, 40, 45, 50, or 75 nucleotides at each target sequence of said cell(s) via the guide(s) RNA(s) or sgRNA(s). The mutations can include the introduction, deletion, or substitution of 40, 45, 50, 75, 100, 200, 300, 400 or 500 nucleotides at each target sequence of said cell(s) via the guide(s) RNA(s) or sgRNA(s).

For minimization of toxicity and off-target effect, it will be important to control the concentration of Cas mRNA and guide RNA delivered. Optimal concentrations of Cas mRNA and guide RNA can be determined by testing different concentrations in a cellular or non-human eukaryote animal model and using deep sequencing the analyze the extent of modification at potential off-target genomic loci. Alternatively, to minimize the level of toxicity and off-target effect, Cas nickase mRNA (for example *S. pyogenes* Cas9 with the D10A mutation) can be delivered with a pair of guide RNAs targeting a site of interest. Guide sequences and strategies to minimize toxicity and off-target effects can be as in WO 2014/093622 (PCT/US2013/074667); or, via mutation as herein.

Typically, in the context of an endogenous CRISPR system, formation of a CRISPR complex (comprising a guide sequence hybridized to a target sequence and complexed with one or more Cas proteins) results in cleavage of one or both strands (if applicable) in or near (e.g. within 1, 2, 3, 4, 5, 6, 7, 8, 9, 10, 20, 50, or more base pairs from) the target sequence. Without wishing to be bound by theory, the tracr sequence (if applicable or present), which may comprise or consist of all or a portion of a wild-type tracr sequence (e.g. about or more than about 20, 26, 32, 45, 48, 54, 63, 67, 85, or more nucleotides of a wild-type tracr sequence), may also form part of a CRISPR complex, such as by hybridization along at least a portion of the tracr sequence to all or a portion of a tracr mate sequence that is operably linked to the guide sequence.

The nucleic acid molecule encoding a Cas is advantageously codon optimized Cas. An example of a codon optimized sequence, is in this instance a sequence optimized for expression in a eukaryote, e.g., humans (i.e. being optimized for expression in humans), or for another eukaryote, animal or mammal as herein discussed; see, e.g., SaCas9 human codon optimized sequence in WO 2014/093622 (PCT/US2013/074667). Whilst this is preferred, it will be appreciated that other examples are possible and codon optimization for a host species other than human, or for codon optimization for specific organs is known. In some embodiments, an enzyme coding sequence encoding a Cas is codon optimized for expression in particular cells, such as eukaryotic cells. The eukaryotic cells may be those of or derived from a particular organism, such as a mammal, including but not limited to human, or non-human eukaryote or animal or mammal as herein discussed, e.g., mouse, rat, rabbit, dog, livestock, or non-human mammal or primate. In some embodiments, processes for modifying the germ line genetic identity of human beings and/or processes for modifying the genetic identity of animals which are likely to cause them suffering without any substantial medical benefit to man or animal, and also animals resulting from such processes, may be excluded. In general, codon optimization refers to a process of modifying a nucleic acid sequence for enhanced expression in the host cells of interest by replacing at least one codon (e.g. about or more than about 1, 2, 3, 4, 5, 10, 15, 20, 25, 50, or more codons) of the native sequence with codons that are more frequently or most frequently used in the genes of that host cell while maintaining the native amino acid sequence. Various species exhibit particular bias for certain codons of a particular amino acid. Codon bias (differences in codon usage between organisms) often correlates with the efficiency of translation of messenger RNA (mRNA), which is in turn believed to be dependent on, among other things, the properties of the codons being translated and the availability of particular transfer RNA (tRNA) molecules. The predominance of selected tRNAs in a cell is generally a reflection of the codons used most frequently in peptide synthesis. Accordingly, genes can be tailored for optimal gene expression in a given organism based on codon optimization. Codon usage tables are readily available, for example, at the "Codon Usage Database" available at www.kazusa.orjp/codon/and these tables can be adapted in a number of ways. See Nakamura, Y., et al. "Codon usage tabulated from the international DNA sequence databases: status for the year 2000" Nucl. Acids Res. 28:292 (2000). Computer algorithms for codon optimizing a particular sequence for expression in a particular host cell are also available, such as Gene Forge (Aptagen; Jacobus, PA), are also available. In some embodiments, one or more codons (e.g. 1, 2, 3, 4, 5, 10, 15, 20, 25, 50, or more, or all codons) in a sequence encoding a Cas correspond to the most frequently used codon for a particular amino acid.

In certain embodiments, the methods as described herein may comprise providing a Cas transgenic cell in which one or more nucleic acids encoding one or more guide RNAs are provided or introduced operably connected in the cell with a regulatory element comprising a promoter of one or more gene of interest. As used herein, the term "Cas transgenic cell" refers to a cell, such as a eukaryotic cell, in which a Cas gene has been genomically integrated. The nature, type, or origin of the cell are not particularly limiting according to the present invention. Also the way how the Cas transgene is introduced in the cell is may vary and can be any method as is known in the art. In certain embodiments, the Cas transgenic cell is obtained by introducing the Cas transgene in an isolated cell. In certain other embodiments, the Cas transgenic cell is obtained by isolating cells from a Cas transgenic organism. By means of example, and without limitation, the Cas transgenic cell as referred to herein may be derived from a Cas transgenic eukaryote, such as a Cas knock-in eukaryote. Reference is made to WO 2014/093622 (PCT/US13/74667), incorporated herein by reference. Methods of US Patent Publication Nos. 20120017290 and 20110265198 assigned to Sangamo BioSciences, Inc. directed to targeting the Rosa locus may be modified to utilize the CRISPR Cas system of the present invention. Methods of US Patent Publication No. 20130236946 assigned to Cellectis directed to targeting the Rosa locus may also be modified to utilize the CRISPR Cas system of the present invention. By means of further example reference is made to Platt et. al. (Cell; 159 (2): 440-455 (2014)), describing a Cas9 knock-in mouse, which is incorporated herein by reference. The Cas transgene can further comprise a Lox-Stop-polyA-Lox (LSL) cassette thereby rendering Cas expression inducible by Cre recombinase. Alternatively, the Cas transgenic cell may be obtained by introducing the Cas transgene in an isolated cell. Delivery systems for transgenes are well known in the art. By means of example, the Cas transgene may be delivered in for instance eukaryotic cell by means of vector (e.g., AAV, adenovirus, lentivirus) and/or particle and/or nanoparticle delivery, as also described herein elsewhere.

It will be understood by the skilled person that the cell, such as the Cas transgenic cell, as referred to herein may comprise further genomic alterations besides having an integrated Cas gene or the mutations arising from the sequence specific action of Cas when complexed with RNA capable of guiding Cas to a target locus, such as for instance one or more oncogenic mutations, as for instance and without limitation described in Platt et al. (2014), Chen et al., (2014) or Kumar et al . . . (2009).

In some embodiments, the Cas sequence is fused to one or more nuclear localization sequences (NLSs), such as about or more than about 1, 2, 3, 4, 5, 6, 7, 8, 9, 10, or more NLSs. In some embodiments, the Cas comprises about or more than about 1, 2, 3, 4, 5, 6, 7, 8, 9, 10, or more NLSs at or near the amino-terminus, about or more than about 1, 2, 3, 4, 5, 6, 7, 8, 9, 10, or more NLSs at or near the carboxy-terminus, or a combination of these (e.g. zero or at least one or more NLS at the amino-terminus and zero or at one or more NLS at the carboxy terminus). When more than one NLS is present, each may be selected independently of the others, such that a single NLS may be present in more than one copy and/or in combination with one or more other NLSs present in one or more copies. In a preferred embodiment of the invention, the Cas comprises at most 6 NLSs. In some embodiments, an NLS is considered near the N- or C-terminus when the nearest amino acid of the NLS is within about 1, 2, 3, 4, 5, 10, 15, 20, 25, 30, 40, 50, or more amino acids along the polypeptide chain from the N- or C-terminus. Non-limiting examples of NLSs include an NLS sequence derived from: the NLS of the SV40 virus large T-antigen, having the amino acid sequence PKKKRKV (SEQ ID No: 3); the NLS from nucleoplasmin (e.g. the nucleoplasmin bipartite NLS with the sequence KRPAATKKAGQAKKKK) (SEQ ID No: 4); the c-myc NLS having the amino acid sequence PAAKRVKLD (SEQ ID No: 5) or RQRRNELKRSP (SEQ ID No: 6); the hRNPAI M9 NLS having the sequence NQSSNFGPMKGGNFGGRSSGPYGGGGQYFAKPRNQGGY (SEQ ID NO: 7); the sequence RMRIZFKNKGKDTAELRRRRVEVSVELRKAKKDEQILKRRNV (SEQ ID No: 8) of the IBB domain from importin-alpha; the sequences VSRKRPRP (SEQ ID NO: 9) and PPKKARED (SEQ ID No: 10) of the myoma T protein; the sequence PQPKKKPL (SEQ ID No: 11) of human p53; the sequence SALIKKKKKMAP (SEQ ID No: 12) of mouse c-abl IV; the sequences DRLRR (SEQ ID No: 13) and PKQKKRK (SEQ ID No: 14) of the influenza virus NS1; the sequence RKLKKKIKKL (SEQ ID No: 15) of the Hepatitis virus delta antigen; the sequence REKKKFLKRR (SEQ ID No: 16) of the mouse Mx1 protein; the sequence KRKGDEVDGVDEVAKKKSKK (SEQ ID No: 17) of the human poly(ADP-ribose) polymerase; and the sequence RKCLQAGMNLEARKTKK (SEQ ID No: 18) of the steroid hormone receptors (human) glucocorticoid. In general, the one or more NLSs are of sufficient strength to drive accumulation of the Cas in a detectable amount in the nucleus of a eukaryotic cell. In general, strength of nuclear localization activity may derive from the number of NLSs in the Cas, the particular NLS(s) used, or a combination of these factors. Detection of accumulation in the nucleus may be performed by any suitable technique. For example, a detectable marker may be fused to the Cas, such that location within a cell may be visualized, such as in combination with a means for detecting the location of the nucleus (e.g. a stain specific for the nucleus such as DAPI). Cell nuclei may also be isolated from cells, the contents of which may then be analyzed by any suitable process for detecting protein, such as immunohistochemistry, Western blot, or enzyme activity assay. Accumulation in the nucleus may also be determined indirectly, such as by an assay for the effect of CRISPR complex formation (e.g. assay for DNA cleavage or mutation at the target sequence, or assay for altered gene expression activity affected by CRISPR complex formation and/or Cas enzyme activity), as compared to a control no exposed to the Cas or complex, or exposed to a Cas lacking the one or more NLSs.

dCas9. It has been shown previously that dCas9 can be used as a generic DNA binding domain to repress gene expression. Applicants report an improved dCas9 design as well as dCas9 fusions to the repressor domains KRAB and SID4x. From the plasmid library created for modulating transcription using Cas9 in Table 1, the following repressor plasmids were functionally characterized by qPCR: pXRP27, pXRP28, pXRP29, pXRP48, pXRP49, pXRP50, pXRP51, pXRP52, pXRP53, pXRP56, pXRP58, pXRP59, pXRP61, and pXRP62.

Each dCas9 repressor plasmid was co-transfected with two guide RNAs targeted to the coding strand of the beta-catenin gene. RNA was isolated 72 hours after transfection and gene expression was quantified by RT-qPCR. The endogenous control gene was GAPDH. Two validated shRNAs were used as positive controls. Negative controls were certain plasmids transfected without gRNA, these are denoted as "pXRP ##control". The plasmids pXRP28, pXRP29, pXRP48, and pXRP49 could repress the beta-catenin gene when using the specified targeting strategy. These plasmids correspond to dCas9 without a functional domain (pXRP28 and pXRP28) and dCas9 fused to SID4x (pXRP48 and pXRP49).

The present invention also contemplates the use of biotinylated Cas9 and crosslinking to pull down neighboring proteins (see, e.g., Fujita et al., Methods Mol Biol. 2015; 1288:43-52. doi: 10.1007/978-1-4939-2474-5_4).

TABLE 1

| TABLE 1 |
| --- |
| pXRP024-pLenti2-EF1a-VP64-NLS-FLAG-Linker-dCas9-NLS-gLuc-2A-GFP-WPRE |
| pXRP025-pLenti2-EF1a-VP64-NLS-GGGGS$_3$Linker-dCas9-NLS-gLuc-2A-GFP-WPRE |
| pXRP026-pLenti2-EF1a-VP64-NLS-EAAAK$_3$Linker-dCas9-NLS-gLuc-2A-GFP-WPRE |
| pXRP027-pLenti2-EF1a-NLS-FLAG-Linker-dCas9-NLS-gLuc-2A-GFP-WPRE |
| pXRP028-pLenti2-EF1a-NLS-GGGGS$_3$Linker-dCas9-NLS-gLuc-2A-GFP-WPRE |
| pXRP029-pLenti2-EF1a-NLS-EAAAK$_3$Linker-dCas9-NLS-gLuc-2A-GFP-WPRE |
| pXRP030-pLenti2-pSV40-VP64-NLS-FLAG-Linker-dCas9-NLS-gLuc-2A-GFP-WPRE |
| pXRP031-pLenti2-pPGK-VP64-NLS-FLAG-Linker-dCas9-NLS-gLuc-2A-GFP-WPRE |
| pXRP032-pLenti2-LTR-VP64-NLS-FLAG-Linker-dCas9-NLS-gLuc-2A-GFP-WPRE |
| pXRP033-pLenti2-pSV40-VP64-NLS-GGGGS$_3$Linker-dCas9-NLS-gLuc-2A-GFP-WPRE |
| pXRP034-pLenti2-pPGK-VP64-NLS-GGGGS$_3$Linker-dCas9-NLS-gLuc-2A-GFP-WPRE |
| pXRP035-pLenti2-LTR-VP64-NLS-GGGGS$_3$Linker-dCas9-NLS-gLuc-2A-GFP-WPRE |
| pXRP036-pLenti2-pSV40-VP64-NLS-EAAAK$_3$Linker-dCas9-NLS-gLuc-2A-GFP-WPRE |
| pXRP037-pLenti2-pPGK-VP64-NLS-EAAAK$_3$Linker-dCas9-NLS-gLuc-2A-GFP-WPRE |
| pXRP038-pLenti2-LTR-VP64-NLS-EAAAK$_3$Linker-dCas9-NLS-gLuc-2A-GFP-WPRE |
| pXRP048-pLenti2-EF1a-SID4x-NLS-FLAG-Linker-dCas9-NLS-gLuc-2A-GFP-WPRE |
| pXRP049-pLenti2-EF1a-SID4X-NLS-GGGGS$_3$Linker-dCas9-NLS-gLuc-2A-GFP-WPRE |
| pXRP050-pLenti2-EF1a-SID4X-NLS-EAAAK$_3$Linker-dCas9-NLS-gLuc-2A-GFP-WPRE |
| pXRP051-pLenti2-EF1a-KRAB-NLS-FLAG-Linker-dCas9-NLS-gLuc-2A-GFP-WPRE |
| pXRP052-pLenti2-EF1a-KRAB-NLS-GGGGS$_3$Linker-dCas9-NLS-gLuc-2A-GFP-WPRE |
| pXRP053-pLenti2-EF1a-KRAB-NLS-EAAAK$_3$Linker-dCas9-NLS-gLuc-2A-GFP-WPRE |
| pXRP054-pLenti2-EF1a-dCas9-Linker-FLAG-NLS-VP64-gLuc-2A-GFP-WPRE |
| pXRP055-pLenti2-EF1a-dCas9-Linker-FLAG-NLS-SID4X-gLuc-2A-GFP-WPRE |
| pXRP056-pLenti2-EF1a-dCas9-Linker-FLAG-NLS-KRAB-gLuc-2A-GFP-WPRE |
| pXRP057-pLenti2-EF1a-dCas9-GGGGGS$_3$-NLS-VP64-gLuc-2A-GFP-WPRE |
| pXRP058-pLenti2-EF1a-dCas9-GGGGGS$_3$-NLS-SID4X-gLuc-2A-GFP-WPRE |
| pXRP059-pLenti2-EF1a-dCas9-GGGGGS$_3$-NLS-KRAB-gLuc-2A-GFP-WPRE |
| pXRP060-pLenti2-EF1a-dCas9-EAAAK$_3$-NLS-VP64-gLuc-2A-GFP-WPRE |
| pXRP061-pLenti2-EF1a-dCas9-EAAAK$_3$-NLS-SID4X-gLuc-2A-GFP-WPRE |
| pXRP062-pLenti2-EF1a-dCas9-EAAAK$_3$-NLS-KRAB-gLuc-2A-GFP-WPRE |
| pXRP024-pLenti2-EF1a-VP64-NLS-FLAG-Linker-Cas9-NLS-gLuc-2A-GFP-WPRE |
| pXRP025-pLenti2-EF1a-VP64-NLS-GGGGS$_3$Linker-Cas9-NLS-gLuc-2A-GFP-WPRE |
| pXRP026-pLenti2-EF1a-VP64-NLS-EAAAK$_3$Linker-Cas9-NLS-gLuc-2A-GFP-WPRE |
| pXRP027-pLenti2-EF1a-NLS-FLAG-Linker-Cas9-NLS-gLuc-2A-GFP-WPRE |
| pXRP028-pLenti2-EF1a-NLS-GGGGS$_3$Linker-Cas9-NLS-gLuc-2A-GFP-WPRE |
| pXRP029-pLenti2-EF1a-NLS-EAAAK$_3$Linker-Cas9-NLS-gLuc-2A-GFP-WPRE |
| pXRP030-pLenti2-pSV40-VP64-NLS-FLAG-Linker-Cas9-NLS-gLuc-2A-GFP-WPRE |
| pXRP031-pLenti2-pPGK-VP64-NLS-FLAG-Linker-Cas9-NLS-gLuc-2A-GFP-WPRE |
| pXRP032-pLenti2-LTR-VP64-NLS-FLAG-Linker-Cas9-NLS-gLuc-2A-GFP-WPRE |
| pXRP033-pLenti2-pSV40-VP64-NLS-GGGGS$_3$Linker-Cas9-NLS-gLuc-2A-GFP-WPRE |
| pXRP034-pLenti2-pPGK-VP64-NLS-GGGGS$_3$Linker-Cas9-NLS-gLuc-2A-GFP-WPRE |
| pXRP035-pLenti2-LTR-VP64-NLS-GGGGS$_3$Linker-Cas9-NLS-gLuc-2A-GFP-WPRE |
| pXRP036-pLenti2-pSV40-VP64-NLS-EAAAK$_3$Linker-Cas9-NLS-gLuc-2A-GFP-WPRE |
| pXRP037-pLenti2-pPGK-VP64-NLS-EAAAK$_3$Linker-Cas9-NLS-gLuc-2A-GFP-WPRE |
| pXRP038-pLenti2-LTR-VP64-NLS-EAAAK$_3$Linker-Cas9-NLS-gLuc-2A-GFP-WPRE |
| pXRP048-pLenti2-EF1a-SID4x-NLS-FLAG-Linker-Cas9-NLS-gLuc-2A-GFP-WPRE |
| pXRP049-pLenti2-EF1a-SID4X-NLS-GGGGS$_3$Linker-Cas9-NLS-gLuc-2A-GFP-WPRE |
| pXRP050-pLenti2-EF1a-SID4X-NLS-EAAAK$_3$Linker-Cas9-NLS-gLuc-2A-GFP-WPRE |

TABLE 1-continued

| |
|---|
| pXRP051-pLenti2-EF1a-KRAB-NLS-FLAG-Linker-Cas9-NLS-gLuc-2A-GFP-WPRE |
| pXRP052-pLenti2-EF1a-KRAB-NLS-$GGGGS_3$Linker-Cas9-NLS-gLuc-2A-GFP-WPRE |
| pXRP053-pLenti2-EF1a-KRAB-NLS-$EAAAK_3$Linker-Cas9-NLS-gLuc-2A-GFP-WPRE |
| pXRP054-pLenti2-EF1a-Cas9-Linker-FLAG-NLS-VP64-gLuc-2A-GFP-WPRE |
| pXRP055-pLenti2-EF1a-Cas9-Linker-FLAG-NLS-SID4X-gLuc-2A-GFP-WPRE |
| pXRP056-pLenti2-EF1a-Cas9-Linker-FLAG-NLS-KRAB-gLuc-2A-GFP-WPRE |
| pXRP057-pLenti2-EF1a-Cas9-$GGGGGS_3$-NLS-VP64-gLuc-2A-GFP-WPRE |
| pXRP058-pLenti2-EF1a-Cas9-$GGGGGS_3$-NLS-SID4X-gLuc-2A-GFP-WPRE |
| pXRP059-pLenti2-EF1a-Cas9-$GGGGGS_3$-NLS-KRAB-gLuc-2A-GFP-WPRE |
| pXRP060-pLenti2-EF1a-Cas9-$EAAAK_3$-NLS-VP64-gLuc-2A-GFP-WPRE |
| pXRP061-pLenti2-EF1a-Cas9-$EAAAK_3$-NLS-SID4X-gLuc-2A-GFP-WPRE |
| pXRP062-pLenti2-EF1a-Cas9-$EAAAK_3$-NLS-KRAB-gLuc-2A-GFP-WPRE |

TABLE 2 sgRNA constructs currently used in genomic locus proteomic applications

| Oligonucleotide name/locus to be targeted | Oligonucleotide sequence |
|---|---|
| pXPR-hTert266bp-R2 (SEQ ID NO. 19) | aaacCGACCCCGGGGAGGCCCACCTGGCGGAAGG |
| pXPR-hTert92bp-F2 (SEQ ID NO. 20) | caccgCCCTGCTGCGCAGCCACTACCGCGAGGTGC |
| pXPR-hTert92bp-R2 (SEQ ID NO. 21) | aaacGCACCTCGCGGTAGTGGCTGCGCAGCAGGG |
| pXPR-hTert959bp-F2 (SEQ ID NO. 22) | caccgGCAGGTGACACCACACAGAAACCACGGTCA |
| pXPR-hTert959bp-R2 (SEQ ID NO. 23) | aaacTGACCGTGGTTTCTGTGTGGTGTCACCTGC |
| pXPR-107hTert-F2 (SEQ ID NO. 24) | caccgCCTTCCAGCTCCGCCTCCTCCGCGCGGACC |
| pXPR-107hTert-R2 (SEQ ID NO. 25) | aaacGGTCCGCGCGGAGGAGGCGGAGCTGGAAGG |
| pXPR-430hTert-F2 (SEQ ID NO. 26) | caccgCTCCGGATCAGGCCAGCGGCCAAAGGGTCG |
| pXPR-430hTert-R2 (SEQ ID NO. 27) | aaacCGACCCTTTGGCCGCTGGCCTGATCCGGAG |
| pXPR-53hMyc-F1 (SEQ ID NO. 28) | caccgCATAACGCGCTCTCCAAGTATACGTGGCAA |
| pXPR-53hMyc-R1 (SEQ ID NO. 29) | aaacTTGCCACGTATACTTGGAGAGCGCGTTATG |
| pXPR-477hMyc-F1 (SEQ ID NO. 30) | caccgAGGTGCTAGACGGGAGAATATGGGAGGGGC |
| pXPR-477hMyc-R1 (SEQ ID NO. 31) | aaacGCCCCTCCCATATTCTCCCGTCTAGCACCT |
| pXPR-hMyc86-F1 (SEQ ID NO. 32) | caccgTCCCTGGGACTCTTGATCAAAGCGCGGCC |
| pXPR-hMyc86-R1 (SEQ ID NO. 33) | aaacGGGCCGCGCTTTGATCAAGAGTCCCAGGGA |
| pXPR-hMyc379-F1 (SEQ ID NO. 34)? | caccgCGAAACTTTGCCCATAGCAGCGGGCGGGCA |
| pXPR-hMyc379-R1 (SEQ ID NO. 35) | aaacTGCCCGCCCGCTGCTATGGGCAAAGTTTCG |
| pXPR-hMyc162-F1 (SEQ ID NO. 36) | caccgACTCGCTGTAGTAATTCCAGCGAGAGGCAG |
| pXPR-hMyc162-R1 (SEQ ID NO. 37) | aaacCTGCCTCTCGCTGGAATTACTACAGCGAGT |

TABLE 2-continued sgRNA constructs currently used in genomic locus proteomic applications

| Oligonucleotide name/locus to be targeted | Oligonucleotide sequence |
|---|---|
| pXPR-hMyc262-F1 (SEQ ID NO. 38) | caccgGAAGGGAGATCCGGAGCGAATAGGGGGCTT |
| pXPR-hMyc262-R1 (SEQ ID NO. 39) | aaacAAGCCCCCTATTCGCTCCGGATCTCCCTTC |
| pXPR-mPou5f1_237-F1 (SEQ ID NO. 40) | caccgATGTCCGCCCGCATACGAGTTCTGCGGAGG |
| pXPR-mPou5f1_237-R1 (SEQ ID NO. 41) | aaacCCTCCGCAGAACTCGTATGCGGGCGGACAT |
| pXPR-406mPou5f1-F1 (SEQ ID NO. 42) | caccgAGACGGGTGGGTAAGCAAGAACTGAGGAGT |
| pXPR-406mPou5f1-R1 (SEQ ID NO. 43) | aaacACTCCTCAGTTCTTGCTTACCCACCCGTCT |
| pXPR-583mNanog-F1 (SEQ ID NO. 44) | caccgAAACACTCCTTAAATTGGGCATGGTGGTAG |
| pXPR-583mNanog-R1 (SEQ ID NO. 45) | aaacCTACCACCATGCCCAATTTAAGGAGTGTTT |
| pXPR-mNanog96-F1 (SEQ ID NO. 46) | caccgCAAATCAGCCTATCTGAAGGCCAACGGCTC |
| pXPR-mNanog96-R1 (SEQ ID NO. 47) | aaacGAGCCGTTGGCCTTCAGATAGGCTGATTTG |
| mPou5f1(SEQ ID NO. 48) | GGTCTCCCTATGAAGCCATA |
| mPou5f1(SEQ ID NO. 49) | GGTCTGCTGTCCCATCTCCA |
| mPou5f1(SEQ ID NO. 50) | GTACTTCAGACACCAGAAGA |
| 1809_mPouf51(SEQ ID NO. 51) | ATGAATGTATAGAAATTGGG |
| mPou5f1(SEQ ID NO. 52) | GAGGACACTAGACTAGAGCA |
| 125_mPouf51(SEQ ID NO. 53) | ATCTGCCTGTGTCTTCCAGA |
| mPouf51_401(SEQ ID NO. 54) | CCAACTTCACGGCATTGGGG |
| mSox1(SEQ ID NO. 55) | GCGCATTTAAACACGACCCA |
| mSox1(SEQ ID NO. 56) | CGATTGGGTTGAAAACCCAG |
| mSox1(SEQ ID NO. 57) | GCCATTAAATGAGCGCGCCG |
| mSox1(SEQ ID NO. 58) | CCGGGAGTGCAGAATAACAG |
| mSox1(SEQ ID NO. 59) | GGAGACTTCGAGCCGACAAG |
| 238_mNanog(SEQ ID NO. 60) | CTTCCCACTAGAGATCGCCA |
| mNanog_531(SEQ ID NO. 61) | GTAGTAGTCATTAACATAAG |
| mNanog_581(SEQ ID NO. 62) | ATCACCGGTCAAACTCAGAG |
| 977_mNanog(SEQ ID NO. 63) | ACTGTGGTAGAGTCTTCACA |
| mNanog_718(SEQ ID NO. 64) | GAGTGGTGTCTTCAGTAGCA |
| mNanog_773(SEQ ID NO. 65) | ATAACCTCACCAAAAAAATG |
| mVpreB1_DNaseHS(SEQ ID NO. 66) | GCAGAAGTGCAGCATGCAGG |
| mVpreB1_DNaseHS(SEQ ID NO. 67) | TTAAAGATGGAAAAAAAGTG |
| mVpreB1_DNaseHS(SEQ ID NO. 68) | GCTGTTGCCAGGTAACTGTG |
| mVpreB1_DNaseHS(SEQ ID NO. 69) | GTTCTTAGCACACATCAGGC |

TABLE 2-continued sgRNA constructs currently used in genomic locus proteomic applications

| Oligonucleotide name/locus to be targeted | Oligonucleotide sequence |
|---|---|
| mSox2(SEQ ID NO. 70) | TCTGGCGGAGAATAGTTGGG |
| mSox2(SEQ ID NO. 71) | GCAGGGCGCTGACGTCGTAG |
| mSox2(SEQ ID NO. 72) | GCGCTGTGCCCCGAACCGCG |
| mSox2(SEQ ID NO. 73) | ACTAATCACAACAATCGCGG |
| mSox2(SEQ ID NO. 74) | GATAAGTACACGCTTCCCGG |
| mSox2(SEQ ID NO. 75) | CGTTCATCGACGAGGCCAAG |
| mSox2(SEQ ID NO. 76) | GGCCAGCTCCAGCCCCCCCG |
| mSox2(SEQ ID NO. 77) | GGGCTCTGTGGTCAAGTCCG |
| mThy1(SEQ ID NO. 78) | GGAAAGCTAGAAAGGATGCG |
| mThy1(SEQ ID NO. 79) | CCCCTTGCCTTGCTTCCGAA |
| mThy1(SEQ ID NO. 80) | CAGAAGCCTGGATAACCAGA |
| mThy1(SEQ ID NO. 81) | TTAGTGGTGCGAATAGAGGG |
| mThy1(SEQ ID NO. 82) | TGAAGGTTCAAGCAAAGAAA |
| mThy1(SEQ ID NO. 83) | AGAGCAGATCTCCAGCCAAG |
| mTert(SEQ ID NO. 84) | GCTGCGCAGCCGATACCGGG |
| mTert(SEQ ID NO. 85) | GCAGCAGAGAGCGCACCGCG |
| mTert(SEQ ID NO. 86) | CCGCGCTCCTCGTTGCCCCG |
| mTert(SEQ ID NO. 87) | GCGCAGCAGAGAGCGCACCG |
| mTert(SEQ ID NO. 88) | ACGCACCCATAGCAAGGCCA |
| mTert(SEQ ID NO. 89) | CCACCAGGTGGGCCTCCAGG |
| TCONS_00011252(SEQ ID NO. 90) | ACGTTGTGTGAGGTTCCTAG |
| TCONS_00011252(SEQ ID NO. 91) | GATTCCTTTGGATATATACC |
| TCONS_00011252(SEQ ID NO. 92) | AAGAGGATTGCTGGATAACG |
| NR_034078(SEQ ID NO. 93) | GACTGCTGCTTAGAAATTCT |
| NR_034078(SEQ ID NO. 94) | CCGTGGGAAGAAACAAAGAA |
| NR_034078(SEQ ID NO. 95) | CCAGAAGAATAGTTAGTAAA |
| TCONS_00009861(SEQ ID NO. 96) | AAGTAGCAAGGGAGATTCTT |
| TCONS_00009861(SEQ ID NO. 97) | TGCAAAGAAGTCACATTCAC |
| TCONS_00009861(SEQ ID NO. 98) | TTATCAACTCAAAGTTCTGG |
| near_A11_TSS_1(SEQ ID NO. 99) | GCCCGTCACTCCGAGCGCGA |
| near_A11_TSS_2(SEQ ID NO. 100) | CCGGGTCCGCGCGAGGTACG |
| near_A11_TSS_3(SEQ ID NO. 101) | CCGAGAGAGCCCGTCCAAGT |
| near_A11_TSS_4(SEQ ID NO. 102) | TCACGCGCGGCTTGCCGGAT |
| near_A11_TSS_5(SEQ ID NO. 103) | CTATTTCCACGCGTTGGCGG |
| near_A11_TSS_6(SEQ ID NO. 104) | TGCATGCGTGTGAGTAGGGC |
| near_A11_TSS_7(SEQ ID NO. 105) | TTACAGGCTTGCACCGCGCC |
| near_A11_TSS_8(SEQ ID NO. 106) | GCGGGGAATCGCTTGAACCC |

TABLE 2-continued sgRNA constructs currently used in genomic locus proteomic applications

| Oligonucleotide name/locus to be targeted | Oligonucleotide sequence |
|---|---|
| near_A11_TSS_9(SEQ ID NO. 107) | GATATGGTGTTTCGCCATGT |
| rs10811660_1(SEQ ID NO. 108) | GCTGGAGGTGAGCTGCTGAC |
| rs10811660_2(SEQ ID NO. 109) | gCGCTTATTGACAAAGAAAA |
| rs12555274_1(SEQ ID NO. 110) | gCTGTCTTAATCAACAAAAT |
| rs12555274_2(SEQ ID NO. 111) | gTATGTTGAAAAGAAAATTA |
| p16(SEQ ID NO. 112) | gTCCCCCGCCTGCCAGCAAA |
| p14/ANRIL(SEQ ID NO. 113) | GCGCACACAGGGCGGGAAAG |
| p15(SEQ ID NO. 114) | gGTCCGCTGTGATCGCCGGG |
| PHACTOR1_1(SEQ ID NO. 115) | gTACTTTTATATGATCTCAA |
| PHACTOR1_2(SEQ ID NO. 116) | GCTCGTGGAAAATATAACTA |
| PHACTOR1_3(SEQ ID NO. 117) | gTATTTTAAAACTCAGCTCG |
| PHACTOR1_4(SEQ ID NO. 118) | gAAAATATGTATAAAGTCTG |
| PHACTOR1_5(SEQ ID NO. 119) | AAAAGTAGCTTAAAATCAT |
| near_A13_TSS_1(SEQ ID NO. 120) | CTGAGAAGTTCAACGGCTAA |
| near_A13_TSS_2(SEQ ID NO. 121) | GGCTGCGTGTTAGTGGCTTC |
| near_A13_TSS_3(SEQ ID NO. 122) | CCCACTAACAGGAAACCTAC |
| near_A13_TSS_4(SEQ ID NO. 123) | GAATGGGCGCATGCGTAAGG |
| near_A13_TSS_5(SEQ ID NO. 124) | GTAGGGCCCCACGTGACGCG |
| near_A13_TSS_6(SEQ ID NO. 125) | AGCTCGCCAATGAGGACGCG |
| near_A13_TSS_7(SEQ ID NO. 126) | ACACCGAACCGGGACCGATC |
| near_A13_TSS_8(SEQ ID NO. 127) | TTCCCAAGGCGGGGCGATAT |
| near_A13_TSS_9(SEQ ID NO. 128) | GAGGTGCGGCGTCCAGAACC |
| rs6983267_1(SEQ ID NO. 129) | gTTTGAGCTCAGCAGATGAA |
| rs6983267_2(SEQ ID NO. 130) | gGACTTTATTTTATTTTATG |
| rs6983267_3(SEQ ID NO. 131) | gTTTCATCTGCTGAGCTCAA |
| cMYC_1(SEQ ID NO. 132) | gCCCCGAGCTGTGCTGCTCG |
| cMYC_2(SEQ ID NO. 133) | gTCCCGGGTTCCCAAAGCAG |
| cMYC_3(SEQ ID NO. 134) | GCGCGCGTAGTTAATTCATG |
| human scramble 1(SEQ ID NO. 135) | AAGAAGGGCCGTACCCGAAA |
| human scramble 2(SEQ ID NO. 136) | AGGTCAAGCCGACCTCGAAC |
| mouse scramble 1(SEQ ID NO. 137) | GCGAGCGCTATCCCGGTGGA |

MS2 Loops, MS2-BirA, RNA-Binding Proteins.

Suitable RNA-binding domains for the fusion protein may include RNA-binding domains of bacteriophage proteins. In some embodiments, the RNA-binding domain of the fusion protein is the RNA-binding domain of the coat protein of the MS2 bacteriophage or R17 bacteriophage. In other embodiments, the RNA-binding domain of the fusion protein is the RNA-binding domain of N-protein of a lambdoid bacteriophage, such as N-protein of lambda bacteriophage, N-protein of P22 bacteriophage, or N-protein of phi21 bacteriophage. Accordingly, suitable RNA-motifs for the cargo RNA may include the corresponding high affinity binding loop of RNA of MS2 bacteriophage to which the MS2 coat protein binds, or the corresponding high affinity binding loop of RNA of the lambdoid bacteriophage to which the N-protein binds.

In some embodiments, the RNA-binding domain of the fusion protein is an RNA-binding domain of coat protein of MS2 bacteriophage or R17 bacteriophage, which may be considered to be interchangeable. (See, Keryer-Bibens et al.; and Stockley et al., "Probing sequence-specific RNA recognition by the bacteriophage MS2 coat protein," Nucl. Acids. Res., 1995, Vol. 23, No. 13, pages 2512-2518, the content of which is incorporated herein by reference in us entirety). The fusion proteins disclosed herein may include the full-length amino acid sequence of the coat protein of MS2 bacteriophage or a variant thereof as contemplated herein having a percentage of sequence identity in comparison to the amino acid sequence of the coat protein of MS2 bacteriophage, or a fragment thereof comprising a portion of the coat protein of MS2 bacteriophage In embodiments where the fusion protein comprises an RNA-binding domain of coat protein of MS2 bacteriophage, the cargo RNA typically comprises an RNA-motif of MS2 bacteriophage RNA which may form a high affinity binding loop that binds to the RNA-binding domain of the fusion protein. (See Peabody et al., "The RNA binding site of bacteriophage MS2 coat protein," The EMBO J., vol. 12, no. 2, pp. 595-600, 1993, Keryer-Bibens et al.; and Stockley et al., the contents of which are incorporated herein by reference in their entireties). The RNA-motif of MS2 bacteriophage and R17 bacteriophage has been characterized. (See id.). The RNA-motif has been determined to comprise minimally a 21-nt stem-loop structure where the identity of the nucleotides forming the stem do not appear to influence the affinity of the coat protein for the RNA-motif, but where the sequence of the loop contains a 4-nt sequence (AUUA), which does influence the affinity of the coat protein for the RNA-motif. Also important, is an unpaired adenosine two nucleotides upstream of the loop.

Aspects of the invention encompass a non-naturally occurring or engineered composition that may comprise a guide RNA (sgRNA) comprising a guide sequence capable of hybridizing to a target sequence in a genomic locus of interest in a cell and a CRISPR enzyme that may comprise at least one or more nuclear localization sequences, wherein the CRISPR enzyme comprises two or more mutations, such that the enzyme has altered or diminished nuclease activity compared with the wild type enzyme, wherein at least one loop of the sgRNA is modified by the insertion of distinct RNA sequence(s) that bind to one or more adaptor proteins, and wherein the adaptor protein further recruits one or more heterologous functional domains. In an embodiment of the invention the CRISPR enzyme comprises two or more mutations in a residue selected from the group comprising, consisting essentially of, or consisting of D10, E762, H840, N854, N863, or D986. In a further embodiment the CRISPR enzyme comprises two or more mutations selected from the group comprising D10A, E762A, H840A, N854A, N863A or D986A. In another embodiment, the functional domain is a transcriptional activation domain, e.g., VP64. In another embodiment, the functional domain is a transcriptional repressor domain, e.g., KRAB domain, SID domain or a SID4X domain. In embodiments of the invention, the one or more heterologous functional domains have one or more activities selected from the group comprising, consisting essentially of, or consisting of methylase activity, demethylase activity, transcription activation activity, transcription repression activity, transcription release factor activity, histone modification activity, RNA cleavage activity and nucleic acid binding activity. In further embodiments of the invention the cell is a eukaryotic cell or a mammalian cell or a human cell. In further embodiments, the adaptor protein is selected from the group comprising, consisting essentially of, or consisting of MS2, PP7, Qβ, F2, GA, fr, JP501, M12, R17, BZ13, JP34, JP500, KU1, M11, MX1, TW18, VK, SP, FI, ID2, NL95, TW19, AP205, ϕCb5, ϕCb8r, ϕCb12r, ϕCb23r, 7s, PRR1. In another embodiment, the at least one loop of the sgRNA is tetraloop and/or loop2. An aspect of the invention emcompasses methods of modifying a genomic locus of interest to change gene expression in a cell by introducing into the cell any of the compositions described herein.

In another embodiment, sequence specific RNA binding proteins are contemplated as an alternative to MS2.

TABLE 3

| RNA-binding proteins for sgRNA delivery of biotinylation enzymes | | |
|---|---|---|
| AP205 | JP501 | R17 |
| BZ13 | KU1 | SP |
| F2 | M11 | TW18 |
| FI | M12 | TW19 |
| Fr | MX1 | VK |
| GA | NL95 | ϕCb12r |
| ID2 | PP7 | ϕCb23r |
| JP34 | PUM | ϕCb5 |
| JP500 | Qβ | ϕCb8r |

The current invention comprehends the use of the compositions disclosed herein to establish and utilize conditional or inducible CRISPR transgenic cell/animals. (See, e.g., Platt et al., Cell (2014), 159 (2): 440-455, or PCT patent publications cited herein, such as WO 2014/093622 (PCT/US2013/074667), which are not believed prior to the present invention or application). For example, the target cell comprises CRISRP enzyme (e.g., Cas9) conditionally or inducibly (e.g., in the form of Cre dependent constructs) and/or the adapter protein conditionally or inducibly and, on expression of a vector introduced into the target cell, the vector expresses that which induces or gives rise to the condition of CRISRP enzyme (e.g., Cas9) expression and/or adaptor expression in the target cell. By applying the teaching and compositions of the current invention with the known method of creating a CRISPR complex, inducible genomic events affected by functional domains are also an aspect of the current invention. One more example of this is the creation of a CRISPR knock-in/conditional transgenic animal (e.g., mouse comprising e.g., a Lox-Stop-polyA-Lox (LSL) cassette) and subsequent delivery of one or more compositions providing one or more modified sgRNA (e.g., −200 nucleotides to TSS of a target gene of interest for gene activation purposes) as described herein (e.g., modified sgRNA with one or more aptamers recognized by coat proteins, e.g., MS2), one or more adapter proteins as described herein (MS2 binding protein linked to one or more VP64) and means for inducing the conditional animal (e.g., Cre recombinase for rendering Cas9 expression inducible). Alternatively, the adaptor protein may be provided as a conditional or inducible element with a conditional or inducible CRISPR enzyme to provide an effective model for screening purposes, which advantageously only requires minimal design and administration of specific sgRNAs for a broad number of applications.

One guide with a first aptamer/RNA-binding protein pair can be linked or fused to an activator, whilst a second guide with a second aptamer/RNA-binding protein pair can be linked or fused to a repressor. The guides are for different targets (loci), so this allows one gene to be activated and one repressed. For example, the following schematic shows such an approach:

Guide 1—MS2 aptamer—MS2 RNA-binding protein—VP64 activator; and

Guide 2—PP7 aptamer—PP7 RNA-binding protein—SID4x repressor.

The present invention also relates to orthogonal PP7/MS2 gene targeting. In this example, sgRNA targeting different loci are modified with distinct RNA loops in order to recruit MS2-VP64 or PP7-SID4X, which activate and repress their target loci, respectively. PP7 is the RNA-binding coat protein of the bacteriophage *Pseudomonas*. Like MS2, it binds a specific RNA sequence and secondary structure. The PP7 RNA-recognition motif is distinct from that of MS2. Consequently, PP7 and MS2 can be multiplexed to mediate distinct effects at different genomic loci simultaneously. For example, an sgRNA targeting locus A can be modified with MS2 loops, recruiting MS2-VP64 activators, while another sgRNA targeting locus B can be modified with PP7 loops, recruiting PP7-SID4X repressor domains. In the same cell, dCas9 can thus mediate orthogonal, locus-specific modifications. This principle can be extended to incorporate other orthogonal RNA-binding proteins such as Q-beta.

An alternative option for orthogonal repression includes incorporating non-coding RNA loops with transactive repressive function into the guide (either at similar positions to the MS2/PP7 loops integrated into the guide or at the 3' terminus of the guide). For instance, guides were designed with non-coding (but known to be repressive) RNA loops (e.g., using the Alu repressor (in RNA) that interferes with RNA polymerase II in mammalian cells). The Alu RNA sequence was located: in place of the MS2 RNA sequences as used herein (e.g., at tetraloop and/or stem loop 2); and/or at 3' terminus of the guide. This gives possible combinations of MS2, PP7 or Alu at the tetraloop and/or stemloop 2 positions, as well as, optionally, addition of Alu at the 3' end of the guide (with or without a linker). As many as 30 different sequence specific RNA binding proteins may be utilized in this system for multiplexing targets by pairing targeted sgRNA with protein specific RNA motifs.

The use of two different aptamers (distinct RNA) allows an activator-adaptor protein fusion and a repressor-adaptor protein fusion to be used, with different guides, to activate expression of one gene, whilst repressing another. They, along with their different guides can be administered together, or substantially together, in a multiplexed approach. A large number of such modified guides can be used all at the same time, for example 10 or 20 or 30 and so forth, whilst only one (or at least a minimal number) of Cas9s to be delivered, as a comparatively small number of Cas9s can be used with a large number modified guides. The adaptor protein may be associated (preferably linked or fused to) one or more activators or one or more repressors. For example, the adaptor protein may be associated with a first activator and a second activator. The first and second activators may be the same, but they are preferably different activators. For example, one might be VP64, whilst the other might be p65, although these are just examples and other transcriptional activators are envisaged. Three or more or even four or more activators (or repressors) may be used, but package size may limit the number being higher than 5 different functional domains. Linkers are preferably used, over a direct fusion to the adaptor protein, where two or more functional domains are associated with the adaptor protein. Suitable linkers might include the GlySer linker.

It is also envisaged that the enzyme-guide complex as a whole may be associated with two or more functional domains. For example, there may be two or more functional domains associated with the enzyme, or there may be two or more functional domains associated with the guide (via one or more adaptor proteins), or there may be one or more functional domains associated with the enzyme and one or more functional domains associated with the guide (via one or more adaptor proteins).

The fusion between the adaptor protein and the activator or repressor may include a linker. For example, GlySer linkers GGGS can be used. They can be used in repeats of 3 ((GGGGS)3) (SEQ. I.D. No. 138) or 6 (Seq. I.D. No. 139), 9 (Seq. I.D. No. 140) or even 12 (Seq. I.D. No. 141) or more, to provide suitable lengths, as required. Linkers can be used between the RNA-binding protein and the functional domain (activator or repressor), or between the CRISPR Enzyme (Cas9) and the functional domain (activator or repressor). The linkers the user to engineer appropriate amounts of "mechanical flexibility".

Biotin concentration and timing: Biotin-protein ligase method: In HEK293T cells, human induced pluripotent stem cells, and mouse embryonic stem cells maintained in appropriate growth media are stably infected with lenti-viral constructs for the versions of the application: dCas9-BirAR118G, MS2-BirAR118G, dCas9-Split-BirAR118G, TALE-BirA, dCas9-APEX respectively at a multiplicity of infection of 1 per cell. Each stable integrant will be selected for with appropriate antibiotic selection for each vector (puromycin, blasticidin, hygromycin, neomycin). Cells are arrested 72 hrs in minimal growth media. Biotinylation is induced by the addition of free biotin to a final concentration of 50 uM in normal growth media for 18 hrs. Both biotin concentration and exposure times can be optimized for improved signal to noise.

APEX method: The peroxidase inducible dCas9-APEX will be stably integrated by lenti-virus into HEK293T, human induced pluripotent stem cells, and mouse embryonic stem cells maintained in appropriate growth media and selected for in appropriate antibiotic selection. Cultures were incubated with 500 mM biotin-phenol for 30 min at 37° C. Then, $H_2O_2$ is added to a final concentration of 1 mM for 1 min at room temperature, after which the probe/$H_2O_2$ solution is replaced with 15 ml of "quencher solution" (10 mM sodium ascorbate, 10 mM sodium azide, and 5 mM Trolox in Dulbecco's Phosphate Buffered Saline [DPBS]). All samples, omcluding a negative control with biotin-phenol and $H_2O_2$ omitted, are washed twice with the quencher solution, twice with DPBS, and once more with the quencher solution. The cells are then collected in 5 ml of quencher solution by gentle pipetting and pelleted at 500 3 g for 3 min at room temperature.

Analysis by ChIP: Each delivery version for directed biotinylation (collectively referred to as dCas9/TALE-fusions) is targeted in positions arrayed across the promoter of a known tumor suppressor gene, TERT in HEK293T cells. The promoter of this gene is known to harbor mutations that significantly impact melanoma risk, further many proteins have previously been shown to interact with this promoter therefore Applicants expect to pull-down these proteins along with unknown proteins at this site. Following biotinylation, cells are cross-linked by formaldehyde covalently binding proteins and proximal DNA. These samples are lysed and sonicated producing a lysate of protein-DNA conjugates. Two parallel ChIPs are performed with each sample, 1) ChIP of dCas9 to measure the interaction of the dCas9/TALE-fusions with their respective target site in the genome. And 2) for each sample a Biotin-streptavidin pull-down is performed to determine if proteins at the cDas9-fusion target location are successfully being biotinylated. Initial results indicate specific recruitment of dCas9/TALE-fusions to the target location as well as specific biotinylation of proteins at the same site. Streptavidin alternatives for biotin purification include, but are not limited to, avidin, NeutrAvidin, CaptAvidin and anti-biotin antibodies.

Analysis by MS/MS: Precise, relative quantitation will be key to successfully differentiate proteins proximal to the target site from background, non-specific labeling. Applicants employ tandem mass tagging (TMT) isobaric peptide labeling to 1) increase the sensitivity of detection with sample multiplexing, 2) unbiasedly identify proteins at the Tert promoter, and 3) to differentiate between specific and non-specific labeling. With TMT-labeling, up to ten samples can be mixed and analysed in a single LC-MS/MS run. This allows a single experiment to include replicates and controls, while minimizing missing data points between samples. Furthermore, because peptides from each state are isobaric after TMT labeling mixing provides summation of signal from each condition (multiplexing), providing substantial improvements in signal to noise. Therefore, overlap of biotinylated regions in the different sgRNA-expressing cell lines will increase the signal of specific proteins, while non-specific signal will be cell line specific. MS/MS of the summed precursor intensity will provide peptide identification as well as reporter ion intensities for each condition allowing relative quantitation between experimental states. The use of a non-specific and a very distant sgRNA will allow us to distinguish between proteins associated with the genomic locus of interest and that of background labeling.

Multiplexing. The methods and uses of the present invention may be multiplexed. It is foreseen to multiplex the system utilizing the sgRNA sequence to identify each protein complex in an arrayed screen method.

For example, sgRNA pools in the presence of the CRISPR-Cas fusion protein of the invention, such as dCas9-BirAR118G in cells may be purified and separated in non-denaturing conditions by electrophoresis or sucrose centrifugation for protein fractionation. Gel electrophoresis or fractions may be split into two samples. One half of each sample may be analyzed by next generation sequencing of each sgRNA to determine target genomic location. The second half of the sample may be separated by standard protein electrophoresis in non-denaturing conditions. Coomassie or silver-stained protein bands may be isolated and submitted for SILAC/MS analysis.

In vivo. The in vivo applications will enable the purification of biotin-labeled proteins from experimental model tissues. In brief, the fusion proteins, polynucleotides and/or systems of the present invention may be delivered using adeno-viral, *lenti*-viral or adeno-associated virus delivery to a target experimental model.

For example, biotin may be administered to the peritoneal cavity and tissues of interest may be extracted. Proteins may be purified from tissue samples by streptavidin pull down and analyzed by mass spectrometry.

The present invention may be used for analysis of human tissues in animal model implants. Pre-implant human cells may be treated with fusion proteins, polynucleotides and/or systems of the present invention, for a target site and implanted into a model organism. Biotin may be administered to the model, and the human material may be explanted and proteins may be purified from tissue samples by streptavidin pull down and analyzed by mass spectrometry.

Ex vivo. The present invention is useful for ex vivo applications. Detection of protein occupancy at regulatory sites of genes in primary tissue can be performed, e.g. by viral delivery of fusion proteins, polynucleotides and/or systems of the present invention, to ex vivo tissues, along with free biotin in culture media.

The present invention could be instrumental for detection of novel proteins at sites known to be important for disease progression. Comparison of protein occupancy at known driver genes of disease in paired healthy and disease samples could identify proteins, in those tissues, that not only control disease gene (mechanism discovery) but these proteins once identified may serve as novel therapeutic targets or act as markers of disease risk/progression (therapeutic/marker discovery; time lapse and monitoring).

Disease mechanism discovery. A key finding from the in depth characterization of disease genetics over about the last 8 years is that he vast majority of disease relevant genomic locations are non-protein coding. The present invention could be applied to cell culture models, in vivo models or ex vivo models in tissues appropriate for each disease. A non-biased method for identifying proteins at genetically nominated sights would provide tremendous insight into disease mechanism. At present only a handful of variants that are associated with disease at a genome wide significant level have been shown to alter protein binding at those sights. The present invention also contemplates genome wide interaction mapping (see, eg., Rao et al., Cell. 2014 Dec. 18; 159 (7): 1665-80. doi: 10.1016/j.cell.2014.11.021. Epub 2014 Dec. 11).

Genomics of cancer biology has compiled a large number of somatic mutations found in disease tissues compared to healthy tissue. With the increased application of next generation sequencing, the number of non-coding somatic mutations has expanded. Recently the Garaway lab has identified a somatic mutation in the promoter of TERT that occurs in ~71% of melanoma samples and in 16% of a panel of different cancer types (Science. 2013 Feb. 22; 339 (6122): 957-9. doi: 10.1126/science.1229259. Epub 2013 Jan. 24. *Highly recurrent TERT promoter mutations in human melanoma*. Huang F W et al.). The number of similar findings in other cancer types in the promoters of known oncogenes/tumor suppressors is coming to light. The present invention has the potential to elucidate which proteins and pathways are disrupted at recurrently mutated non-coding sites such as the one at the TERT promoter.

The target polynucleotide of the complex of the present invention may include a number of disease-associated genes and polynucleotides as well as signaling biochemical pathway-associated genes and polynucleotides as listed in U.S. provisional patent applications 61/736,527 and 61/748,427 having Broad reference BI-2011/008/WSGR Docket No. 44063-701.101 and BI-2011/008/WSGR Docket No. 44063-701.102 respectively, both entitled SYSTEMS METHODS AND COMPOSITIONS FOR SEQUENCE MANIPULATION filed on Dec. 12, 2012 and Jan. 2, 2013, respectively, the contents of all of which are herein incorporated by reference in their entirety.

Examples of target polynucleotides include a sequence associated with a signaling biochemical pathway, e.g., a signaling biochemical pathway-associated gene or polynucleotide. Examples of target polynucleotides include a disease associated gene or polynucleotide. A "disease-associated" gene or polynucleotide refers to any gene or polynucleotide which is yielding transcription or translation products at an abnormal level or in an abnormal form in cells derived from a disease-affected tissues compared with tissues or cells of a non-disease control. It may be a gene that becomes expressed at an abnormally high level; it may be a gene that becomes expressed at an abnormally low level, where the altered expression correlates with the occurrence and/or progression of the disease. A disease-associated gene also refers to a gene possessing mutation(s) or genetic variation that is directly responsible or is in linkage disequilibrium with a gene(s) that is responsible for the etiology of a disease. The transcribed or translated products may be known or unknown, and may be at a normal or abnormal level.

Examples of disease-associated genes and polynucleotides are listed in Tables A and B. Disease specific information is available from McKusick-Nathans Institute of Genetic Medicine, Johns Hopkins University (Baltimore, Md.) and National Center for Biotechnology Information, National Library of Medicine (Bethesda, Md.), available on the World Wide Web. Examples of signaling biochemical pathway-associated genes and polynucleotides are listed in Table C.

Mutations in these genes and pathways can result in production of improper proteins or proteins in improper amounts which affect function. Further examples of genes, diseases and proteins are hereby incorporated by reference from U.S. Provisional application 61/736,527 filed Dec. 12, 2012. Such genes, proteins and pathways may be the target polynucleotide of a complex of the present invention.

TABLE A

| DISEASE/DISORDERS | GENE(S) |
|---|---|
| Neoplasia | PTEN; ATM; ATR; EGFR; ERBB2; ERBB3; ERBB4; Notch1; Notch2; Notch3; Notch4; AKT; AKT2; AKT3; HIF; HIF1a; HIF3a; Met; HRG; Bcl2; PPAR alpha; PPAR gamma; WT1 (Wilms Tumor); FGF Receptor Family members (5 members: 1, 2, 3, 4, 5); CDKN2a; APC; RB (retinoblastoma); MEN1; VHL; BRCA1; BRCA2; AR (Androgen Receptor); TSG101; IGF; IGF Receptor; Igf1 (4 variants); Igf2 (3 variants); Igf 1 Receptor; Igf 2 Receptor; Bax; Bcl2; caspases family (9 members: 1, 2, 3, 4, 6, 7, 8, 9, 12); Kras; Apc |
| Age-related Macular Degeneration | Abcr; Ccl2; Cc2; cp (ceruloplasmin); Timp3; cathepsinD; Vldlr; Ccr2 |
| Schizophrenia | Neuregulin1 (Nrg1); Erb4 (receptor for Neuregulin); Complexin1 (Cplx1); Tph1 Tryptophan hydroxylase; Tph2 Tryptophan hydroxylase 2; Neurexin 1; GSK3; GSK3a; GSK3b |
| Disorders | 5-HTT (Slc6a4); COMT; DRD (Drd1a); SLC6A3; DAOA; DTNBP1; Dao (Dao1) |
| Trinucleotide Repeat Disorders | HTT (Huntington's Dx); SBMA/SMAX1/AR (Kennedy's Dx); FXN/X25 (Friedrich's Ataxia); ATX3 (Machado-Joseph's Dx); ATXN1 and ATXN2 (spinocerebellar ataxias); DMPK (myotonic dystrophy); Atrophin-1 and Atn1 (DRPLA Dx); CBP (Creb-BP - global instability); VLDLR (Alzheimer's); Atxn7; Atxn10 |
| Fragile X Syndrome | FMR2; FXR1; FXR2; mGLUR5 |
| Secretase Related Disorders | APH-1 (alpha and beta); Presenilin (Psen1); nicastrin (Ncstn); PEN-2 |
| Others | Nos1; Parp1; Nat1; Nat2 |
| Prion-related disorders | Prp |
| ALS | SOD1; ALS2; STEX; FUS; TARDBP; VEGF (VEGF-a; VEGF-b; VEGF-c) |
| Drug addiction | Prkce (alcohol); Drd2; Drd4; ABAT (alcohol); GRIA2; Grm5; Grin1; Htr1b; Grin2a; Drd3; Pdyn; Gria1 (alcohol) |
| Autism | Mecp2; BZRAP1; MDGA2; Sema5A; Neurexin 1; Fragile X (FMR2 (AFF2); FXR1; FXR2; Mglur5) |
| Alzheimer's Disease | E1; CHIP; UCH; UBB; Tau; LRP; PICALM; Clusterin; PS1; SORL1; CR1; Vldlr; Uba1; Uba3; CHIP28 (Aqp1, Aquaporin 1); Uchl1; Uchl3; APP |
| Inflammation | IL-10; IL-1 (IL-1a; IL-1b); IL-13; IL-17 (IL-17a (CTLA8); IL-17b; IL-17c; IL-17d; IL-17f); II-23; Cx3cr1; ptpn22; TNFa; NOD2/CARD15 for IBD; IL-6; IL-12 (IL-12a; IL-12b); CTLA4; Cx3cl1 |
| Parkinson's Disease | x-Synuclein; DJ-1; LRRK2; Parkin; PINK1 |

TABLE B

| | |
|---|---|
| Blood and coagulation diseases and disorders | Anemia (CDAN1, CDA1, RPS19, DBA, PKLR, PK1, NT5C3, UMPH1, PSN1, RHAG, RH50A, NRAMP2, SPTB, ALAS2, ANH1, ASB, ABCB7, ABC7, ASAT); Bare lymphocyte syndrome (TAPBP, TPSN, TAP2, ABCB3, PSF2, RING11, MHC2TA, C2TA, RFX5, RFXAP, RFX5), Bleeding disorders (TBXA2R, P2RX1, P2X1); Factor H and factor H-like 1 (HF1, CFH, HUS); Factor V and factor VIII (MCFD2); Factor VII deficiency (F7); Factor X deficiency (F10); Factor XI deficiency (F11); Factor XII deficiency (F12, HAF); Factor XIIIA deficiency (F13A1, F13A); Factor XIIIB deficiency (F13B); Fanconi anemia (FANCA, FACA, FA1, FA, FAA, FAAP95, FAAP90, FLJ34064, FANCB, FANCC, FACC, BRCA2, FANCD1, FANCD2, FANCD, FACD, FAD, FANCE, FACE, FANCF, XRCC9, FANCG, BRIP1, BACH1, FANCJ, PHF9, FANCL, FANCM, KIAA1596); Hemophagocytic lymphohistiocytosis disorders (PRF1, HPLH2, |

TABLE B-continued

| | |
|---|---|
| | UNC13D, MUNC13-4, HPLH3, HLH3, FHL3); Hemophilia A (F8, F8C, HEMA); Hemophilia B (F9, HEMB), Hemorrhagic disorders (PI, ATT, F5); Leukocyde deficiencies and disorders (ITGB2, CD18, LCAMB, LAD, EIF2B1, EIF2BA, EIF2B2, EIF2B3, EIF2B5, LVWM, CACH, CLE, EIF2B4); Sickle cell anemia (HBB); Thalassemia (HBA2, HBB, HBD, LCRB, HBA1). |
| Cell dysregulation and oncology diseases and disorders | B-cell non-Hodgkin lymphoma (BCL7A, BCL7); Leukemia (TAL1, TCL5, SCL, TAL2, FLT3, NBS1, NBS, ZNFN1A1, IK1, LYF1, HOXD4, HOX4B, BCR, CML, PHL, ALL, ARNT, KRAS2, RASK2, GMPS, AF10, ARHGEF12, LARG, KIAA0382, CALM, CLTH, CEBPA, CEBP, CHIC2, BTL, FLT3, KIT, PBT, LPP, NPM1, NUP214, D9S46E, CAN, CAIN, RUNX1, CBFA2, AML1, WHSC1L1, NSD3, FLT3, AF1Q, NPM1, NUMA1, ZNF145, PLZF, PML, MYL, STAT5B, AF10, CALM, CLTH, ARL11, ARLTS1, P2RX7, P2X7, BCR, CML, PHL, ALL, GRAF, NF1, VRNF, WSS, NFNS, PTPN11, PTP2C, SHP2, NS1, BCL2, CCND1, PRAD1, BCL1, TCRA, GATA1, GF1, ERYF1, NFE1, ABL1, NQO1, DIA4, NMOR1, NUP214, D9S46E, CAN, CAIN). |
| Inflammation and immune related diseases and disorders | AIDS (KIR3DL1, NKAT3, NKB1, AMB11, KIR3DS1, IFNG, CXCL12, SDF1); Autoimmune lymphoproliferative syndrome (TNFRSF6, APT1, FAS, CD95, ALPS1A); Combined immunodeficiency, (IL2RG, SCIDX1, SCIDX, IMD4); HIV-1 (CCL5, SCYA5, D17S136E, TCP228), HIV susceptibility or infection (IL10, CSIF, CMKBR2, CCR2, CMKBR5, CCCKR5 (CCR5)); Immunodeficiencies (CD3E, CD3G, AICDA, AID, HIGM2, TNFRSF5, CD40, UNG, DGU, HIGM4, TNFSF5, CD40LG, HIGM1, IGM, FOXP3, IPEX, AIID, XPID, PIDX, TNFRSF14B, TACI); Inflammation (IL-10, IL-1 (IL-1a, IL-1b), IL-13, IL-17 (IL-17a (CTLA8), IL-17b, IL-17c, IL-17d, IL-17f), II-23, Cx3cr1, ptpn22, TNFa, NOD2/CARD15 for IBD, IL-6, IL-12 (IL-12a, IL-12b), CTLA4, Cx3cl1); Severe combined immunodeficiencies (SCIDs)(JAK3, JAKL, DCLRE1C, ARTEMIS, SCIDA, RAG1, RAG2, ADA, PTPRC, CD45, LCA, IL7R, CD3D, T3D, IL2RG, SCIDX1, SCIDX, IMD4). |
| Metabolic, liver, kidney and protein diseases and disorders | Amyloid neuropathy (TTR, PALB); Amyloidosis (APOA1, APP, AAA, CVAP, AD1, GSN, FGA, LYZ, TTR, PALB); Cirrhosis (KRT18, KRT8, CIRH1A, NAIC, TEX292, KIAA1988); Cystic fibrosis (CFTR, ABCC7, CF, MRP7); Glycogen storage diseases (SLC2A2, GLUT2, G6PC, G6PT, G6PT1, GAA, LAMP2, LAMPB, AGL, GDE, GBE1, GYS2, PYGL, PFKM); Hepatic adenoma, 142330 (TCF1, HNF1A, MODY3), Hepatic failure, early onset, and neurologic disorder (SCOD1, SCO1), Hepatic lipase deficiency (LIPC), Hepatoblastoma, cancer and carcinomas (CTNNB1, PDGFRL, PDGRL, PRLTS, AXIN1, AXIN, CTNNB1, TP53, P53, LFS1, IGF2R, MPRI, MET, CASP8, MCH5; Medullary cystic kidney disease (UMOD, HNFJ, FJHN, MCKD2, ADMCKD2); Phenylketonuria (PAH, PKU1, QDPR, DHPR, PTS); Polycystic kidney and hepatic disease (FCYT, PKHD1, ARPKD, PKD1, PKD2, PKD4, PKDTS, PRKCSH, G19P1, PCLD, SEC63). |
| Muscular/Skeletal diseases and disorders | Becker muscular dystrophy (DMD, BMD, MYF6), Duchenne Muscular Dystrophy (DMD, BMD); Emery-Dreifuss muscular dystrophy (LMNA, LMN1, EMD2, FPLD, CMD1A, HGPS, LGMD1B, LMNA, LMN1, EMD2, FPLD, CMD1A); Facioscapulohumeral muscular dystrophy (FSHMD1A, FSHD1A); Muscular dystrophy (FKRP, MDC1C, LGMD2I, LAMA2, LAMM, LARGE, KIAA0609, MDC1D, FCMD, TTID, MYOT, CAPN3, CANP3, DYSF, LGMD2B, SGCG, LGMD2C, DMDA1, SCG3, SGCA, ADL, DAG2, LGMD2D, DMDA2, SGCB, LGMD2E, SGCD, SGD, LGMD2F, CMD1L, TCAP, LGMD2G, CMD1N, TRIM32, HT2A, LGMD2H, FKRP, MDC1C, LGMD2I, TTN, CMD1G, TMD, LGMD2J, POMT1, CAV3, LGMD1C, SEPN1, SELN, RSMD1, PLEC1, PLTN, EBS1); Osteopetrosis (LRP5, BMND1, LRP7, LR3, OPPG, VBCH2, CLCN7, CLC7, OPTA2, OSTM1, GL, TCIRG1, TIRC7, OC116, OPTB1); Muscular atrophy (VAPB, VAPC, ALS8, SMN1, SMA1, SMA2, SMA3, SMA4, BSCL2, SPG17, GARS, SMAD1, CMT2D, HEXB, IGHMBP2, SMUBP2, CATF1, SMARD1). |
| Neurological and neuronal diseases and disorders | ALS (SOD1, ALS2, STEX, FUS, TARDBP, VEGF (VEGF-a, VEGF-b, VEGF-c); Alzheimer disease (APP, AAA, CVAP, AD1, APOE, AD2, PSEN2, AD4, STM2, APBB2, FE65L1, NOS3, PLAU, URK, ACE, DCP1, ACE1, MPO, PACIP1, PAXIP1L, PTIP, A2M, BLMH, BMH, PSEN1, AD3); Autism (Mecp2, BZRAP1, MDGA2, Sema5A, Neurexin1, GLO1, MECP2, RTT, PPMX, MRX16, MRX79, NLGN3, NLGN4, KIAA1260, AUTSX2); Fragile X Syndrome (FMR2, FXR1, FXR2, mGLUR5); Huntington's disease and disease like disorders (HD, IT15, PRNP, PRIP, JPH3, JP3, HDL2, TBP, SCA17); Parkinson disease (NR4A2, NURR1, NOT, TINUR, SNCAIP, TBP, SCA17, SNCA, NACP, PARK1, PARK4, DJ1, PARK7, LRRK2, PARK8, PINK1, PARK6, UCHL1, PARK5, SNCA, NACP, PARK1, PARK4, PRKN, PARK2, PDJ, DBH, NDUFV2); Rett syndrome (MECP2, RTT, PPMX, MRX16, MRX79, CDKL5, STK9, MECP2, RTT, PPMX, MRX16, MRX79, x-Synuclein, DJ-1); Schizophrenia (Neuregulin1 (Nrg1), Erb4 (receptor for Neuregulin), Complexin1 (Cplx1), Tph1 Tryptophan hydroxylase, Tph2, Tryptophan hydroxylase 2, Neurexin 1, GSK3, GSK3a, GSK3b, 5-HTT (Slc6a4), COMT, DRD (Drd1a), SLC6A3, DAOA, DTNBP1, Dao (Dao1)); Secretase Related Disorders (APH-1 |

TABLE B-continued

| | |
|---|---|
| | (alpha and beta), Presenilin (Psen1), nicastrin, (Ncstn), PEN-2, Nos1, Parp1, Nat1, Nat2); Trinucleotide Repeat Disorders (HTT (Huntington's Dx), SBMA/SMAX1/AR (Kennedy's Dx), FXN/X25 (Friedrich's Ataxia), ATX3 (Machado-Joseph's Dx), ATXN1 and ATXN2 (spinocerebellar ataxias), DMPK (myotonic dystrophy), Atrophin-1 and Atn1 (DRPLA Dx), CBP (Creb-BP-global instability), VLDLR (Alzheimer's), Atxn7, Atxn10). |
| Occular diseases and disorders | Age-related macular degeneration (Abcr, Ccl2, Cc2, cp (ceruloplasmin), Timp3, cathepsinD, Vldlr, Ccr2); Cataract (CRYAA, CRYA1, CRYBB2, CRYB2, PITX3, BFSP2, CP49, CP47, CRYAA, CRYA1, PAX6, AN2, MGDA, CRYBA1, CRYB1, CRYGC, CRYG3, CCL, LIM2, MP19, CRYGD, CRYG4, BFSP2, CP49, CP47, HSF4, CTM, HSF4, CTM, MIP, AQP0, CRYAB, CRYA2, CTPP2, CRYBB1, CRYGD, CRYG4, CRYBB2, CRYB2, CRYGC, CRYG3, CCL, CRYAA, CRYA1, GJA8, CX50, CAE1, GJA3, CX46, CZP3, CAE3, CCM1, CAM, KRIT1); Corneal clouding and dystrophy (APOA1, TGFBI, CSD2, CDGG1, CSD, BIGH3, CDG2, TACSTD2, TROP2, M1S1, VSX1, RINX, PPCD, PPD, KTCN, COL8A2, FECD, PPCD2, PIP5K3, CFD); Cornea plana congenital (KERA, CNA2); Glaucoma (MYOC, TIGR, GLC1A, JOAG, GPOA, OPTN, GLC1E, FIP2, HYPL, NRP, CYP1B1, GLC3A, OPA1, NTG, NPG, CYP1B1, GLC3A); Leber congenital amaurosis (CRB1, RP12, CRX, CORD2, CRD, RPGRIP1, LCA6, CORD9, RPE65, RP20, AIPL1, LCA4, GUCY2D, GUC2D, LCA1, CORD6, RDH12, LCA3); Macular dystrophy (ELOVL4, ADMD, STGD2, STGD3, RDS, RP7, PRPH2, PRPH, AVMD, AOFMD, VMD2). |

TABLE C

| CELLULAR FUNCTION | GENES |
|---|---|
| PI3K/AKT Signaling | PRKCE; ITGAM; ITGA5; IRAK1; PRKAA2; EIF2AK2; PTEN; EIF4E; PRKCZ; GRK6; MAPK1; TSC1; PLK1; AKT2; IKBKB; PIK3CA; CDK8; CDKN1B; NFKB2; BCL2; PIK3CB; PPP2R1A; MAPK8; BCL2L1; MAPK3; TSC2; ITGA1; KRAS; EIF4EBP1; RELA; PRKCD; NOS3; PRKAA1; MAPK9; CDK2; PPP2CA; PIM1; ITGB7; YWHAZ; ILK; TP53; RAF1; IKBKG; RELB; DYRK1A; CDKN1A; ITGB1; MAP2K2; JAK1; AKT1; JAK2; PIK3R1; CHUK; PDPK1; PPP2R5C; CTNNB1; MAP2K1; NFKB1; PAK3; ITGB3; CCND1; GSK3A; FRAP1; SFN; ITGA2; TTK; CSNK1A1; BRAF; GSK3B; AKT3; FOXO1; SGK; HSP90AA1; RPS6KB1 |
| ERK/MAPK Signaling | PRKCE; ITGAM; ITGA5; HSPB1; IRAK1; PRKAA2; EIF2AK2; RAC1; RAP1A; TLN1; EIF4E; ELK1; GRK6; MAPK1; RAC2; PLK1; AKT2; PIK3CA; CDK8; CREB1; PRKCI; PTK2; FOS; RPS6KA4; PIK3CB; PPP2R1A; PIK3C3; MAPK8; MAPK3; ITGA1; ETS1; KRAS; MYCN; EIF4EBP1; PPARG; PRKCD; PRKAA1; MAPK9; SRC; CDK2; PPP2CA; PIM1; PIK3C2A; ITGB7; YWHAZ; PPP1CC; KSR1; PXN; RAF1; FYN; DYRK1A; ITGB1; MAP2K2; PAK4; PIK3R1; STAT3; PPP2R5C; MAP2K1; PAK3; ITGB3; ESR1; ITGA2; MYC; TTK; CSNK1A1; CRKL; BRAF; ATF4; PRKCA; SRF; STAT1; SGK |
| Glucocorticoid Receptor Signaling | RAC1; TAF4B; EP300; SMAD2; TRAF6; PCAF; ELK1; MAPK1; SMAD3; AKT2; IKBKB; NCOR2; UBE2I; PIK3CA; CREB1; FOS; HSPA5; NFKB2; BCL2; MAP3K14; STAT5B; PIK3CB; PIK3C3; MAPK8; BCL2L1; MAPK3; TSC22D3; MAPK10; NRIP1; KRAS; MAPK13; RELA; STAT5A; MAPK9; NOS2A; PBX1; NR3C1; PIK3C2A; CDKN1C; TRAF2; SERPINE1; NCOA3; MAPK14; TNF; RAF1; IKBKG; MAP3K7; CREBBP; CDKN1A; MAP2K2; JAK1; IL8; NCOA2; AKT1; JAK2; PIK3R1; CHUK; STAT3; MAP2K1; NFKB1; TGFBR1; ESR1; SMAD4; CEBPB; JUN; AR; AKT3; CCL2; MMP1; STAT1; IL6; HSP90AA1 |
| Axonal Guidance Signaling | PRKCE; ITGAM; ROCK1; ITGA5; CXCR4; ADAM12; IGF1; RAC1; RAP1A; EIF4E; PRKCZ; NRP1; NTRK2; ARHGEF7; SMO; ROCK2; MAPK1; PGF; RAC2; PTPN11; GNAS; AKT2; PIK3CA; ERBB2; PRKCI; PTK2; CFL1; GNAQ; PIK3CB; CXCL12; PIK3C3; WNT11; PRKD1; GNB2L1; ABL1; MAPK3; ITGA1; KRAS; RHOA; PRKCD; PIK3C2A; ITGB7; GLI2; PXN; VASP; RAF1; FYN; ITGB1; MAP2K2; PAK4; ADAM17; AKT1; PIK3R1; GLI1; WNT5A; ADAM10; MAP2K1; PAK3; ITGB3; |

TABLE C-continued

| CELLULAR FUNCTION | GENES |
|---|---|
| | CDC42; VEGFA; ITGA2; EPHA8; CRKL; RND1; GSK3B; AKT3; PRKCA |
| Ephrin Receptor Signaling | PRKCE; ITGAM; ROCK1; ITGA5; CXCR4; IRAK1; PRKAA2; EIF2AK2; RAC1; RAP1A; GRK6; ROCK2; MAPK1; PGF; RAC2; PTPN11; GNAS; PLK1; AKT2; DOK1; CDK8; CREB1; PTK2; CFL1; GNAQ; MAP3K14; CXCL12; MAPK8; GNB2L1; ABL1; MAPK3; ITGA1; KRAS; RHOA; PRKCD; PRKAA1; MAPK9; SRC; CDK2; PIM1; ITGB7; PXN; RAF1; FYN; DYRK1A; ITGB1; MAP2K2; PAK4; AKT1; JAK2; STAT3; ADAM10; MAP2K1; PAK3; ITGB3; CDC42; VEGFA; ITGA2; EPHA8; TTK; CSNK1A1; CRKL; BRAF; PTPN13; ATF4; AKT3; SGK |
| Actin Cytoskeleton Signaling | ACTN4; PRKCE; ITGAM; ROCK1; ITGA5; IRAK1; PRKAA2; EIF2AK2; RAC1; INS; ARHGEF7; GRK6; ROCK2; MAPK1; RAC2; PLK1; AKT2; PIK3CA; CDK8; PTK2; CFL1; PIK3CB; MYH9; DIAPH1; PIK3C3; MAPK8; F2R; MAPK3; SLC9A1; ITGA1; KRAS; RHOA; PRKCD; PRKAA1; MAPK9; CDK2; PIM1; PIK3C2A; ITGB7; PPP1CC; PXN; VIL2; RAF1; GSN; DYRK1A; ITGB1; MAP2K2; PAK4; PIP5K1A; PIK3R1; MAP2K1; PAK3; ITGB3; CDC42; APC; ITGA2; TTK; CSNK1A1; CRKL; BRAF; VAV3; SGK |
| Huntington's Disease Signaling | PRKCE; IGF1; EP300; RCOR1; PRKCZ; HDAC4; TGM2; MAPK1; CAPNS1; AKT2; EGFR; NCOR2; SP1; CAPN2; PIK3CA; HDAC5; CREB1; PRKCI; HSPA5; REST; GNAQ; PIK3CB; PIK3C3; MAPK8; IGF1R; PRKD1; GNB2L1; BCL2L1; CAPN1; MAPK3; CASP8; HDAC2; HDAC7A; PRKCD; HDAC11; MAPK9; HDAC9; PIK3C2A; HDAC3; TP53; CASP9; CREBBP; AKT1; PIK3R1; PDPK1; CASP1; APAF1; FRAP1; CASP2; JUN; BAX; ATF4; AKT3; PRKCA; CLTC; SGK; HDAC6; CASP3 |
| Apoptosis Signaling | PRKCE; ROCK1; BID; IRAK1; PRKAA2; EIF2AK2; BAK1; BIRC4; GRK6; MAPK1; CAPNS1; PLK1; AKT2; IKBKB; CAPN2; CDK8; FAS; NFKB2; BCL2; MAP3K14; MAPK8; BCL2L1; CAPN1; MAPK3; CASP8; KRAS; RELA; PRKCD; PRKAA1; MAPK9; CDK2; PIM1; TP53; TNF; RAF1; IKBKG; RELB; CASP9; DYRK1A; MAP2K2; CHUK; APAF1; MAP2K1; NFKB1; PAK3; LMNA; CASP2; BIRC2; TTK; CSNK1A1; BRAF; BAX; PRKCA; SGK; CASP3; BIRC3; PARP1 |
| B Cell Receptor Signaling | RAC1; PTEN; LYN; ELK1; MAPK1; RAC2; PTPN11; AKT2; IKBKB; PIK3CA; CREB1; SYK; NFKB2; CAMK2A; MAP3K14; PIK3CB; PIK3C3; MAPK8; BCL2L1; ABL1; MAPK3; ETS1; KRAS; MAPK13; RELA; PTPN6; MAPK9; EGR1; PIK3C2A; BTK; MAPK14; RAF1; IKBKG; RELB; MAP3K7; MAP2K2; AKT1; PIK3R1; CHUK; MAP2K1; NFKB1; CDC42; GSK3A; FRAP1; BCL6; BCL10; JUN; GSK3B; ATF4; AKT3; VAV3; RPS6KB1 |
| Leukocyte Extravasation Signaling | ACTN4; CD44; PRKCE; ITGAM; ROCK1; CXCR4; CYBA; RAC1; RAP1A; PRKCZ; ROCK2; RAC2; PTPN11; MMP14; PIK3CA; PRKCI; PTK2; PIK3CB; CXCL12; PIK3C3; MAPK8; PRKD1; ABL1; MAPK10; CYBB; MAPK13; RHOA; PRKCD; MAPK9; SRC; PIK3C2A; BTK; MAPK14; NOX1; PXN; VIL2; VASP; ITGB1; MAP2K2; CTNND1; PIK3R1; CTNNB1; CLDN1; CDC42; F11R; ITK; CRKL; VAV3; CTTN; PRKCA; MMP1; MMP9 |
| Integrin Signaling | ACTN4; ITGAM; ROCK1; ITGA5; RAC1; PTEN; RAP1A; TLN1; ARHGEF7; MAPK1; RAC2; CAPNS1; AKT2; CAPN2; PIK3CA; PTK2; PIK3CB; PIK3C3; MAPK8; CAV1; CAPN1; ABL1; MAPK3; ITGA1; KRAS; RHOA; SRC; PIK3C2A; ITGB7; PPP1CC; ILK; PXN; VASP; RAF1; FYN; ITGB1; MAP2K2; PAK4; AKT1; PIK3R1; TNK2; MAP2K1; PAK3; ITGB3; CDC42; RND3; ITGA2; CRKL; BRAF; GSK3B; AKT3 |
| Acute Phase Response Signaling | IRAK1; SOD2; MYD88; TRAF6; ELK1; MAPK1; PTPN11; AKT2; IKBKB; PIK3CA; FOS; NFKB2; MAP3K14; PIK3CB; MAPK8; RIPK1; MAPK3; IL6ST; KRAS; MAPK13; IL6R; RELA; SOCS1; MAPK9; FTL; NR3C1; |

TABLE C-continued

| CELLULAR FUNCTION | GENES |
|---|---|
| | TRAF2; SERPINE1; MAPK14; TNF; RAF1; PDK1; IKBKG; RELB; MAP3K7; MAP2K2; AKT1; JAK2; PIK3R1; CHUK; STAT3; MAP2K1; NFKB1; FRAP1; CEBPB; JUN; AKT3; IL1R1; IL6 |
| PTEN Signaling | ITGAM; ITGA5; RAC1; PTEN; PRKCZ; BCL2L11; MAPK1; RAC2; AKT2; EGFR; IKBKB; CBL; PIK3CA; CDKN1B; PTK2; NFKB2; BCL2; PIK3CB; BCL2L1; MAPK3; ITGA1; KRAS; ITGB7; ILK; PDGFRB; INSR; RAF1; IKBKG; CASP9; CDKN1A; ITGB1; MAP2K2; AKT1; PIK3R1; CHUK; PDGFRA; PDPK1; MAP2K1; NFKB1; ITGB3; CDC42; CCND1; GSK3A; ITGA2; GSK3B; AKT3; FOXO1; CASP3; RPS6KB1 |
| p53 Signaling | PTEN; EP300; BBC3; PCAF; FASN; BRCA1; GADD45A; BIRC5; AKT2; PIK3CA; CHEK1; TP53INP1; BCL2; PIK3CB; PIK3C3; MAPK8; THBS1; ATR; BCL2L1; E2F1; PMAIP1; CHEK2; TNFRSF10B; TP73; RB1; HDAC9; CDK2; PIK3C2A; MAPK14; TP53; LRDD; CDKN1A; HIPK2; AKT1; PIK3R1; RRM2B; APAF1; CTNNB1; SIRT1; CCND1; PRKDC; ATM; SFN; CDKN2A; JUN; SNAI2; GSK3B; BAX; AKT3 |
| Aryl Hydrocarbon Receptor Signaling | HSPB1; EP300; FASN; TGM2; RXRA; MAPK1; NQO1; NCOR2; SP1; ARNT; CDKN1B; FOS; CHEK1; SMARCA4; NFKB2; MAPK8; ALDH1A1; ATR; E2F1; MAPK3; NRIP1; CHEK2; RELA; TP73; GSTP1; RB1; SRC; CDK2; AHR; NFE2L2; NCOA3; TP53; TNF; CDKN1A; NCOA2; APAF1; NFKB1; CCND1; ATM; ESR1; CDKN2A; MYC; JUN; ESR2; BAX; IL6; CYP1B1; HSP90AA1 |
| Xenobiotic Metabolism Signaling | PRKCE; EP300; PRKCZ; RXRA; MAPK1; NQO1; NCOR2; PIK3CA; ARNT; PRKCI; NFKB2; CAMK2A; PIK3CB; PPP2R1A; PIK3C3; MAPK8; PRKD1; ALDH1A1; MAPK3; NRIP1; KRAS; MAPK13; PRKCD; GSTP1; MAPK9; NOS2A; ABCB1; AHR; PPP2CA; FTL; NFE2L2; PIK3C2A; PPARGC1A; MAPK14; TNF; RAF1; CREBBP; MAP2K2; PIK3R1; PPP2R5C; MAP2K1; NFKB1; KEAP1; PRKCA; EIF2AK3; IL6; CYP1B1; HSP90AA1 |
| SAPK/JNK Signaling | PRKCE; IRAK1; PRKAA2; EIF2AK2; RAC1; ELK1; GRK6; MAPK1; GADD45A; RAC2; PLK1; AKT2; PIK3CA; FADD; CDK8; PIK3CB; PIK3C3; MAPK8; RIPK1; GNB2L1; IRS1; MAPK3; MAPK10; DAXX; KRAS; PRKCD; PRKAA1; MAPK9; CDK2; PIM1; PIK3C2A; TRAF2; TP53; LCK; MAP3K7; DYRK1A; MAP2K2; PIK3R1; MAP2K1; PAK3; CDC42; JUN; TTK; CSNK1A1; CRKL; BRAF; SGK |
| PPAr/RXR Signaling | PRKAA2; EP300; INS; SMAD2; TRAF6; PPARA; FASN; RXRA; MAPK1; SMAD3; GNAS; IKBKB; NCOR2; ABCA1; GNAQ; NFKB2; MAP3K14; STAT5B; MAPK8; IRS1; MAPK3; KRAS; RELA; PRKAA1; PPARGC1A; NCOA3; MAPK14; INSR; RAF1; IKBKG; RELB; MAP3K7; CREBBP; MAP2K2; JAK2; CHUK; MAP2K1; NFKB1; TGFBR1; SMAD4; JUN; IL1R1; PRKCA; IL6; HSP90AA1; ADIPOQ |
| NF-KB Signaling | IRAK1; EIF2AK2; EP300; INS; MYD88; PRKCZ; TRAF6; TBK1; AKT2; EGFR; IKBKB; PIK3CA; BTRC; NFKB2; MAP3K14; PIK3CB; PIK3C3; MAPK8; RIPK1; HDAC2; KRAS; RELA; PIK3C2A; TRAF2; TLR4; PDGFRB; TNF; INSR; LCK; IKBKG; RELB; MAP3K7; CREBBP; AKT1; PIK3R1; CHUK; PDGFRA; NFKB1; TLR2; BCL10; GSK3B; AKT3; TNFAIP3; IL1R1 |
| Neuregulin Signaling | ERBB4; PRKCE; ITGAM; ITGA5; PTEN; PRKCZ; ELK1; MAPK1; PTPN11; AKT2; EGFR; ERBB2; PRKCI; CDKN1B; STAT5B; PRKD1; MAPK3; ITGA1; KRAS; PRKCD; STAT5A; SRC; ITGB7; RAF1; ITGB1; MAP2K2; ADAM17; AKT1; PIK3R1; PDPK1; MAP2K1; ITGB3; EREG; FRAP1; PSEN1; ITGA2; MYC; NRG1; CRKL; AKT3; PRKCA; HSP90AA1; RPS6KB1 |
| Wnt & Beta catenin Signaling | CD44; EP300; LRP6; DVL3; CSNK1E; GJA1; SMO; AKT2; PIN1; CDH1; BTRC; GNAQ; MARK2; PPP2R1A; WNT11; SRC; DKK1; PPP2CA; SOX6; SFRP2; ILK; LEF1; SOX9; TP53; MAP3K7; CREBBP; TCF7L2; AKT1; PPP2R5C; WNT5A; LRP5; CTNNB1; TGFBR1; CCND1; |

TABLE C-continued

| CELLULAR FUNCTION | GENES |
|---|---|
| | GSK3A; DVL1; APC; CDKN2A; MYC; CSNK1A1; GSK3B; AKT3; SOX2 |
| Insulin Receptor Signaling | PTEN; INS; EIF4E; PTPN1; PRKCZ; MAPK1; TSC1; PTPN11; AKT2; CBL; PIK3CA; PRKCI; PIK3CB; PIK3C3; MAPK8; IRS1; MAPK3; TSC2; KRAS; EIF4EBP1; SLC2A4; PIK3C2A; PPP1CC; INSR; RAF1; FYN; MAP2K2; JAK1; AKT1; JAK2; PIK3R1; PDPK1; MAP2K1; GSK3A; FRAP1; CRKL; GSK3B; AKT3; FOXO1; SGK; RPS6KB1 |
| IL-6 Signaling | HSPB1; TRAF6; MAPKAPK2; ELK1; MAPK1; PTPN11; IKBKB; FOS; NFKB2; MAP3K14; MAPK8; MAPK3; MAPK10; IL6ST; KRAS; MAPK13; IL6R; RELA; SOCS1; MAPK9; ABCB1; TRAF2; MAPK14; TNF; RAF1; IKBKG; RELB; MAP3K7; MAP2K2; IL8; JAK2; CHUK; STAT3; MAP2K1; NFKB1; CEBPB; JUN; IL1R1; SRF; IL6 |
| Hepatic Cholestasis | PRKCE; IRAK1; INS; MYD88; PRKCZ; TRAF6; PPARA; RXRA; IKBKB; PRKCI; NFKB2; MAP3K14; MAPK8; PRKD1; MAPK10; RELA; PRKCD; MAPK9; ABCB1; TRAF2; TLR4; TNF; INSR; IKBKG; RELB; MAP3K7; IL8; CHUK; NR1H2; TJP2; NFKB1; ESR1; SREBF1; FGFR4; JUN; IL1R1; PRKCA; IL6 |
| IGF-1 Signaling | IGF1; PRKCZ; ELK1; MAPK1; PTPN11; NEDD4; AKT2; PIK3CA; PRKCI; PTK2; FOS; PIK3CB; PIK3C3; MAPK8; IGF1R; IRS1; MAPK3; IGFBP7; KRAS; PIK3C2A; YWHAZ; PXN; RAF1; CASP9; MAP2K2; AKT1; PIK3R1; PDPK1; MAP2K1; IGFBP2; SFN; JUN; CYR61; AKT3; FOXO1; SRF; CTGF; RPS6KB1 |
| NRF2-mediated Oxidative Stress Response | PRKCE; EP300; SOD2; PRKCZ; MAPK1; SQSTM1; NQO1; PIK3CA; PRKCI; FOS; PIK3CB; PIK3C3; MAPK8; PRKD1; MAPK3; KRAS; PRKCD; GSTP1; MAPK9; FTL; NFE2L2; PIK3C2A; MAPK14; RAF1; MAP3K7; CREBBP; MAP2K2; AKT1; PIK3R1; MAP2K1; PPIB; JUN; KEAP1; GSK3B; ATF4; PRKCA; EIF2AK3; HSP90AA1 |
| Hepatic Fibrosis/Hepatic Stellate Cell Activation | EDN1; IGF1; KDR; FLT1; SMAD2; FGFR1; MET; PGF; SMAD3; EGFR; FAS; CSF1; NFKB2; BCL2; MYH9; IGF1R; IL6R; RELA; TLR4; PDGFRB; TNF; RELB; IL8; PDGFRA; NFKB1; TGFBR1; SMAD4; VEGFA; BAX; IL1R1; CCL2; HGF; MMP1; STAT1; IL6; CTGF; MMP9 |
| PPAR Signaling | EP300; INS; TRAF6; PPARA; RXRA; MAPK1; IKBKB; NCOR2; FOS; NFKB2; MAP3K14; STAT5B; MAPK3; NRIP1; KRAS; PPARG; RELA; STAT5A; TRAF2; PPARGC1A; PDGFRB; TNF; INSR; RAF1; IKBKG; RELB; MAP3K7; CREBBP; MAP2K2; CHUK; PDGFRA; MAP2K1; NFKB1; JUN; IL1R1; HSP90AA1 |
| Fc Epsilon RI Signaling | PRKCE; RAC1; PRKCZ; LYN; MAPK1; RAC2; PTPN11; AKT2; PIK3CA; SYK; PRKCI; PIK3CB; PIK3C3; MAPK8; PRKD1; MAPK3; MAPK10; KRAS; MAPK13; PRKCD; MAPK9; PIK3C2A; BTK; MAPK14; TNF; RAF1; FYN; MAP2K2; AKT1; PIK3R1; PDPK1; MAP2K1; AKT3; VAV3; PRKCA |
| G-Protein Coupled Receptor Signaling | PRKCE; RAP1A; RGS16; MAPK1; GNAS; AKT2; IKBKB; PIK3CA; CREB1; GNAQ; NFKB2; CAMK2A; PIK3CB; PIK3C3; MAPK3; KRAS; RELA; SRC; PIK3C2A; RAF1; IKBKG; RELB; FYN; MAP2K2; AKT1; PIK3R1; CHUK; PDPK1; STAT3; MAP2K1; NFKB1; BRAF; ATF4; AKT3; PRKCA |
| Inositol Phosphate Metabolism | PRKCE; IRAK1; PRKAA2; EIF2AK2; PTEN; GRK6; MAPK1; PLK1; AKT2; PIK3CA; CDK8; PIK3CB; PIK3C3; MAPK8; MAPK3; PRKCD; PRKAA1; MAPK9; CDK2; PIM1; PIK3C2A; DYRK1A; MAP2K2; PIP5K1A; PIK3R1; MAP2K1; PAK3; ATM; TTK; CSNK1A1; BRAF; SGK |
| PDGF Signaling | EIF2AK2; ELK1; ABL2; MAPK1; PIK3CA; FOS; PIK3CB; PIK3C3; MAPK8; CAV1; ABL1; MAPK3; KRAS; SRC; PIK3C2A; PDGFRB; RAF1; MAP2K2; JAK1; JAK2; PIK3R1; PDGFRA; STAT3; SPHK1; MAP2K1; MYC; JUN; CRKL; PRKCA; SRF; STAT1; SPHK2 |
| VEGF Signaling | ACTN4; ROCK1; KDR; FLT1; ROCK2; MAPK1; PGF; AKT2; PIK3CA; ARNT; PTK2; BCL2; PIK3CB; PIK3C3; BCL2L1; MAPK3; KRAS; HIF1A; NOS3; PIK3C2A; PXN; RAF1; MAP2K2; ELAVL1; AKT1; PIK3R1; MAP2K1; SFN; VEGFA; AKT3; FOXO1; PRKCA |

TABLE C-continued

| CELLULAR FUNCTION | GENES |
|---|---|
| Natural Killer Cell Signaling | PRKCE; RAC1; PRKCZ; MAPK1; RAC2; PTPN11; KIR2DL3; AKT2; PIK3CA; SYK; PRKCI; PIK3CB; PIK3C3; PRKD1; MAPK3; KRAS; PRKCD; PTPN6; PIK3C2A; LCK; RAF1; FYN; MAP2K2; PAK4; AKT1; PIK3R1; MAP2K1; PAK3; AKT3; VAV3; PRKCA |
| Cell Cycle: G1/S Checkpoint Regulation | HDAC4; SMAD3; SUV39H1; HDAC5; CDKN1B; BTRC; ATR; ABL1; E2F1; HDAC2; HDAC7A; RB1; HDAC11; HDAC9; CDK2; E2F2; HDAC3; TP53; CDKN1A; CCND1; E2F4; ATM; RBL2; SMAD4; CDKN2A; MYC; NRG1; GSK3B; RBL1; HDAC6 |
| T Cell Receptor Signaling | RAC1; ELK1; MAPK1; IKBKB; CBL; PIK3CA; FOS; NFKB2; PIK3CB; PIK3C3; MAPK8; MAPK3; KRAS; RELA; PIK3C2A; BTK; LCK; RAF1; IKBKG; RELB; FYN; MAP2K2; PIK3R1; CHUK; MAP2K1; NFKB1; ITK; BCL10; JUN; VAV3 |
| Death Receptor Signaling | CRADD; HSPB1; BID; BIRC4; TBK1; IKBKB; FADD; FAS; NFKB2; BCL2; MAP3K14; MAPK8; RIPK1; CASP8; DAXX; TNFRSF10B; RELA; TRAF2; TNF; IKBKG; RELB; CASP9; CHUK; APAF1; NFKB1; CASP2; BIRC2; CASP3; BIRC3 |
| FGF Signaling | RAC1; FGFR1; MET; MAPKAPK2; MAPK1; PTPN11; AKT2; PIK3CA; CREB1; PIK3CB; PIK3C3; MAPK8; MAPK3; MAPK13; PTPN6; PIK3C2A; MAPK14; RAF1; AKT1; PIK3R1; STAT3; MAP2K1; FGFR4; CRKL; ATF4; AKT3; PRKCA; HGF |
| GM-CSF Signaling | LYN; ELK1; MAPK1; PTPN11; AKT2; PIK3CA; CAMK2A; STAT5B; PIK3CB; PIK3C3; GNB2L1; BCL2L1; MAPK3; ETS1; KRAS; RUNX1; PIM1; PIK3C2A; RAF1; MAP2K2; AKT1; JAK2; PIK3R1; STAT3; MAP2K1; CCND1; AKT3; STAT1 |
| Amyotrophic Lateral Sclerosis Signaling | BID; IGF1; RAC1; BIRC4; PGF; CAPNS1; CAPN2; PIK3CA; BCL2; PIK3CB; PIK3C3; BCL2L1; CAPN1; PIK3C2A; TP53; CASP9; PIK3R1; RAB5A; CASP1; APAF1; VEGFA; BIRC2; BAX; AKT3; CASP3; BIRC3 |
| JAK/Stat Signaling | PTPN1; MAPK1; PTPN11; AKT2; PIK3CA; STAT5B; PIK3CB; PIK3C3; MAPK3; KRAS; SOCS1; STAT5A; PTPN6; PIK3C2A; RAF1; CDKN1A; MAP2K2; JAK1; AKT1; JAK2; PIK3R1; STAT3; MAP2K1; FRAP1; AKT3; STAT1 |
| Nicotinate and Nicotinamide Metabolism | PRKCE; IRAK1; PRKAA2; EIF2AK2; GRK6; MAPK1; PLK1; AKT2; CDK8; MAPK8; MAPK3; PRKCD; PRKAA1; PBEF1; MAPK9; CDK2; PIM1; DYRK1A; MAP2K2; MAP2K1; PAK3; NT5E; TTK; CSNK1A1; BRAF; SGK |
| Chemokine Signaling | CXCR4; ROCK2; MAPK1; PTK2; FOS; CFL1; GNAQ; CAMK2A; CXCL12; MAPK8; MAPK3; KRAS; MAPK13; RHOA; CCR3; SRC; PPP1CC; MAPK14; NOX1; RAF1; MAP2K2; MAP2K1; JUN; CCL2; PRKCA |
| IL-2 Signaling | ELK1; MAPK1; PTPN11; AKT2; PIK3CA; SYK; FOS; STAT5B; PIK3CB; PIK3C3; MAPK8; MAPK3; KRAS; SOCS1; STAT5A; PIK3C2A; LCK; RAF1; MAP2K2; JAK1; AKT1; PIK3R1; MAP2K1; JUN; AKT3 |
| Synaptic Long Term Depression | PRKCE; IGF1; PRKCZ; PRDX6; LYN; MAPK1; GNAS; PRKCI; GNAQ; PPP2R1A; IGF1R; PRKD1; MAPK3; KRAS; GRN; PRKCD; NOS3; NOS2A; PPP2CA; YWHAZ; RAF1; MAP2K2; PPP2R5C; MAP2K1; PRKCA |
| Estrogen Receptor Signaling | TAF4B; EP300; CARM1; PCAF; MAPK1; NCOR2; SMARCA4; MAPK3; NRIP1; KRAS; SRC; NR3C1; HDAC3; PPARGC1A; RBM9; NCOA3; RAF1; CREBBP; MAP2K2; NCOA2; MAP2K1; PRKDC; ESR1; ESR2 |
| Protein Ubiquitination Pathway | TRAF6; SMURF1; BIRC4; BRCA1; UCHL1; NEDD4; CBL; UBE2I; BTRC; HSPA5; USP7; USP10; FBXW7; USP9X; STUB1; USP22; B2M; BIRC2; PARK2; USP8; USP1; VHL; HSP90AA1; BIRC3 |
| IL-10 Signaling | TRAF6; CCR1; ELK1; IKBKB; SP1; FOS; NFKB2; MAP3K14; MAPK8; MAPK13; RELA; MAPK14; TNF; IKBKG; RELB; MAP3K7; JAK1; CHUK; STAT3; NFKB1; JUN; IL1R1; IL6 |
| VDR/RXR Activation | PRKCE; EP300; PRKCZ; RXRA; GADD45A; HES1; NCOR2; SP1; PRKCI; CDKN1B; PRKD1; PRKCD; RUNX2; KLF4; YY1; NCOA3; CDKN1A; NCOA2; SPP1; LRP5; CEBPB; FOXO1; PRKCA |

TABLE C-continued

| CELLULAR FUNCTION | GENES |
|---|---|
| TGF-beta Signaling | EP300; SMAD2; SMURF1; MAPK1; SMAD3; SMAD1; FOS; MAPK8; MAPK3; KRAS; MAPK9; RUNX2; SERPINE1; RAF1; MAP3K7; CREBBP; MAP2K2; MAP2K1; TGFBR1; SMAD4; JUN; SMAD5 |
| Toll-like Receptor Signaling | IRAK1; EIF2AK2; MYD88; TRAF6; PPARA; ELK1; IKBKB; FOS; NFKB2; MAP3K14; MAPK8; MAPK13; RELA; TLR4; MAPK14; IKBKG; RELB; MAP3K7; CHUK; NFKB1; TLR2; JUN |
| p38 MAPK Signaling | HSPB1; IRAK1; TRAF6; MAPKAPK2; ELK1; FADD; FAS; CREB1; DDIT3; RPS6KA4; DAXX; MAPK13; TRAF2; MAPK14; TNF; MAP3K7; TGFBR1; MYC; ATF4; IL1R1; SRF; STAT1 |
| Neurotrophin/TRK Signaling | NTRK2; MAPK1; PTPN11; PIK3CA; CREB1; FOS; PIK3CB; PIK3C3; MAPK8; MAPK3; KRAS; PIK3C2A; RAF1; MAP2K2; AKT1; PIK3R1; PDPK1; MAP2K1; CDC42; JUN; ATF4 |
| FXR/RXR Activation | INS; PPARA; FASN; RXRA; AKT2; SDC1; MAPK8; APOB; MAPK10; PPARG; MTTP; MAPK9; PPARGC1A; TNF; CREBBP; AKT1; SREBF1; FGFR4; AKT3; FOXO1 |
| Synaptic Long Term Potentiation | PRKCE; RAP1A; EP300; PRKCZ; MAPK1; CREB1; PRKCI; GNAQ; CAMK2A; PRKD1; MAPK3; KRAS; PRKCD; PPP1CC; RAF1; CREBBP; MAP2K2; MAP2K1; ATF4; PRKCA |
| Calcium Signaling | RAP1A; EP300; HDAC4; MAPK1; HDAC5; CREB1; CAMK2A; MYH9; MAPK3; HDAC2; HDAC7A; HDAC11; HDAC9; HDAC3; CREBBP; CALR; CAMKK2; ATF4; HDAC6 |
| EGF Signaling | ELK1; MAPK1; EGFR; PIK3CA; FOS; PIK3CB; PIK3C3; MAPK8; MAPK3; PIK3C2A; RAF1; JAK1; PIK3R1; STAT3; MAP2K1; JUN; PRKCA; SRF; STAT1 |
| Hypoxia Signaling in the Cardiovascular System | EDN1; PTEN; EP300; NQO1; UBE2I; CREB1; ARNT; HIF1A; SLC2A4; NOS3; TP53; LDHA; AKT1; ATM; VEGFA; JUN; ATF4; VHL; HSP90AA1 |
| LPS/IL-1 Mediated Inhibition of RXR Function | IRAK1; MYD88; TRAF6; PPARA; RXRA; ABCA1; MAPK8; ALDH1A1; GSTP1; MAPK9; ABCB1; TRAF2; TLR4; TNF; MAP3K7; NR1H2; SREBF1; JUN; IL1R1 |
| LXR/RXR Activation | FASN; RXRA; NCOR2; ABCA1; NFKB2; IRF3; RELA; NOS2A; TLR4; TNF; RELB; LDLR; NR1H2; NFKB1; SREBF1; IL1R1; CCL2; IL6; MMP9 |
| Amyloid Processing | PRKCE; CSNK1E; MAPK1; CAPNS1; AKT2; CAPN2; CAPN1; MAPK3; MAPK13; MAPT; MAPK14; AKT1; PSEN1; CSNK1A1; GSK3B; AKT3; APP |
| IL-4 Signaling | AKT2; PIK3CA; PIK3CB; PIK3C3; IRS1; KRAS; SOCS1; PTPN6; NR3C1; PIK3C2A; JAK1; AKT1; JAK2; PIK3R1; FRAP1; AKT3; RPS6KB1 |
| Cell Cycle: G2/M DNA Damage Checkpoint Regulation | EP300; PCAF; BRCA1; GADD45A; PLK1; BTRC; CHEK1; ATR; CHEK2; YWHAZ; TP53; CDKN1A; PRKDC; ATM; SFN; CDKN2A |
| Nitric Oxide Signaling in the Cardiovascular System | KDR; FLT1; PGF; AKT2; PIK3CA; PIK3CB; PIK3C3; CAV1; PRKCD; NOS3; PIK3C2A; AKT1; PIK3R1; VEGFA; AKT3; HSP90AA1 |
| Purine Metabolism | NME2; SMARCA4; MYH9; RRM2; ADAR; EIF2AK4; PKM2; ENTPD1; RAD51; RRM2B; TJP2; RAD51C; NT5E; POLD1; NME1 |
| cAMP-mediated Signaling | RAP1A; MAPK1; GNAS; CREB1; CAMK2A; MAPK3; SRC; RAF1; MAP2K2; STAT3; MAP2K1; BRAF; ATF4 |
| Mitochondrial Dysfunction | SOD2; MAPK8; CASP8; MAPK10; MAPK9; CASP9; PARK7; PSEN1; PARK2; APP; CASP3 |
| Notch Signaling | HES1; JAG1; NUMB; NOTCH4; ADAM17; NOTCH2; PSEN1; NOTCH3; NOTCH1; DLL4 |
| Endoplasmic Reticulum Stress Pathway | HSPA5; MAPK8; XBP1; TRAF2; ATF6; CASP9; ATF4; EIF2AK3; CASP3 |
| Pyrimidine Metabolism | NME2; AICDA; RRM2; EIF2AK4; ENTPD1; RRM2B; NT5E; POLD1; NME1 |
| Parkinson's Signaling | UCHL1; MAPK8; MAPK13; MAPK14; CASP9; PARK7; PARK2; CASP3 |
| Cardiac & Beta Adrenergic Signaling | GNAS; GNAQ; PPP2R1A; GNB2L1; PPP2CA; PPP1CC; PPP2R5C |
| Glycolysis/Gluconeogenesis | HK2; GCK; GPI; ALDH1A1; PKM2; LDHA; HK1 |
| Interferon Signaling | IRF1; SOCS1; JAK1; JAK2; IFITM1; STAT1; IFIT3 |
| Sonic Hedgehog Signaling | ARRB2; SMO; GLI2; DYRK1A; GLI1; GSK3B; DYRK1B |
| Glycerophospholipid Metabolism | PLD1; GRN; GPAM; YWHAZ; SPHK1; SPHK2 |

TABLE C-continued

| CELLULAR FUNCTION | GENES |
|---|---|
| Phospholipid Degradation | PRDX6; PLD1; GRN; YWHAZ; SPHK1; SPHK2 |
| Tryptophan Metabolism | SIAH2; PRMT5; NEDD4; ALDH1A1; CYP1B1; SIAH1 |
| Lysine Degradation | SUV39H1; EHMT2; NSD1; SETD7; PPP2R5C |
| Nucleotide Excision Repair Pathway | ERCC5; ERCC4; XPA; XPC; ERCC1 |
| Starch and Sucrose Metabolism | UCHL1; HK2; GCK; GPI; HK1 |
| Aminosugars Metabolism | NQO1; HK2; GCK; HK1 |
| Arachidonic Acid Metabolism | PRDX6; GRN; YWHAZ; CYP1B1 |
| Circadian Rhythm Signaling | CSNK1E; CREB1; ATF4; NR1D1 |
| Coagulation System | BDKRB1; F2R; SERPINE1; F3 |
| Dopamine Receptor Signaling | PPP2R1A; PPP2CA; PPP1CC; PPP2R5C |
| Glutathione Metabolism | IDH2; GSTP1; ANPEP; IDH1 |
| Glycerolipid Metabolism | ALDH1A1; GPAM; SPHK1; SPHK2 |
| Linoleic Acid Metabolism | PRDX6; GRN; YWHAZ; CYP1B1 |
| Methionine Metabolism | DNMT1; DNMT3B; AHCY; DNMT3A |
| Pyruvate Metabolism | GLO1; ALDH1A1; PKM2; LDHA |
| Arginine and Proline Metabolism | ALDH1A1; NOS3; NOS2A |
| Eicosanoid Signaling | PRDX6; GRN; YWHAZ |
| Fructose and Mannose Metabolism | HK2; GCK; HK1 |
| Galactose Metabolism | HK2; GCK; HK1 |
| Stilbene, Coumarine and Lignin Biosynthesis | PRDX6; PRDX1; TYR |
| Antigen Presentation Pathway | CALR; B2M |
| Biosynthesis of Steroids | NQO1; DHCR7 |
| Butanoate Metabolism | ALDH1A1; NLGN1 |
| Citrate Cycle | IDH2; IDH1 |
| Fatty Acid Metabolism | ALDH1A1; CYP1B1 |
| Glycerophospholipid Metabolism | PRDX6; CHKA |
| Histidine Metabolism | PRMT5; ALDH1A1 |
| Inositol Metabolism | ERO1L; APEX1 |
| Metabolism of Xenobiotics by Cytochrome p450 | GSTP1; CYP1B1 |
| Methane Metabolism | PRDX6; PRDX1 |
| Phenylalanine Metabolism | PRDX6; PRDX1 |
| Propanoate Metabolism | ALDH1A1; LDHA |
| Selenoamino Acid Metabolism | PRMT5; AHCY |
| Sphingolipid Metabolism | SPHK1; SPHK2 |
| Aminophosphonate Metabolism | PRMT5 |
| Androgen and Estrogen Metabolism | PRMT5 |
| Ascorbate and Aldarate Metabolism | ALDH1A1 |
| Bile Acid Biosynthesis | ALDH1A1 |
| Cysteine Metabolism | LDHA |
| Fatty Acid Biosynthesis | FASN |
| Glutamate Receptor Signaling | GNB2L1 |
| NRF2-mediated Oxidative Stress Response | PRDX1 |
| Pentose Phosphate Pathway | GPI |
| Pentose and Glucuronate Interconversions | UCHL1 |
| Retinol Metabolism | ALDH1A1 |
| Riboflavin Metabolism | TYR |
| Tyrosine Metabolism | PRMT5, TYR |
| Ubiquinone Biosynthesis | PRMT5 |
| Valine, Leucine and Isoleucine Degradation | ALDH1A1 |
| Glycine, Serine and Threonine Metabolism | CHKA |

TABLE C-continued

| CELLULAR FUNCTION | GENES |
|---|---|
| Lysine Degradation | ALDH1A1 |
| Pain/Taste | TRPM5; TRPA1 |
| Pain | TRPM7; TRPC5; TRPC6; TRPC1; Cnr1; cnr2; Grk2; Trpa1; Pomc; Cgrp; Crf; Pka; Era; Nr2b; TRPM5; Prkaca; Prkacb; Prkar1a; Prkar2a |
| Mitochondrial Function | AIF; CytC; SMAC (Diablo); Aifm-1; Aifm-2 |
| Developmental Neurology | BMP-4; Chordin (Chrd); Noggin (Nog); WNT (Wnt2; Wnt2b; Wnt3a; Wnt4; Wnt5a; Wnt6; Wnt7b; Wnt8b; Wnt9a; Wnt9b; Wnt10a; Wnt10b; Wnt16); beta-catenin; Dkk-1; Frizzled related proteins; Otx-2; Gbx2; FGF-8; Reelin; Dab1; unc-86 (Pou4f1 or Brn3a); Numb; Reln |

Therapeutic/disease markers. The present invention provides a non-biased protein discovery tool. Mapping of regions of the genome that either harbor inherited or somatic mutations that cause disease have greatly outpaced one's ability to interpret the data. Therefore, the present invention has the potential to magnify the number of proteins implicated in disease etiology. Systematic detection of proteins at disease relevant locations could expand the number of potential therapeutic targets for any given condition or nominate these proteins as markers for disease risk/progression.

Although the present invention and its advantages have been described in detail, it should be understood that various changes, substitutions and alterations can be made herein without departing from the spirit and scope of the invention as defined in the appended claims.

The present invention will be further illustrated in the following Examples which are given for illustration purposes only and are not intended to limit the invention in any way.

EXAMPLES

The activation or repression of a gene's expression is primarily controlled by changes in the proteins that occupy its regulatory elements. The most common method to identify proteins associated with genomic loci is chromatin immunoprecipitation (ChIP). While having greatly advanced our understanding of gene expression regulation, ChIP requires specific, high quality, IP-competent antibodies against nominated proteins, which can limit its utility and scope for discovery. Thus, a method able to discover and identify proteins associated with a particular genomic locus within the native cellular context would be extremely valuable. Here, we present a novel technology combining recent advances in chemical biology, genome targeting, and quantitative mass spectrometry to develop genomic locus proteomics, a method able to identify proteins which occupy a specific genomic locus.

Example 1: Fusion of dCas9-BirAR118G

This approach creates a fusion protein consisting of the enzyme-deactivated Cas9 (Nature. 2015 Jan. 29; 517 (7536): 583-8. doi: 10.1038/nature14136. Epub 2014 Dec. 10. Genome-scale transcriptional activation by an engineered CRISPR-Cas9 complex. Konermann S et al.) linked to the BirAR118G biotin protein ligase. This approach only requires ATP, free biotin, dCas9-BirAR118G and sgRNA per target location.

Figure 1:
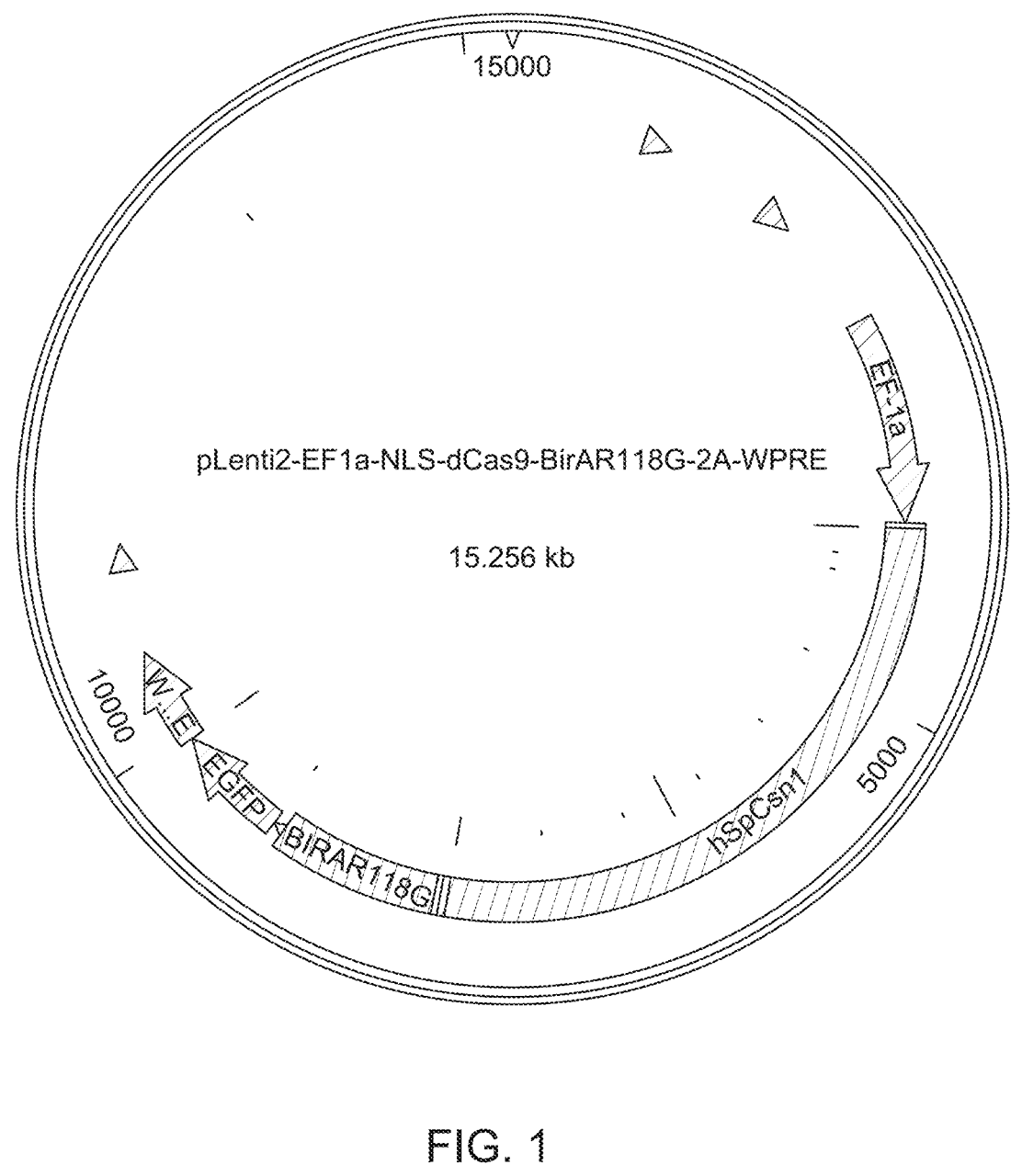

Sequence and map of the corresponding vector (pLenti2-dCas9-NLS-BirAR118G-2A-GFP) are shown on FIG. 1.

The advantages of this method are it requires the fewest number of components, increasing the likely-hood of high copy delivery.

Example 2: dCas9-BirAR118G/MS2-BirA

This approach uses the fusion protein described in Example 1 in combination with an MS2-BirAR118G fusion protein. This approach combines dCas9-BirAR118G with a second BirAR118-G bound to a recognition motif of the guide RNA itself. The design and location of the MS2-BirAR118G fusion is based on designs from (Nature. 2015 Jan. 29; 517 (7536): 583-8. doi: 10.1038/nature14136. Epub 2014 Dec. 10. Genome-scale transcriptional activation by an engineered CRISPR-Cas9 complex. Konermann S et al.) for delivery of transactivator enzymes. The advantages of this method are it increases the number of BirA enzymes at the target site thus potentially increasing signal to noise ratios.

Sequence and map of the corresponding vector (pLenti2-EF1a-MS2-NLS-BirA-2A-GFP-WPRE) are shown on FIG. 2.

Example 3: Split-enzyme

Figure 3A:
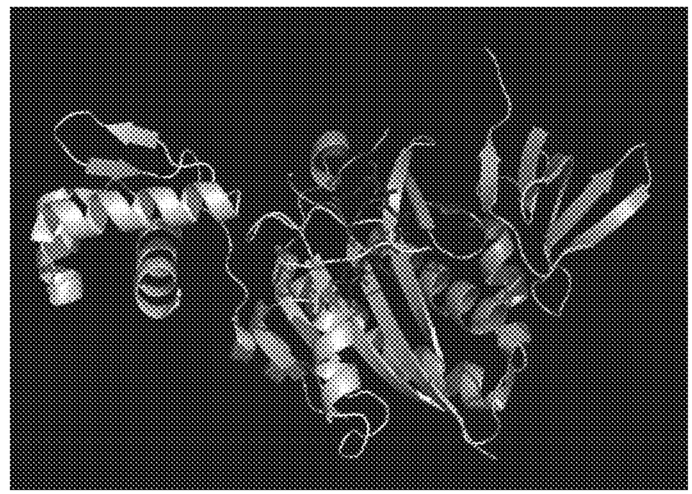
FIG. 3A—depicts yellow and green the two halves are the split protein neither act by themselves, but together they are active (predicted to be active).
Figure 3B:
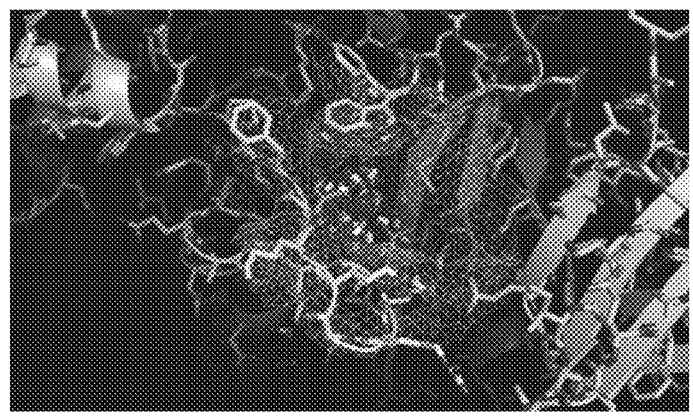
FIG. 3B—depicts coloring the same, red is the biotin. complex between BirA and the biotinyl-AMP. The mesh shows the solvent accessible binding pocket.
Figure 3C:
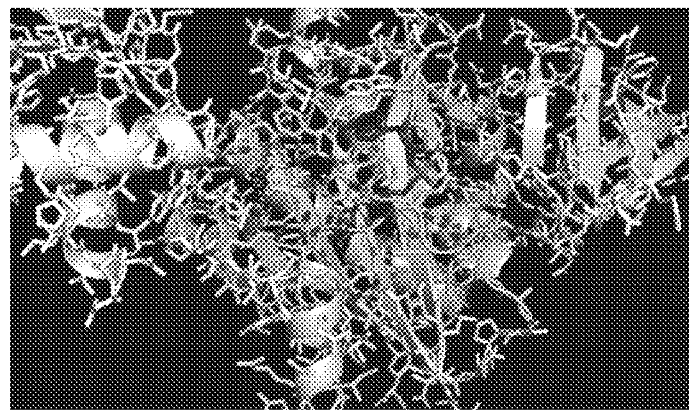
FIG. 3C—depicts the red the biotinylated AMP. The blue is inhibitory loop. Variant of BirA that a mutation in the loop that makes it more "promiscuous". Without this mutation it is an inhibits the activity of BirA biotinylation. The loop may be utilized to give greater control over the activity of BirA.

This approach divides the BirAR118G enzyme into two fragments (amino-acids 1-140 and 141-320 FIG. 3A), which will only biotinylate targets when both fragments are present. This entails removing the ATP/biotin interaction loop from the Biotin pocket (FIG. 3B). The BirA-Biotin pocket component is fused to a dCas9 (dCas9-pocket) and delivered by the first of a pair of sgRNAs to a target. A second dCas9 is fused to the ATP/biotin interaction loop (dCas9-loop) and delivered to the target site by the second of the two sgRNAs. A catalytic and inhibitory loop (residues 112-130) that partially composes the active site of BirA (FIG. 3C). 3 dimensional folding of the BirA protein immobilizes ATP, biotin and biotinyl-AMP within the BirA protein. Only when dCas9-pocket and dCas9-loop are present at the target will biotinylation take place. The advantages of this method are that the enzymatic reaction requires the presence of both constructs to be co-located, therefore off target biotinylation should be greatly reduced.

Figure 4A:
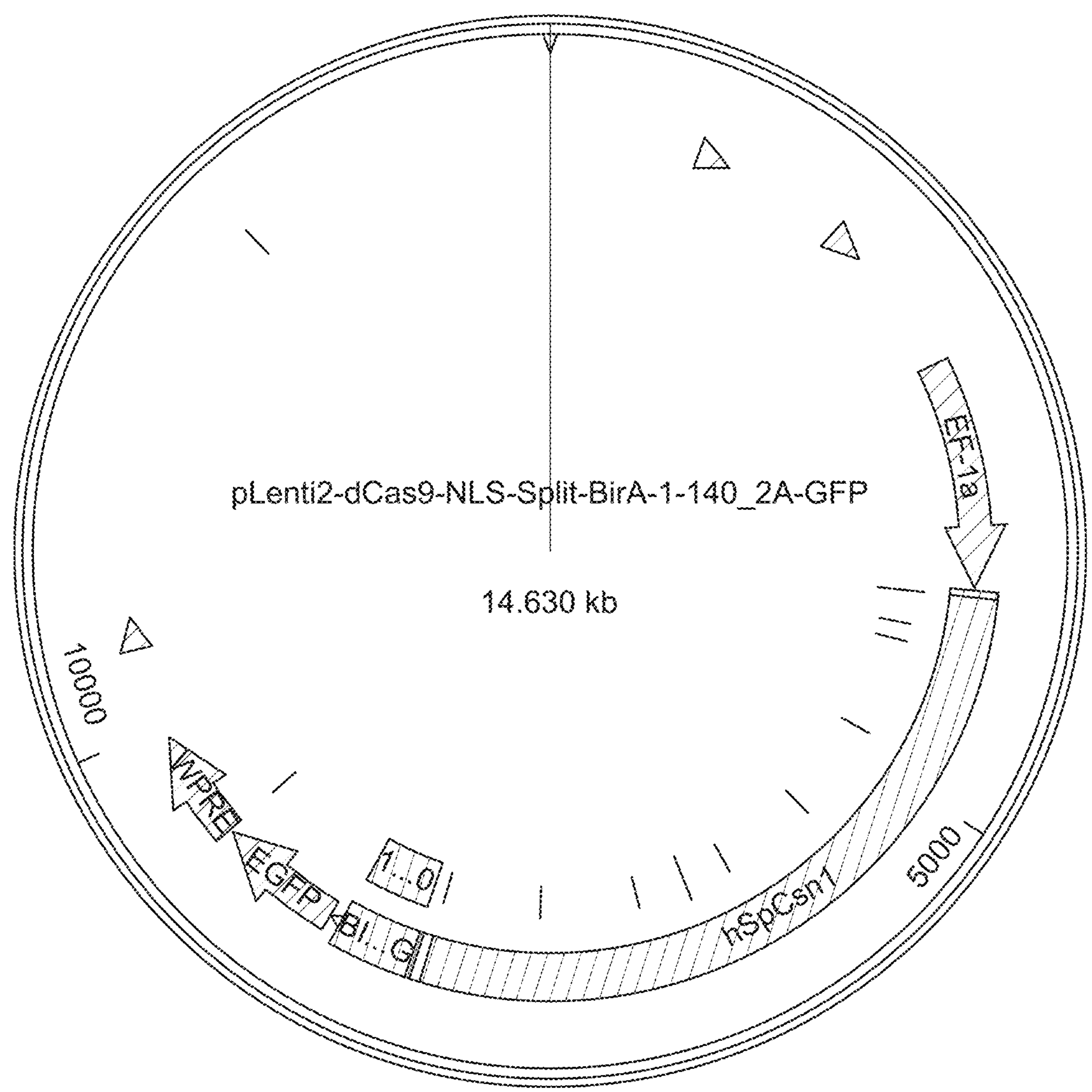
FIG. 4—depicts a split dCas9-BirA vector maps. A. dCas9_BirA_1-140, B. dCas9_BirA_141-329, in accordance with certain example embodiments.
Figure 4B:
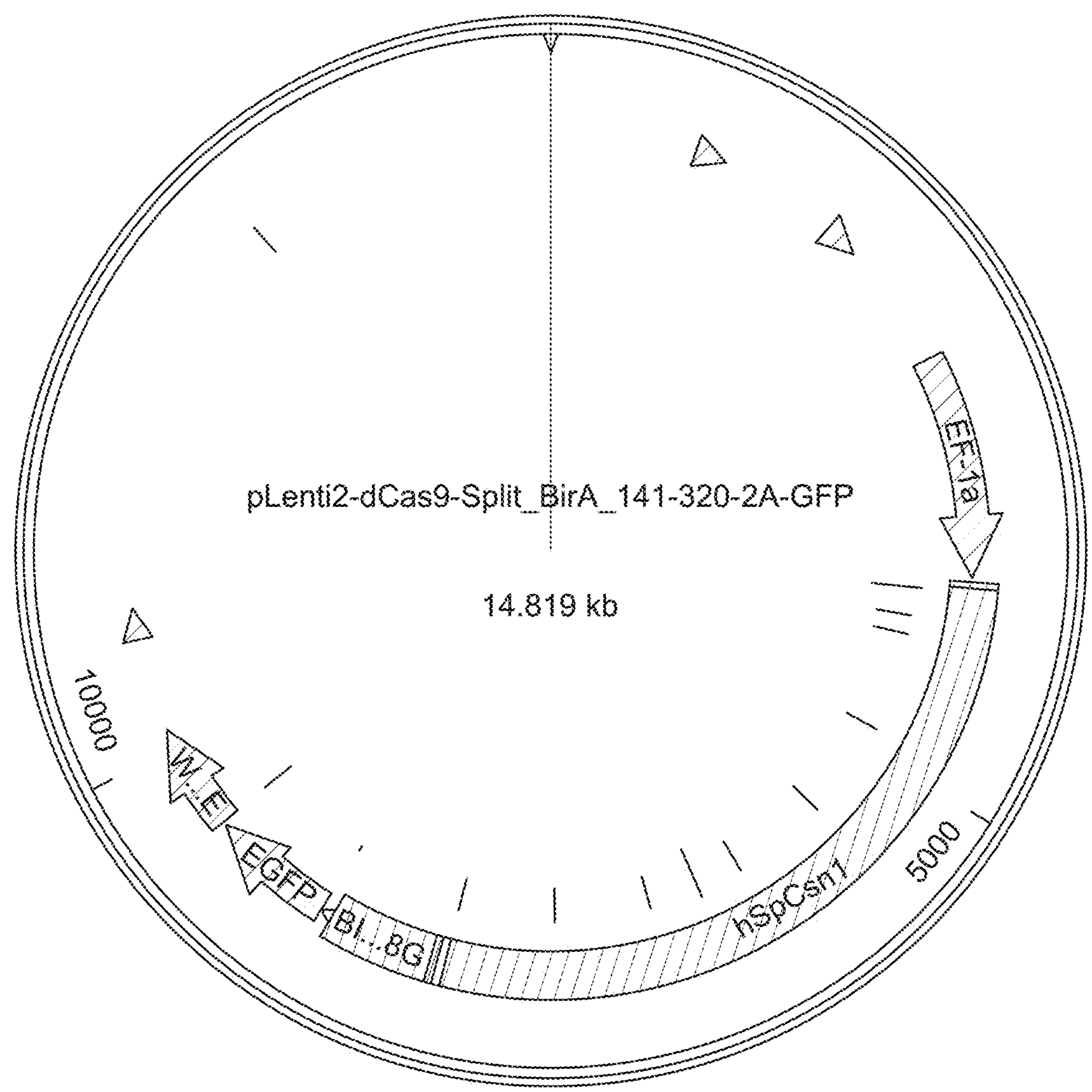

The constructs for this method on shown in FIG. 4.

Example 4: TALE-BirA

In an orthogonal approach to achieving proximity dependent biotinylation of target loci, one delivers a TALE-BirAR118G fusion to a target location. This involves replacing the FokI domain of a TALEN fusion cassette (Sanjana et al., 2011, t Protoc. 2012 Jan. 5; 7 (1): 171-92. doi: 10.1038/nprot.2011.431. *A transcription activator-like effector toolbox for genome engineering*. Sanjana N E et al.) with a BirAR118G cassette. The advantage of this is that the TALE-binding domain has a lower impact on the chromatin state of a target location, which might alter protein-DNA interactions. This method could be used as in Example 3 as a dual delivery system.

Figure 5:
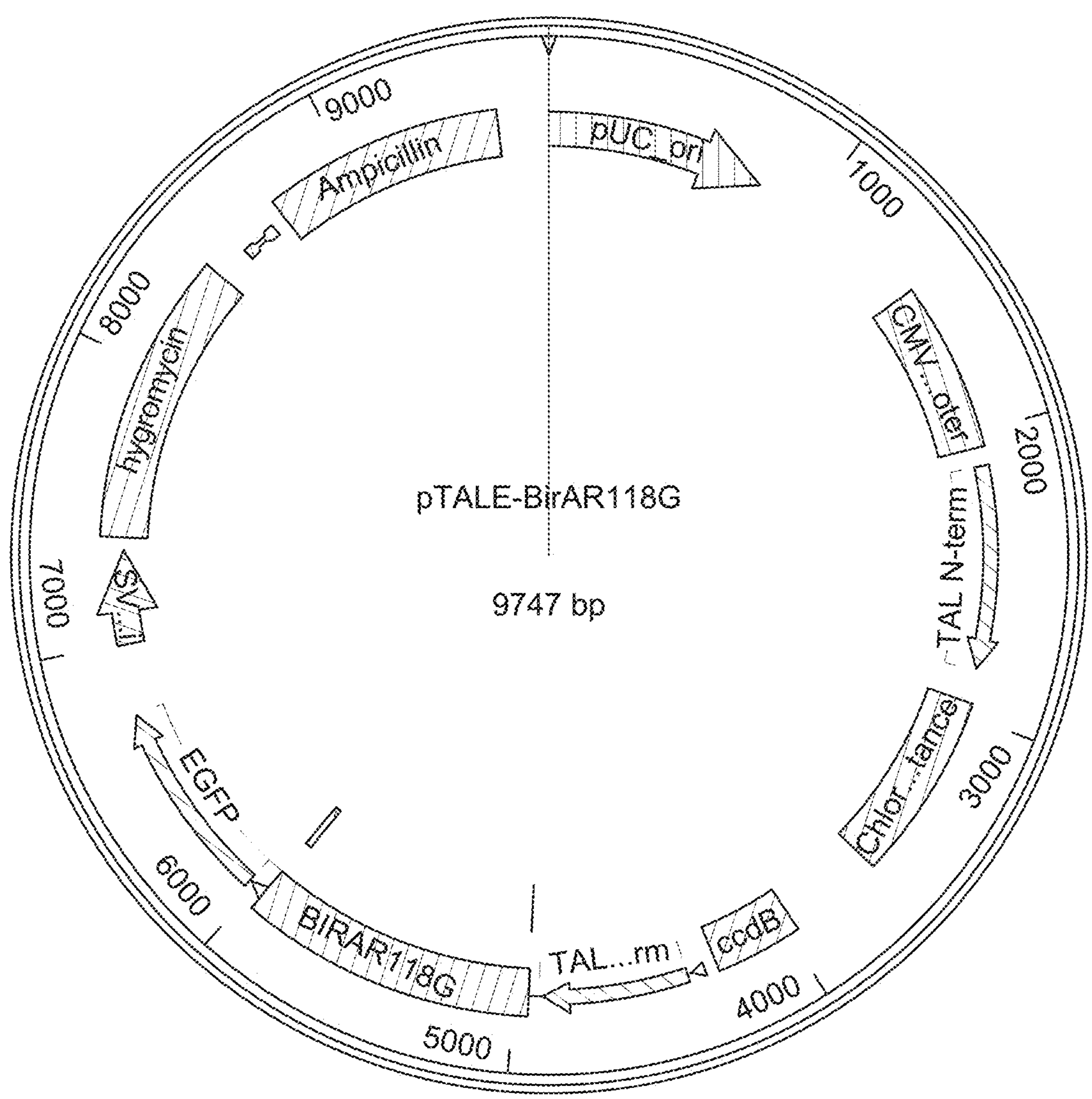
FIG. 5—depicts a vector map of TALE-BirAR118G-2A-WPRE, in accordance with certain example embodiments.

Sequence and map of the corresponding vector (TALE-backbone-BirAR118G-2A-WPRE) are shown on FIG. 5.

Example 5: Purification of Bound DNA

In this approach one biotinylates target DNA of a target location. For this one may utilize each method described above, and may purify biotinylated DNA fragments. This has a number of potential applications. First, one may use next generation sequencing to identify all biotinylated DNA-sites upon fusion-BirAR118G treatment. This provides an unbiased snapshot of all locations in the genome in which the enzyme is acting. Therefore potential off-target sites can be mapped compared to off-target prediction. Further, one may determine if the site is in close proximity to other locations in the genome via genomic loops. This could readily be evaluated by comparison of biotinylated DNA fragments to previously identified chromatin loops (Cell. 2014 Dec. 18; 159 (7): 1665-80. doi: 10.1016/j.cell.2014.11.021. Epub 2014 Dec. 11. *A 3D) map of the human genome at kilobase resolution reveals principles of chromatin looping*. Rao S S et al.).

Example 6: Testing Genomic Sites

Based on the above examples, one may test genomic sites, which have been well characterized for protein binding and one may measure the specificity of this method for proteins previously known to bind the target location. This may be done by standard western blot of the known protein. Using this assay Applicants optimize technical variables of the technology such as time course assays and biotin titrations. One may also determine potential toxicity of each method by cell death assays across a panel of commonly used cell models including HEK293T cells, and hESCs.

Examples of an inherited disease variant using the present invention include Science. 2013 Oct. 11; 342 (6155): 253-7. doi: 10.1126/science.1242088. An erythroid enhancer of BCL11A subject to genetic variation determines fetal hemoglobin level. Bauer D E et al.

Example of somatic disease mutation using the present invention include Science. 2013 Feb. 22; 339 (6122): 957-9. doi: 10.1126/science.1229259. Epub 2013 Jan. 24. Highly recurrent TERT promoter mutations in human melanoma. Huang F W et al.

Example 7: dCas9-APEX

The goal of this Example is to:

(a) Test specific recruitment to Cas9 to a given target (b) Test detection of biotinylation-of DNA binding proteins at a genomic target (c) Measure the resolution of the biotinylation for a single target (d) Compare the resolution of biotinylation with the resolution of dCas9 binding dCas9-APEX were delivered into HEKCATG07 cells targeting sites spanning ~1 kb centered on the TERT promoter. Biotinylation was induced with timed peroxidase treatment (see methods). Each cell condition was cross-linked and lysed for anti-flag immune-precipitation of flag-tagged dCas-9/DNA complexes and streptavidin purification of biotin-protein/DNA complexes at targeted sites across the TERT promoter. The interaction of flag-tagged dCas9/DNA interaction at each target location was assessed by droplet digital PCR with target droplet digital probes designed for each site queried. Likewise, biotinylated-protein/DNA interactions were assessed by droplet digital PCR with custom target specific probes. Purified target DNA was confirmed by direct Sanger sequencing of the resultant amplicon.

Figure 6A:
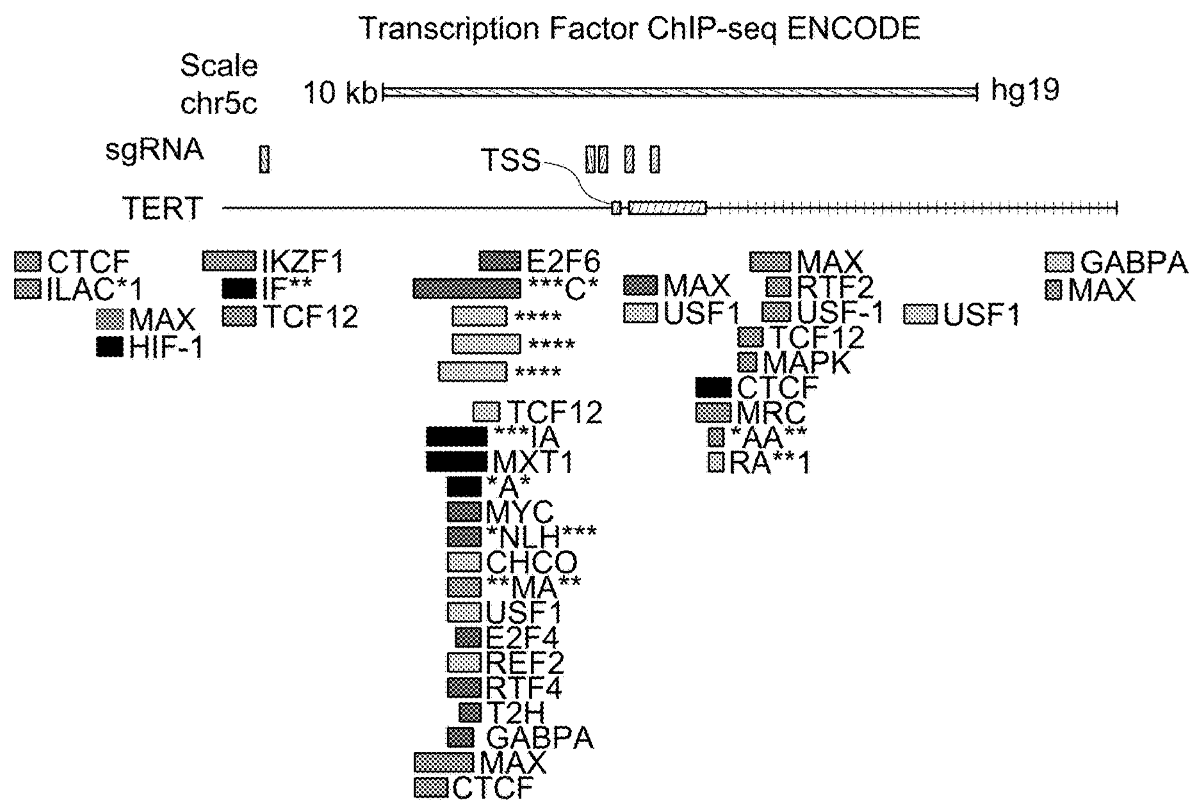
FIG. 6—depicts a design of a pilot experiment in accordance with certain example embodiments. A) Target locations of dCas9-APEX sgRNAs (colored bars) and their positions relative to the promoter of TERT. Below, gray, known proteins bound by publically available ChIP-seq below. B) Diagram of determination of dCas9 binding in relation to potential biotinylation of proximal proteins at the TERT promoter.
Figure 6B:
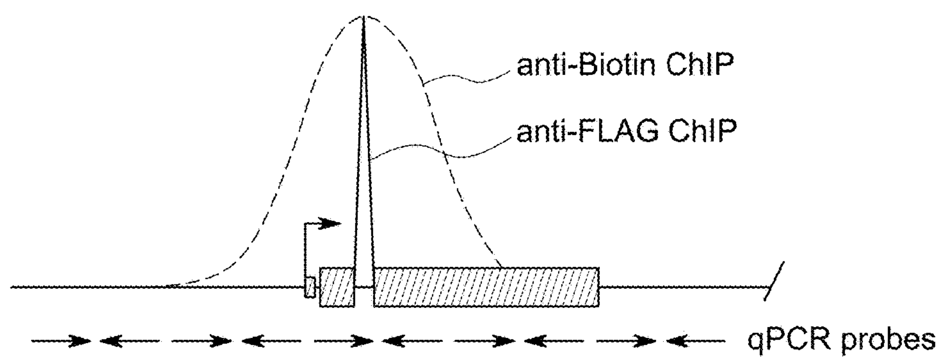

FIG. 6 depicts a design of the pilot experiment.

Figure 7A:
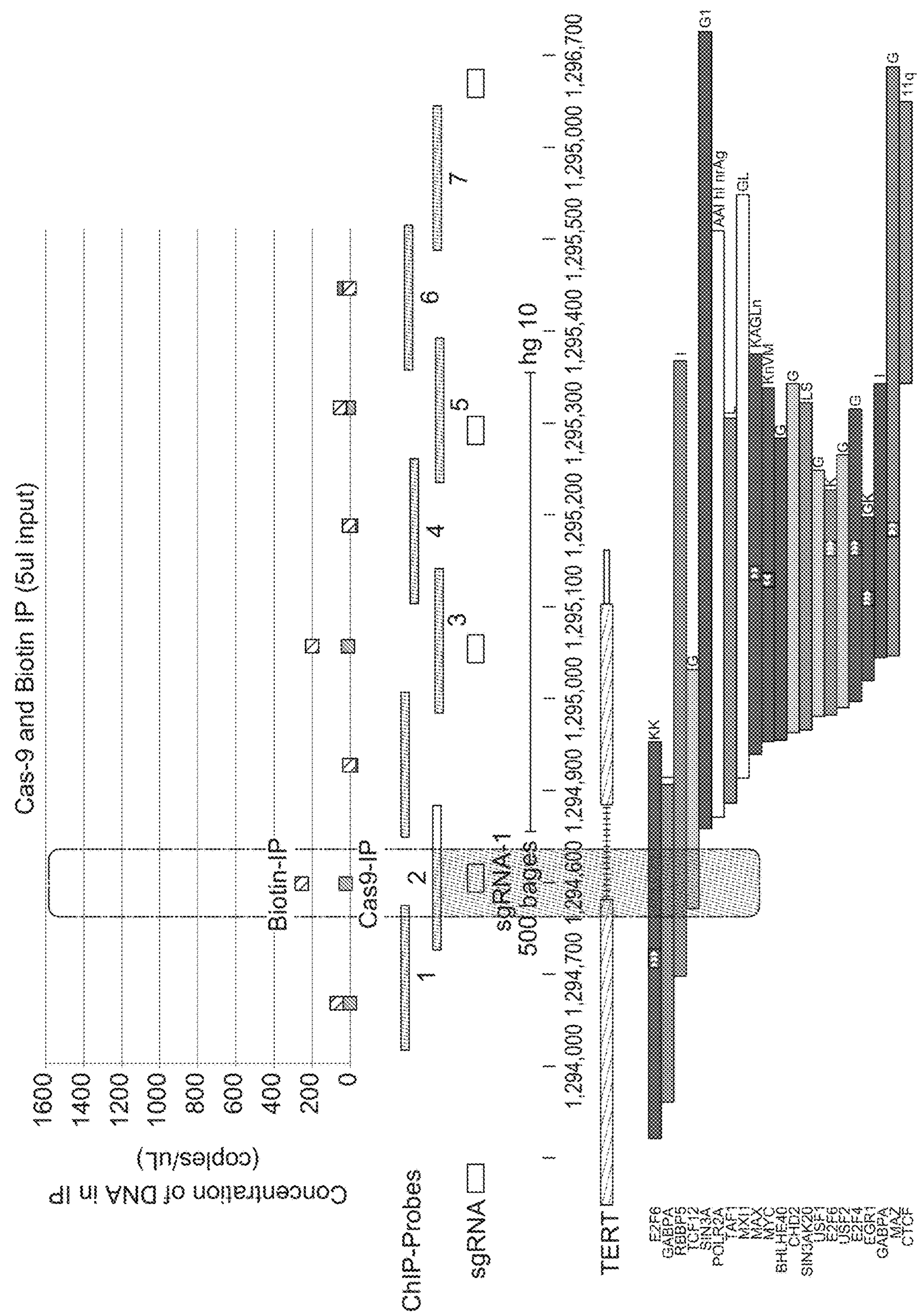
FIG. 7—depicts results of immunoprecipitation for dCas9 and streptavidin purification of biotinylated protein complexes at the TERT promoter. A) ChIP of flag-tagged Cas9 (Green) at the TERT promoter displays 98 fold enrichment of interaction at the target site relative to controls, with a resolution of between ~300 bp. Purification by streptavidin of biotinylated protein/DNA complexes (Blue) at the TERT promoter displays a 215 fold enrichment over controls with a resolution under 200 bp. B) Probe design tiled across the TERT promoter. C) Orientation of the TERT promoter and known proteins bound to the site (ENCODE).
Figure 7B:
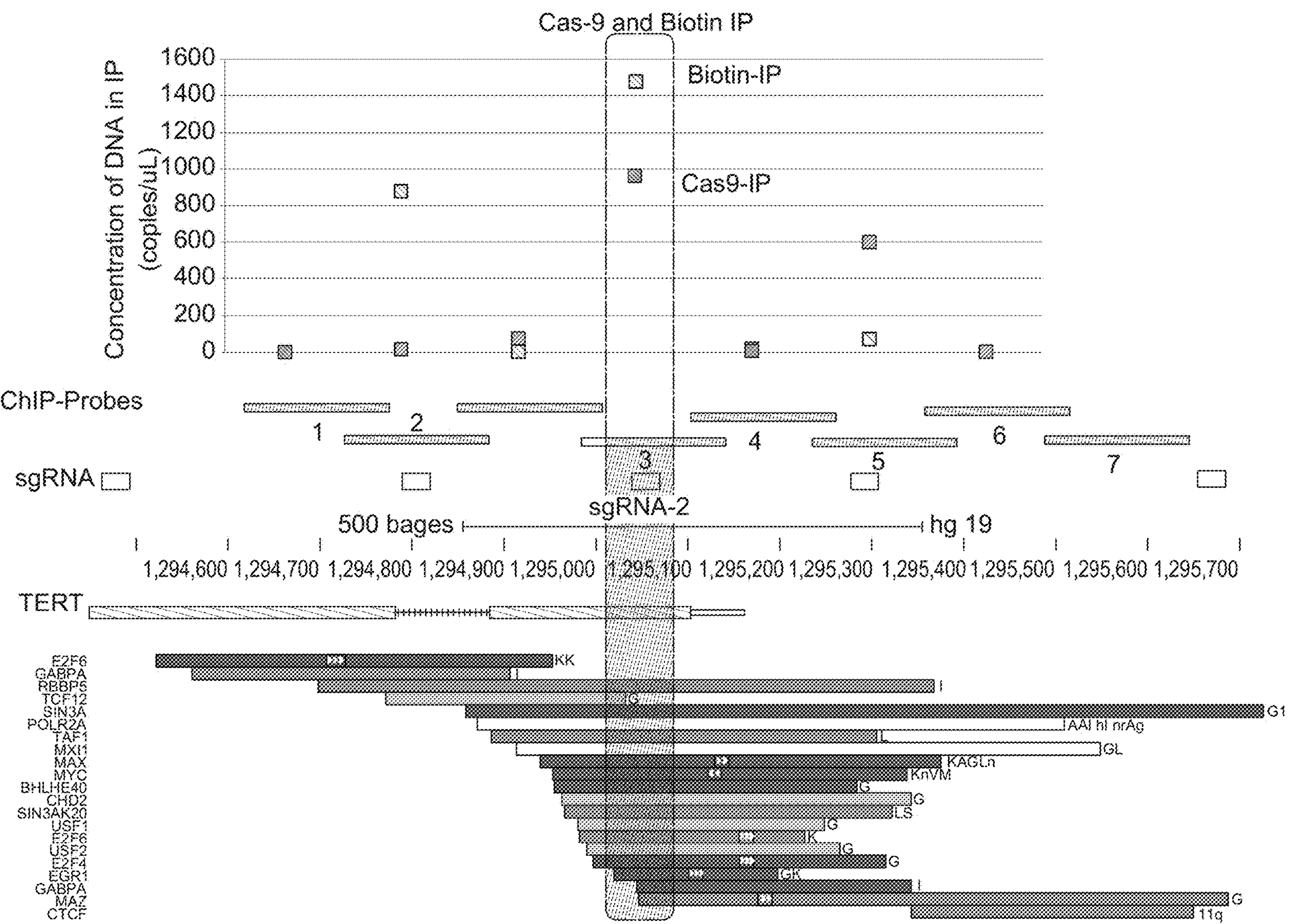
Figure 7C:
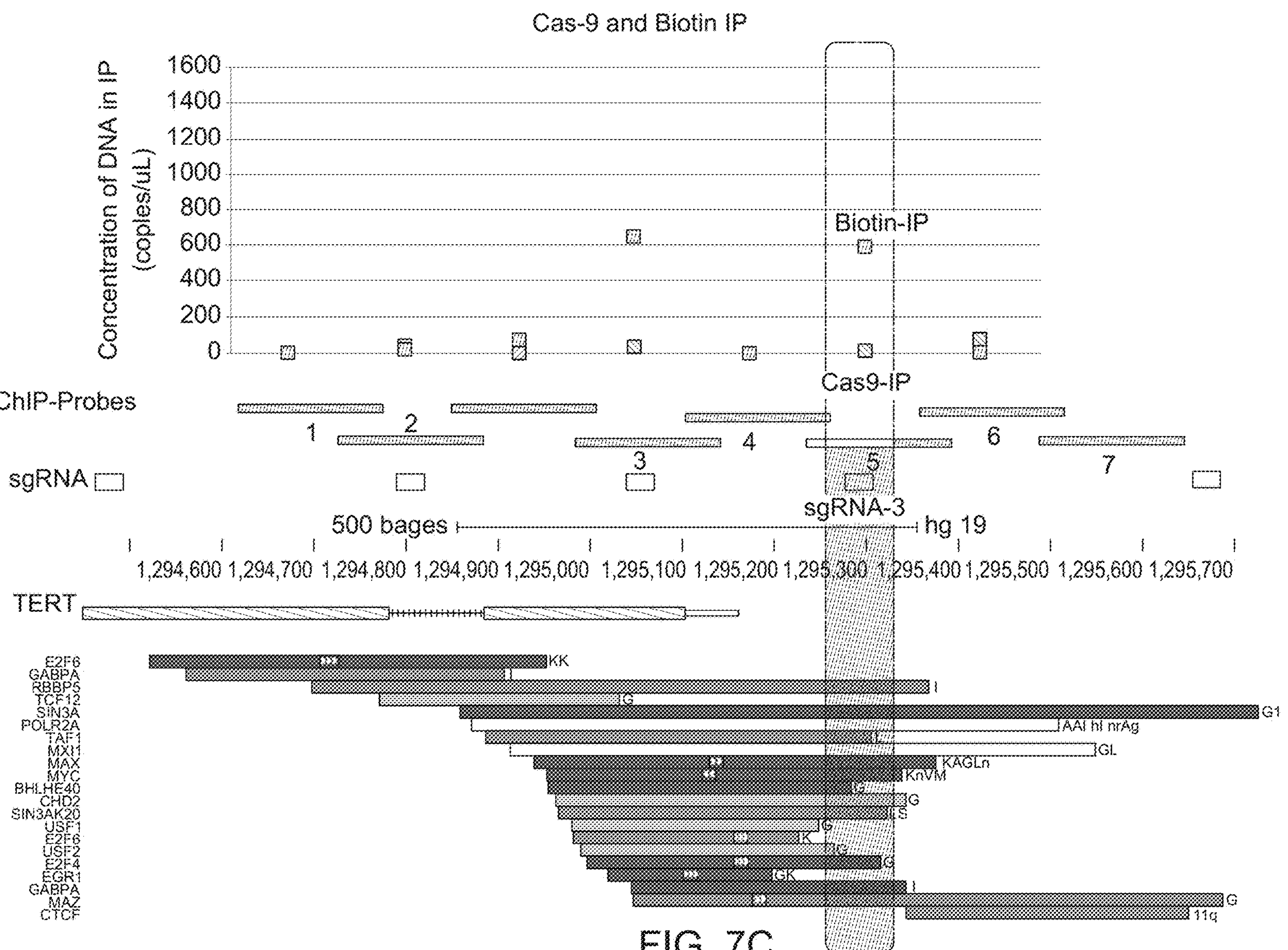
Figure 8A:
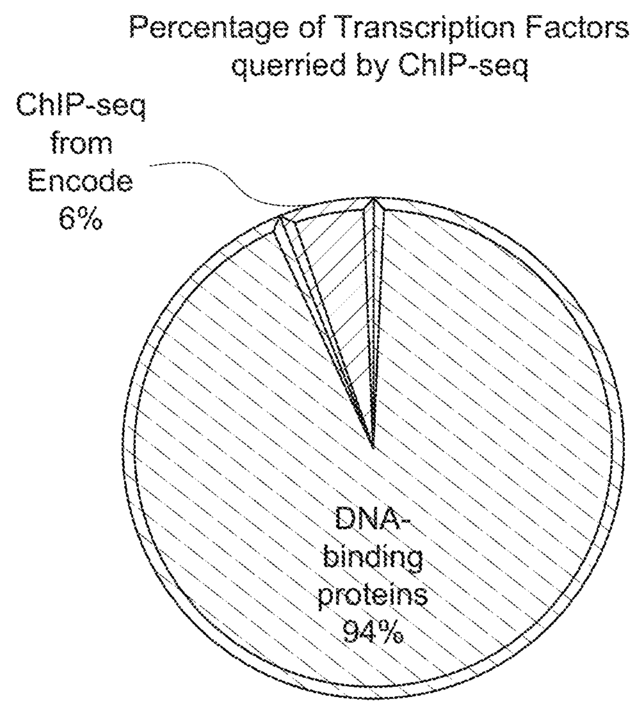
FIG. 8—depicts an outline of the dCas9-APEX mediated biotinylation in accordance with certain example embodiments. A) Pie chart of all proteins with DNA binding domains and the fraction that have been characterized by ChIP (Babu et al., 2004, Gerstein et al., 2012). B) Schematic representation of APEX: rapid biotinylation of nearby proteins depicting a genetically encoded peroxidase, rapid labeling and a small labeling radius (Rhee et al., Science, 2013, Hung et al., Nat. Protoc. 2016) C) Schematic representation of a promoter/regulatory element with all known protein interactions identified by ChIP-seq (Minimum of two target loci i.e. TERT promoter, c-MYC promoter, CDKN2A promoter, these are all well characterized genes that are expressed in HEK293 Ts and have known distal interactions). D) Schematic of the protocol for dCas9-APEX mediated biotinylation of proximal proteins. E) Schematic presentation of tiling hTERT for redundant coverage. F) Testing CasPEX efficacy via ChIP-qPCR. G: Experimental design and analysis pipeline.
Figure 8B:
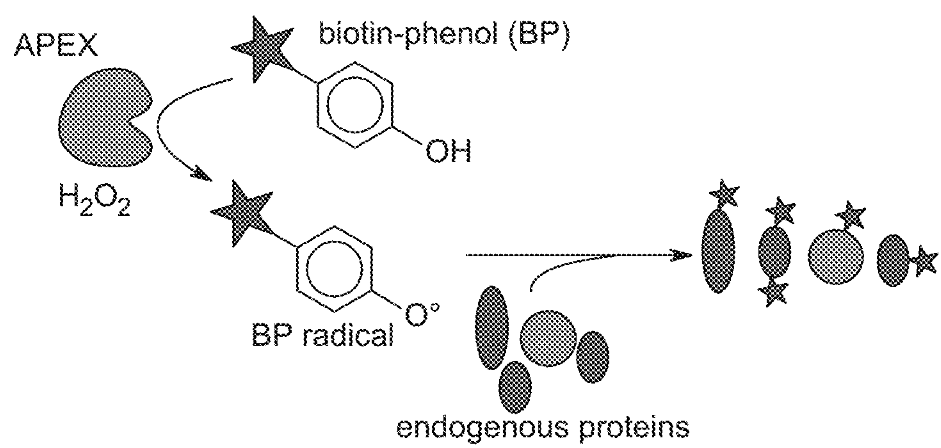
Figure 8C:
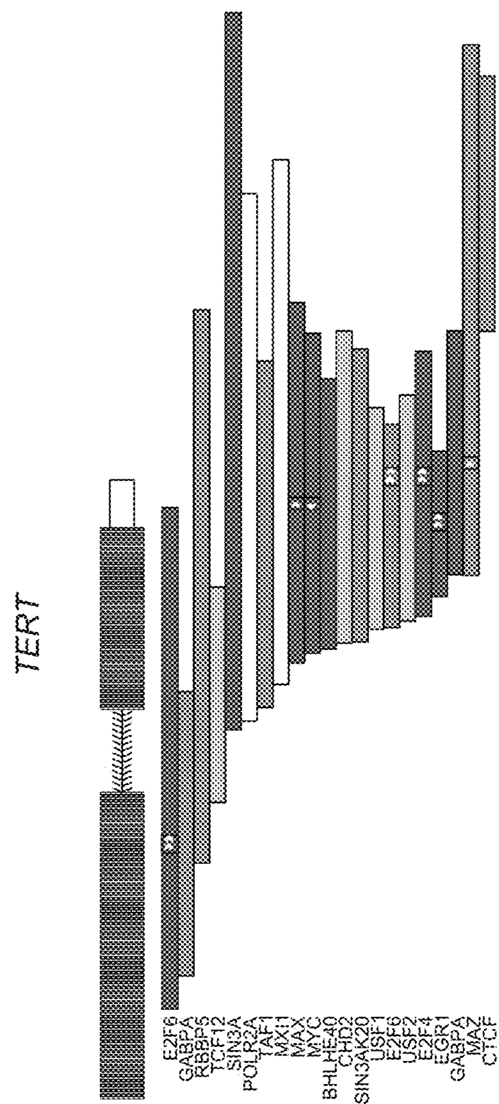
Figure 8D:
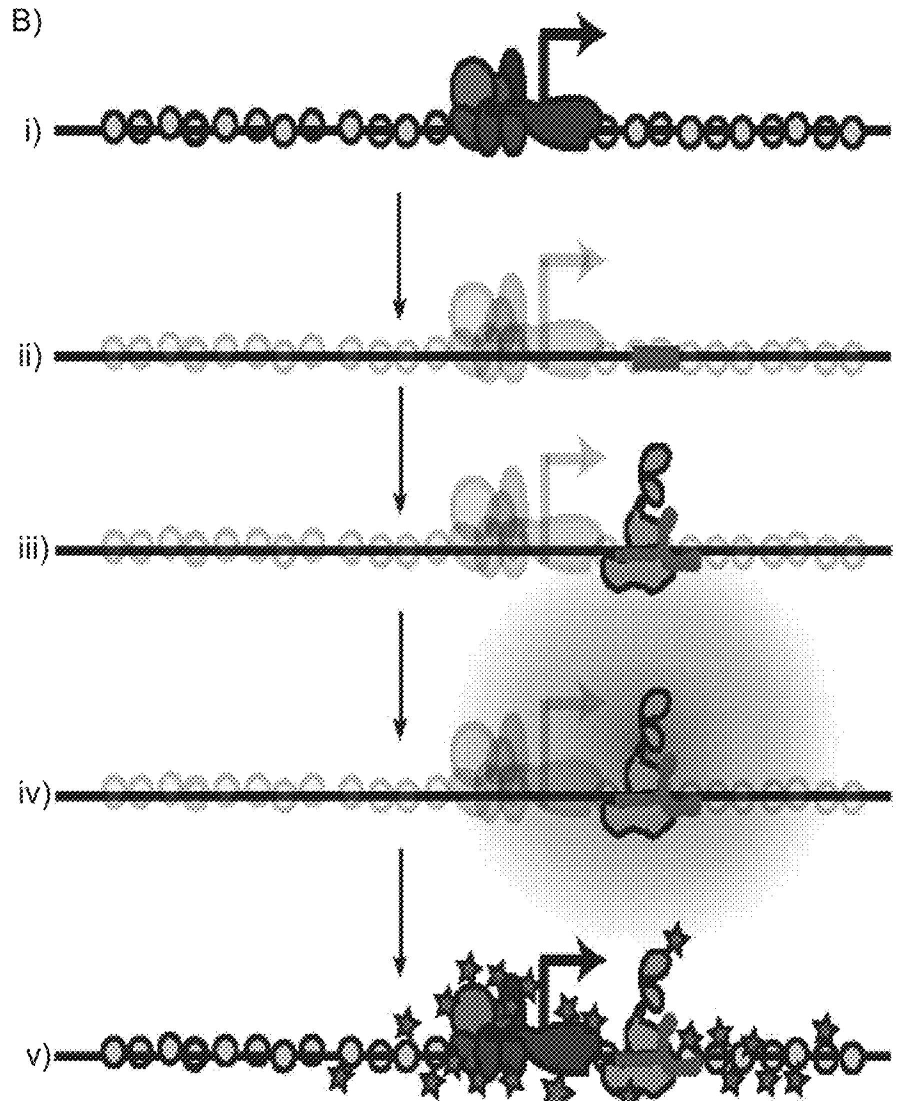
Figure 8D:
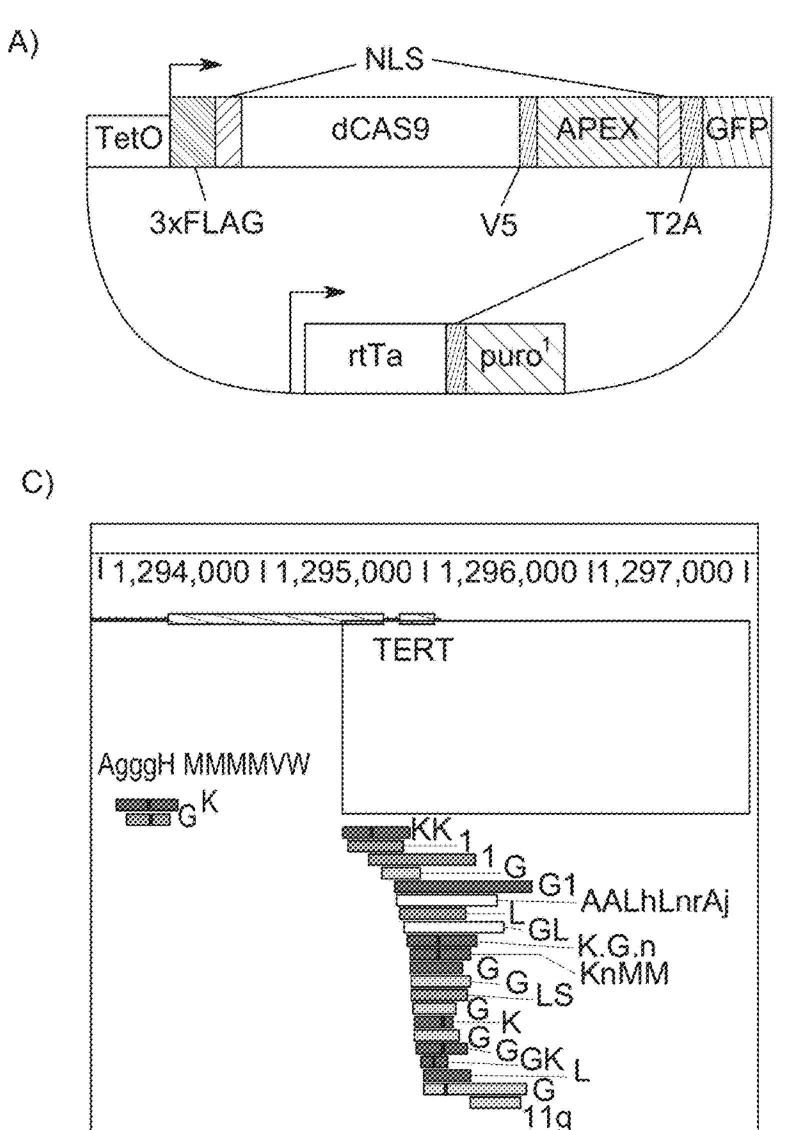
Figure 8E:
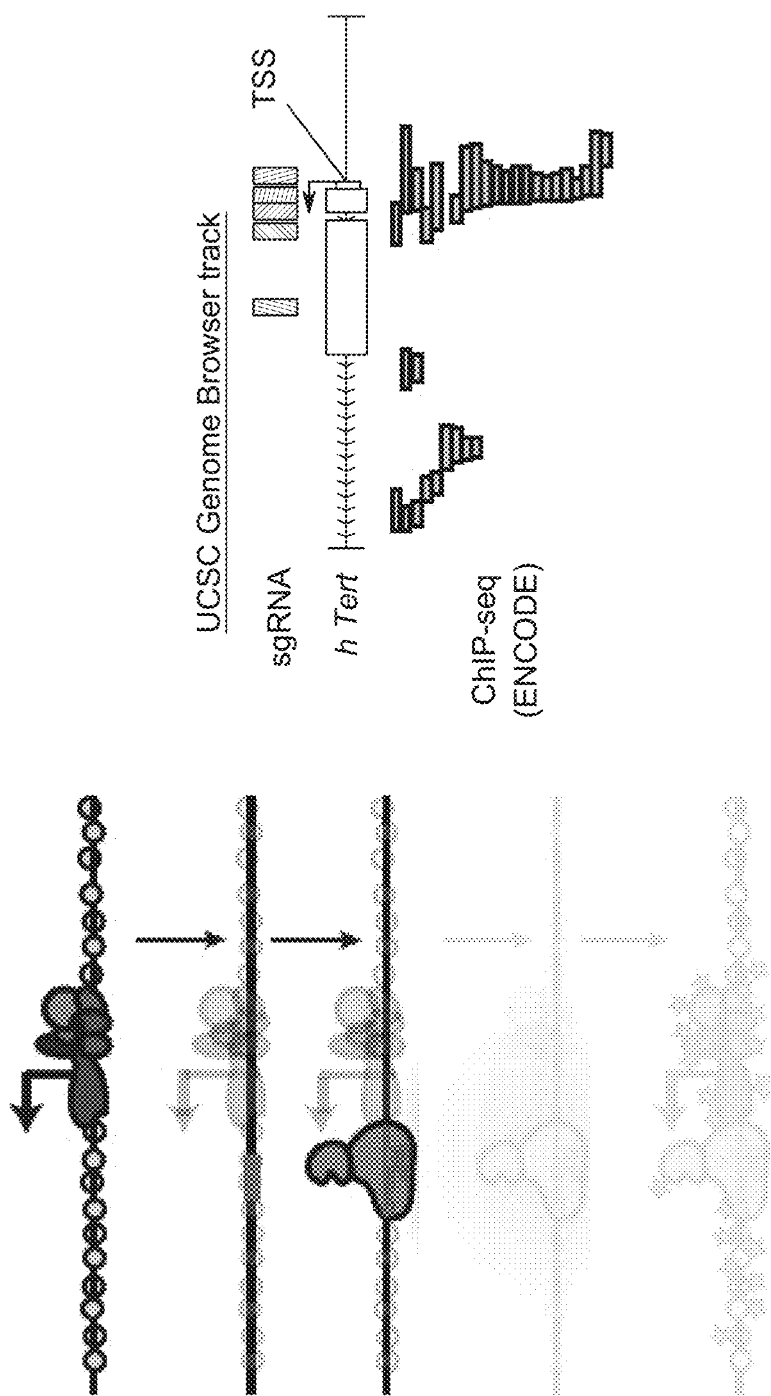
Figure 8F:
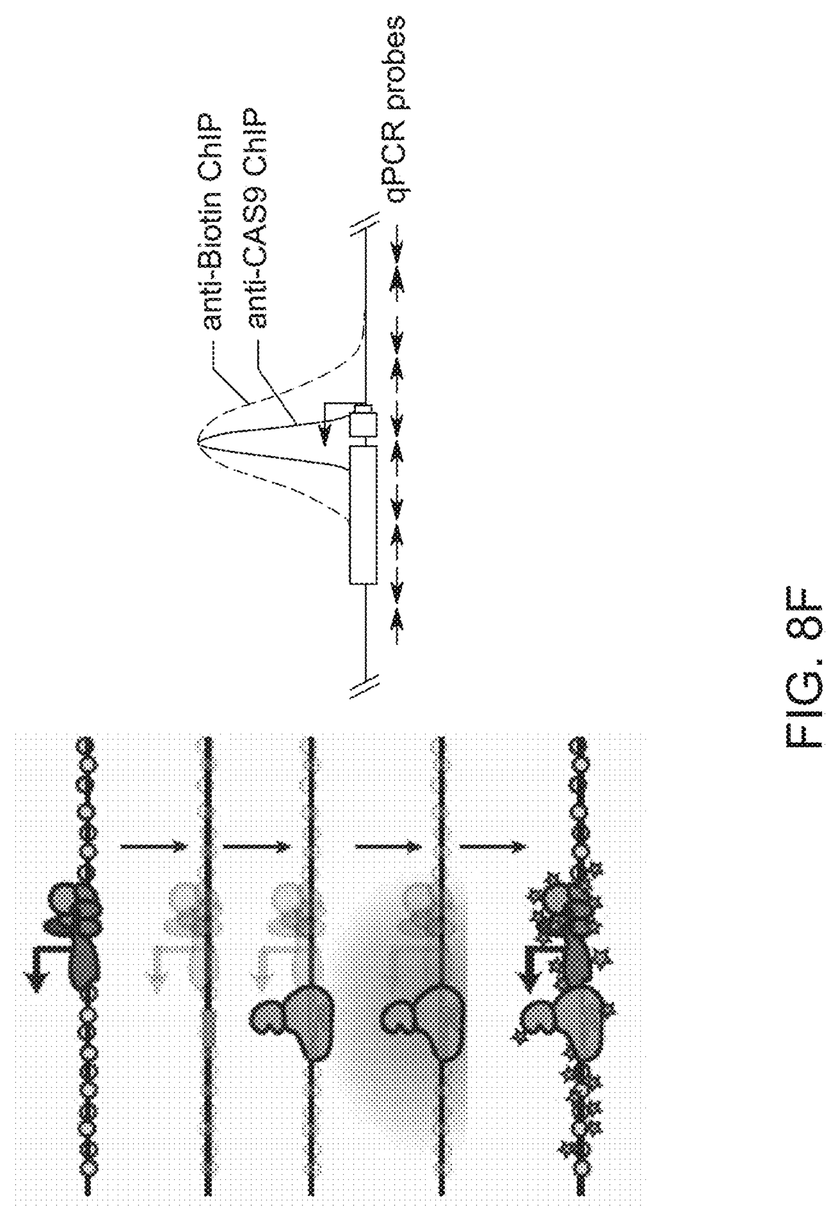
Figure 8G:
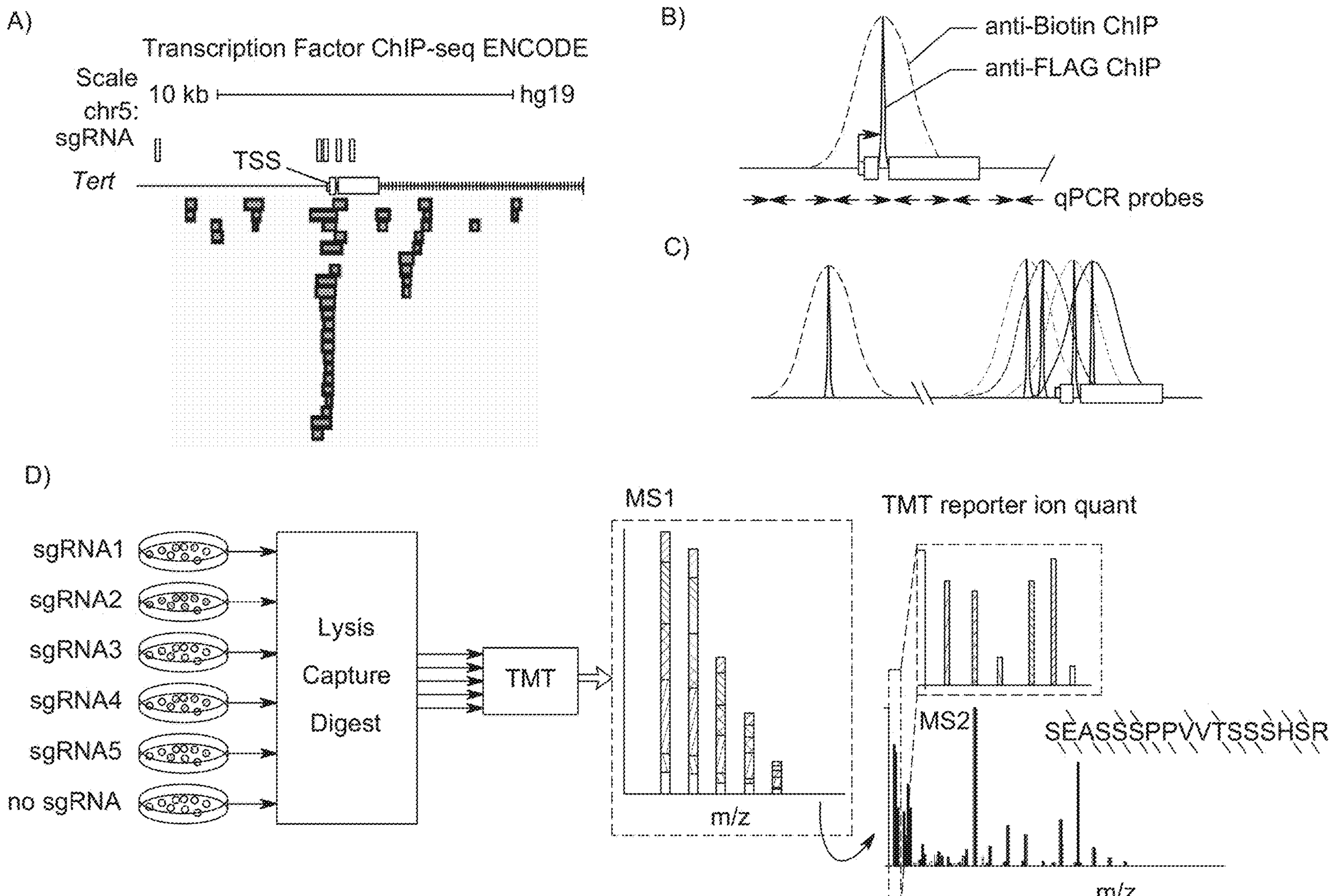

FIG. 7 depicts results of immunoprecipitation for dCas9 and streptavidin purification of biotinylated protein complexes at the TERT promoter.

This data supports the principal that the DNA-binding affinity of engineered nucleases to deliver enzymes which mediate the specific biotinylation of proteins at specific target locations in the genome may be utilized. Further this data supports that the proximity of biotinylation is restricted to an area within ~200 bp of the targeted location, a distance that closely approximates the distance between nucleosomes. Next steps include: (1) applying this approach to a additional target sites with multiple guides and multiple derivations of the technology (SaCas9, TALE, split Enzyme) to compare each strategy, assess the technologies robustness, and the range of applicability and (2) performing next generation sequencing of purified flag-dCas9/DNA and Biotin-protein/DNA to identify i. off-target dCas9 binding sites and ii. Distal regulatory elements that loop to be brought in close proximity to the target promoter.

The following example vector sequences are provided herein.

Vector sequence of pLenti2-dCas9-NLS-BirAR118G-2A-GFP: (Seq. I.D. No. 142)

Vector sequence of pLenti2-EF1a-MS2-NLS-BirA-2A-GFP-WPRE (Seq. I.D. No. 143)

Vector sequence of dCas9_SplitBirA_1-140 (Seq. I.D. No. 144)

Vector sequence of dCas9_SplitBirA_141-320 (Seq. I.D. No. 145)

Vector Sequence of TALE-BirAR118G (Seq. I.D. No. 146)

Example 8: Unbiased Identification and Quantitation of Proteins at Single Genomic Loci FIG. 8 depicts an outline of the dCas9-APEX mediated biotinylation. A: Pie chart of all proteins with DNA binding domains and the fraction that have been characterized by ChIP (Babu et al., 2004, Gerstein et al., 2012). B: Schematic representation of a promoter/regulatory element with all known protein interactions identified by ChIP-seq (Minimum of two target loci i.e. TERT promoter, c-MYC promoter, CDKN2A promoter, these are all well characterized genes that are expressed in HEK293 Ts and have known distal interactions). C: Schematic of the protocol for dCas9-APEX mediated biotinylation of proximal proteins. D: Experimental design and analysis pipeline.

To analyze the proteomic data in the context of predicted, known and novel protein occupancy at target sites an analysis pipe-line is developed. The bioinformatic pipeline begins with three inputs for a given loci of interest, each outputting a p-value per sgRNA loci per protein of interest. The p-value is an indication of the probability Applicants observe that particular protein at that site over background:

1. Mass Spectrometer RAW output files, the format can be variable, but essentially these are spectrometer readings. Applicants identify spectra by using a traditional database search approach, this provides observed peptides. Tallying up the observed peptides and comparing to control (no sgRNA) Applicants get a TMT based log 2 fold change, this is used to output a p-value per protein per sgRNA. Maxquant (http://medusa.biochem.mpg.de/maxquant_doku/) or OpenMS (http://open-ms.sourceforge.net/) software packages are used for this.

2. (In-vivo ChiP). Genomic coordinates of the probed region. This is overlapped with all available ChiP-Seq ENCODE peaks, those peak intensities are then turned into p-values using a normalization approach which looks at the surrounding binding profile for each particular ChiP-Seq experiment.

3. (In-silico). Genomic coordinates of the probed region. This is overlapped with the reference genome fetching the raw nucleotide sequence for the loci of interest. The raw sequence is then chunked into 20 bp regions, each time stepping by 10 bp so the 20 bp regions overlap. Each 20 bp chunk is then fed to DeepBind, estimating the probability of known TFs to bind there. The rolling average is then taken across these probabilities producing p-values for all TFs across the locus.

These approaches each produce three sets of p-values that are then visualized using R (http://shiny.rstudio.com/, may be used). The user can interactively determine the quality of the output.

Figure 9:
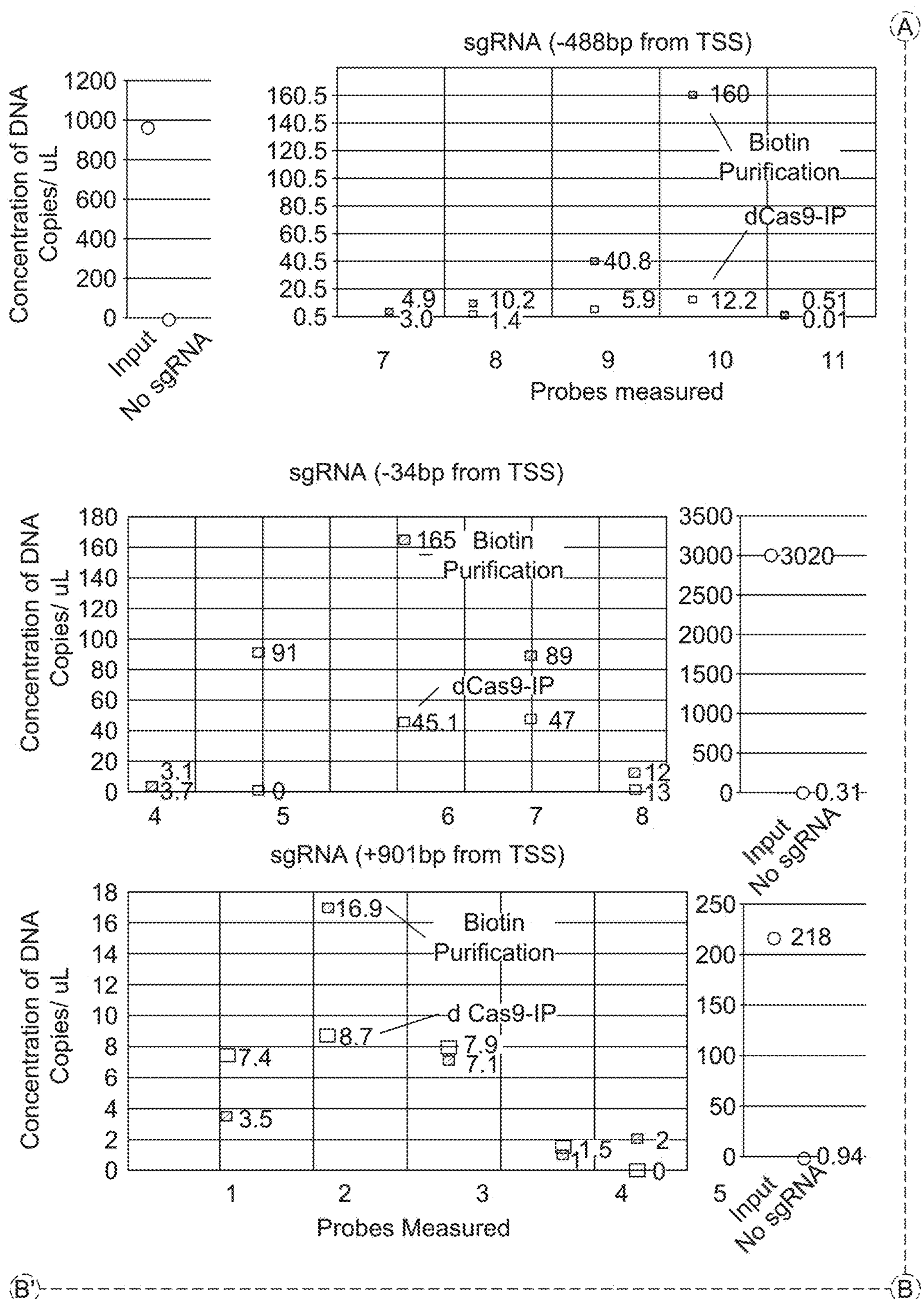
FIG. 9—depicts characterization of dCas9-APEX site-specific biotinylation. Locus specific biotinylation and measurement by streptavidin pull-down and ddPCR at target loci. 5 sgRNAs tiled across the promoter of TERT in HEK293T cells were designed to deliver the biotin transferase APEX2. Biotinylated proteins were purified from each sgRNA treatment, and DNA concentration of the target was measured by probes tiling the locus, and readout by partitioned droplet digital PCR. In parallel, the dCas9-APEX fusion proteins were purified by V5 antibody precipitation, and each site was assayed by ddPCR. For Each purification, no sgRNA treatment was used as a negative control. The probe that includes each respective sgRNA is shown for the negative and positive (input) controls.
Figure 9:
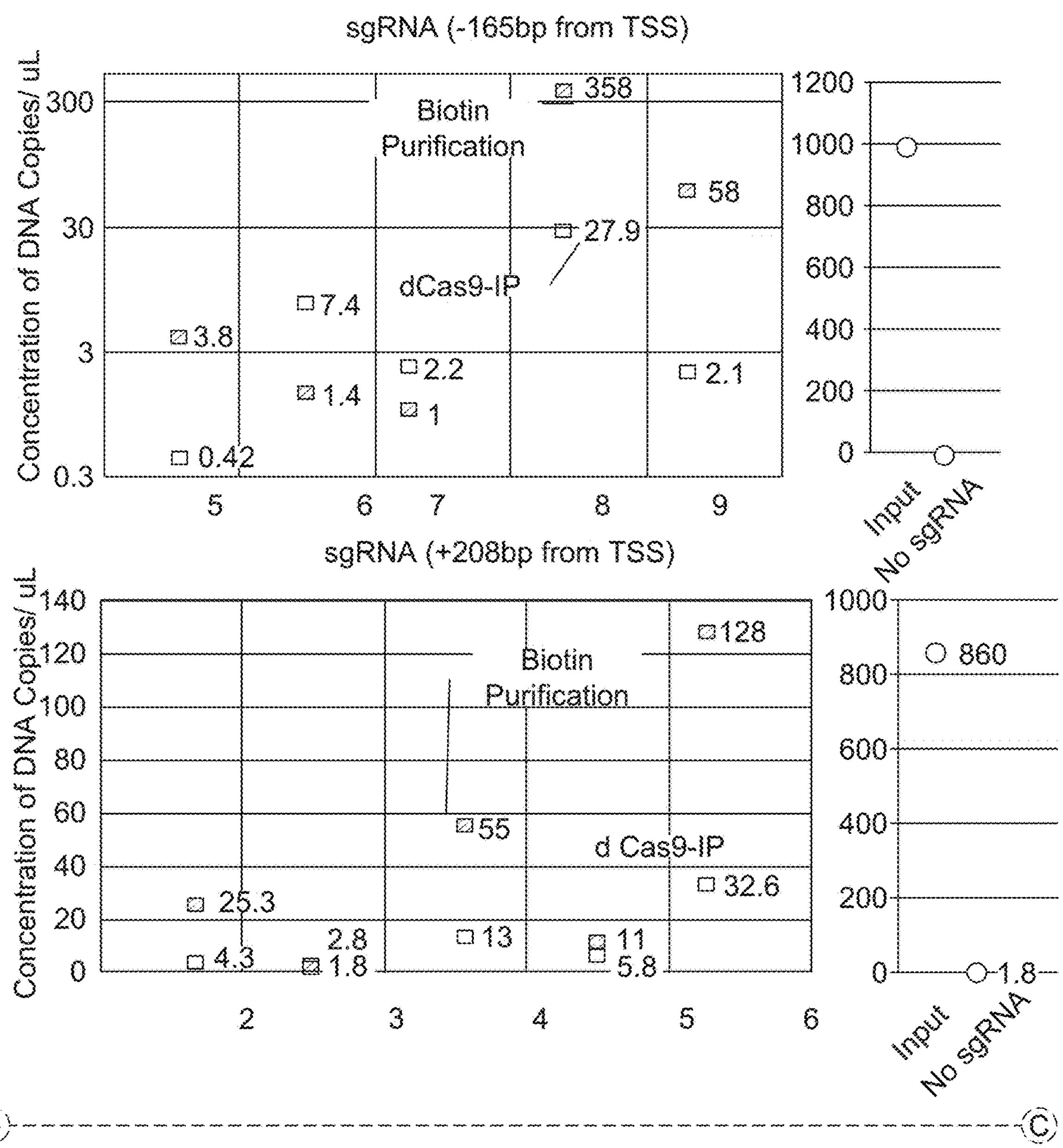
Figure 9:
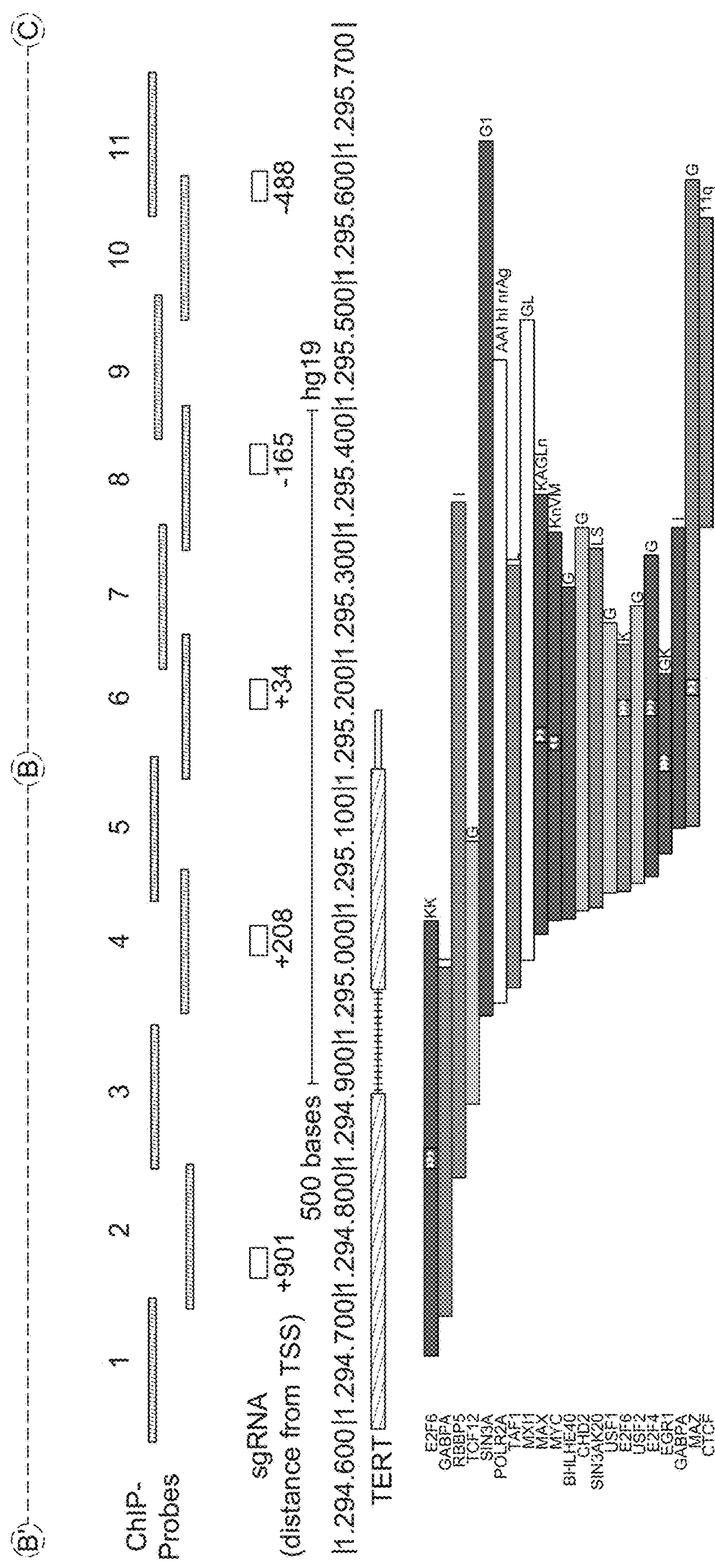

FIG. 9 depicts parameterization of dCas9-APEX site-specific biotinylation. Locus specific biotinylation were measured by streptavidin pull-down and ddPCR at target loci. 5 sgRNAs tiled across the promoter of TERT in HEK293T cells were designed to deliver the biotin transferase APEX2. Position of the target DNA of each sgRNA relative to the TERT promoter (488, 165, 34, 208, 901) was selected to minimize off-target effect. Biotinylated proteins were purified from each sgRNA treatment, and DNA concentration of the target was measured by probes tiling the locus, and readout by partitioned droplet digital PCR. In parallel, the dCas9-APEX fusion proteins were purified by V5 antibody precipitation, and each site was assayed by ddPCR. For Each purification, no sgRNA treatment was used as a negative control. The probe that includes each respective sgRNA is shown for the negative and positive (input) controls.

Figure 10:
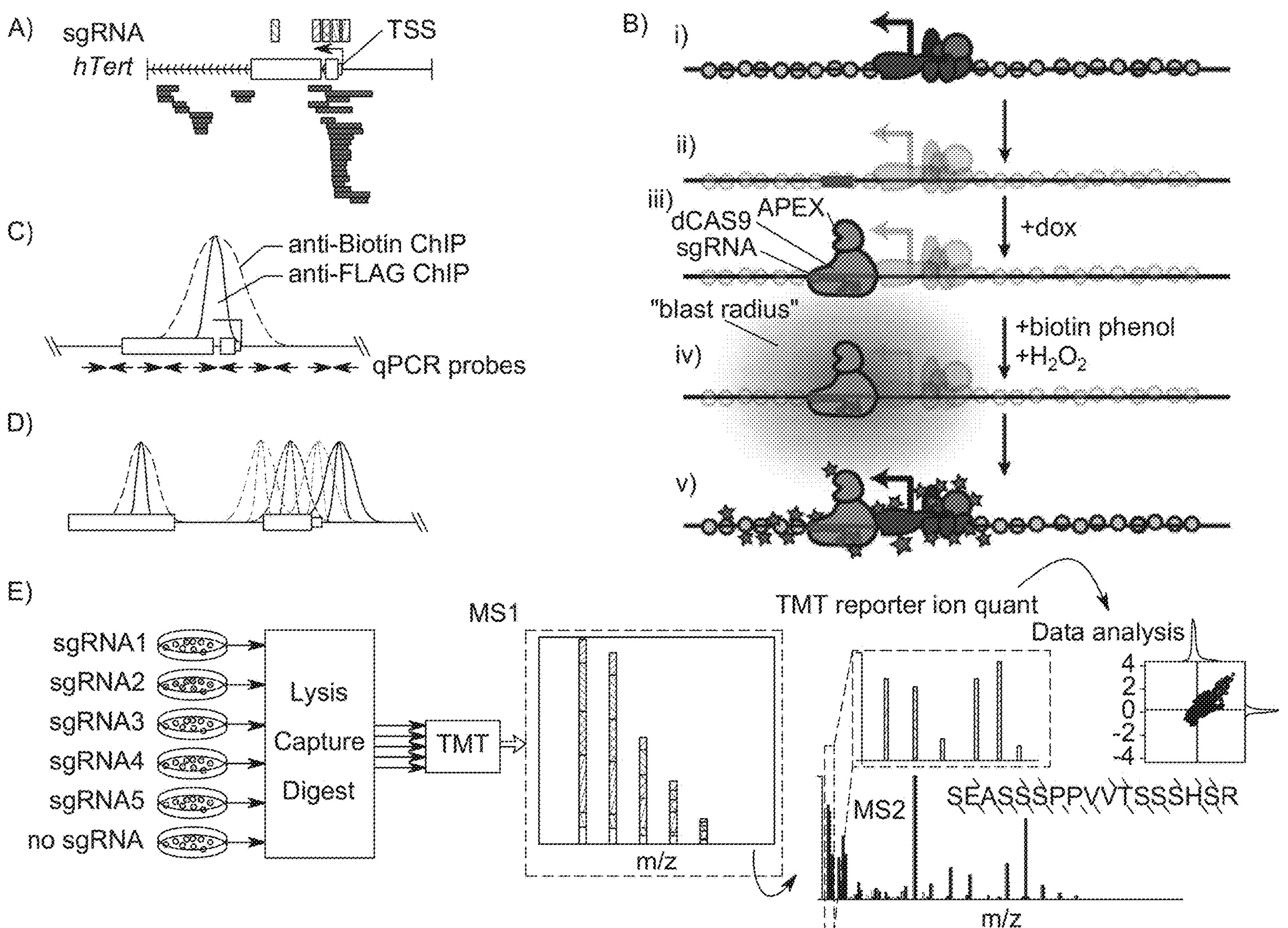
FIG. 10—depicts proteomic analysis of TERT promoter. A) Layout of sgRNA targets relative to hTert. B) Scheme of Caspex expression induction and proximal biotinylation of proteins C) Diagram of expected result of ChIP-ddPCR against Caspex and biotin in cells taken through the procedure in FIG. 10 B. D) Same as C but for all guides in the experiment. E) Proteomic workflow for hTert characterization by genomic locus proteomics. 2*10^9 HEK293T cells across 6 conditions, 5 sgRNAs spanning the TERT promoter. dCas9-APEX expression was induced with dox, and cells were treated with biotin-peroxide to induce biotinylation for 30 min. The reaction was halted with reducing solution. Cells were harvested and biotinylated proteins were isolated by magnetic streptavidin and analyzed by MS/MS. Proteins isolated from each sgRNA treated cell population were normalized to no sgRNA control. Enriched proteins were identified. The correlation of proteins common between proximal sgRNAs are displayed above. Of note, the most distal sgRNA to the promoter of TERT, (nT901), displays the least similarity with the other 4 sgRNAs which show striking consistency of protein purification between the sgRNAs n488T, n165T, n34T and nT208.
Figure 11A:
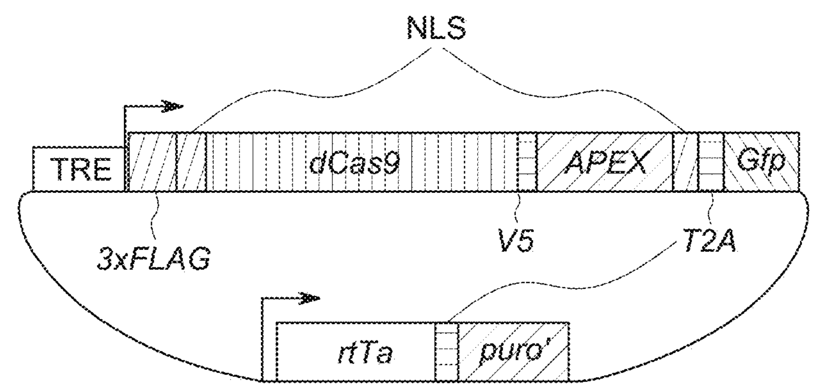
FIG. 11—provides characterization of sgRNA-293-CasPEX cells A) Diagram of CasPEX plasmid. NLS, nuclear localization sequence; 3xFLAG, triple FLAG epitope tag; V5, V5 epitope tag; T2A, T2A self-cleaving peptide; GFP, Green fluorescent protein; TRE, Tetracycline response element; rtTA, reverse tetracycline-controlled transactivator; puror; puromycin acetyltransferase. B) ChIP-ddPCR against biotin (blue boxes) and FLAG (green boxes) in 293-CasPEX cells transfected with either no sgRNA or the T92 sgRNA construct and induced to affinity label proximal proteins. ChIP probes refer to regions amplified and detected by ddPCR. hTert is below to show the tiling spacing of PCR probes with respect to the sgRNA target (red block). C) Anti-biotin Western blot analysis of all sgRNA-293-CasPEX stable lines after induction of affinity labeling in the presence or absence of dox for 24 hours. Endogenous biotinylated proteins (stars) are used for the loading control for the whole cell lysate (left) and nuclear lysate (right) analysis.
Figure 11B:
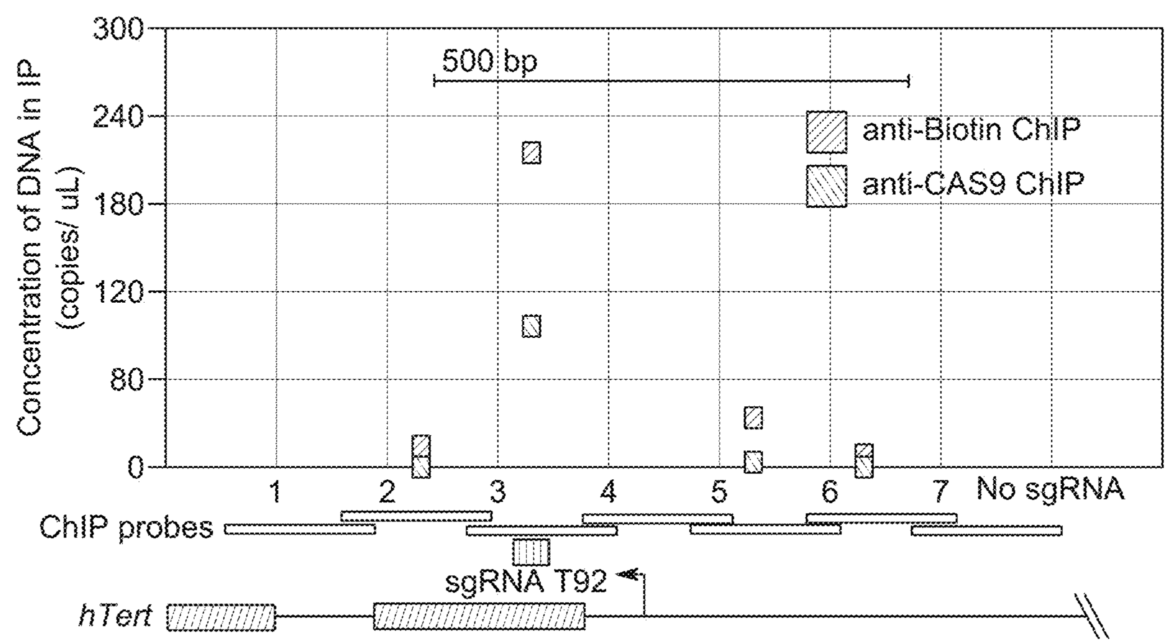
Figure 11C:
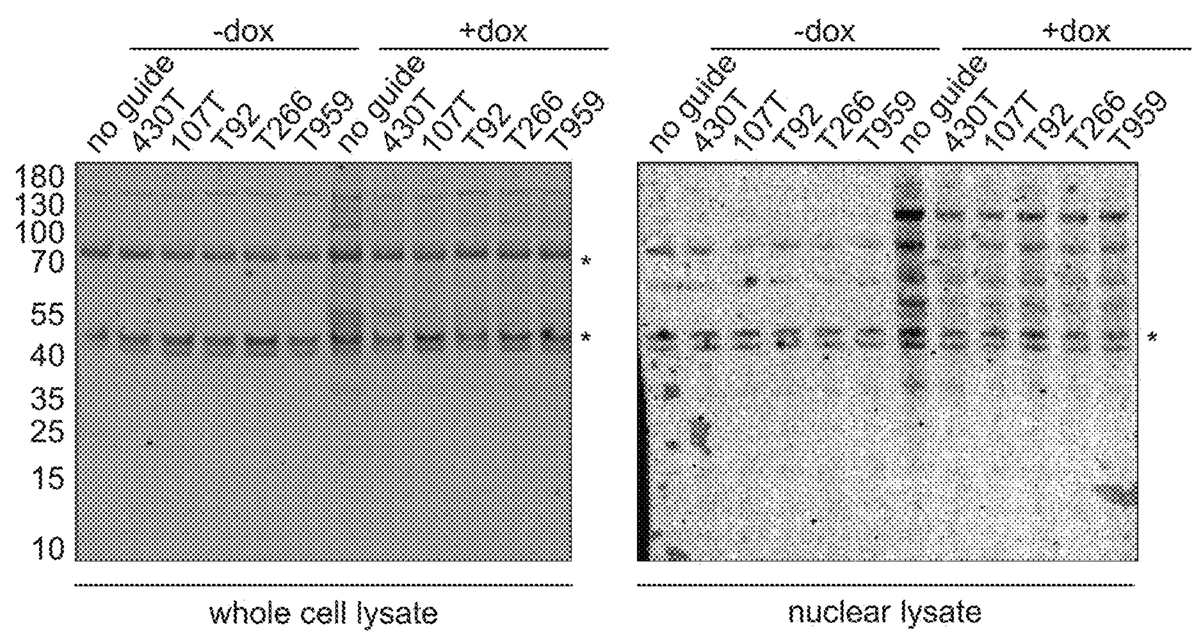
Figure 12:
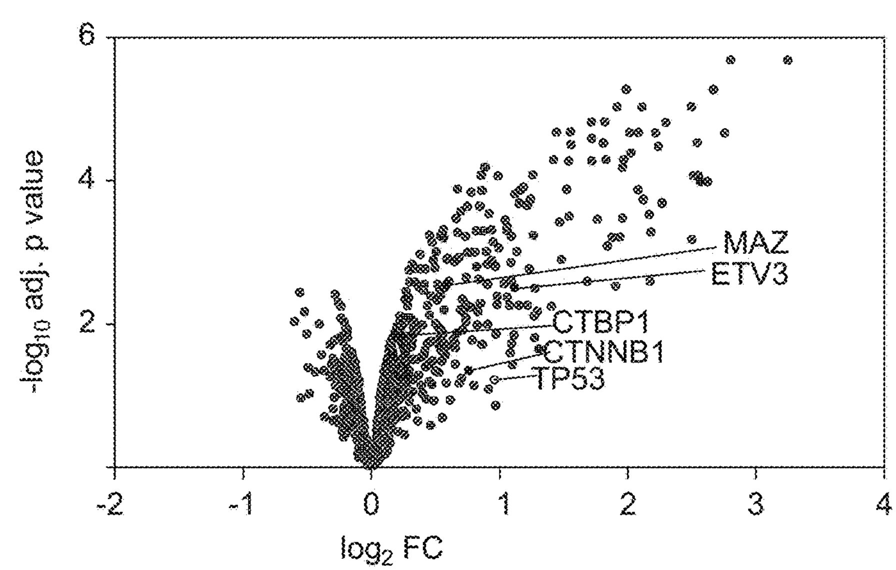
FIG. 12—Genomic locus proteomics of hTert in HEK293T cells A) Volcano plot of proteins quantified across the four overlapping sgRNA-293-CasPEX cell lines compared to the no sgRNA control. Proteins known to associate with hTert are labeled. Red indicates an enrichment p value of <0.05, blue indicates a p value of 0.058. B) GSEA enrichment analysis of proteins identified by GLoPro of hTert in HEK293T cells. Only gene sets with an FDR≤0.15 are shown. C) Correlation analysis of proteomic log 2 fold enrichment values between overlapping sgRNA-293-CasPEX cells and the distal T959 CasPEX line, compared to the no sgRNA control line. D) Positional heatmap of anti-V5 ChIP-ddPCR tiling hTert of candidates identified by GLoPro analysis and negative controls. The mean GLoPro enrichment value for the overlapping sgRNA lines was used to rank order ChIP values. E) Correlation between mean ChIP-ddPCR and GLoPro enrichment values of the four overlapping sgRNAs and their corresponding genomic loci. Black, open circles indicate that the protein was not identified by GLoPro. Purple, open circles indicate the protein was identified but was not statistically enriched. Red open circles indicate proteins that are enriched according to the GLoPro analysis. Previously described hTert binders are labeled. F) Native ChIP results.
Figure 12:
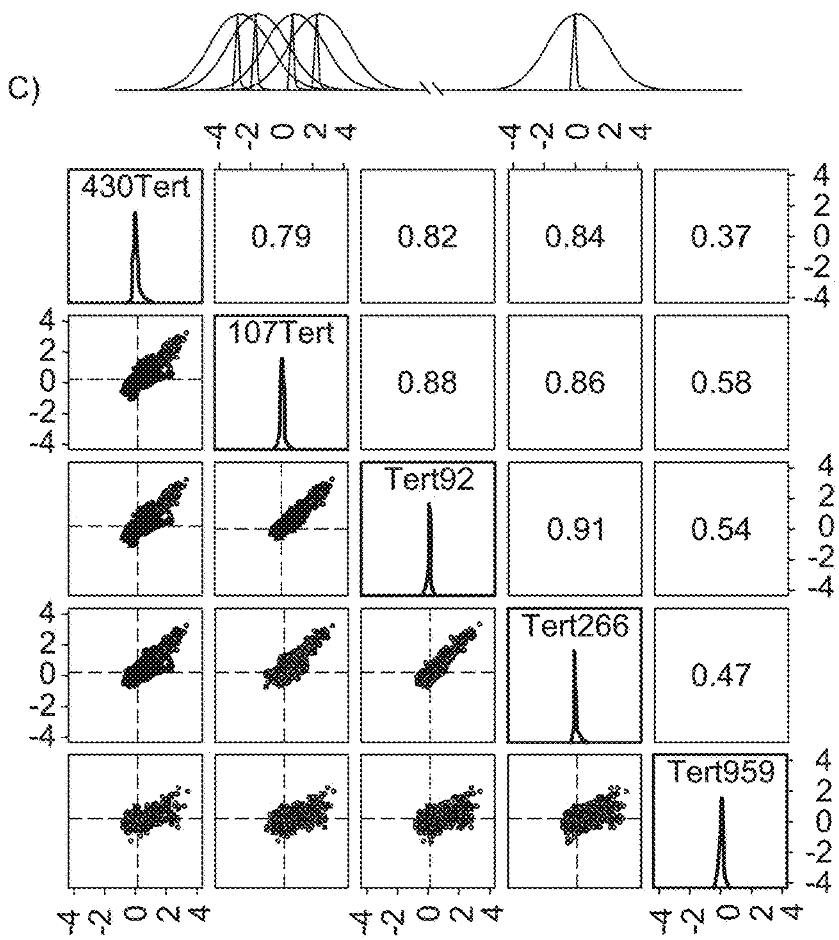
Figure 12:
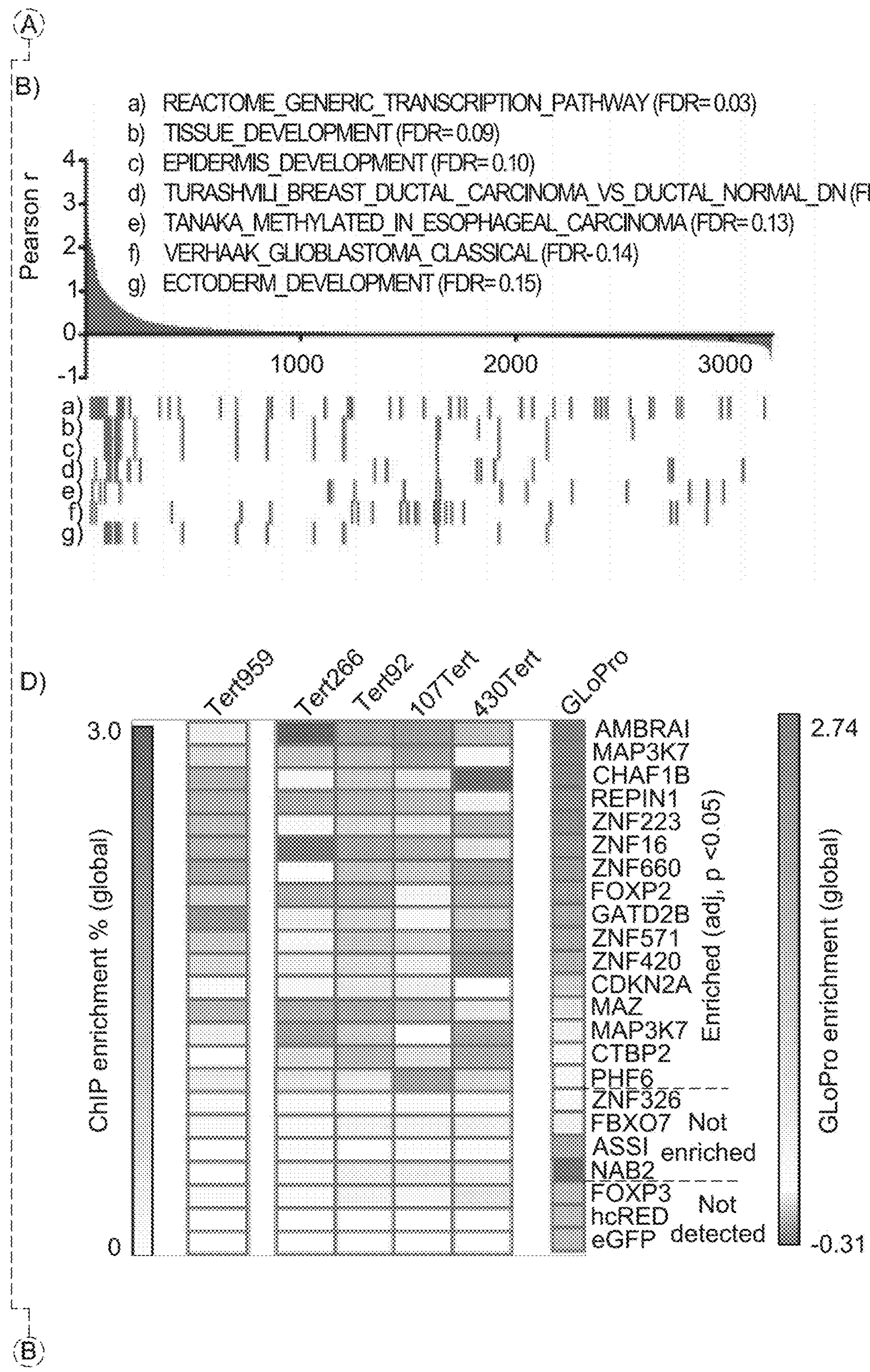
Figure 12:
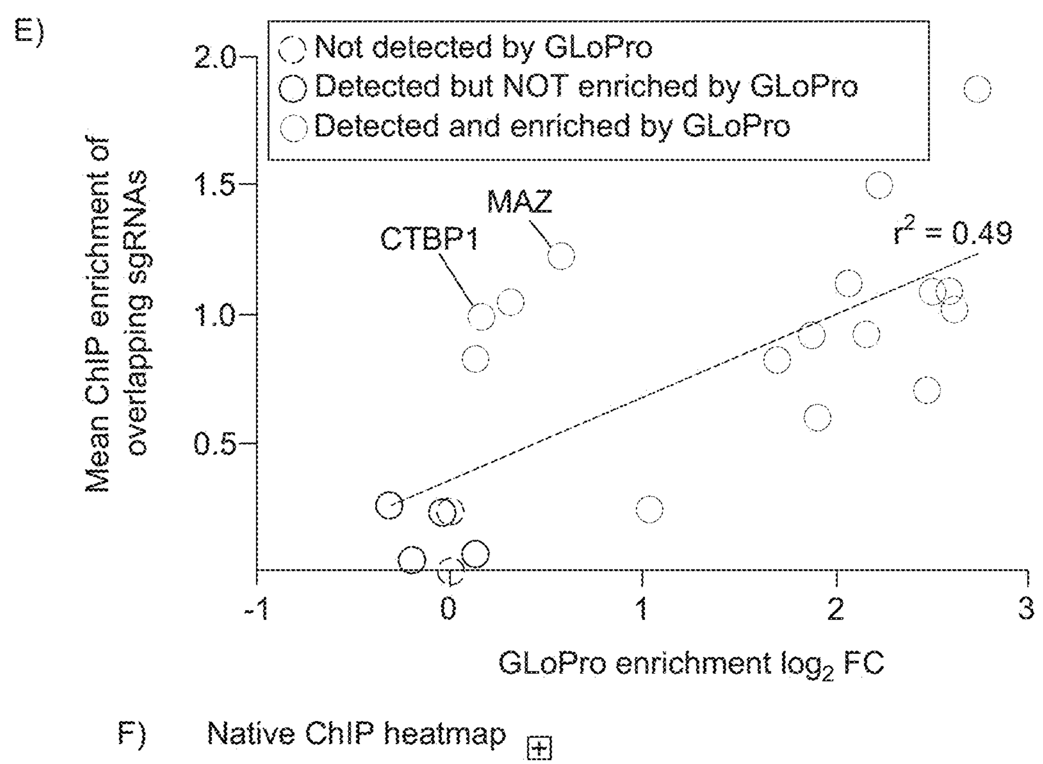
Figure 13:
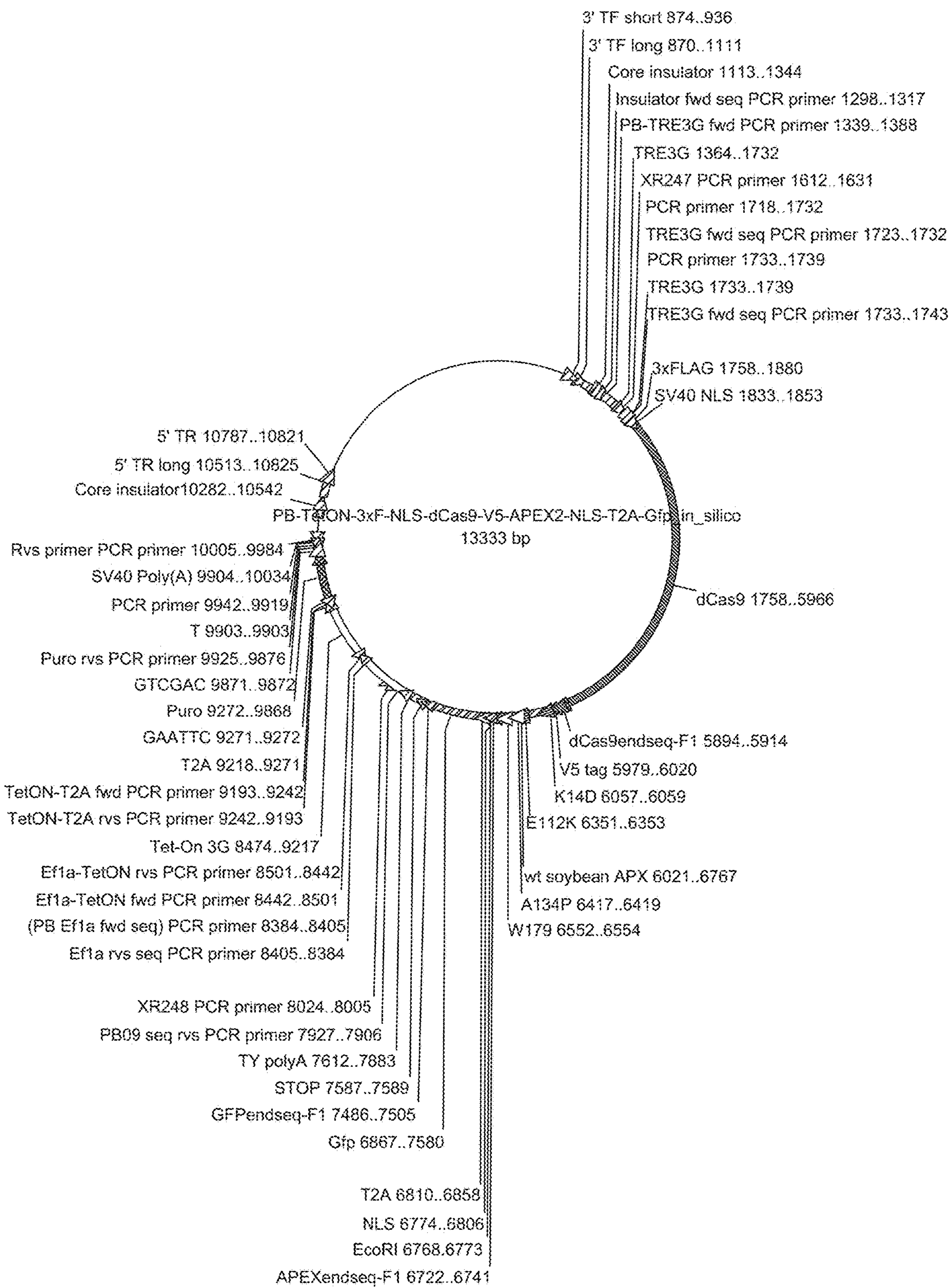
FIG. 13—Current version of plasmid used for genomic locus proteomics. Plasmid contains tetracycline inducible system driving the dCas9-APEX2-T2A-GFP. Puromycin selectable marker is co-expressed with the rtTA transcriptional activator.
Figure 14:
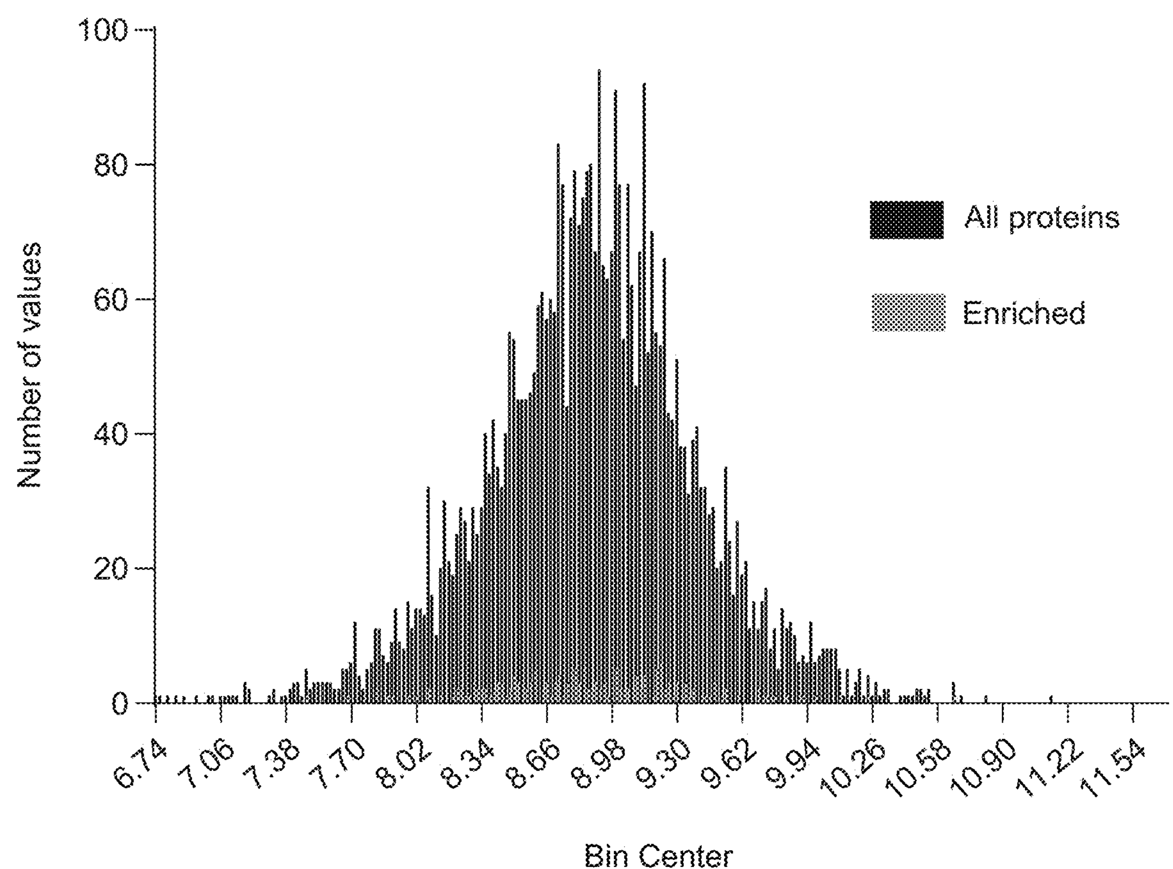
FIG. 14—Distribution of peptide precursor intensity for all proteins identified in a GLoPro experiment (black) compared to proteins identified to be significantly enriched (grey). These data show that not only low abundant proteins are found as enriched at the genomic locus of interest.
Figure 15A:
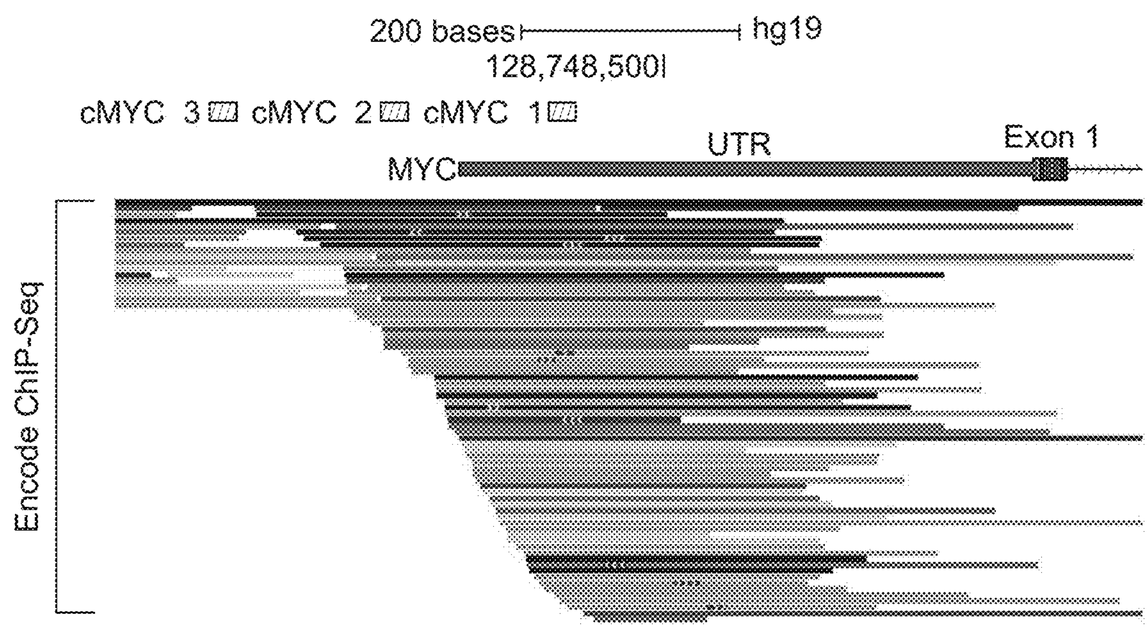
FIG. 15—A) Initial design of sgRNAs to characterize the human c-Myc promoter. Relative the transcription start site, Myc1=3 bp into the gene, Myc2=85 bp before TSS and Myc3=208 bp before TSS. B) ChIP-qPCR analysis of c-Myc targeted GLOPro.
Figure 15B:
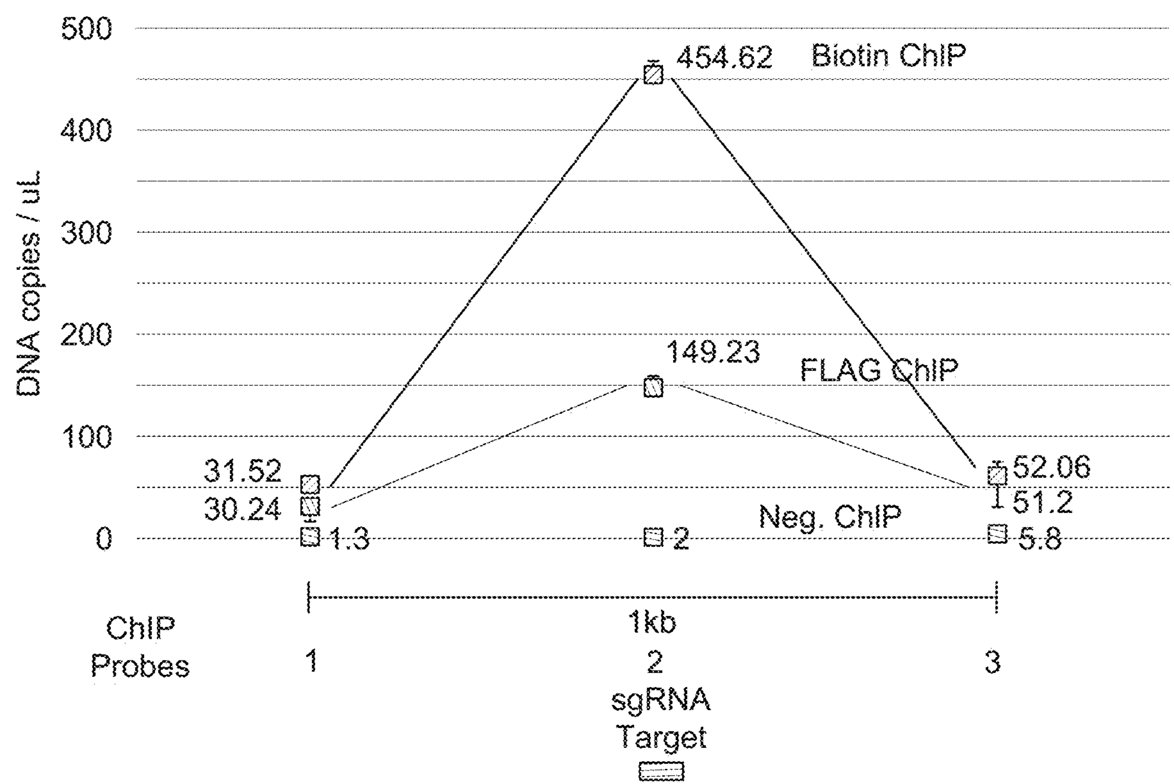
Figure 16A:
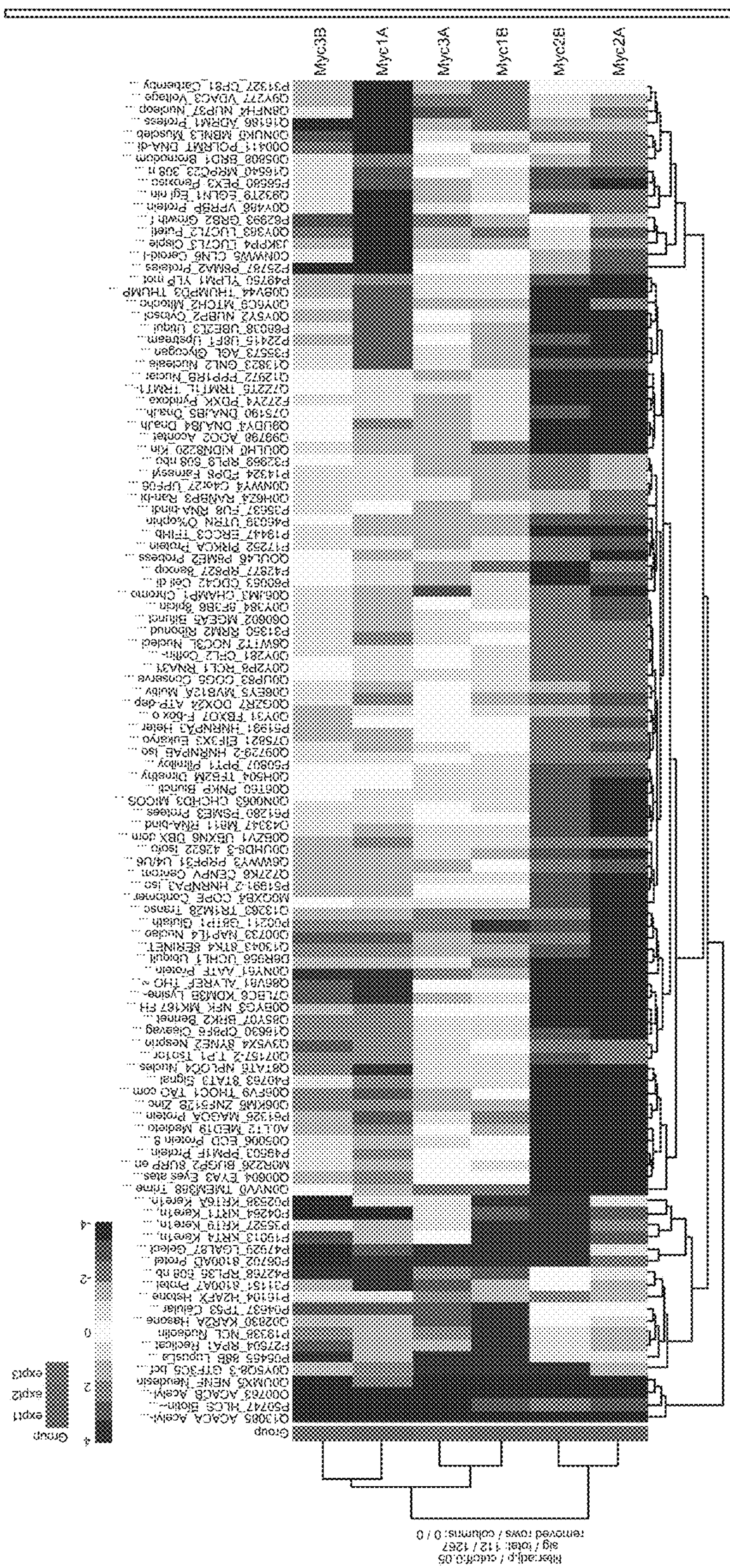
FIG. 16—A) Heatmap of proteins identified to be significantly enriched or depleted at the human Myc promoter compared to the no guide control in 293T cells. Samples from Myc1 and Myc3 show similar enrichment patterns when compared to Myc2. Applicants hypothesize that binding of Caspex at the Myc2 locus displaces proteins that would be identified by Myc1 and 3, illustrating there may be a spacing requirement between guides of aobut 200 bp. B) Heatmap of enriched proteins between Myc1 and 3 only. Pathway analysis by Genets (Broad Institute, unpublished) shows that the PID MYC ACTIVPATHWAY is enriched with a Bonferroni p-value of 0.0018.
Figure 16B:
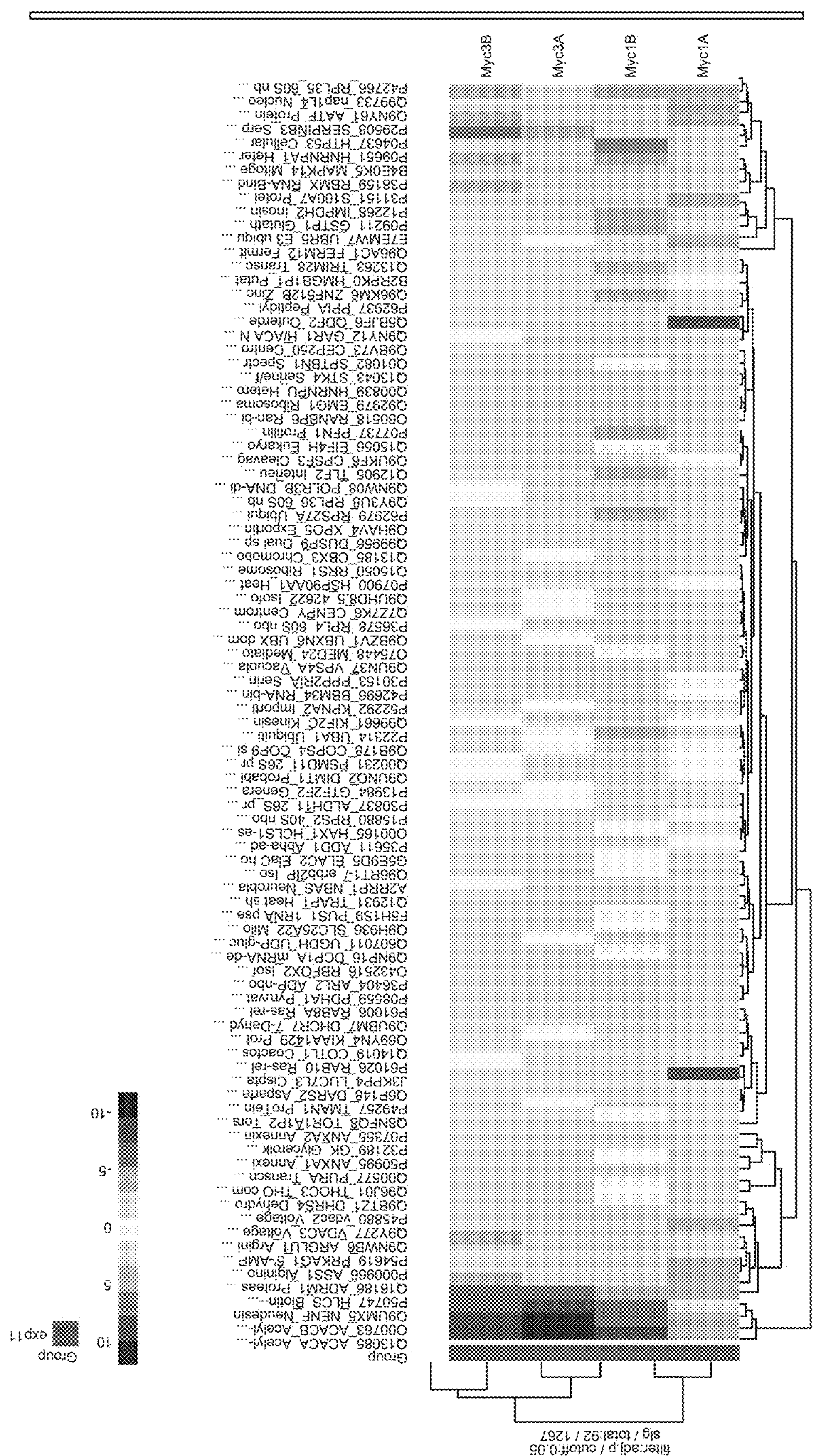
Figure 17:
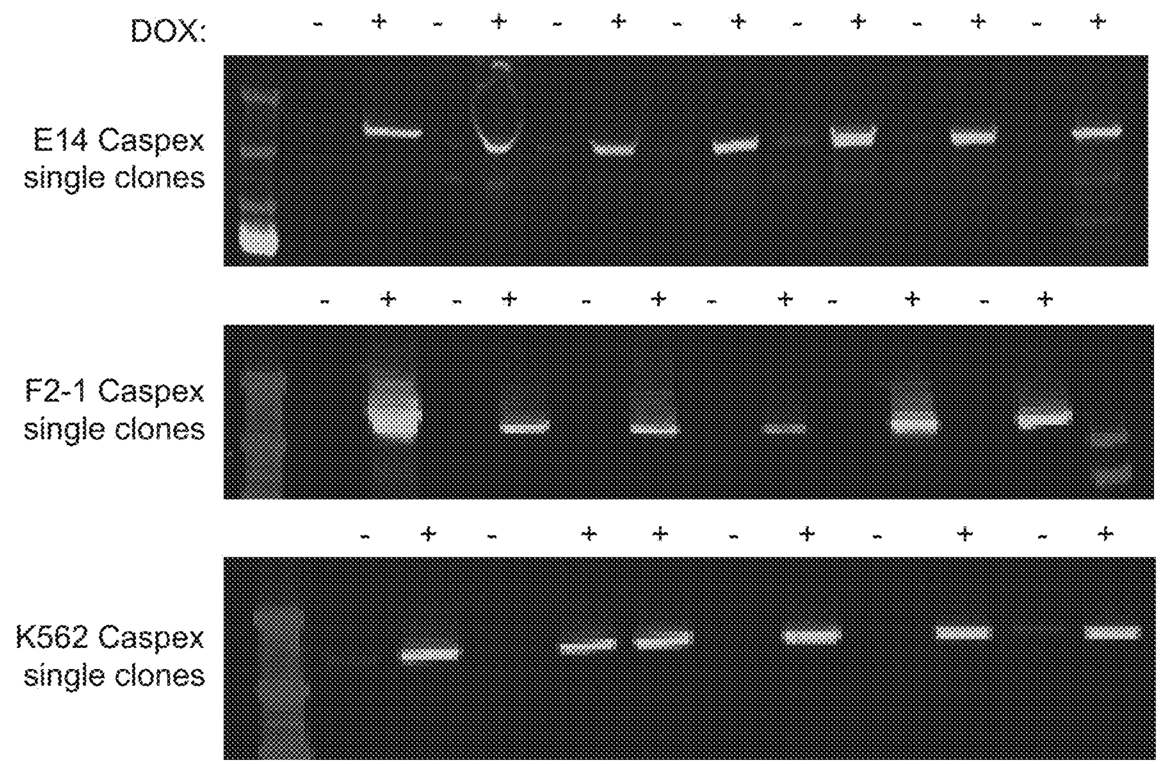
FIG. 17—Creation of inducible Caspex lines in two mouse embryonic stem cell lines, E14 and F2-1/Castaneous, and in K562 cells. Each single colony clone (+/− doxycycline) was tested for inducibility of the FLAG tagged Caspex protein (green band). Red in molecular weight marker showing a FLAG band between 200 and 250 kDa.
Figure 18:
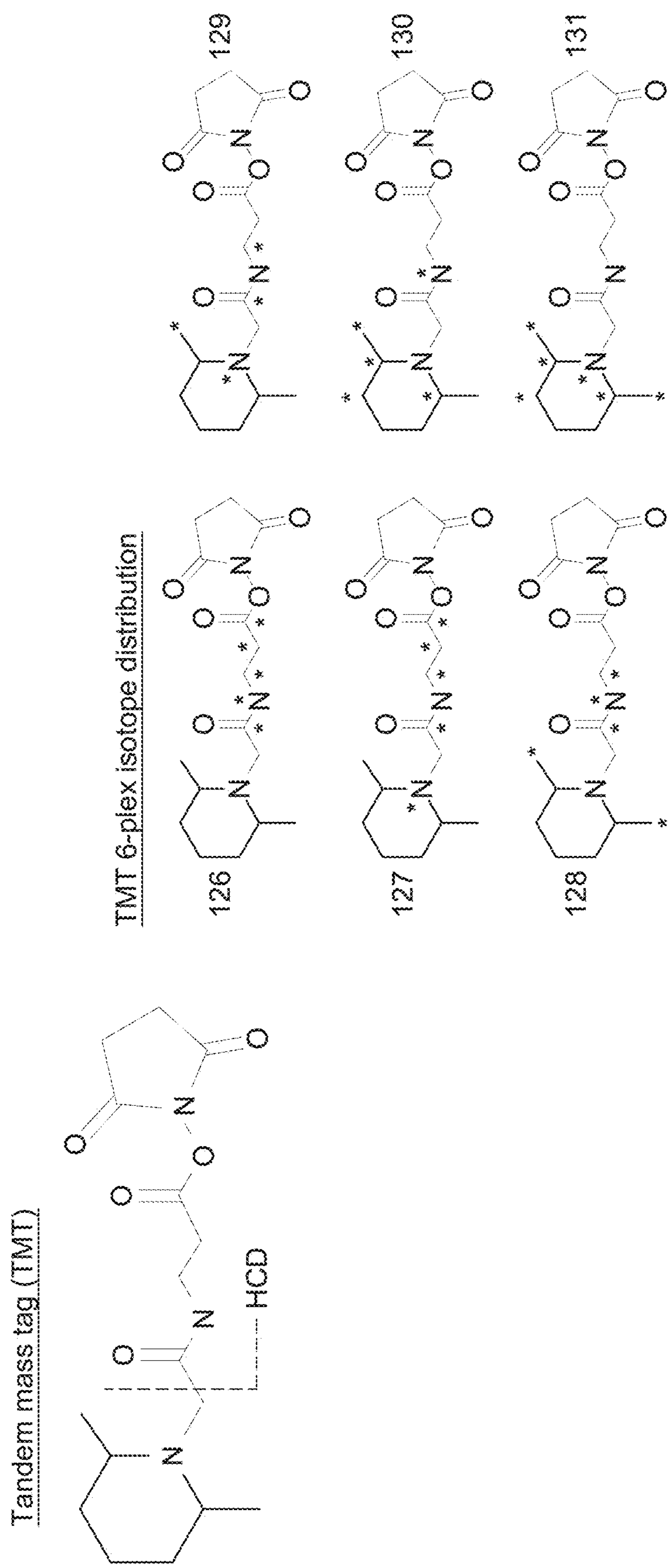
FIG. 18—Isobaric labeling enables multiplexing.
Figure 19:
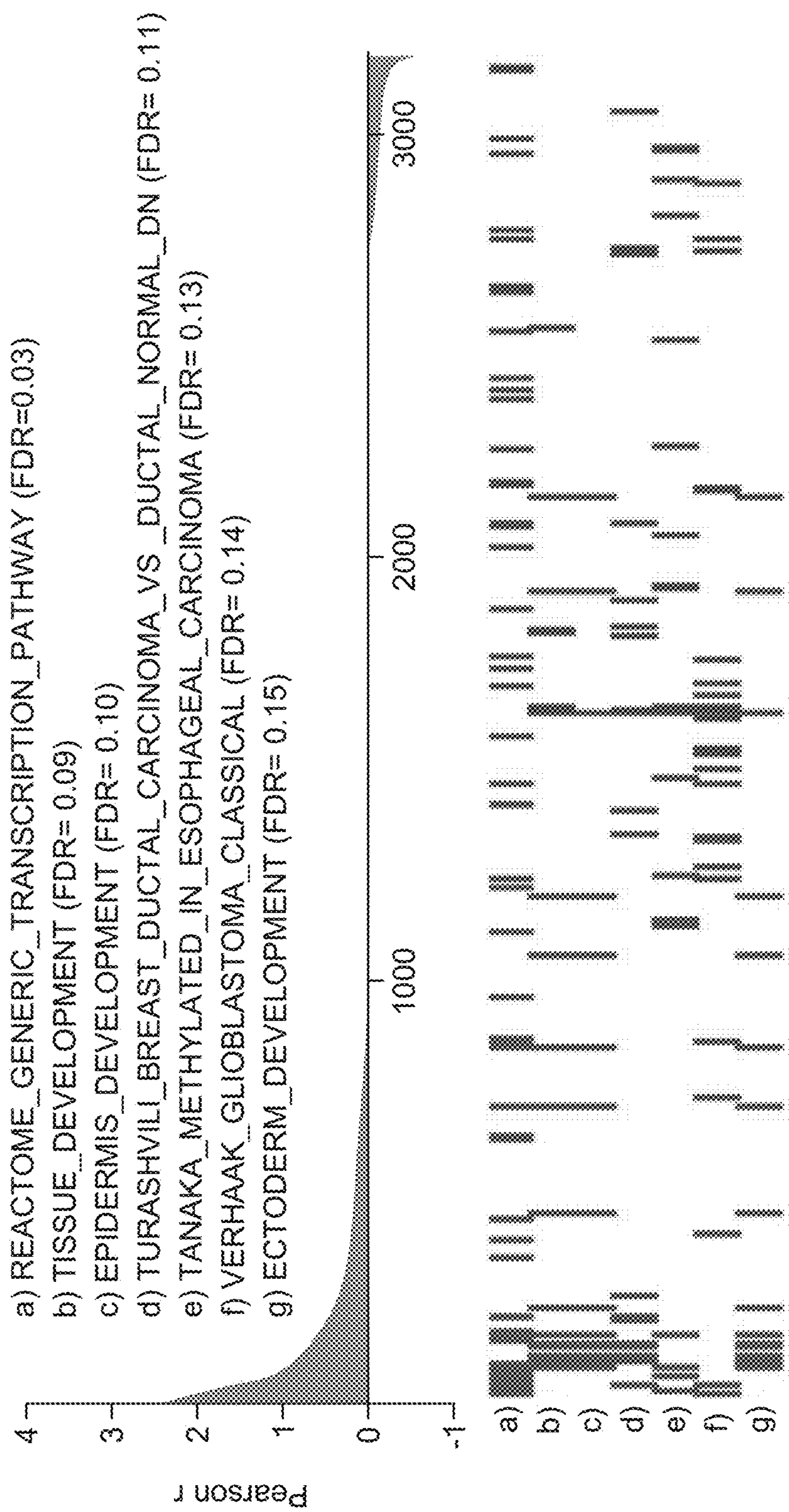
FIG. 19—GSEA reveals expected pathways.
Figure 20:
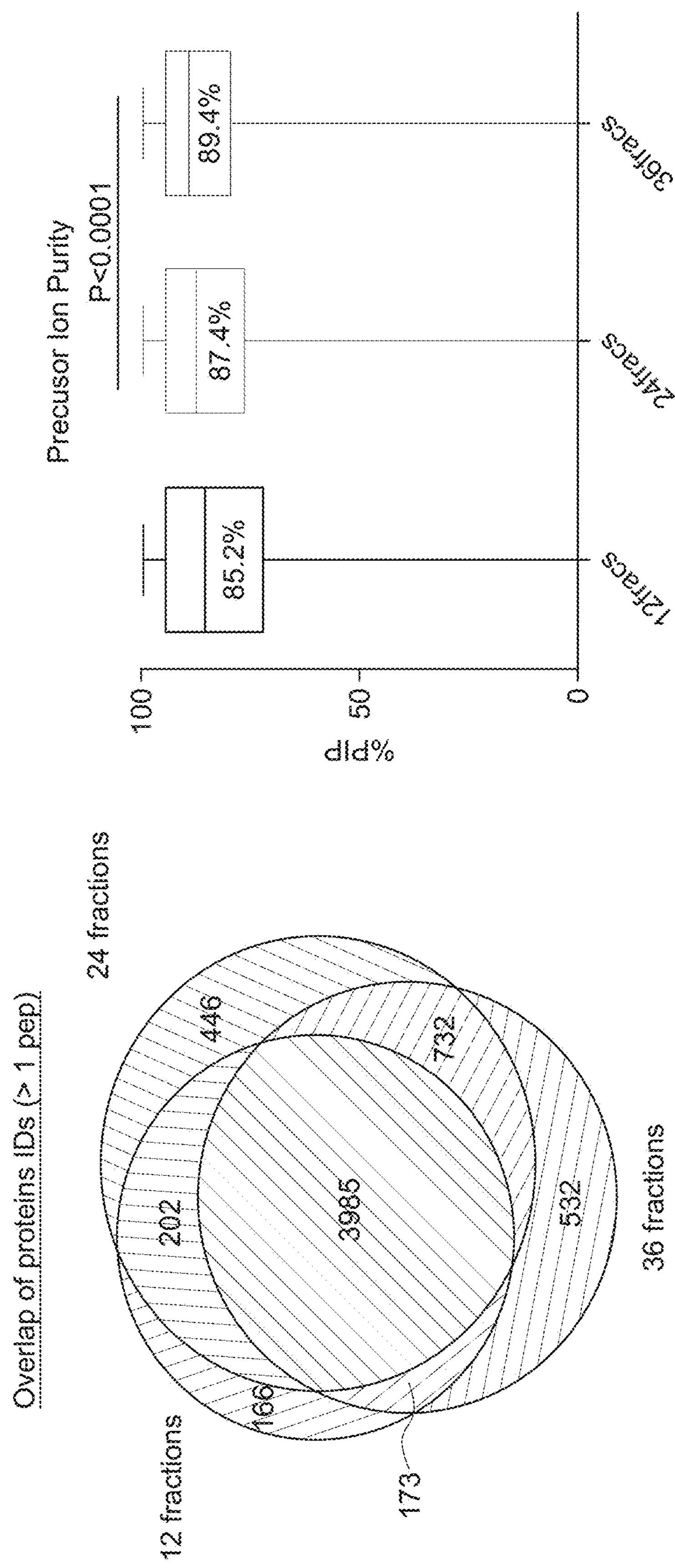
FIG. 20—Graphs demonstrate that with more fractions, more accuracy.
Figure 21:
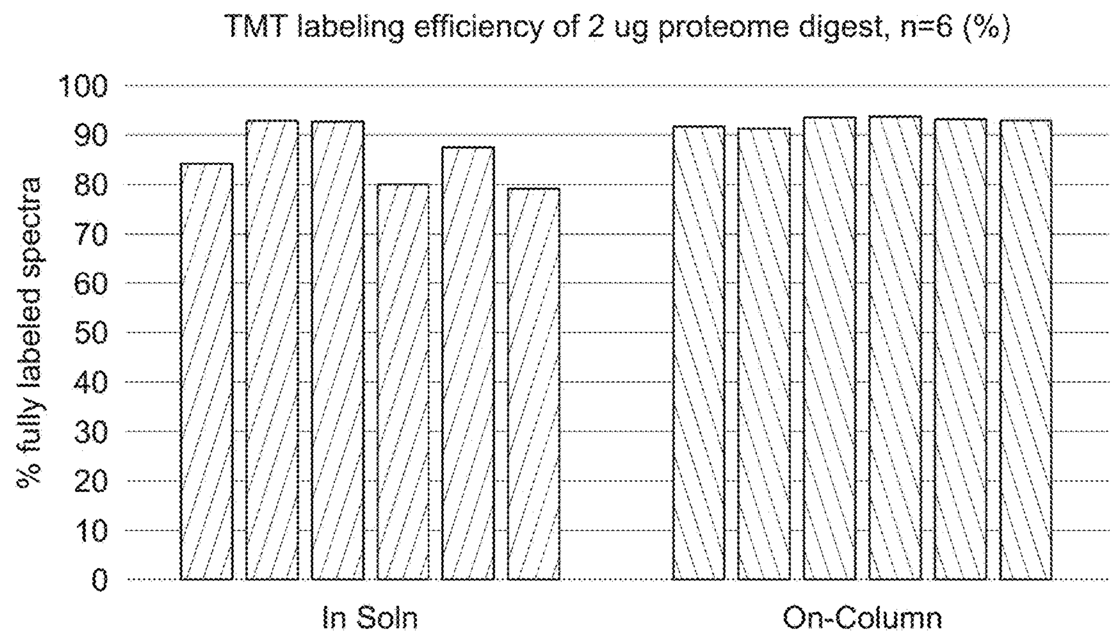
FIG. 21—Graphs showing more consistent TMT labeling on-column.
Figure 22:
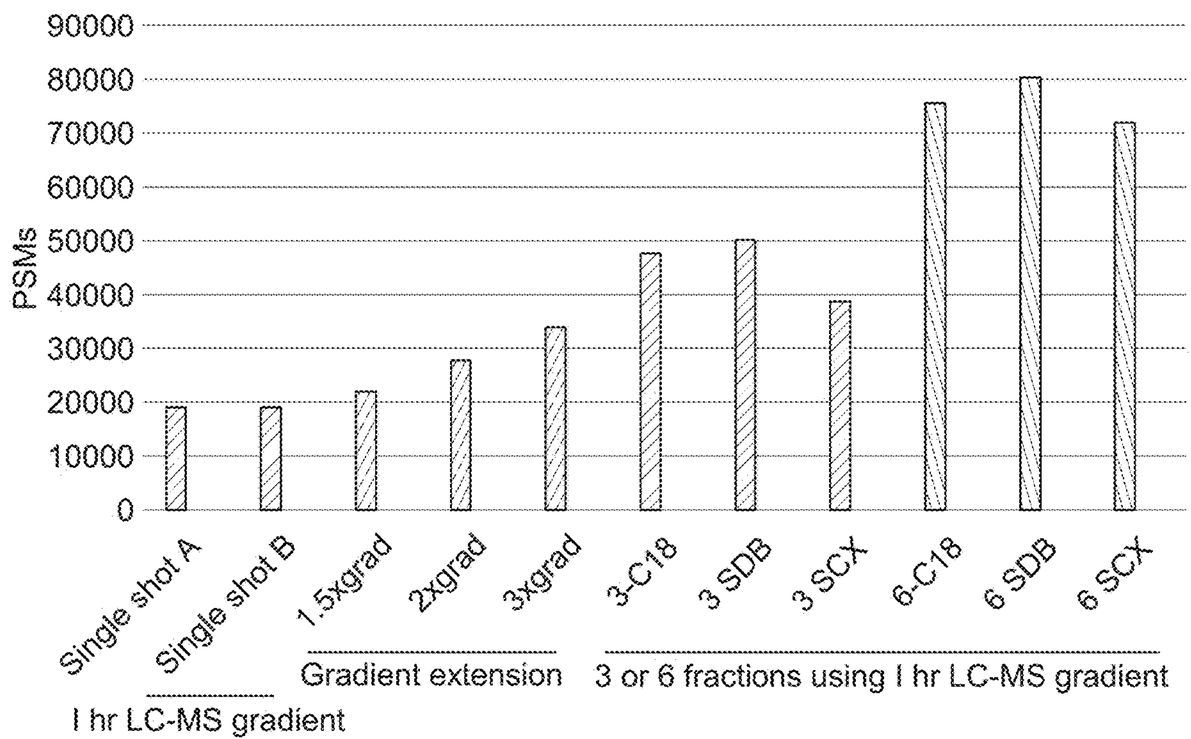
FIG. 22—provide spectral matches for Stage tip fractionation and longer gradients.

FIG. 10 depicts proteomic analysis of TERT promoter. 2*10^9 HEK293T cells were divided across 6 conditions, 5 sgRNAs spanning the TERT promoter. dCas9-APEX was induced with dox, and cells were treated with biotin-peroxide to induce biotinylation for 30 min. The reaction was halted with reducing solution. Cells were harvested and biotinylated proteins were isolated by magnetic streptavidin and analyzed by MS/MS. Proteins isolated from each sgRNA treated cell population were normalized to no sgRNA control. Enriched proteins were identified. The correlation of proteins common between proximal sgRNAs are displayed above. Of note, the most distal sgRNA to the promoter of TERT (nT901), displays the least similarity with the other 4 sgRNAs which show striking consistency of protein purification between the sgRNAs n488T, n165T, n34T and nT208.

Example 9. Genomic Locus Proteomics: A Method for the Unbiased Detection of Proteins Associated with a Particular Genomic Locus Transcriptional regulation is a highly-coordinated process largely controlled by changes in protein occupancy at regulatory elements of the modulated genes. Chromatin immunoprecipitation (ChIP), followed by quantitative polymerase chain reaction (qPCR) or next generation sequencing (NGS), has been invaluable towards our understanding of transcriptional regulation and chromatin structure at both the genome-wide and individual loci levels[1-6, 7-11]. However, because ChIP requires the use of antibodies its utility can often be limited by the presupposition of protein occupancy and lack of highly specific and high affinity reagents. Therefore, Applicants sought to develop a method to unbiasedly identify proteins bound at a specific genomic locus in the native cellular context. Previously developed "reverse ChIP" type methods have several drawbacks, including loss of cellular or chromatin context, extensive engineering and locus disruption, reliance on repetitive DNA sequences, and chemical crosslinking, which reduces sensitivity for mass spectrometric-based approaches (refs). Here, Applicants use recent advancements in sequence specific DNA targeting and affinity labeling in cells to develop genomic locus proteomics (GLoPro) to characterize proteins bound at a specific genomic locus.

Figure 23:
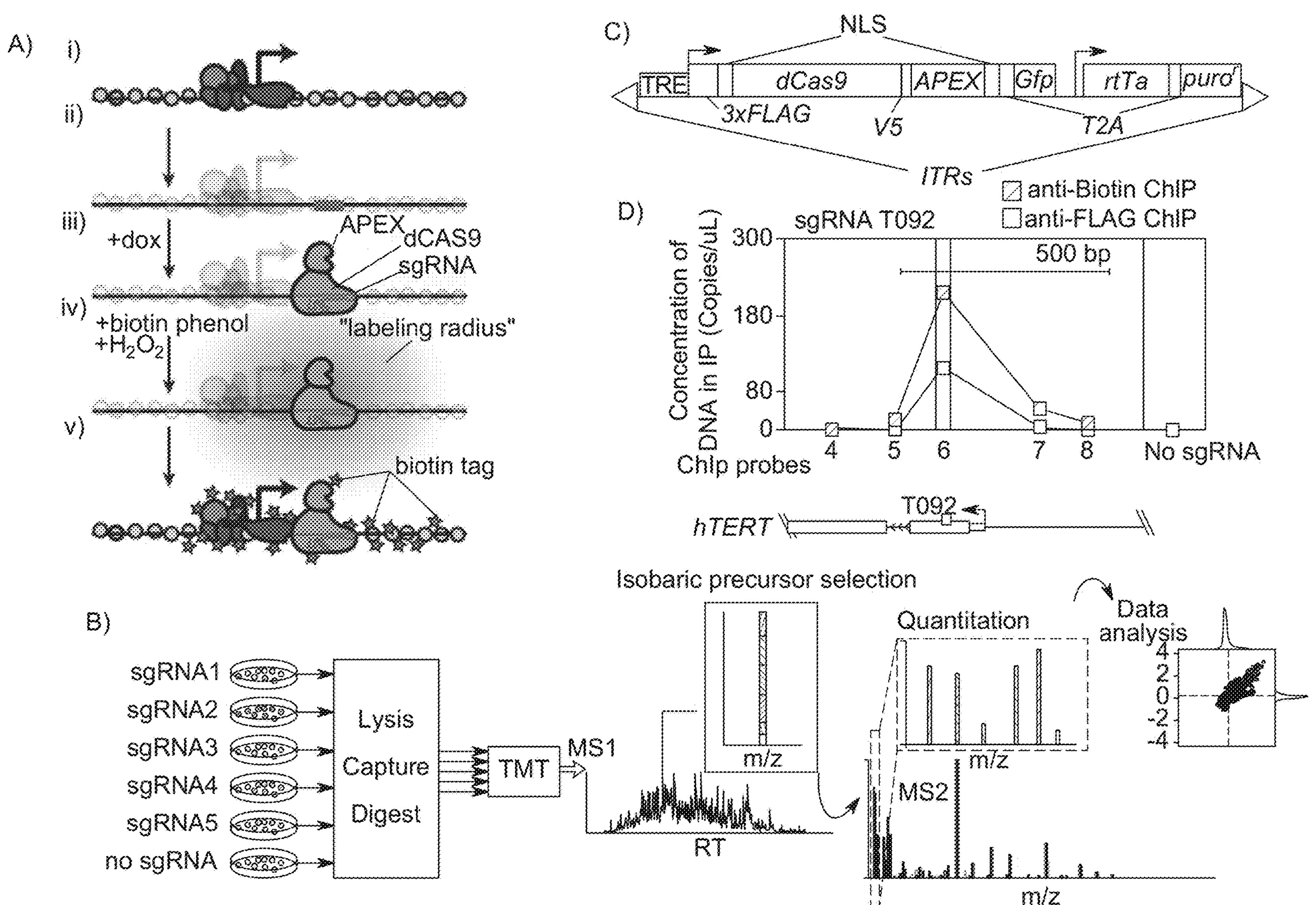
FIG. 23—Diagram for Genomic Locus Proteomics workflow A) Illustration of CASPEX targeting and affinity labeling reaction. i) A genomic locus of interest is identified. ii) A targeting sequence for the sgRNA is designed (red bar). iii) CASPEX expression is induced with doxycycline and, after association with sgRNA, binds region of interest. iv) After biotin-phenol incubation, $H_2O_2$ induces the CASPEX-mediated labeling of proximal proteins, where the "labeling radius" of the reactive biotin-phenol is represented by the red cloud. v) Proteins proximal to CASPEX are labeled with biotin (orange star) for subsequent enrichment. B) Workflow for the proteomic aspect of GLoPro. Each individual sgRNA-293T-Caspex line is independently affinity labeled, lysed, enriched for biotinylated proteins by streptavidin-coated beads, digested, and TMT labeled. After mixing, the peptides are analyzed by LC-MS/MS, where the isobarically-labeled peptides from each condition is co-isolated (MS1), co-fragmented for peptide sequencing (MS2), and the relative quantitation of the TMT reporter ions are measured. Subsequent data analysis compares the TMT reporter ions for each sgRNA line to the non-spatially constrained no guide control line (grey) to identify reproducibly enriched proteins. C) Diagram of Caspex plasmid. NLS, nuclear localization sequence; 3xFLAG, triple FLAG epitope tag; V5, V5 epitope tag; T2A, T2A self-cleaving peptide; GFP, Green fluorescent protein; TRE, Tetracycline response element; rtTA, reverse tetracycline-controlled transactivator; puror; puromycin acetyltransferase, ITRs, inverted terminal repeats. D) ChIP-qPCR against biotin (blue boxes) and FLAG (green boxes) in 293T-CasPEX cells expressing either no sgRNA (far right) or T092 sgRNA. ChIP probes refer to regions amplified and detected by qPCR as in FIG. 26. hTERT is below to show the gene structure with respect to the sgRNA target (red box).

Applicants fused the catalytically dead RNA-guided nuclease Cas9 (dCas9)[12, 13] to the ascorbate peroxidase APEX214 to affinity label proximal proteins at a particular genomic locus for subsequent enrichment and identification by liquid chromatography-mass spectrometry (LC-MS/MS) (FIG. 23A-B). For this proof-of-principle experiment dCAS9 was chosen over of transcription activator-like effectors (TALEs) or engineered zinc finger nucleases (ZFNs) due to the easily reprogrammable nature of the RNA base pairing to the target locus[15]. APEX2, in the presence of $H_2O_2$, will oxidize the phenol moiety of biotin-phenol compounds to phenoxyl radicals that react with nearby tyrosine residues, labeling proximal proteins with biotin derivatives (14, 16, 17). Affinity labeling in cells also circumvents the need for chemical crosslinking, a method used to stabilize biomolecular interactions that diminish LC-MS/MS sensitivity. APEX2 was chosen over biotin ligase BirA derivatives due its smaller labeling radius and shorter labeling times (18-20). The dCas9-APEX (Caspex) gene was cloned in frame with the self-cleaving T2A peptide and green fluorescent protein (Gfp) under the control of a tetracycline response element into a puromycin-selectable piggybac plasmid (21) (FIG. 23C).

HEK293T cells were transfected with the Caspex plasmid, selected for, and single-colony cloned before characterization for doxycycline (dox) inducible expression of GFP, hereinafter referred to as 293T-Caspex cells. To test whether the CASPEX protein correctly localized to the genomic site of interest, we expressed a single guide RNA (sgRNA) targeting 92 base pairs (bp) 3' of the transcription start site (TSS) of the TERT gene (sgRNA position is referred to as T092). We chose to focus on the TERT promoter (hTERT) as TERT expression is a hallmark of cancer and recurrent promoter mutations in hTERT have been shown to re-activate TERT expression[22]. Biotinylation in T092 sgRNA expressing 293T-CasPEX cells was accomplished by incubating cells with dox for 18 hours, followed by incubation with biotin-phenol for 30 minutes, and finally with hydrogen peroxide for 60 seconds. ChIP against the FLAG epitope of CASPEX was then performed, or biotin, followed by quantitative PCR (qPCR) of probes tiling hTERT (FIG. 23D). ChIP-qPCR showed proper localization of CASPEX with the peak of the anti-FLAG signal overlapping with the destination of the sgRNA. The anti-biotin ChIP-qPCR signal showed a similar trend of enrichment, indicating that CASPEX biotinylates proteins within approximately 400 base pairs on either side of its target locus. No enrichment was observed at T092 for the no sgRNA control, which is not spatially constrained to the targeted locus (FIG. 23D).

Figure 24:
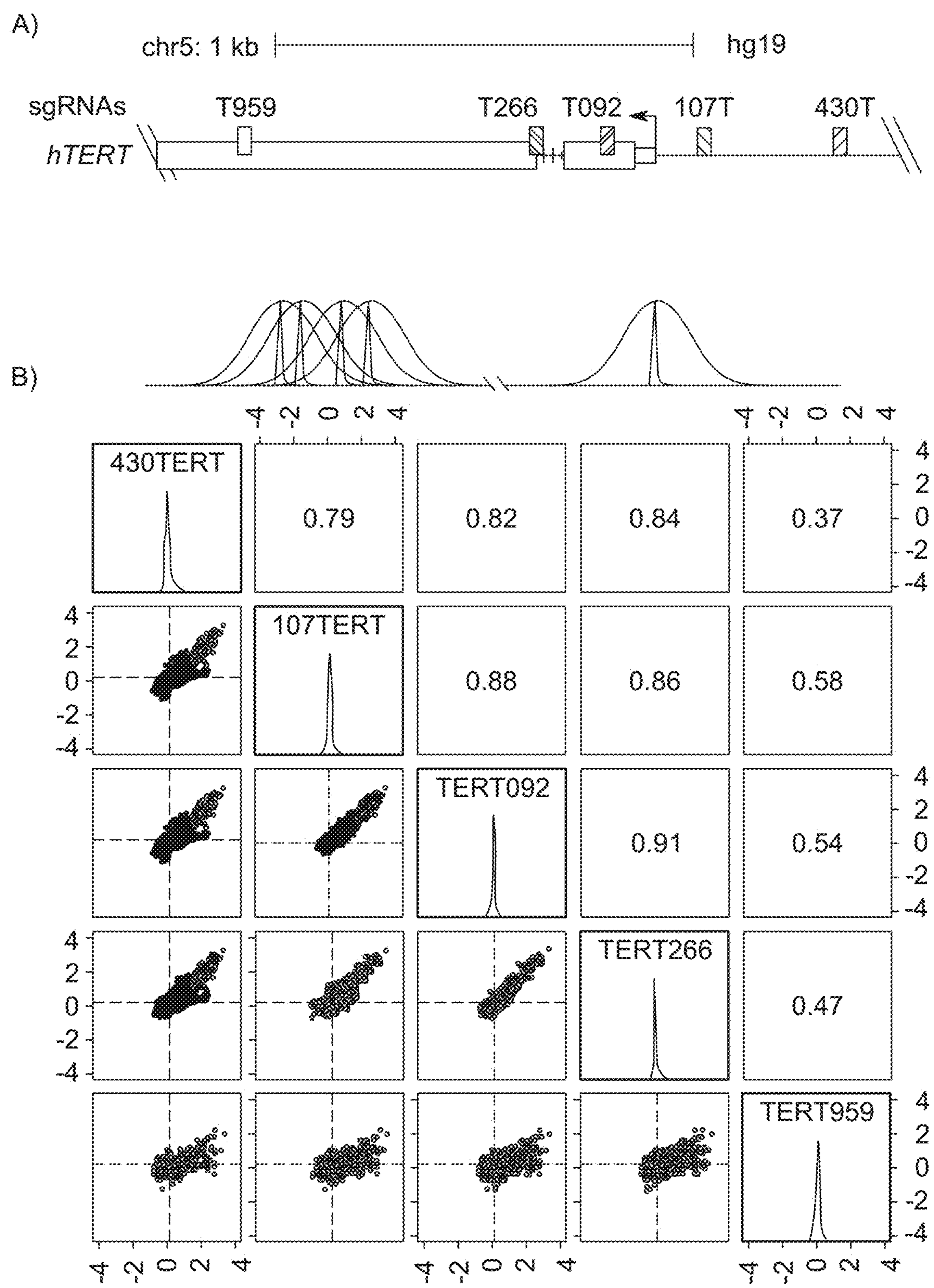
FIG. 24—Genomic locus proteomic analysis of hTERT A) UCSC Genome Browser representation of hTERT (hg19). sgRNAs (colored bars) are shown to scale relative to the transcription start site (black arrow). B) Multi-scatter plots and Pearson correlation coefficients of $\log_2$ fold enrichment values of proteins identified and quantified between hTERT-293T-Caspex cells compared to the no sgRNA control line. C) Volcano plot of proteins quantified across the four overlapping hTERT-293T-Caspex cell lines compared to the no sgRNA control. Data points representing proteins enriched with an adjusted p-value of less than 0.05 are labeled in red. Proteins known to associate with hTERT and identified as enriched by GLoPro are highlighted. TP53, a known hTERT binder, had an adj. p val.=0.058 and is highlighted blue. D) Mean GLoPro enrichment values for V5-tagged ORFs selected to ChIP-qPCR corroboration. Red indicates the protein was enriched at hTERT, blue that the protein was detected in the analysis but not statistically enriched. Grey proteins were not detected. E) Correlation between ChIP-qPCR and GLoPro enrichment of the four overlapping sgRNAs at hTERT. Black, open circles indicate that the protein was not identified by GLoPro. Blue, open circles indicate the protein was identified but was not statistically enriched. Red open circles indicate proteins that are enriched according to the GLoPro analysis. Previously described hTERT binders are labeled. Dotted line separates ChIP-qPCR data tested for statistical significance via the Mann-Whitney test, and the p-value is shown.
Figure 24:
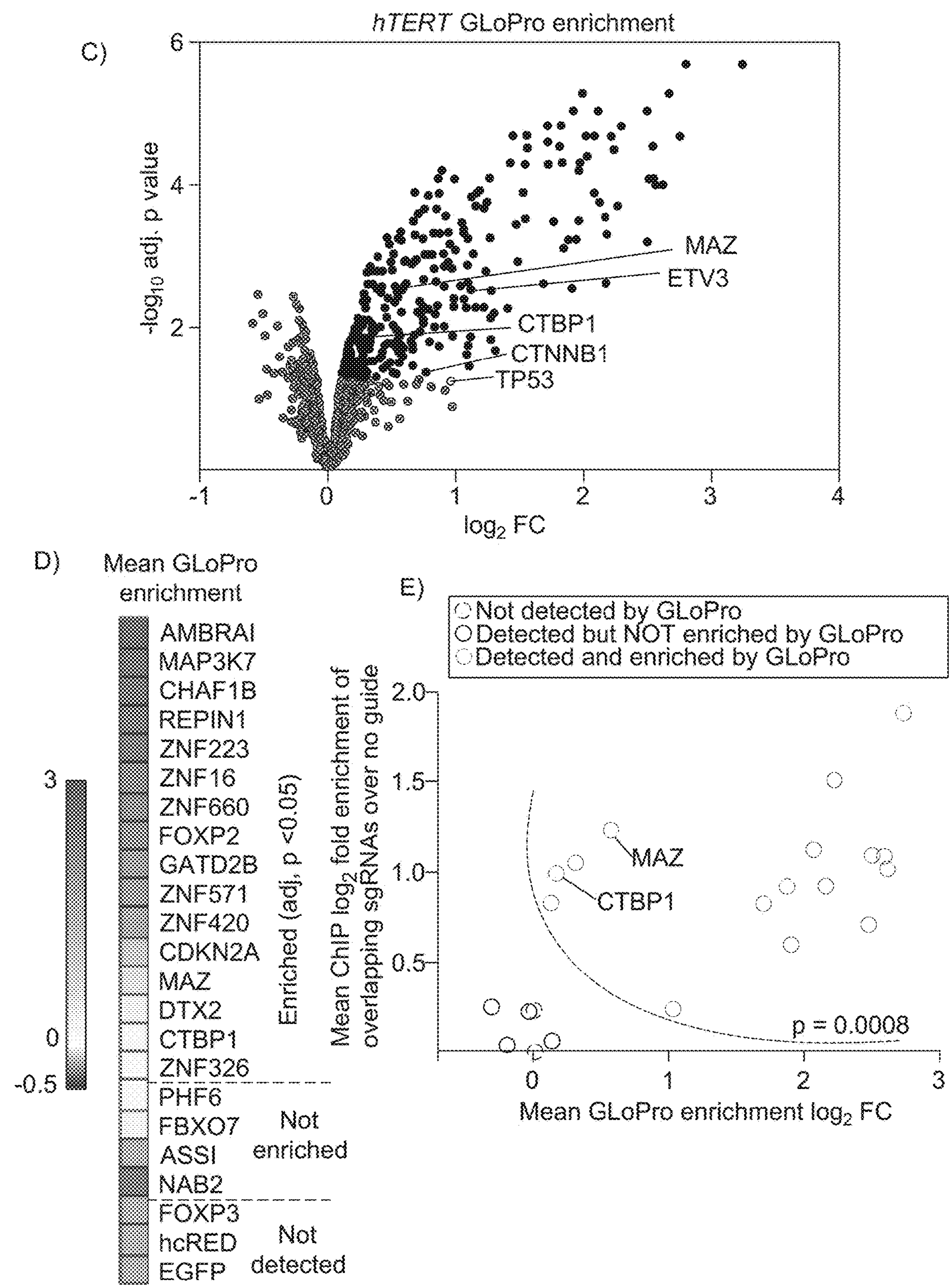
Figure 26:
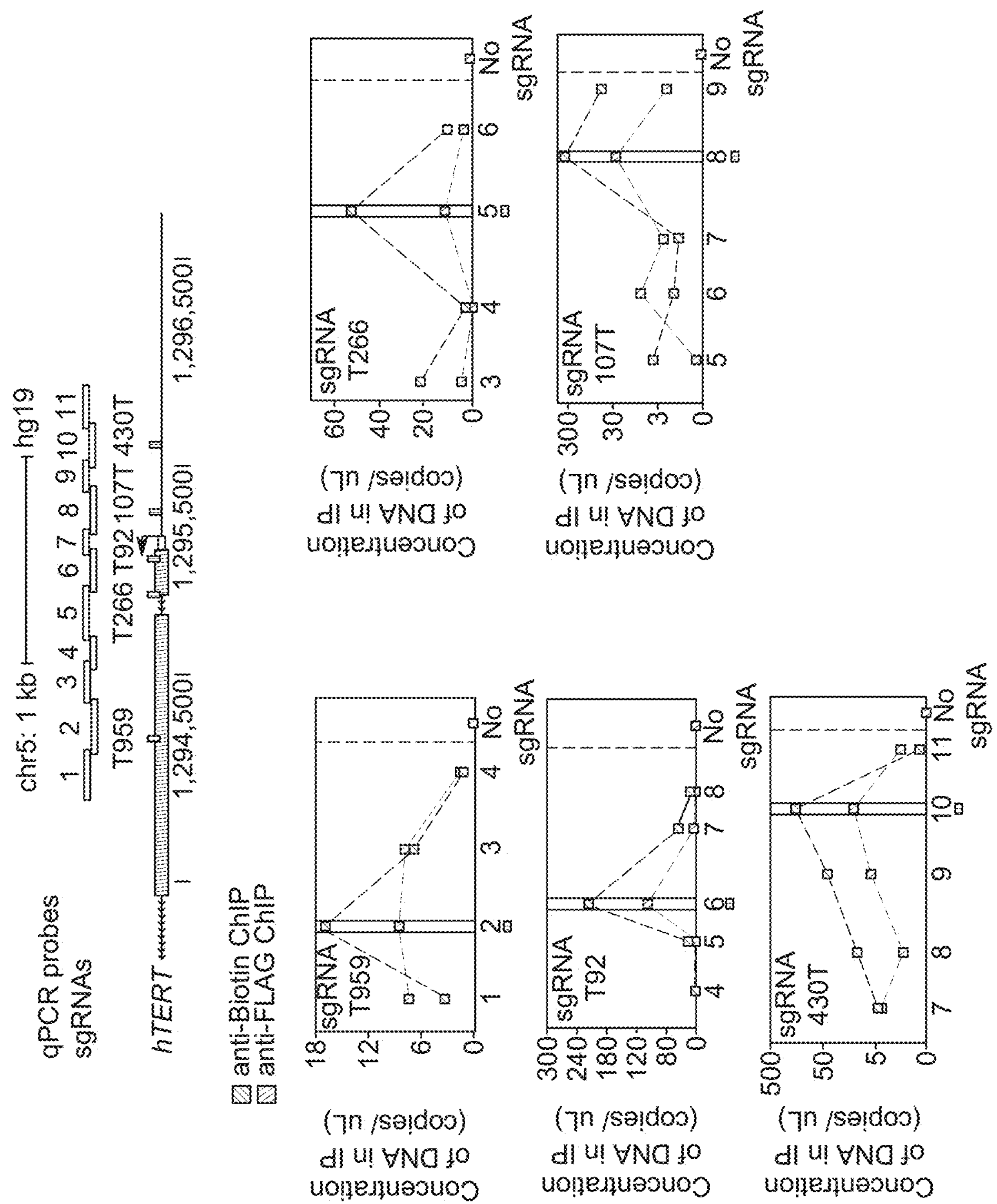
FIG. 26—A) UCSC Genome Browser representation (hg19) of the TERT promoter, including genomic coordinates, and the location of sgRNA sites relative to the TSS. qPCR probes are numbered. B) ChIP-qPCR against biotin (blue boxes) and FLAG (green boxes) in hTERT-CasPEX cells expressing either no sgRNA (far right) their respective sgRNA. ChIP probes refer to regions amplified and detected by qPCR. The location of the sgRNA in each ChIP-qPCR is highlighted in red.
Figure 27:
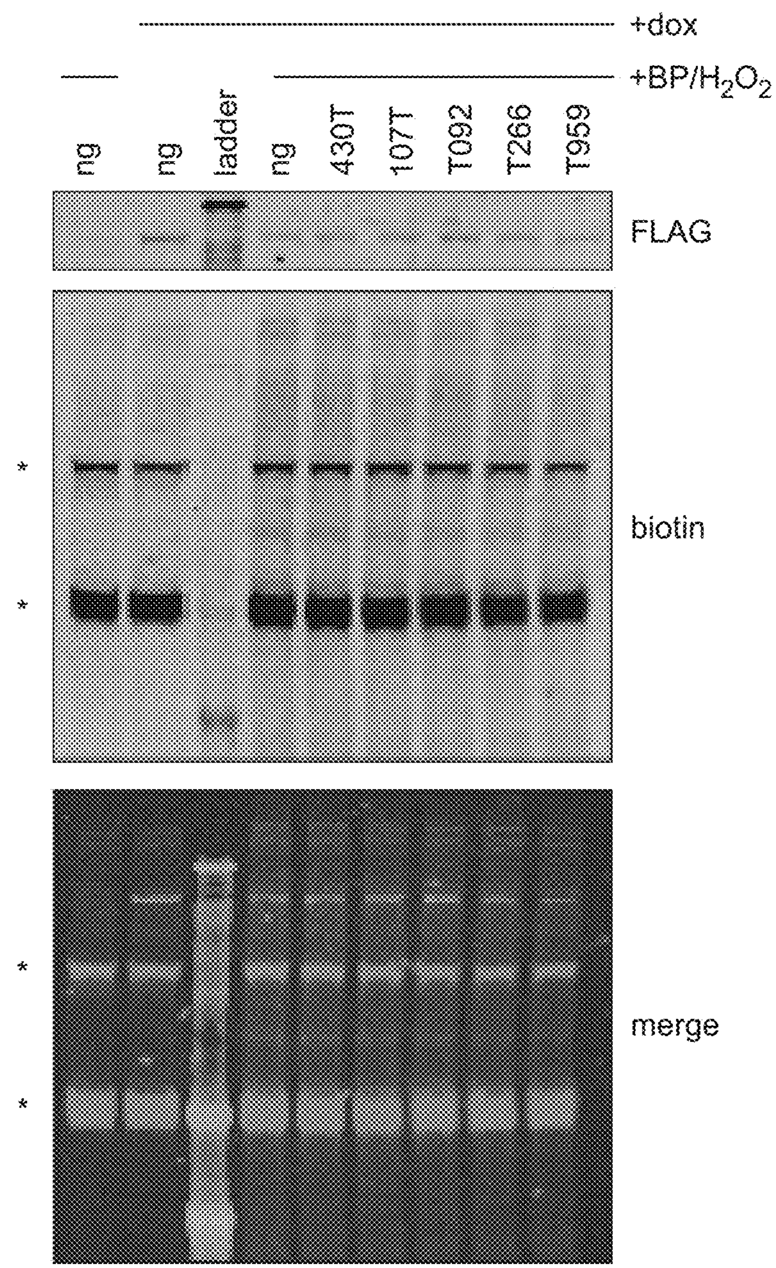
FIG. 27—Anti-FLAG and anti-biotin Western blots of TERT Caspex lines treated for 12 hours with 0.5 ug/mL dox or vehicle, and labeled via Caspex-mediated biotinylation. Top panel shows anti-FLAG signals for cells treated with dox or vehicle. Middle panel shows anti-biotin signal from cells exposed to labeling protocols with or without dox treatment. Endogenous biotinylated proteins (stars) are used as the loading control. Bottom panel is a merge of both signals. Protein molecular weight ladder separates the no-guide line from the TERT Caspex lines.

Four additional sgRNA constructs were then tested tiling hTERT: 430T, 107T, T266 and T959, where the number indicates the targeted position relative to TERT's TSS denoted by "T" (FIG. 24A). After performing the labeling reaction in stable sgRNA-expressing 293T-Caspex lines ChIP-qPCR against FLAG and biotin showed all constructs correctly targeted and labeled the region of interest, where the peak of enrichment resided at the sgRNA site (FIG. 26). While biotinylation was dependent on CASPEX expression, no difference in biotin patterns between hTERT sgRNA lines could be seen by Western blot (FIG. 27). These data demonstrate that CASPEX targeting can be reprogrammed by substitution of the sgRNAs and that proximal protein biotinylation is CASPEX mediated.

To test whether CASPEX could identify proteins associated with hTERT, we enriched biotinylated proteins with streptavidin from hTERT-targeted 293T-Caspex lines, followed by analysis by quantitative LC-MS/MS. Biotinylation was initiated in the five individual hTERT targeting 293T-Caspex lines that tiled the genomic loci of interest 18 hours after doxycycline addition, along with the no guide control 293T-Caspex line. Tiling is an important feature of this method as "noise" from off-target binding of dCas9 from each individual line will be diluted and only reproducibly enriched proteins from on-target occupancy contribute to the "signal"[23, 24]. Whole cell lysates from each individual line were then incubated with streptavidin-coated magnetic beads, stringently washed, and subjected to on-bead trypsin digestion. Digests of the enriched proteins were labeled with isobaric tandem mass tags (TMT)[25] for relative quantitation, multiplexed, and analyzed by LC-MS/MS (FIG. 23B). We used a ratiometric approach for each individual sgRNA 293T-Caspex line compared to the no guide control line[26]. Enrichment from four of the hTERT Caspex lines that according to the ChIP-qPCR results had overlapping labeling radii (430T, 107T, T266 and T092; FIG. 26), showed high correlation of protein enrichment (FIG. 24B). The T959 Caspex line, which lies ≥2 labeling radii from its closest neighbor, showed decreased correlation of protein enrichment. We performed a moderated T-test by treating the four overlapping sgRNA lines as replicates, using the non-spatially constrained no sgRNA 293T-CasPEX line as the control. The null distributions for the statistical tests were provided by the large number of background proteins typically associated with APEX-proteomics[19, 20, 26]. 371 of the 3,199 proteins identified with at least two peptides were significantly enriched (adj. p value<0.05) at hTERT over the no sgRNA control, including five proteins known to occupy hTERT in various cell types (TP53; [27, 28], MAZ; [29, 30], CTNNB1; [31-33], ETV3; [34], CTBP1; [35] (FIG. 24C). These results indicate GLoPro is able enrich proteins from the native cellular context, and suggests this method is capable of distinguishing reproducibly enriched proteins at a particular genomic locus.

The inability to detect differences in biotinylation patterns between the sgRNA-293-CasPEX lines is likely due to the inadequate sensitivity and specificity of WBs for a promiscuous labeling reaction. Therefore, Applicants used quantitative proteomics to identify proteins enriched at hTert compared to the non-targeted background. The five individual hTert targeting 293-CasPEX lines, along with the no guide control 293-CasPEX line, were cultured with dox for 24 hours prior to CasPEX-mediated labeling, after which biotinylated proteins were enriched with streptavidin. Enriched proteins were individually digested with trypsin, labeled with isobaric tandem mass tags (TMT) for relative quantitation, mixed and analyzed by LC-MS/MS. Applicants used a ratiometric approach of each individual sgRNA 293-CasPEX line compared to the no guide control line, which is not spatially constrained to a locus in the genome by a sgRNA. From this analysis, Applicants identified 3,199 proteins with at least two quantifiable peptides, 1,249 of which had a gene ontology annotation of "nuclear". Since four of the sgRNAs had biotin labeling radii that overlap with each other according to the ChIP-ddPCR results (430T, 107T, T266 and T92), Applicants performed a moderated T-test using each of the four sgRNA lines as quasi-replicates of each other, using the non-spatially constrained no sgRNA 293-CasPEX line as the control. 371 proteins were statistically enriched at hTert over the no sgRNA control, including five proteins known to occupy hTert in various cell lines. Gene set enrichment analysis (GSEA) of the proteins identified showed that "Generic Transcription Pathways" (FDR=0.03) was the most enriched gene set in our data, indicating our method enriches for proteins involved in transcriptional regulation. GSEA also identified glioblastoma and epidermal developmental pathways as enriched (FDR=0.15 and 0.10, respectively), two cancer or tissue types with a high frequency of recurrent hTert mutations (ref). These results suggest that GLoPro is capable of distinguishing proteins at a particular genomic locus involved transcriptional regulation.

To test whether GLoPro was indeed able to spatially distinguish proteins at hTert over background, Applicants performed a correlation analysis of enrichment values of the four overlapping sgRNA 293-CasPEX lines compared to T959-293-CasPEX cells, where the sgRNA is targeted approximately two linear DNA labeling radii away from the nearest guide T266. Correlation analysis of enrichment values between the four overlapping sgRNA lines showed high to very high correlation between each pairwise comparison. However, when the four overlapping sgRNA lines were compared T959-293-CasPEX cells the correlation was only low to moderate. These data indicate GLoPro can identify proteins associated with hTert.

To validate whether the proteins identified by GLoPro associate with hTert Applicants performed ChIP-ddPCR on a number of candidates. Since many of the candidate proteins identified by GLoPro do not have ChIP grade antibodies Applicants turned to V5-tagged ORF expression in HEK293T cells. 23 individual V5-tagged ORFs (≥99% amino acid homology and in-frame V5 tag) were transiently transfected into HEK293T cells at one-fourth the recommended DNA concentration to moderate gross overexpression. After 48 hours the cells were subjected to anti-V5 ChIP-ddPCR with probes tiling the regions targeted by the sgRNAs. Applicants chose 16 V5-tagged ORFs significantly enriched according to GLoPro that spanned the mean fold enrichment scores between the four overlapping sgRNA-CasPEX lines. Applicants also chose four V5-tagged ORFs for proteins that were detected by GLoPro but not identified as enriched at hTert, and three that were not detected, as negative controls. A spatially resolved heatmap of ChIP-ddPCR enrichment values spanning hTert showed the majority of candidate proteins identified in the GLoPro analysis showed enrichment at hTert. Applicants next took the mean ChIP-ddPCR enrichment value across the four overlapping guides and compared these values to the fold change enrichment values as determined by the GLoPro analysis. There was a moderate correlation (r2=0.56) between the GLoPro and ChIP-ddPCR enrichment analyses, where most candidates separated the statistically enriched proteins according to the GLoPro analysis compared to those not enriched or not detected. Two proteins previously described to bind hTert, CTBP1 and MAZ, were found in a regime of high ChIP enrichment and low GLoPro enrichment, suggesting the null distribution of background enrichment provides high specificity of GLoPro candidate identification.

Overexpression of DNA binding proteins can often lead to high rates of false positives (ref). To further validate a subset of candidates generated by our GLoPro analyses, Applicants performed ChIP-ddPCR on proteins for which ChIP-grade antibodies were available against the endogenous proteins. ChIP-ddPCR against FOXP2, MAZ, ZKSCAN1, ETV3, CTBP2, CTBP1, ZKSCAN4, TBPL1 and CTNNB1. Results from native ChIP show the method still successfully validates candidates. Together, these data demonstrate GLoPro can be used with high specificity to identify candidate proteins associated with a particular genomic locus.

In addition to detecting proteins known to associate with hTERT, several novel candidates were also identified and associated with this region. To corroborate whether a subset the proteins identified by GLoPro associate with hTERT, ChIP-qPCR was performed for candidates spanning the GLoPro enrichment range (FIG. 24D). Many of these proteins do not have ChIP grade antibodies V5-tagged ORF expression in unmodified HEK293T cells were used instead [36]. Twenty-three individual V5-tagged ORFs were chosen by availability, having ≥99% amino acid homology, and having an in-frame V5 tag. Sixteen V5-tagged ORFs were selected that spanned a range of significant enrichment values (FIG. 24D). Four V5-tagged ORFs for proteins not identified as significantly enriched at hTERT were chosen, and three proteins that were not detected as negative controls. To moderate overexpression, each ORF was individually expressed in HEK293T cells at one-fourth of the recommended DNA concentration. After 48 hours, the cells were subjected to anti-V5 ChIP-qPCR with probes tiling the regions targeted by the sgRNAs. Comparing ChIP-qPCR signals from each individual ORF to their respective GLoPro enrichment values (proteins not detected were assigned a GLoPro enrichment value of 0) we found that all proteins enriched in the GLoPro analysis were, as a group, statistically enriched by ChIP-qPCR (Mann-Whitney test, $p=0.0008$) (FIG. 24E). Most candidates deemed statistically enriched according to the GLoPro analysis were separated in the ChIP enrichment space from those not enriched or not detected. Two proteins previously described to bind hTERT, CTBP1 and MAZ [29, 30, 35], were found in a regime of high ChIP enrichment and low GLoPro enrichment, suggesting ChIP-qPCR provides orthogonal information to GLoPro for protein occupancy at a genomic locus. These data show that GLoPro can identify known and novel proteins that can be corroborated by ChIP-qPCR, that associate with hTERT.

Figure 25:
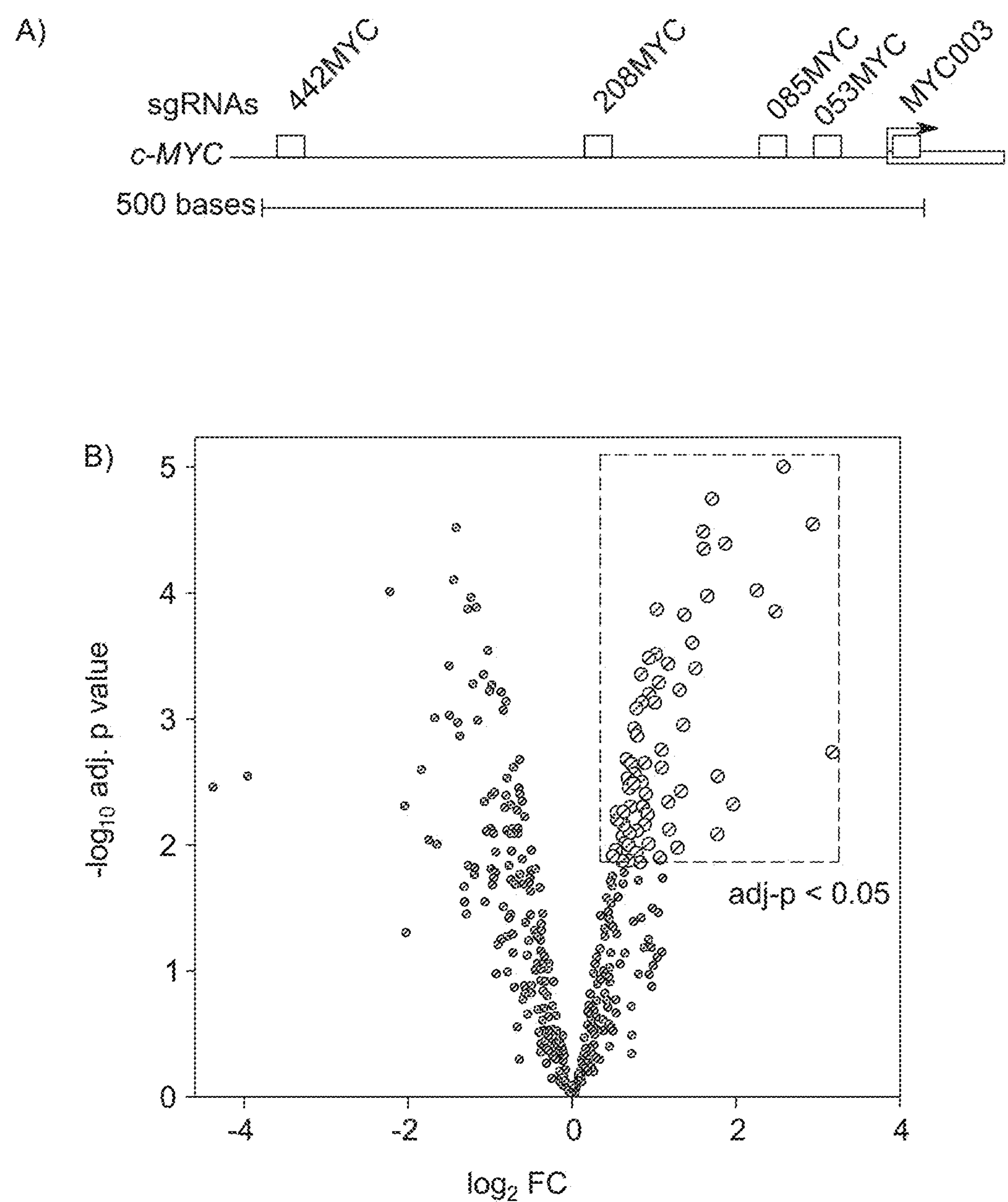
FIG. 25—Genomic locus proteomic analysis of c-MYC promoter A) UCSC Genome Browser representation (hg19) of the c-MYC promoter and the location of sgRNA sites relative to the TSS. B) Volcano plot of proteins quantified across the five MYC-Caspex cell lines compared to the no sgRNA control Caspex line. Data points representing proteins with an adjusted p-value of less than 0.05 are labeled green. C) Significantly enriched gene sets from proteins identified to associate with the c-MYC promoter by GLoPro. Only gene sets with an adjusted p-value of less than 0.01 are shown. MYC ACTIVE PATHWAY is highlighted in red and discussed in the text D) ChIP-qPCR of candidate proteins identified by GLoPro at the c-MYC promoter. V5 tagged dsRED served as the negative control for V5-tagged proteins ENO1, RBMX, RUVBL1 and MAPK14, whereas HA-tagged HUWE1 was used for MYC-tagged HUWE1. * indicates T-test p-value<0.05, **p<0.01.
Figure 25:
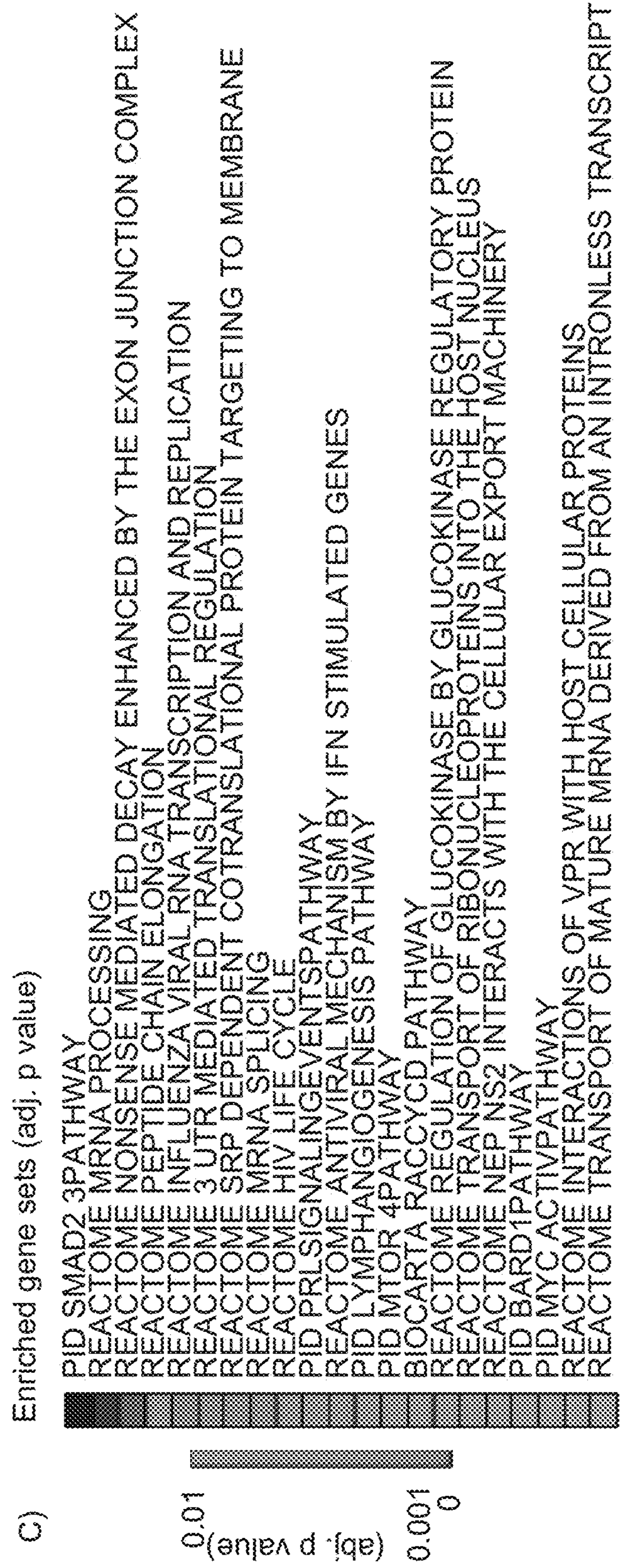
Figure 25:
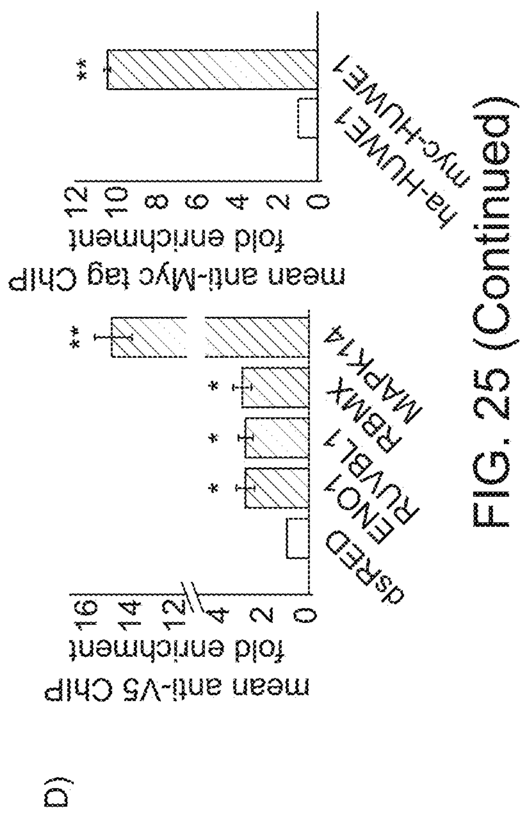
Figure 28A:
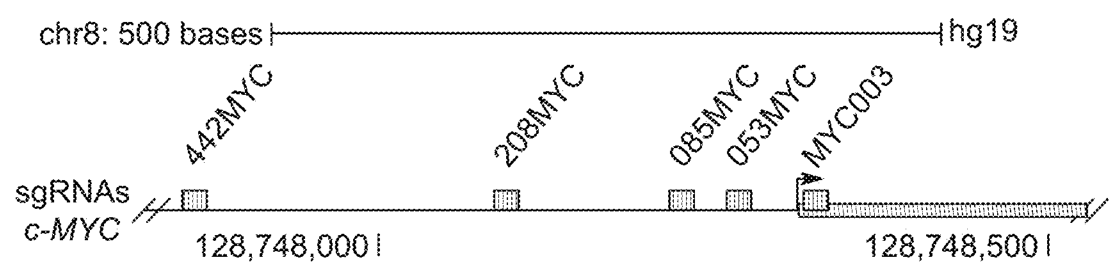
FIG. 28—UCSC Genome Browser representation (hg19) of the c-MYC promoter, including genomic coordinates, and the location of sgRNA sites relative to the TSS. B) ChIP-qPCR against CASPEX (FLAG epitope) in MYC-Caspex cells expressing their respective sgRNAs. ChIP probes either span the region targeted by the respective sgRNA or a non-overlapping regions approximately 500 bp on either side of the sgRNA target site. Caspex cells expressing no sgRNA was used as the negative control.
Figure 28B:
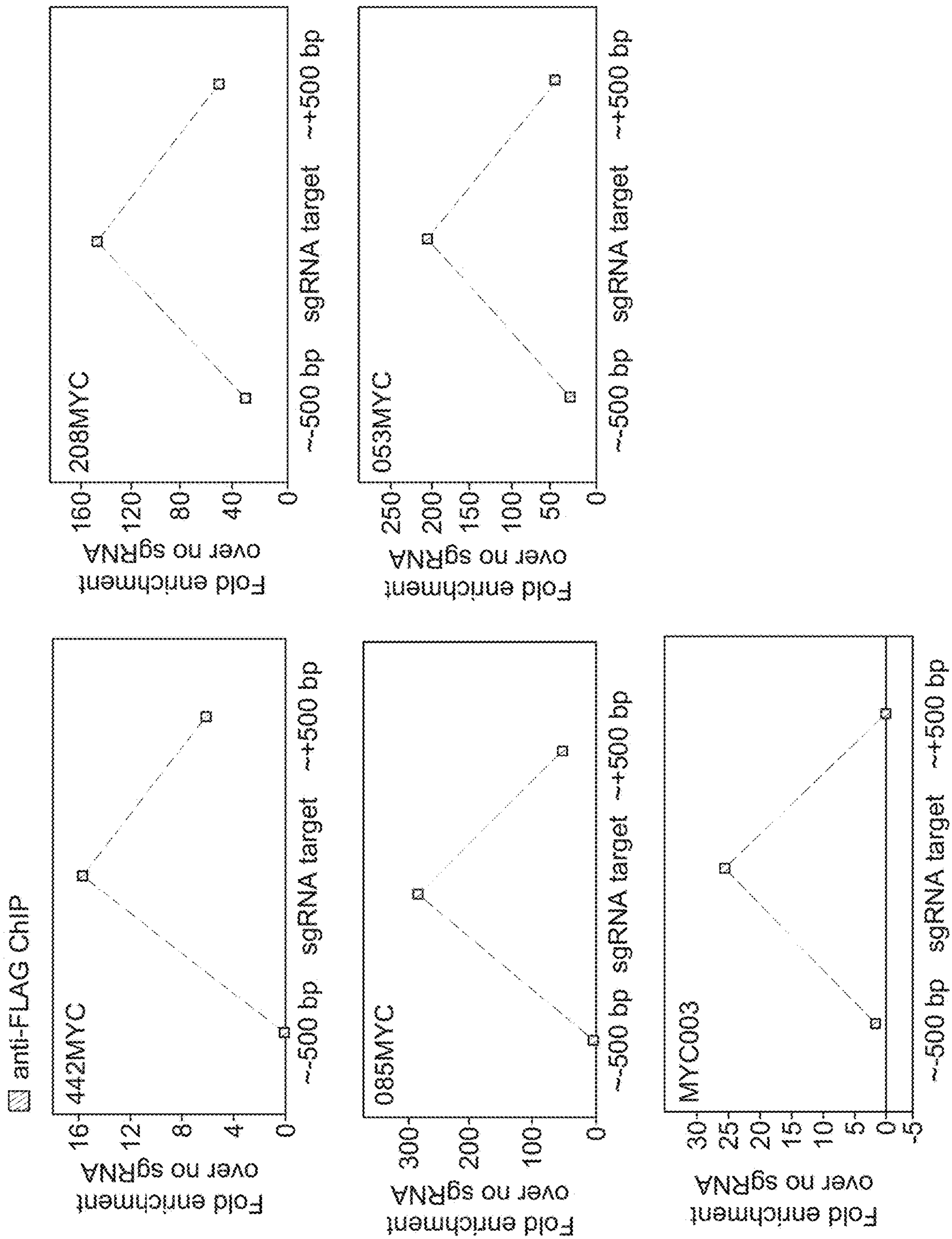

To explore the generalizability of GLoPro at another site in the genome, 293T-Caspex cells were created that express individual sgRNAs tiling the c-MYC promoter (FIG. 25A). ChIP-qPCR against CASPEX verified the proper localization of each c-MYC 293T-Caspex line (FIG. 28). GLoPro analysis of the c-MYC promoter identified 66 proteins as significantly enriched (adj. p val<0.05) compared to the no guide control line (FIG. 25B). We applied a machine learning algorithm to identify association of GLoPro-enriched proteins with canonical pathways from Molecular the Signature Database [37, 38], (http://apps.broadinstitute.org/genets). We identified 21 statistically enriched networks (adj. p val.<0.01), including the "MYC Active Pathway", a gene set of validated targets responsible for activating c-MYC transcription [38] (FIG. 25C). To corroborate the association of proteins with the c-MYC promoter, we focused on components of enriched gene sets using ChIP-qPCR. ChIP-qPCR confirmed the presence of pathway components at the c-MYC promoter, including HUWE1, RUVBL1, and ENO1 for MYC active pathway, RBMX for mRNA splicing pathway, and MAPK14 (a.k.a. P38a/MXI2) for the Lymph_angiogenesis pathway (FIG. 25D). Taken together, these results illustrate that GLoPro enriches and identifies proteins associated in multiple pathways that are known to activate c-MYC expression, while directly implicating specific proteins potentially involved in regulating c-MY (transcription through association with its promoter.

Embodiments disclosed herein provide a method for the unbiased discovery of proteins associated with particular genomic loci in live cells without genetically engineering the site of interest. We applied GLoPro to identify proteins associated with the hTERT and c-MYC promoters. Both well-established and previously unreported interactors of the respective promoter regions identified by GLoPro were validated using ChIP-qPCR, demonstrating that this method enables the discovery of proteins and pathways that potentially regulate a gene of interest without the need for prior knowledge of potential occupants.

GLoPro relies on the localization of the affinity labeling enzyme APEX2 directed by the catalytically dead CRISPR/Cas9 system to biotinylate proteins within a small labeling radius at a specific site in the genome in living cells. Other than the expression of Caspex and its associated sgRNA, no genome engineering or cell disruption is required to capture a snapshot of proteins associated with the genomic locus of interest. This advantage, in combination with the generalizability of dCAS9 and APEX2, suggests that GLoPro can be used in a wide variety of cell types and at any dCAS9-targetable genomic element. Beyond circumventing the need for antibodies for discovery, LC-MS/MS analysis using isobaric peptide labeling allows for sample multiplexing, enabling multiple sgRNA lines and/or replicates to be measured in a single experiment with little or no missing data for relative quantitation of enrichment. GLoPro-derived candidate proteins can be further validated for association with the genomic region of interest by ChIP, the current gold standard for interrogation of protein-DNA interactions. While GLoPro in this initial work only identifies association with a locus and not functional relevance, we expect that analyzing promoters or enhancer elements during relevant perturbations may provide novel functional insights into transcriptional regulation. In addition, we envision CASPEX can be used for enrichment of genomic locus entities such as locus-associated RNAs (i.e. nascent or non-coding RNAs) or DNA elements not targeted directly by CASPEX, but in close three-dimensional space within the nucleus (i.e. enhancers or promoters associated with an enhancer). Further work will be needed to assess the extended capabilities of CASPEX.

While we have demonstrated that GLoPro will be a powerful tool to study chromatin structure and transcriptional regulation, there are several drawbacks that should be noted, mainly concerning receptive cell systems and analyte sensitivity. We designed GLoPro to have an inducible expression system to prevent constant CASPEX association with the locus of interest, potentially disrupting gene expression. Thus, the inducible expression and selection cassette is currently too large for viral transduction (FIG. 23C). Ongoing work in our laboratory has found that co-transfecting the piggybac transposase aids the generation of stable Caspex lines in cell culture systems with poor transfection efficiency (data not shown). Thus, in its current form, Caspex can only be used in electroporation- or cationic lipid-based transfectable cells. The second major challenge is sensitivity. Avoidance of chemical crosslinking, the high affinity of streptavidin for biotin, and sample multiplexing were boons for the development of GLoPro, but due to the inherent sensitivity limits of current mass spectrometers and the unavoidable sample loss at each sample handling step, a large amount of input material is needed, currently on the order of a few hundred million cells per guide. These input requirements are readily attainable with many cell culture systems but may prove more challenging with recalcitrant or limited passaging cells.

In summary, Applicants describe a novel approach to identify proteins at hTert. Combining the genome targeting function of dCAS9 with the affinity labeling of proximal proteins in live cells with APEX, GLoPro allows the unbiased characterization of proteins associated with a particular genomic locus.

Methods

Plasmid Construction

The Caspex construct (dox inducible dCas9-APEX2-T2-GFP) was created by subcloning 3xFLAG-dCas9 and T2A-Gfp from pLV-hUBC-dCas9-VP64-T2A-GFP (Addgene 53192), and V5-APEX2-NLS from mito-V5-APEX2 (Addgene 42607) into an all in one piggybac, TREG/Tet-3G plasmid (Church lab) via ligation independent cloning (In-Fusion, Clontech). Guide sequences were selected and cloned as previously described (Doench et al). All V5 ORF constructs were purchased through the Broad Genetics Perturbation Platform and were expressed from the pLX-TRC_317 backbone. V5 ORFs were only selected for validation if the construct was available, had protein homology >99%, and an in frame V5 tag. The Caspex plasmid is available through Addgene (plasmid #TBA upon publication).

Cell Line Construction and Culture

HEK293T cells were grown in DMEM supplemented with 10% fetal bovine serum, glutamine and non-essential amino acids (Gibco). All constructs were transfected with Lipofectamine 2000. After Caspex transfection, puromycin was added to a final concentration of 4 ug/ml and selected for two weeks. Single colonies were picked, expanded and tested for doxycycline inducibility of the Caspex construct monitored by GFP detection. The HEK293T cell line with the best inducibility (now referred to as 293-Caspex cells) was expanded and used for all subsequent experiments. For stable sgRNA expression, single sgRNA constructs were transfected into 293-Caspex cells and were selected for stable incorporation by hygroMYCin treatment at 200 ug/ml for two weeks. Caspex binding was tested using ChIP followed by digital droplet PCR (ddPCR) or qPCR.

APEX-Mediated Labeling

Prior to labeling, doxycycline dissolved in 70% ethanol was added to cell culture media to a final concentration of either 500 ng/mL for 18-24 hours (hTERT) or 12 hours at 1 ug/mL (c-MYC). Biotin tyramide phenol (Iris Biotech) in DMSO was added directly to cell culture media, which was swirled until the precipitate dissolved, to a final concentration of 500 uM. After 30 minutes at 37° C. hydrogen peroxide was added to media to a final concentration of 1 mM to induce biotinylation. After 60 seconds the media was decanted and the cells were washed with ice cold PBS containing 100 mM sodium azide, 100 mM sodium ascorbate and 50 mM TROLOX (6-hydroxy-2,5,7,8-tetramethylchroman-2-carboxylic acid) three times. Cells were lifted and transferred to 15 ml Falcon tubes with ice cold PBS, spun at 500 g for 3 minutes, flash frozen in liquid nitrogen and stored at −80° C.

Chromatin Immunoprecipitation Followed by Quantitative POR

Cells were trypsinized to single cell suspension and fresh formaldehyde was added to a final concentration of 1% and incubated at 37° C. for 10 minutes, being inverted several times every two minutes or so. Formaldehyde was quenched with 5% glycine and the samples were aliquoted into 3e6 cell aliquots, spun down and flash frozen in 0.5 mL Axygen tubes. Chromatin was sheared using a QSonica Q800R2 Sonicator at and amplitude of 50 for 30 seconds on/30 off, for 7.5 minutes, until 60% of fragments were between 150 and 700 bp. Lysis buffer was comprised of 1% SDS, 10 mM EDTA and Tris HCl, pH 8.0. For ChIP, streptavidin (SA) conjugated to magnetic beads (Thermo), M2 anti-FLAG antibody (Sigma) or anti-V5 antibodies (MBL Life Sciences) was conjugated to a 50:50 mix of Protein A: Protein G Dynabeads (Invitrogen) was incubated with sheared chromatin at 4° C. overnight. qPCR was performed with either Roche 2x Sybr mix (biological triplicates, measurement triplicates) on a Lightcycler (Agilent) or via digital droplet PCR (biological quadruplicates, measurement singlicate) (Bio-Rad).

Western Blot Analysis sgRNA-293-Caspex cells were labeled as described above. 40 ug of whole cell lysate was separated by SDS-PAGE, transferred to nitrocellulose and blotted against FLAG (Sigma) or biotin (Li-Cor IRdye 800 CW Streptavidin and IRdye 680RD anti-Mouse IgG).

Enrichment of Biotinylated Proteins for Proteomic Analysis

Eight 15 cm2 plates of each sgRNA-293-Caspex line, or no guide as a negative control, were used for proteomic experiments. Labeled whole cell pellets were lysed with RIPA (50 mM TRIS pH 8.0, 150 mM NaCl, 1% NP-40 and 0.5% sodium deoxycholate, 0.1% sodium dodecyl sulfate) with protease inhibitors (Roche) and probe sonicated to shear genomic DNA. Whole cell lysates were clarified by centrifugation at 14,000 g for 30 minutes at 4° C. and protein concentration was determined by Bradford. 500 uL SA magnetic bead slurry (Thermo) was used for each sgRNA line (between 60-90 mgs of protein/state). Lysates of equal protein concentrations were incubated with SA for 120 minutes at room temperature, washed twice with cold lysis buffer, once with cold IM KCl, once with cold 100 mM $Na_3CO_2$, and twice with cold 2 M urea in 50 mM ammonium bicarbonate (ABC). Beads were resuspended in 50 mM ABC and 300 ng trypsin and digested at 37° C. overnight.

Isobaric Labeling and Liquid Chromatography Tandem Mass Spectrometry

On-bead digests were desalted via Stage tip [39] and labeled with TMT (Thermo) using an on-column protocol. For on-column TMT labeling, Stage tips were packed with one punch C18 mesh (Empore), washed with 50 uL methanol, 50 uL 50% acetonitrile (ACN)/0.1% formic acid (FA), and equilibrated with 75 uL 0.1% FA twice. The digest was loaded by spinning at 3,500 g until the entire digest passed through. The bound peptides were washed twice with 75 uL 0.1% FA. One uL of TMT reagent in 100% ACN was added to 100 uL freshly made HEPES, pH 8, and passed over the C18 resin at 2,000 g for 2 minutes. The HEPES and residual TMT was washed away with 75 uL 0.1% FA twice and peptides were eluted with 50 uL 50% ACN/0.1% FA followed by a second elution with 50% ACN/20 mM ammonium hydroxide, pH 10. Peptide concentrations were estimated using an absorbance reading at 280 nm and mixed at equal ratios. Mixed TMT labeled peptides were step fractionated by basic reverse phase on a sulfonated divinylbenzene (SDB-RPS, Empore) packed Stage tip into 6 fractions (5, 10, 15, 20, 30 and 55% ACN in 20 mM ammonium hydroxide, pH 10). Each fraction was dried via vacuum centrifugation and resuspended in 0.1% formic acid for subsequent LC-MS/MS analysis.

Chromatography was performed using a Proxeon UHPLC at a flow rate of 200 nl/min. Peptides were separated at 50° C. using a 75 micron i.d. PicoFit (New Objective) column packed with 1.9 um AQ-C18 material (Dr. Maisch) to 20 cm in length over a 94 min gradient. Mass spectrometry was performed on a Thermo Scientific Q Exactive Plus (hTERT data) or a Lumos (c-MYC data) mass spectrometer. After a precursor scan from 300 to 2,000 m/z at 70,000 resolution the top 12 most intense multiply charged precursors were selected for HCD at a resolution of 35,000. Data were searched with Spectrum Mill (Agilent) using the Uniprot Human database, in which the CASPEX protein was amended. A fixed modification of carbamidomethylation of cysteine and variable modifications of N-terminal protein acetylation, oxidation of methionine, and TMT-10plex labels were searched. The enzyme specificity was set to trypsin and a maximum of three missed cleavages was used for searching. The maximum precursor-ion charge state was set to 6. The precursor mass tolerance and MS/MS tolerance were set to 20 ppm. The peptide and protein false discovery rates were set to 0.01.

Data Analysis

All non-human proteins and human proteins identified with only one peptide were excluded from downstream analyses. Human keratins were included in all analyses but were removed from the figures. The moderated T-test was used to determine proteins statistically enriched in the sgRNA-293-Caspex lines compared to the no sgRNA control. After correcting for multiple comparisons (Benjamini-Hochberg procedure), any proteins with an adjusted p-value of less than 0.05 were considered statistically enriched.

Pathway analysis was performed using the Quack algorithm incorporated into Genets (http://apps.broadinstitute.org/genets) to test for enrichment of canonical pathways in the Molecular Signature Database (MSigDB). Proteins identified as significantly enriched (adj. p-val.<0.05) by GLoPro were input into Genets and were queried against MSigDB. Pathways enriched (FDR<0.05) were investigated manually for specific proteins for follow-up.

Data Availability

The original mass spectra may be downloaded from MassIVE (http: \\massive.ucsd.edu) under the identifier: To be determined. The data are directly accessible via ftp://massive.ucsd.edu/tobedetermined.

Oligonucleotides Used in this Study

| sgRNAs | Guide matching seq | Chromosome | start | end |
|---|---|---|---|---|
| Myc003<br>SEQ ID NO. 149 | CCCCGAGCTGTGCTGCTCG | chr8 | 128748313 | 128748336 |
| 053Myc<br>SEQ ID NO. 150 | gtgggcggagattagcgagag | chr8 | 128748259 | 128748279 |
| 085Myc<br>SEQ ID NO. 151 | TCCCGGGTTCCCAAAGCAG | chr8 | 128748207 | 128748234 |
| 208Myc<br>SEQ ID NO. 152 | GCGCGCGTAGTTAATTCATG | chr8 | 128748087 | 128748106 |
| 442Myc<br>SEQ ID NO. 153 | tgggactcttgatcaaagcg | chr8 | 128747853 | 128747872 |
| 1021Myc<br>SEQ ID NO. 154 | gcccctcccatattctcccgtctagcacct | chr8 | 128747264 | 128747293 |
| Tert959<br>SEQ ID NO. 155 | GCAGGTGACACCACACAGAAACCACGGTCA | chr5 | 1294174 | 1294203 |
| Tert266<br>SEQ ID NO. 156 | CCTTCCGCCAGGTGGGCCTCCCCGGGGTCG | chr5 | 1294867 | 1294896 |
| Tert092<br>SEQ ID NO. 157 | CCCTGCTGCGCAGCCACTACCGCGAGGTGC | chr5 | 1295041 | 1295070 |
| 107Tert<br>SEQ ID NO. 158 | CCTTCCAGCTCCGCCTCCTCCGCGCGGACC | chr5 | 1295270 | 1295299 |
| 430Tert<br>SEQ ID NO. 159 | CTCCGGATCAGGCCAGCGGCCAAAGGGTCG | chr5 | 1295593 | 1295622 |

| ChIP primers | |
|---|---|
| ChIP-hMyc-F1<br>SEQ ID NO. 160 | GGGAGATCCGGAGCGAATAG |
| ChIP-hMyc-R1<br>SEQ ID NO. 161 | GGAGAGTCGCGTCCTTGCTC |
| ChIP-hMyc-F2<br>SEQ ID NO. 162 | AGGGATCGCGCTGAGTATAAAAG |
| ChIP-hMyc-R2<br>SEQ ID NO. 163 | CTATTCGCTCCGGATCTCCC |
| ChIP-hMyc-F3<br>SEQ ID NO. 164 | aagatcctctctcgctaatctcc |
| ChIP-hMyc-R3<br>SEQ ID NO. 165 | CTGCCCTTCTCGAGGCAGGA |

-continued

| ChIP primers | |
|---|---|
| ChIP-hMyc-F4 SEQ ID NO. 166 | gtttgtcaaacagtactgctacgga |
| ChIP-hMyc-R4 SEQ ID NO. 167 | gaggagactcagccgggcag |
| ChIP-hMyc-F5 SEQ ID NO. 168 | tacactaacatcccacgctctg |
| ChIP-hMyc-R5 SEQ ID NO. 169 | gtataaatcatcgcaggcggaac |
| ChIP-hMyc-F6 SEQ ID NO. 170 | CAGGACCCGCTTCTCTGAAAG |
| ChIP-hMyc-R6 SEQ ID NO. 171 | GACACCCTATTTAGGCATTCGACTC |
| ChIP-hMyc-F7 SEQ ID NO. 172 | ggtccacaagctctccacttg |
| ChIP-hMyc-R7 SEQ ID NO. 173 | ccggtttgcaacagtctcgg |
| ChIP-hTert-F11 SEQ ID NO. 174 | CAGCAGGAGCGCCTGGCTCCATTTCC |
| ChIP-hTert-R11 SEQ ID NO. 175 | GACGAACCCGAGGACGCATTGCTCC |
| ChIP-hTert-F10 SEQ ID NO. 176 | GGAGCAATGCGTCCTCGGGTTCGTC |
| ChIP-hTert-R10 SEQ ID NO. 177 | CATGATGTGGAGGCCCTGGGAAC |
| ChIP-hTert-F9 SEQ ID NO. 178 | GTTCCCAGGGCCTCCACATCATG |
| ChIP-hTert-R9 SEQ ID NO. 179 | GGAAGCGCGGTCCTGGGCGTCTGTG |
| ChIP-hTert-F8 SEQ ID NO. 180 | CACAGACGCCCAGGACCGCGCTTCC |

-continued

| ChIP primers | |
|---|---|
| ChIP-hTert-R8 SEQ ID NO. 181 | CAGCAGGACGCAGCGCTGCCTGAAACTC |
| ChIP-hTert-F7 SEQ ID NO. 182 | GAGTTTCAGGCAGCGCTGCGTCCTGCTG |
| ChIP-hTert-R7 SEQ ID NO. 183 | CAGCACCTCGCGGTAGTGGCTGC |
| ChIP-hTert-F6 SEQ ID NO. 184 | GCAGCCACTACCGCGAGGTGCTG |
| ChIP-hTert-R6 SEQ ID NO. 185 | CACCAGCTCCTTCAGGCAGGACACCTG |
| ChIP-hTert-F5 SEQ ID NO. 186 | CAGGTGTCCTGCCTGAAGGAGCTGGTG |
| ChIP-hTert-R5 SEQ ID NO. 187 | CAGTGCGTCGGTCACCGTGTTGGGCAG |
| ChIP-hTert-F4 SEQ ID NO. 188 | CTGCCCAACACGGTGACCGACGCACTG |
| ChIP-hTert-R4 SEQ ID NO. 189 | CTTCGGGGTCCACTAGCGTGTG |
| ChIP-hTert-F3 SEQ ID NO. 190 | GAAGAAGCCACCTCTTTGGAG |
| ChIP-hTert-R3 SEQ ID NO. 191 | CTCCAAAGAGGTGGCTTCTTC |
| ChIP-hTert-F2 SEQ ID NO. 192 | GAAGAAGCCACCTCTTTGGAG |
| ChIP-hTert-R2 SEQ ID NO. 193 | CTGGAACCCAGAAAGATGGTCTCCACGAG |
| ChIP-hTert-F1 SEQ ID NO. 194 | CTCGTGGAGACCATCTTTCTGGGTTCCAG |
| ChIP-hTert-R1 SEQ ID NO. 195 | CCACAGAGCCCTGGGGCTTCTC |

| Construct primers | | |
|---|---|---|
| 3xFdCAS-tetON-F1 SEQ ID NO. 196 | taccacttcctaccctcgtaaaggtctaga gctagccaccATGGACTACAAAGACCATGA | COMMON PRIMER amplifies 3xF-dCas9 with homology to PB-TetON cut with Nhe1 |
| dCASapex-R1 SEQ ID NO. 197 | GTTGGGGATGGGCTTGCCagaaccccgcac GTCTCCACCGAGCTGAGAGA | amps the 3' end of 3xFdCas9 with *homo* to V5-APEX2-NLS |
| V5-APEXdcas-F1 SEQ ID NO. 198 | AGAATCGACCTCTCTCAGCTCGGTGGAGAC gtgcggggttctGGCAAGC | amps V5-APEX2 with *homo* to cas9 |
| APEXt2agfp-F1 SEQ ID NO. 199 | accgcatgttagaagacttcctctgccctc CACCTTCCTCTTCTTCTTGGG | amps APEX2 with *homo* to T2A-Gfp |
| T2AGFPapex-F1 SEQ ID NO. 200 | agggccgaccccaagaagaagaggaaggtg GAGGGCAGAGGAAGTCTTCT | amps T2-Gfp with *homo* to apex |
| GFPtetOn-R1 SEQ ID NO. 201 | cctcccccgtttaaactcattactaaccgg TCAAccggTcttgtacagctc | amps Gfp with *homo* to PB-TetON cut with AgeI |

Having thus described in detail preferred embodiments of the present invention, it is to be understood that the invention defined by the above paragraphs is not to be limited to particular details set forth in the above description as many apparent variations thereof are possible without departing from the spirit or scope of the present invention.

REFERENCES CITED

1. Bernstein, B. E. et al. A bivalent chromatin structure marks key developmental genes in embryonic stem cells. *Cell* 125, 315-326 (2006).
2. Boyer, L. A. et al. Core transcriptional regulatory circuitry in human embryonic stem cells. *Cell* 122, 947-956 (2005).
3. Boyer, L. A. et al. Polycomb complexes repress developmental regulators in murine embryonic stem cells. *Nature* 441, 349-353 (2006).
4. Kagey, M. H. et al. Mediator and cohesin connect gene expression and chromatin architecture. *Nature* 467, 430-435 (2010).
5. Liber, D. et al. Epigenetic priming of a pre-B cell-specific enhancer through binding of Sox2 and Foxd3 at the ESC stage. *Cell Stem Cell* 7, 114-126 (2010).
6. Samstein, R. M. et al. Foxp3 exploits a pre-existent enhancer landscape for regulatory T cell lineage specification. *Cell* 151, 153-166 (2012).
7. Mittler, G., Butter, F. & Mann, M. A SILAC-based DNA protein interaction screen that identifies candidate binding proteins to functional DNA elements. *Genome Res* 19, 284-293 (2009).
8. Dejardin, J. & Kingston, R. E. Purification of proteins associated with specific genomic Loci. *Cell* 136, 175-186 (2009).
9. Fujita, T. & Fujii, H. Efficient isolation of specific genomic regions and identification of associated proteins by engineered DNA-binding molecule-mediated chromatin immunoprecipitation (enChIP) using CRISPR. *Biochem Biophys Res Commun* 439, 132-136 (2013).
10. Fujita, T. & Fujii, H. Efficient isolation of specific genomic regions retaining molecular interactions by the iChIP system using recombinant exogenous DNA-binding proteins. *BMC Mol Biol* 15, 26 (2014).
11. Pourfarzad, F. et al. Locus-specific proteomics by TChP: targeted chromatin purification. *Cell Rep* 4, 589-600 (2013).
12. Jinek, M. et al. A programmable dual-RNA-guided DNA endonuclease in adaptive bacterial immunity. *Science* 337, 816-821 (2012).
13. Qi, L. S. et al. Repurposing CRISPR as an RNA-guided platform for sequence-specific control of gene expression. *Cell* 152, 1173-1183 (2013).
14. Lam, S. S. et al. Directed evolution of APEX2 for electron microscopy and proximity labeling. *Nat Methods* 12, 51-54 (2015).
15. Cong, L. et al. Multiplex Genome Engineering Using CRISPR/Cas Systems. *Science* 339, 819-823 (2013).
16. Hung, V. et al. Proteomic mapping of cytosol-facing outer mitochondrial and ER membranes in living human cells by proximity biotinylation. *Elife* 6 (2017).
17. Rhee, H. W. et al. Proteomic Mapping of Mitochondria in Living Cells via Spatially Restricted Enzymatic Tagging. *Science* 339, 1328-1331 (2013).
18. Roux, K. J., Kim, D. I., Raida, M. & Burke, B. A promiscuous biotin ligase fusion protein identifies proximal and interacting proteins in mammalian cells. *J Cell Biol* 196, 801-810 (2012).
19. Paek, J. et al. Multidimensional Tracking of GPCR Signaling via Peroxidase-Catalyzed Proximity Labeling. *Cell* 169, 338-349 (2017).
20. Lobingier, B. T. et al. An Approach to Spatiotemporally Resolve Protein Interaction Networks in Living Cells. *Cell* 169, 350-360 (2017).
21. Wang, G. et al. Modeling the mitochondrial cardiomyopathy of Barth syndrome with induced pluripotent stem cell and heart-on-chip technologies. *Nat Med* 20, 616-623 (2014).
22. Huang, F. W. et al. Highly Recurrent TERT Promoter Mutations in Human Melanoma. *Science* 339, 957-959 (2013).
23. Thakore, P. I. et al. Highly specific epigenome editing by CRISPR-Cas9 repressors for silencing of distal regulatory elements. *Nature Methods* 12, 1143-+ (2015).
24. Wu, X. B. et al. Genome-wide binding of the CRISPR endonuclease Cas9 in mammalian cells. *Nat Biotechnol* 32, 670-+ (2014).
25. Thompson, A. et al. Tandem mass tags: A novel quantification strategy for comparative analysis of complex protein mixtures by MS/MS. *Anal Chem* 75, 1895-1904 (2003).
26. Hung, V. et al. Proteomic Mapping of the Human Mitochondrial Intermembrane Space in Live Cells via Ratiometric APEX Tagging. *Mol Cell* 55, 332-341 (2014).
27. Xu, D. W. et al. Downregulation of telomerase reverse transcriptase mRNA expression by wild type p53 in human tumor cells. *Oncogene* 19, 5123-5133 (2000).
28. Kanaya, T. et al. Adenoviral expression of p53 represses telomerase activity through down-regulation of human telomerase reverse transcriptase transcription. *Clin Cancer Res* 6, 1239-1247 (2000).
29. Su, J. M. et al. X protein of hepatitis B virus functions as a transcriptional corepressor on the human telomerase promoter. *Hepatology* 46, 402-413 (2007).
30. Xu, M., Katzenellenbogen, R. A., Grandori, C. & Galloway, D. A. An unbiased in vivo screen reveals multiple transcription factors that control HPV E6-regulated hTERT in keratinocytes. *Virology* 446, 17-24 (2013).
31. Hoffmeyer, K. et al. Wnt/beta-Catenin Signaling Regulates Telomerase in Stem Cells and Cancer Cells. *Science* 336, 1549-1554 (2012).
32. Jaitner, S. et al. Human telomerase reverse transcriptase (hTERT) is a target gene of beta-catenin in human colorectal tumors. *Cell Cycle* 11, 3331-3338 (2012).
33. Zhang, Y., Toh, L., Lau, P. & Wang, X. Y. Human Telomerase Reverse Transcriptase (hTERT) Is a Novel Target of the Wnt/beta-Catenin Pathway in Human Cancer. *J Biol Chem* 287, 32494-32511 (2012).
34. Bell, R. J. A. et al. The transcription factor GABP selectively binds and activates the mutant TERT promoter in cancer. *Science* 348, 1036-1039 (2015).
35. Glasspool, R. M., Burns, S., Hoare, S. F., Svensson, C. & Keith, W. N. The hTERT and hTERC telomerase gene promoters are activated by the second exon of the adenoviral protein, E1A, identifying the transcriptional corepressor CtBP as a potential repressor of both genes. *Neoplasia* 7, 614-622 (2005).
36. Yang, X. P. et al. A public genome-scale lentiviral expression library of human ORFs. *Nature Methods* 8, 659-U680 (2011).
37. Li, T. B. et al. A scored human protein-protein interaction network to catalyze genomic interpretation. *Nature Methods* 14, 61-64 (2017).
38. Subramanian, A. et al. Gene set enrichment analysis: A knowledge-based approach for interpreting genome-wide expression profiles. *P Natl Acad Sci USA* 102, 15545-15550 (2005).
39. Rappsilber, J., Mann, M. & Ishihama, Y. Protocol for micro-purification, enrichment, pre-fractionation and storage of peptides for proteomics using StageTips. Nature Protocols 2, 1896-1906 (2007).

What is claimed is:

1. A fusion protein comprising:

(a) a nucleotide-editing protein, wherein the nucleotide-editing protein is a *Streptococcus pyogenes* or *Staphylococcus aureus* catalytically-inactive Cas9 (dCas9) protein, and (b) a proximity-dependent protein to catalyze ligation of biotin, or an ATP-biotin interaction loop or a biotin pocket thereof, wherein said proximity-dependent protein is a mutated *E. coli* Bir A, or a biotin-peroxide dependent ascorbate peroxidase (APEX) or a Split Biotin protein ligase separated at amino-acid positions (1-149, 141-320).

2. The fusion protein according to claim 1, wherein said proximity-dependent protein is *E. coli* BirA (RI 18G).

3. The fusion protein according to claim 1 wherein the nucleotide editing protein comprises a DIOA mutation combined with one or more of H840A, N854A, or N863A mutations, with reference to residue position numbering of a *Streptococcus pyogenes* Cas9 (SpCas9) protein or a *Staphylococcus aureus* Cas9 (SaCas9) protein.

4. The fusion protein according to claim 1, further comprising one or more nuclear localization signals (NLS).

5. A polynucleotide comprising a nucleotide sequence encoding the fusion protein of claim 1.

6. The polynucleotide according to claim 5, wherein the polynucleotide is:

selected from vectors and messenger RNAs;

selected from any one of retroviral, lentiviral, adenoviral, adeno-associated or herpes simplex viral vectors; or codon-optimized for expression in a host of interest.

7. The fusion protein of claim 1 further comprising an MS2 bacteriophage coat protein.

8. A polynucleotide comprising a nucleotide sequence encoding the fusion protein according to claim 7.

9. The fusion protein of claim 1, further comprising one or more CRISPR guide RNA(s) that hybridize(s) with a target sequence within a genomic locus of interest, wherein said CRISPR guide RNA(s) each comprise(s) a guide sequence, a tracr sequence, and a tracr mate sequence.

10. The fusion protein of claim 9, wherein the one or more CRISPR guide RNA(s) each comprise one or two MS2-binding RNA aptamer sequence(s).

11. The fusion protein of claim 9, wherein said genomic locus of interest is located in a non-coding genomic region.

12. A method for protein purification, comprising the steps of:

(A) selecting a genomic locus of interest in a cell, (B) providing the fusion protein of claim 1, (C) contacting said genomic locus of interest with the component(s) of the system provided at step (B), wherein the proximity-dependent protein to catalyze ligation of biotin, or the ATP-biotin interaction loop or the biotin pocket thereof, is directed to a genomic locus of interest, (D) causing endogenous ATP and free biotin uptake by said cell, so as to allow proximity-dependent biotinylation of one or more proteins located at the genomic locus of interest, and (E) following flushing of free biotin, performing streptavidin-mediated purification of said one or more proteins biotinylated at step (D).

13. A method for identifying proteins located at a genomic locus of interest, comprising the method for protein purification according to claim 12, and further comprising the step of (F) performing protein analysis on the proteins purified at step (E).

14. The method according to claim 13, wherein performing protein analysis further comprises protein electrophoresis and/or mass spectroscopy (MS).

15. The method according to claim 12, wherein the method is for performing chromatin analysis, and/or identifying a medically or therapeutically relevant marker, and/or identifying a medically or therapeutically relevant target, and/or monitoring protein occupancy at a genomic locus of interest.

16. A method for DNA purification, comprising the steps of:

(A) selecting a genomic locus of interest in a cell, (B) providing the fusion protein of claim 1, (C) contacting said genomic locus of interest with the component(s) of the system provided at step (B), wherein the proximity-dependent protein to catalyze ligation of biotin, or the ATP-biotin interaction loop or the biotin pocket thereof, is directed to the genomic locus of interest, (D) causing endogenous ATP and free biotin uptake by said cell, so as to allow proximity-dependent biotinylation of DNA at the genomic locus of interest, and (E) following flushing of free biotin, performing streptavidin mediated purification of said DNA biotinylated at step (D).

17. The method of claim 15, for identifying genomic targets, comprising:

(A) selecting a genomic locus of interest in a cell, (B) providing a fusion protein comprising: (i) a nucleotide-editing protein, wherein the nucleotide-editing protein is a *Streptococcus pyogenes* or *Staphylococcus aureus* catalytically-inactive Cas9 (dCas9) protein, and (ii) a proximity-dependent protein to catalyze ligation of biotin, or an ATP-biotin interaction loop or a biotin pocket thereof, wherein said proximity-dependent protein is a mutated *E. coli* Bir A, or a biotin-peroxide dependent ascorbate peroxidase (APEX) or a Split Biotin protein ligase separated at amino-acid positions (1-149, 141-320), (C) contacting said genomic locus of interest with the component(s) of the system provided at step (B), wherein the proximity-dependent protein to catalyze ligation of biotin, or the ATP-biotin interaction loop or the biotin pocket thereof, is directed to the genomic locus of interest, (D) causing endogenous ATP and free biotin uptake by said cell, so as to allow proximity-dependent biotinylation of DNA at the genomic locus of interest, (E) following flushing of free biotin, performing streptavidin mediated purification of said DNA biotinylated at step (D)

(F) performing DNA analysis on the DNA purified at step (E).

18. The method according to claim 17, wherein step (F) comprises DNA electrophoresis and/or DNA sequencing.

19. The method according to claim 17, wherein the method is for determining off-target activity of a TALE or CRISPR-Cas system.

20. The method of claim 16, further comprising the step of (F) performing DNA analysis on the DNA purified at step (E).

21. The method according to claim 20, wherein DNA analysis comprises DNA electrophoresis and/or DNA sequencing.

22. The method according to claim 12, wherein the method is selected from in vivo, in vitro and ex vivo methods.

23. A kit comprising:

the fusion protein of claim 1 or a polynucleotide encoding the fusion protein of claim 1;

free biotin;

ATP; and instructions for its use.

24. The kit of claim 23, further comprising streptavidin.

25. The kit of claim 24, wherein the streptavidin is bound to a solid support.

26. The kit of claim 25, wherein the solid support comprises magnetic beads.

* * * * *